(12) United States Patent
Baty et al.

(10) Patent No.: US 10,385,137 B2
(45) Date of Patent: *Aug. 20, 2019

(54) PRODUCTION OF ANTIBODY FORMATS AND IMMUNOLOGICAL APPLICATIONS OF SAID FORMATS

(71) Applicants: INSERM (Institut National de la Sante et de la Recherche Medicale), Paris (FR); Centre National de la Recherche Scientifique—CNRS, Paris (FR); Universite d'Aix Marseille, Marseilles (FR); Universite de Montpellier, Montpellier (FR); Institut Regional du Cancer de Montpellier-Val d'Aurelle, Montpellier (FR); Institut Paoli Calmettes, Marseilles (FR)

(72) Inventors: Daniel Baty, Marseilles (FR); Ghislaine Behar, Marseilles (FR); Martine Mansais, Marseilles (FR); Andre Pelegrin, Montpellier (FR); Jean-luc Teillaud, Paris (FR); Isabelle Teulon, Saint Gely du Fesc (FR)

(73) Assignees: INSERM (Institut National de la Sante et de la Recherche Medicale), Paris (FR); Centre National de la Recherche Scientifique (CNRS), Paris (FR); Universite d'Aix Marseille, Marseilles (FR); Universite de Montpellier, Montpellier (FR); Institut Regional du Cancer de Montpellier-Val D'Aurelle, Montpellier (FR); Institut Paoli Calmettes, Marseilles (FR)

(*) Notice: Subject to any disclaimer, the term of this patent is extended or adjusted under 35 U.S.C. 154(b) by 72 days.

This patent is subject to a terminal disclaimer.

(21) Appl. No.: 14/856,016

(22) Filed: Sep. 16, 2015

(65) Prior Publication Data

US 2016/0083476 A1 Mar. 24, 2016

Related U.S. Application Data

(63) Continuation of application No. 11/818,218, filed on Jun. 13, 2007, now Pat. No. 9,169,316, which is a continuation of application No. PCT/FR2005/003151, filed on Dec. 15, 2005.

(30) Foreign Application Priority Data

Dec. 16, 2004 (FR) .................................. 04 13433

(51) Int. Cl.
*A61K 39/00* (2006.01)
*C07K 16/30* (2006.01)
*C07K 16/28* (2006.01)
*C07K 16/00* (2006.01)

(52) U.S. Cl.
CPC .......... *C07K 16/3007* (2013.01); *C07K 16/00* (2013.01); *C07K 16/283* (2013.01); *C07K 2317/21* (2013.01); *C07K 2317/22* (2013.01); *C07K 2317/24* (2013.01); *C07K 2317/52* (2013.01); *C07K 2317/522* (2013.01); *C07K 2317/53* (2013.01); *C07K 2317/54* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 9,169,316 B2* | 10/2015 | Baty | C07K 16/00 |
| 2002/0155604 A1 | 10/2002 | Ledbetter et al. | |
| 2004/0220388 A1* | 11/2004 | Mertens | C07K 16/00 530/388.8 |
| 2004/0253250 A1 | 12/2004 | Ledbetter et al. | |
| 2007/0135621 A1 | 6/2007 | Bourel et al. | |
| 2007/0298033 A1 | 12/2007 | Gauthier et al. | |
| 2009/0053233 A1 | 2/2009 | De Romeuf et al. | |
| 2009/0163410 A1 | 6/2009 | Baty et al. | |

FOREIGN PATENT DOCUMENTS

| | | |
|---|---|---|
| EP | 0618292 | 10/1994 |
| WO | 1994/025591 | 11/1994 |
| WO | 2005/075515 | 8/2005 |

OTHER PUBLICATIONS

Bond et al. (Journal of Molecular Biology, 2003, 332:643-655).*
Weinblatt et al. (Arthritis and Rheumatism, 2003, 48:35-45).*
Muller et al. (FEBS Letters, 1998, 422:259-264).*
Zhu et al. (Protein Engineering, 2000, 13:361-367.*
Shahied et al. (Journal of Biological Chemistry, 2004, 279:53907-53914).*
Casset et al., "A peptide mimetic of an anti-CD4 monoclonal antibody by rational design," Biochem. Biophys. Res. Commun., 307:198-205 (2003).
Chen et al., "Selection and analysis of an optimized anti-VEGF antibody: crystal structure of an affinity-matured Fab in complex with antigen," J. Mol. Biol., 293(4):865-881 (1999).
Chomczynski et al., "Single-Step Method of RNA Isolation by Acid Guanidinium Thiocyanate-Phenol-Chloroform Extraction," Anal. Biochem., 162:156-159 (1987).
Colman, "Effects of amino acid sequence changes on antibody-antigen interactions," Res. Immunol., 145:33-36 (1994).
Cortez-Retamozo et al., "Efficient tumor targeting by single-domain antibody fragments of camels," Int. J. Cancer, 98(3):456-462 (2002).
Credo, Definition of "valence" from "Mosby's Dental Dictionary" (2013).

(Continued)

*Primary Examiner* — Julie Wu
(74) *Attorney, Agent, or Firm* — W&C IP

(57) ABSTRACT

The invention concerns antibody formats comprising VH sequence of Camelidae, such as llamas; antibodies of various formats have anti-CEA or anti-CD16 VH sequences thereof; vectors expressing the antibody formats, and methods for producing the same.

3 Claims, 93 Drawing Sheets

Specification includes a Sequence Listing.

(56) References Cited

OTHER PUBLICATIONS

De Pascalis et al., "Grafting of "abbreviated" complementarity-determining regions containing specificity-determining residues essential for ligand contact to engineer a less immunogenic humanized monoclonal antibody," J. Immunol., 169(6):3076-3084 (2002).
Frenken et al., "Isolation of antigen specific llama VHH antibody fragments and their high level secretion by *Saccharomyces cerevisiae*," J. Biotechnol., 78:11-21 (2000).
Ghahroudi et al., "Selection and identification of single domain antibody fragments from camel heavy-chain antibodies," FEBS Lett., 414(3):521-526 (1997).
Hamers-Casterman et al., "Naturally occurring antibodies devoid of light chains," Nature, 363(6428):446-448 (1993).
Harmsen et al., "Properties, production, and applications of camelid single-domain antibody fragments," Appl. Microbiol. Biotechnol., 77:13-22 (2007).
Holm et al., "Functional mapping and single chain construction of the anti-cytokeratin 8 monoclonal antibody TS1," Mol. Immunol., 44(6):1075-1084 (2007).
International Search Report in PCT/FR2005/003151 dated Mar. 22, 2006, 2 pages.
Le Calvez et al., "Increased efficiency of alkaline phosphatase production levels in *Escherichia coli* using a degenerate PelB signal sequence," Gene, 170:51-55 (1996).
Le Calvez et al., "Paratope characterization by structural modelling of two anti-cortisol single-chain variable fragments produced in *E. coli*," Mol. Immunol., 32(3):185-198 (1995).
MacCallum et al., "Antibody-antigen interactions: contact analysis and binding site topography," J. Mol. Biol., 262(5):732-745 (1996).
McCall et al., "Isolation and characterization of an anti-CD16 single chain Fv fragment and construction of an anti-HER2/neu/anti-CD16 bispecific svFv that triggers CD16 dependent tumor cytolysis," Mol. Immunol., 36(7):433-445 (1999).
Muller et al., "The first constant domain (C(H)1 and C(L)) of an antibody used as heterodimerization domain for bispecific miniantibodies,"FEBS Lett., 442(2):259-264 (1998).
Muyldermans et al., "Unique single-domain antigen binding fragments derived from naturally occurring camel heavy-chain antibodies," J. Mol. Recognit., 12(2):131-140 (1999).
Muyldermans, "Single domain camel antibodies: current status," J. Biotechnol., 74(4):277-302 (2001).

Padlan et al., "Identification of specificity-determining residues in antibodies," FASEB J., 9:133-139 (1995).
Paul, Fundamental Immunology, 3rd Edition, pp. 292-295 (1993).
Pluckthun et al., "New protein engineering approaches to multivalent and bispecific antibody fragments," Immunotechnology, 3(2):83-105 (1997).
Rahbarizadeh et al., "The production and characterization of novel heavy-chain antibodies against the tandem repeat region of MUC1 mucin," Immunol. Invest., 34(4):431-452 (2005).
Riechmann et al., "Single domain antibodies: comparison of camel VH and camelised human VH domains," J. Immunol. Methods, 231(1-2):25-38 (1999).
Roguska et al., "A comparison of two murine monoclonal antibodies humanized by CDR-grafting and variable domain resurfacing," Protein Eng., 9(10):895-904 (1996).
Rudikoff et al., "Single amino acid substitution altering antigen-binding specificity," Proc. Natl. Acad. Sci. USA, 79(6):1979-1983 (1982).
Teillaud et al., "Soluble CD16 binds peripheral blood mononuclear cells and inhibits pokeweed-mitogen-induced responses," Blood, 82(10):3081-3090 (1993).
Terskikh et al., "Marked increase in the secretion of a fully antigenic recombinant carcinoembryonic antigen obtained by deletion of its hydrophobic tail," Mol. Immunol., 30(10):921-927 (1993).
Vajdos et al., "Comprehensive functional maps of the antigen-binding site of an anti-ErbB2 antibody obtained with shotgun scanning mutagenesis," J. Mol. Biol., 320(2):415-428 (2002).
Vely et al., "A new set of monoclonal antibodies against human Fc gamma RII (CD32) and FC gamma RIII (CD16): characterization and use in various assays," Hybridoma, 16(6):519-528 (1997).
Vivier et al., "Signaling function of reconstituted CD16: zeta: gamma receptor complex isoforms," Int. Immunol., 4(11):1313-1323 (1992).
Wright et al., "Genetically engineered antibodies: progress and prospects," Crit. Rev. Immunol., 12(3-4):125-168 (1992).
Wu et al., "Humanization of a murine monoclonal antibody by simultaneous optimization of framework and CDR residues," J. Mol. Biol., 294:151-162 (1999).
Zhu et al., "Inhibition of human leukemia in an animal model with human antibodies directed against vascular endothelial growth factor receptor 2. Correlation between antibody affinity and biological activity," Leukemia, 17(3):604-611 (2003).
Zuo et al., "An efficient route to the production of an IgG-like bispecific antibody," Protein Eng., 13(5):361-367 (2000).

* cited by examiner

```
                        /         FR1        /      CDR1    /        FR2      /   CDR2    /              FR3                   /          CDR3           /    FR4
                        1         10        20        30            40        50         60         70        80         90       100             110
                        123456789012345678901234 56 78901ab2345 6789012345 6789012345 012abc 3456789012345 6789012345678901234abc345678901234 567890abcde 12 34567890123

VHH ANTI-CD16

CD16 c13
/SEQ ID N°73/           EVQLVQSGGGLVQPGGSLRLSCSFPG  SIFSLITMG***  WYRQAPGKERELVT  SAT***  PGGDTNYADFVKG  RFTISRDNARSIIYLQMNSLKPEDTAVYYCYA  RTRNWG*****  TV  WGQGTQVTVSS
/SEQ ID N°103/          EVQLVESGGGLVQPGGSLRLSCSFPG  SIFSLITMG***  WYRQAPGKERELVT  SAT***  PGGDTNYADFVKG  RFTISRDNARSIIYLQMNSLKPEDTAVYYCYA  RTRNWG*****  TV  WGQGTQVTVSS

CD16 c21
/SEQ ID N°74/           EVQLVQSGGGELVQAGGSLRLSCAASG LTFSSYNMG**   WFRRAPGKEREFVA  SITW**  SGRDTFYADSVKG  RFTISRDNAKNTVYLQMSSLKPEDTAVYYCAA  NPWPVAAPRSG  TY  WGQGTQVTVSS
/SEQ ID N°104/          EVQLVESGGGELVQAGGSLRLSCAASG LTFSSYNMG**   WFRRAPGKEREFVA  SITW**  SGRDTFYADSVKG  RFTISRDNAKNTVYLQMSSLKPEDTAVYYCAA  NPWPVAAPRSG  TY  WGQGTQVTVSS

CD16 c28
/SEQ ID N°75/           EVQLVESGGGLVQPGESLITLSCVVAG SIFSFAMS***   WYRQAPGKERELVA  RIG***  SDDRVTYADSVKG  RFTISRDNIKRTAGLQMNSLKPEDTAVYYCNA  QTDLRDWTVR*  EY  WGQGTQVTVSS

CD16 c72
/SEQ ID N°76/           EVQLVESGGGLVQPGGSLITLSCVAAG SIFTFAMS***   WYRQAPRKERELVA  RIG***  TDDETMYKDSVKG  RFTISRDNVKRTAGLQMNNLKPEDTAVYYCNA  RTDYRDWTVR*  EY  WGQGTQVTVSS

VHH ANTI-CEA

CEA 3
/SEQ ID N°77/           EVQLVESGGGLVQAGGSIRLSCTSST  VTFTPYQMG**   WYRQAPGKQRALVA  DIST**  GGSRTNYADFAKG  RFTISRDDVQNTVYLQMNNLKPEDTAVYYCNT  YYAMIGHA***  RN  WGQGTQVTVSS

CEA 17
/SEQ ID N°78/           EVQLVESGGGFVQAGESLTLSCTSST  LTFTPYRMA**   WYRQAPGKQRDIVA  DISSG*  DGRTTNYADFAKG  RFTISRDNIKNTVFLRMTNLKPEDTAVYYCNT  FVSFVGIA***  RS  WGQGTQVTVSS

CEA 25
/SEQ ID N°79/           EVQLVESGGGLVQAGDSLTLICTSPT  LTFTPYRMG**   WYRQAPGKQRDIVA  DISGG*  DGRTTNYADFAKG  RFTISRDNVKNAVVLQMNNLKPEDTALYYCNT  YVAIVGHA***  RS  WGQGTQVTVSS

CEA 43
/SEQ ID N°80/           QVQLQESGGGLVQAGGSLTLSCTSST  LTFTPYRMG**   WYRQTPGKQRDLVA  DISPG*  DGSTKNYAGFAQG  RFTISRDNIKNTVYLQMNDLKPEDTAVYYCNT  YVAFVGRA***  RT  WGQGTQVTVTS
/SEQ ID N°105/          EVQLVESGGGLVQAGGSLTLSCTSST  LTFTPYRMG**   WYRQTPGKQRDLVA  DISPG*  DGSTKNYAGFAQG  RFTISRDNIKNTVYLQMNDLKPEDTAVYYCNT  YVAFVGRA***  RT  WGQGTQVTVTS
```

Figure 1

VHH anti-CD16

CD16 c13
/SEQ ID N° 81/
GAGGTGCAGCTGGTGCAGTCTGGGGGAGGCTTGGTGCAGCCTGGGGGGTCTCTGAGACTCTCCTGTTCATTCCCTGGAAGCATCTTCAGTCTCA
CCATGGGCTGGTACCGTCAGGCTCCAGGGAAGGAGCGCGAGTTGGTCACAAGTGCTACTCCTGGTGGTGACACAAACTATGCAGACTTCGTGAA
GGGCCGATTCACCATCTCCAGAGACAACGCCAGGAGCATCATATATCTACAAATGAATAGCCTGAAACCTGAGGACACGGCCGTCTATTATTGT
TATGCACGTACGAGGAATTGGGGTACGGTCTGGGGCCAGGGGACCCAGGTCACCGTCTCCTCA
/SEQ ID N° 106/
GAGGTGCAGCTGGTGGAGTCTGGGGGAGGCTTGGTGCAGCCTGGGGGGTCTCTGAGACTCTCCTGTTCATTCCCTGGAAGCATCTTCAGTCTCA
CCATGGGCTGGTACCGTCAGGCTCCAGGGAAGGAGCGCGAGTTGGTCACAAGTGCTACTCCTGGTGGTGACACAAACTATGCAGACTTCGTGAA
GGGCCGATTCACCATCTCCAGAGACAACGCCAGGAGCATCATATATCTACAAATGAATAGCCTGAAACCTGAGGACACGGCCGTCTATTATTGT
TATGCACGTACGAGGAATTGGGGTACGGTCTGGGGCCAGGGGACCCAGGTCACCGTCTCCTCA

CD16 c21
/SEQ ID N° 82/
GAGGTGCAGCTGGTGCAGTCTGGGGGAGAGTTGGTGCAGGCTGGGGGCTCTCTGAGACTCTCCTGTGCAGCCTCTGGCCTCACCTTCAGTAGCT
ATAACATGGGCTGGTTCCGCCGGGCTCCAGGGAAGGAGCGTGAGTTTGTAGCATCTATTACCTGGAGTGGTCGGGACACATTCTATGCAGACTC
CGTGAAGGGCCGATTCACCATCTCCAGAGACAACGCCAAGAACACTGTTTATCTGCAAATGAGCAGCCTGAAACCTGAGGACACGGCCGTTTAT
TATTGTGCTGcAAAcCCCTGGCCAGTGGCGGCGCCACGTAGTGGCACCTACTGGGGCCAAGGGACCCAGGTCACCGTCTCCTCA
/SEQ ID N° 107/
GAGGTGCAGCTGGTGGAGTCTGGGGGAGAGTTGGTGCAGGCTGGGGGCTCTCTGAGACTCTCCTGTGCAGCCTCTGGCCTCACCTTCAGTAGCT
ATAACATGGGCTGGTTCCGCCGGGCTCCAGGGAAGGAGCGTGAGTTTGTAGCATCTATTACCTGGAGTGGTCGGGACACATTCTATGCAGACTC
CGTGAAGGGCCGATTCACCATCTCCAGAGACAACGCCAAGAACACTGTTTATCTGCAAATGAGCAGCCTGAAACCTGAGGACACGGCCGTTTAT
TATTGTGCTGcAAAcCCCTGGCCAGTGGCGGCGCCACGTAGTGGCACCTACTGGGGCCAAGGGACCCAGGTCACCGTCTCCTCA

CD16 c28
SEQ ID NO:83
GAGGTGCAGCTGGTGGAGTCTGGGGGAGGCTTAGTGCAGCCTGGGGAGTCTcTGACACTCTCCTGtGTAGTTGCTGGAAGCATCTTCAGCTTCG
CCATGAGCTGGTATCGCCAGGCTCCAGGAAAAGAGCGCGAATTGGTCGCACGTATTGGTTCGGATGATCGGGTAACGTACGCAGATTCCGTGAA
GGGCCGATTTACCATCTCCAGAGACAACATCAAGCGCACGGCGGGCCTGCAGATGAACAGCCTGAAACCTGAGGACACGGCCGTCTACTACTGC
AAtGcCCAAACAGATTTGAGGGATTGGACTGTGCGAGAGTACTGGGGCCAGGGGACCCAGGTCACCGTCTCCTCA

CD16 c72
SEQ ID NO:84
GAGGTGCAGCTGGTGGAGTCTGGGGGAGGCTTGGTGCAGCCTGGGGGTCTCTGACACTCTCCTGTGTTGCCGCTGGAAGCATCTTCACCTTCG
CCATGAGCTGGTACCGCCAGGCTCCACGAAAAGAGCGCGAATTGGTCGCACGTATTGGTACGGATGACGAAACAATGTACAAAGACTCCGTGAA
GGGTCGATTCACCATCTCCAGAGACAACGTCAAGCGCACGGCGGGTCTGCAGATGAACAACCTGAAACCCGAGGACACGGCCGTCTACTACTGC
AATGCCCGGACAGATTATAGGGACTGGACTGTCCGTGAGTACTGGGGCCAGGGGACCCAGGTCACCGTCTCCTCA

VHH anti-CEA

CEA 3
/SEQ ID N° 85/
GAGGTGCAGCTGGTGGAGTCTGGGGGAGGCTTGGTGCAGGCTGGGGGCTCTCTGAGACTCTCCTGTACCAGCTCTACGGTTACCTTCACTCCGT
ATCAAATGGGCTGGTACCGCCAGGCTCCAGGGAAGCAGCGTGCTTTGGTCGCAGATATTAGTACGGGTGGTAGCCGCACAAATTATGCGGATTT
CGCGAAGGGCCGATTCACCATCTCCAGAGACGACGTTAAGAACACGGTGTATCTGCAAATGAACAACCTGAAACCTGAGGACACGGCCGTCTAC
TACtGTAACACCTACTACGCGATGATAGGGCATGCGCGTAATTGGGGCCAGGGGACCCAGGTCACTGTCTCCTCA

CEA 17
/SEQ ID N° 86/
GAGGTGCAGCTGGTGGAGTCTGGGGGAGGCTTCGTGCAGGCGGGGGAATCTCTGACGCTCTCCTGTACAagTTCTACACTGACCTTCACTCCGT
ATCGCATGGCCTGGTACCGCCAGGCTCCAGGGAAGCAGCGTGATTTAGTCGCGGATATTAGTAGTGGTGATGGTAGGACCACAAACTATGCGGA
CTTCGCGAAGGGCCGATTCACCATCTCCAGAGACAACATCAAGAACACGGTCTTTCTGCAATGACTAACCTGAAACCTGAGGACACGGCCGTC
TACTACTGTAACACCTTCGTTTCGTTTGTGGGGATTGCGCGTTCTTGGGGCCAGGGGACCCAGGTCACTGTCTCCTCA

CEA 25
/SEQ ID N° 87/
GAGGTGCAGCTGGTGGAGTCTGGGGGAGGCTTGGTGCAGGCGGGGGACTCTCTGACACTGACCTGTACAAGCCCTACACTTACCTTCACTCCGT
ATCGCATGGGCTGGTACCGCCAAGCTCCAGGGAAGCAGCGTGATTGGTCGCAGATATTAGTGGTGGTGATGGTCGTACCACAAACTATGCAGA
CTTCGCGAAGGGCCGATTCACCATCTCCAGAGACAACGTCAAGAACGCGGTCTATCTGCAAATGAACAACCTGAAACCTGAAGACACGGCCATT
TATTACTGTAACACCTACGTCGCGATTGTGGGCCATGCGCGTTCCTGGGGCCAGGGGACCCAGGTCACCGTCTCCTCA

CEA 43
/SEQ ID N° 88/
CAGGTGCAGCTGCAGGAGTCTGGGGGAGGCTTGGTGCAGGCGGGGGGCTCTCTGACACTCTCCTGCACAAGTTCTACACTTACCTTCACTCCGT
ATCGCATGGGCTGGTACCGCCAGACTCCAGGGAAGCAGCGTGATTTGGTCGCGGACATTAGTCCTGGTGATGGTAGTACCAAAAAATTATGCAGG
CTTCGCGCAGGGCCGATTCACCATCTCCAGAGACAACATCAAGAACACGGTGTATCTGCAAATGAACGACCTGAAACCTGAGGACACGGCCGTC
TATTAcTGCAACACCTACGTCGCGTTTGTGGGCGTGCGCGTACTTGGGGCCAGGGGACCCAGGTCACTGTCACCTCA
/SEQ ID N° 108/
GAGGTGCAGCTGGTGGAGTCTGGGGGAGGCTTGGTGCAGGCGGGGGGCTCTCTGACACTCTCCTGCACAAGTTCTACACTTACCTTCACTCCGT
ATCGCATGGGCTGGTACCGCCAGACTCCAGGGAAGCAGCGTGATTTGGTCGCGGACATTAGTCCTGGTGATGGTAGTACCAAAAAATTATGCAGG
CTTCGCGCAGGGCCGATTCACCATCTCCAGAGACAACATCAAGAACACGGTGTATCTGCAAATGAACGACCTGAAACCTGAGGACACGGCCGTC
TATTAcTGCAACACCTACGTCGCGTTTGTGGGCGTGCGCGTACTTGGGGCCAGGGGACCCAGGTCACTGTCACCTCA

Figure 2

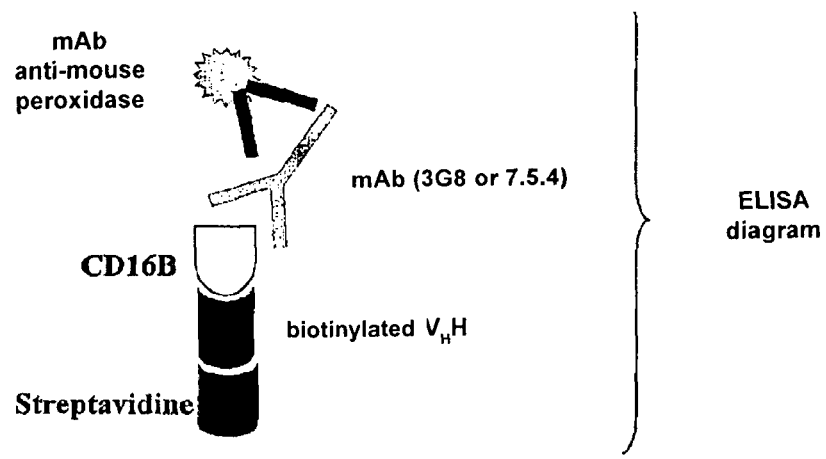
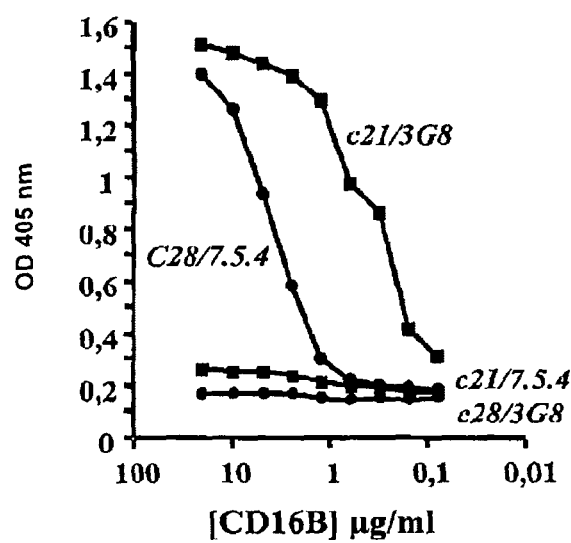
Figure 6

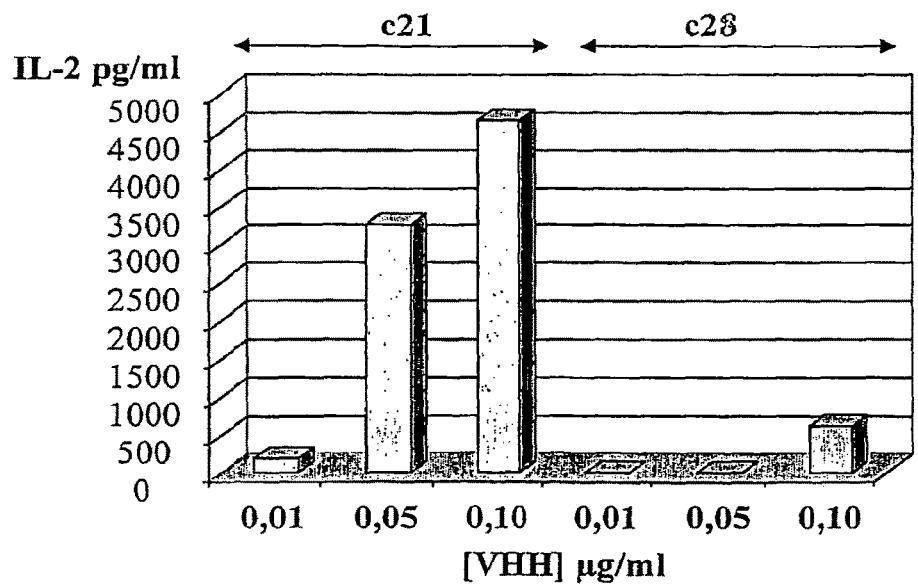
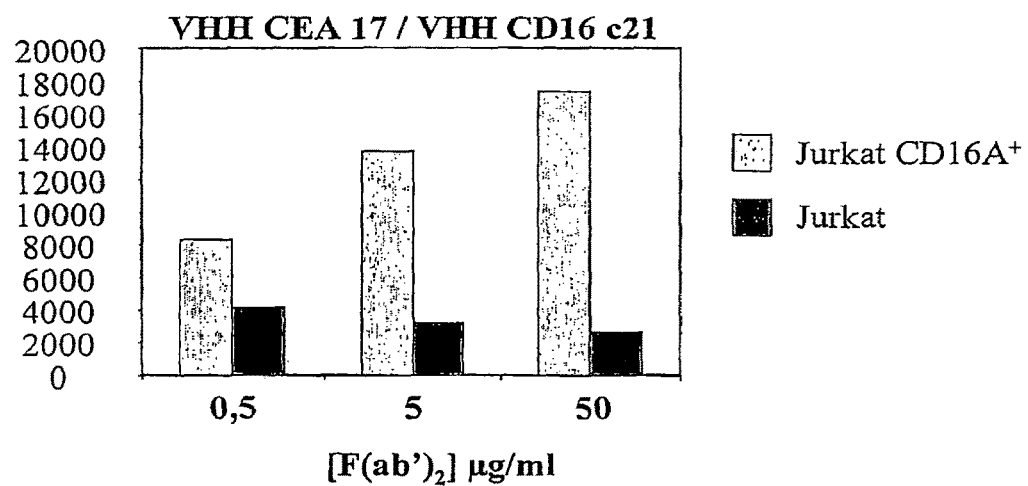
Figure 8

Figure 9 p55PhoA6HisGS/N- (SEQ ID NO:89)

```
ttgtttattttttctaaatacattcaaatatgtatccgctcatgagacaataaccctgataaatgcttca
ataatattgaa
aaaggaagagtatgagtattcaacatttccgtgtcgccttattcccttttttgcggcattttgccttc
ctgttttttgct
cacccagaaacgctggtgaaagtaaaagatgctgaagatcagttgggtgcacgagtgggttacatcgaa
ctggatctcaa
cagcggtaagatccttgagagttttcgccccgaagaacgttttccaatgatgagcacttttaaagttct
gctatgtggcg
cggtattatccgtgttgacgccgggcaagagcaactcggtcgccgcatacactattctcagaatgact
tggttgagtac
tcaccagtcacagaaaagcatcttacggatggcatgacagtaagagaattatgcagtgctgccataacc
atgagtgataa
cactgcggccaacttacttctgacaacgatcggaggaccgaaggagctaaccgcttttttgcacaacat
gggggatcatg
taactcgccttgatcgttgggaaccggagctgaatgaagccataccaaacgacgagcgtgacaccacga
tgcctgtagca
atggcaacaacgttgcgcaaactattaactggcgaactacttactctagcttcccggcaacaattaata
gactggatgga
ggcggataaagttgcaggaccacttctgcgctcggcccttccggctggctggtttattgctgataaatc
tggagccggtg
agcgtgggtctcgcggtatcattgcagcactggggccagatggtaagccctcccgtatcgtagttatct
acacgacgggg
agtcaggcaactatggatgaacgaaatagacagatcgctgagataggtgcctcactgattaagcattgg
taactgtcaga
ccaagtttactcatatatactttagattgatttaaaacttcattttaatttaaaaggatctaggtgaa
gatccttttg
ataatctcatgaccaaaatcccttaacgtgagttttcgttccactgagcgtcagacccgtagaaaaga
tcaaaggatct
tcttgagatcctttttttctgcgcgtaatctgctgcttgcaaacaaaaaaaccaccgctaccagcggtg
gtttgtttgcc
ggatcaagagctaccaactcttttttccgaaggtaactggcttcagcagagcgcagataccaaatactgt
ccttctagtgt
agccgtagttaggccaccacttcaagaactctgtagcaccgcctacatacctcgctctgctaatcctgt
taccagtggct
gctgccagtggcgataagtcgtgtcttaccgggttggactcaagacgatagttaccggataaggcgcag
cggtcgggctg
aacggggggttcgtgcacacagcccagcttggagcgaacgacctacaccgaactgagatacctacagcg
tgagcattgag
aaagcgccacgcttcccgaagggagaaaggcggacaggtatccggtaagcggcagggtcggaacaggag
agcgcacgagg
gagcttccaggggggaaacgcctggtatctttatagtcctgtcgggtttcgccacctctgacttgagcgt
cgatttttgtg
atgctcgtcagggggcggagcctatggaaaaacgccagcaacgcggccttttacggttcctggcctt
ttgctggcctt
ttgctcacatgttctttcctgcgttatccctgattctgtggataaccgtattaccgcctttgagtgag
ctgataccgct
cgccgcagccgaacgaccgagcgcagcgagtcagtgagcgaggaagcggaagagcgcctgatgcggtat
tttctccttac
gcatctgtgcggtatttcacaccgcatatatggtgcactctcagtacaatctgctctgatgccgcatag
ttaagccagta
tacactccgctatcgctacgtgactgggtcatggctgcgccccgacacccgccaacacccgctgacgcg
ccctgacgggc
ttgtctgctcccggcatccgcttacagacaagctgtgaccgtctccgggagctgcatgtgtcagaggtt
ttcaccgtcat
```

Figure 9 (Cont.)

```
caccgaaacgcgcgaggcagctgcggtaaagctcatcagcgtggtcgtgaagcgattcacagatgtctg
cctgttcatcc
gcgtccagctcgttgagtttctccagaagcgttaatgtctggcttctgataaagcgggccatgttaagg
gcggttttttc
ctgtttggtcacttgatgcctccgtgtaagggggaatttctgttcatgggggtaatgataccgatgaaa
cgagagaggat
gctcacgatacgggttactgatgatgaacatgcccggttactggaacgttgtgagggtaaacaactggc
ggtatggatgc
ggcgggaccagagaaaaatcactcagggtcaatgccagcgcttcgttaatacagatgtaggtgttccac
agggtagccag
cagcatcctgcatgcagatccggaacataatggtgcagggcgctgacttccgcgtttccagactttac
gaaacacggaa
accgaagaccattcatgttgttgctcaggtcgcagacgttttgcagcagcagtcgcttcacgttcgctc
gcgtatcggtg
attcattctgctaaccagtaaggcaacccgccagcctagccgggtcctcaacgacaggagcacgatca
tgcgcacccgt
ggccaggacccaacgctgccgagatgcgccgcgtgcggctgctggagatggcggacgcgatggatatg
ttctgccaagg
gttggtttgcgcattcacagttctccgcaagaattgattggctccaattcttggagtggtgaatccgtt
agcgaggtgcc
gccggcttccattcaggtcgaggtggcccggctccatgcacgcgacgcaacgcggggaggcagacaag
gtatagggcgg
cgcctacaatccatgccaacccgttccatgtgctcgccgaggcggcataaatcgcgtgacgatcagcg
gtccagtgatc
gaagttaggctggtaagagccgcgagcgatccttgaagctgtccctgatggtcgtcatctacctgcctg
gacagcatggc
ctgcaacgcgggcatcccgatgccgccggaagcgagaagaatcataatggggaaggccatccagcctcg
cgtcgcgaacg
ccagcaagacgtagcccagcgcgtcggccagcttgcaattcgcgctaacttacattaattgcgttgcgc
tcactgcccgc
tttccagtcgggaaacctgtcgtgccagctgcattaatgaatcggccaacgcgcggggagaggcggttt
gcgtattgggc
gccagggtggttttctttcaccagtgagacgggcaacagctgattgcccttcaccgcctggccctga
gagagttgcag
caagcggtccacgctggtttgccccagcaggcgaaaatcctgtttgatggtggttgacggcgggatata
acatgagctgt
cttcggtatcgtcgtatcccactaccgagatatccgcaccaacgcgcagcccggactcggtaatggcgc
gcattgcgccc
agcgccatctgatcgttggcaaccagcatcgcagtgggaacgatgccctcattcagcatttgcatggtt
tgttgaaaacc
ggacatggcactccagtcgccttcccgttccgctatcggctgaatttgattgcgagtgagatatttatg
ccagccagcca
gacgcagacgcgccgagacagaacttaatgggccgctaacagcgcgatttgctggtgacccaatgcga
ccagatgctcc
acgcccagtcgcgtaccgtcttcatgggagaaaataatactgttgatgggtgtctggtcagagacatca
agaaataacgc
cggaacattagtgcaggcagcttccacagcaatggcatcctggtcatccagcggatagttaatgatcag
cccactgacgc
gttgcgcgagaagattgtgcaccgccgctttacaggcttcgacgccgcttcgttctaccatcgacacca
ccacgctggca
cccagttgatcggcgcgagatttaatcgccgcgacaatttgcgacggcgcgtgcagggccagactggag
gtggcaacgcc
aatcagcaacgactgtttgccgccagttgttgtgccacgcggttgggaatgtaattcagctccgccat
cgccgcttcca
cttttttccgcgttttcgcagaaacgtggctggcctggttcaccacgcgggaaacggtctgataagaga
caccggcatac
tctgcgacatcgtataacgttactggtttcacattcaccaccctgaattgactctcttccgggcgctat
catgccatacc
```

Figure 9 (Cont.)

```
gcgaaaggttttgcgccattcgatggtgtcaacgtaaatgcatgccgcttcgccttcgcgcgcgaattg
caagctgatcc
ggagcttatcgactgcacggtgcaccaatgcttctggcgtcaggcagccatcggaagctgtggtatggc
tgtgcaggtcg
taaatcactgcataattcgtgtcgctcaaggcgcactcccgttctggataatgttttttgcgccgacat
cataacggttc
tggcaaatattctgaaatgagctgttgacaattaatcatcggctcgtataatgtgtggaattgtgagcg
gataacaattt
cacacaggaaacaGAATTCcatATGAAATACCTATTACCAACAGCAGCAGCTGGGTTATTATTGCTCGC
TGCGCAGCCGG
CCATGGCGgccgatcctcgagagctcccgggCTGCAGccctgttctggaaaaccgggctgctcagggcg
atattactgca
cccggcggtgctcgccgtttaacgggtgatcagactgccgctctgcgtgattctcttagcgataaacct
gcaaaaaatat
tattttgctgattggcgatgggatgggggactcggaaattactgccgcacgtaattatgccgaaggtgc
gggcggctttt
ttaaaggtatagatgccttaccgcttaccggcaatacactcactatgcgctgaataaaaaaaccggca
aaccggactac
gtcaccgactcggctgcatcagcaaccgcctggtcaaccggtgtcaaaacctataacggcgcgctgggc
gtcgatattca
cgaaaaagatcacccaacgattctggaaatggcaaaagccgcaggtctggcgaccggtaacgtttctac
cgcagagttgc
aggatgccacgcccgctgcgctggtggcacatgtgacctcgcgcaaatgctacggtccgagcgcgacca
gtgaaaaatgt
ccgggtaacgctctggaaaaaggcggaaaaggatcgattaccgaacagctgcttaacgctcgtgccgac
gttacgcttgg
cggcggcgcaaaaacctttgctgaaacggcaaccgctggtgaatggcagggaaaaacgctgcgtgaaca
ggcacaggcgc
gtggttatcagttggtgagcgatgctgcctcactgaattcggtgacggaagcgaatcagcaaaaacccc
tgcttggcctg
tttgctgacggcaatatgccagtgcgctggctaggaccgaaagcaacgtaCCACGGcaatatcgataag
cccgcagtcac
ctgtacgccaaatccgcaacgtaatgacagtgtaccaaccctggcgcagatgaccgacaaagccattga
attgttgagta
aaaatgagaaaggcttttttcctgcaagttgaaggtgcgtcaatcgataaacaggatcatgctgcgaatc
cttgtgggcaa
attggcgagacggtcgatctcgatgaagccgtacaacgggcgctggaattcgctaaaaaggagggtaac
acgctggtcat
agtcaccgctgatcacgccacgccagccagattgttgcgccggataccaaagctccgggcctcaccca
ggcgctaaata
ccaaagatggcgcagtgatggtgatgagttacgggaactccgaagaggattcacaagaacataccggca
gtcagttgcgt
attgcggcgtatggcccgcatgccgccaatgttgttggactgaccgaccagaccgatctcttctacacc
atgaaagccgc
tctggggctgaaaCATCATCATCACCATCACGGGAGCtaatAAGCTTctgttttggcggatgagagaag
attttcagcct
gatacagattaaatcagaacgcagaagcggtctgataaaacagaatttgcctggcggcagtagcgcggt
ggtcccacctg
accccatgccgaactcagaagtgaaacgccgtagcgccgatggtagtgtggggtctcccatgcgagag
tagggaactgc
caggcatcaaataaaacgaaaggctcagtcgaaagactgggcctttcgttttatctgttgtttgtcggt
gaacgctctcc
tgagtaggacaaatccgccgggagcggatttgaacgttgcgaagcaacggcccggaggaccctggcggg
caggacgcccg
ccataaactgccaggcatcaaattaagcagaaggccatcctgacggatggcctttttgcgtttctacaa
actctt
``` p55PhoA6HisGS/NAB⁻ (SEQ ID NO:90)

Figure 9 (Cont.)

```
ttgtttattttttctaaatacattcaaatatgtatccgctcatgagacaataaccctgataaatgcttcaataata
ttgaa
aaaggaagagtatgagtattcaacatttccgtgtcgccttattcctttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtatttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
```

Figure 9 (Cont.)

```
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttcttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatgggcccgctaacagcgcgatttgctggtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttttccgcgcgttttcgcagaaacgtggctggcctggttcaccacgcgggaaacggtctgataagagacaccgg
catac
tctgcgacatcgtataacgttactggtttcacattccaccccctgaattgactctcttccgggcgctatcatgcc
atacc
gcgaaaggttttgcgccattcgatggtgtcaacgtaaatgcatgccgcttcgccttcgcgcgcgaattgcaagct
gatcc
```

Figure 9 (Cont.)

```
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgcgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGCGgccgatcctcgagagctcccgggCTGCAGccctgttctggaaaaccgggctgctcagggcgatatta
ctgca
cccggcggtgctcgccgtttaacgggtgatcagactgccgctctgcgtgattctcttagcgataaacctgcaaaa
aatat
tattttgctgattggcgatgggatgggggactcggaaattactgccgcacgtaattatgccgaaggtgcgggcgg
ctttt
ttaaaggtatagatgccttaccgcttaccgggcaatacactcactatgcgctgaataaaaaaaccggcaaaccgg
actac
gtcaccgactcggctgcatcagcaaccgcctggtcaaccggtgtcaaaacctataacggcgcgctgggcgtcgat
attca
cgaaaaagatcacccaacgattctggaaatggcaaaagccgcaggtctggcgaccggtaacgtttctaccgcaga
gttgc
aggatgccacgcccgctgcgctggtggcacatgtgacctcgcgcaaatgctacggtccgagcgcgaccagtgaaa
aatgt
ccgggtaacgctctggaaaaaggcggaaaaggatcgattaccgaacagctgcttaacgctcgtgccgacgttacg
cttgg
cggcggcgcaaaaacctttgctgaaacggcaaccgctggtgaatggcagggaaaaacgctgcgtgaacaggcaca
ggcgc
gtggttatcagttggtgagcgatgctgcctcactgaattcggtgacggaagcgaatcagcaaaaaccctgcttg
gcctg
tttgctgacggcaatatgccagtgcgctggctaggaccgaaagcaacgtaCCACGGcaatatcgataagcccgca
gtcac
ctgtacgccaaatccgcaacgtaatgacagtgtaccaaccctggcgcagatgaccgacaaagccattgaattgtt
gagta
aaaatgagaaaggcttttcctgcaagttgaaggtgcgtcaatcgataaacaggatcatgctgcgaatccttgtg
ggcaa
attggcgagacggtcgatctcgatgaagccgtacaacgggcgctggaattcgctaaaaaggagggtaacacgctg
gtcat
agtcaccgctgatcacgccacgccagccagattgttgcgccggataccaaagctccgggcctcacccaggcgct
aaata
ccaaagatggcgcagtgatggtgatgagttacgggaactccgaagaggattcacaagaacataccggcagtcagt
tgcgt
attgcggcgtatggcccgcatgccgccaatgttgttggactgaccgaccagaccgatctcttctacaccatgaaa
gccgc
tctgggctgaaaCATCATCATCACCATCACGGGAGCtaatAAGCTTctgttttggcggatgagagaagatttc
agcct
gatacagattaaatcagaacgcagaagcggtctgataaaacagaatttgcctggcggcagtagcgcggtggtccc
acctg
acccatgccgaactcagaagtgaaacgccgtagcgccgatggtagtgtggggtctcccatgcgagagtaggga
actgc
caggcatcaaataaaacgaaaggctcagtcgaaagactgggcctttcgttttatctgttgtttgtcggtgaacgc
tctcc
tgagtaggacaaatccgccgggagcggatttgaacgttgcgaagcaacggcccggaggaccctggcgggcaggac
gcccg
ccataaactgccaggcatcaaattaagcagaaggccatcctgacggatggccttttttgcgtttctacaaactctt
``` p55/PhoA6HisGS⁻/NAB⁻ (SEQ ID NO:91)

Figure 9 (Cont.)

ttgtttatttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccagggggaaacgcctggtatctttatagtcctgtcgggtttcgccacctctgacttgagcgtcgattt
ttgtg
atgctcgtcaggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgcctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc

Figure 9 (Cont.)

```
gcgtccagctcgttgagtttctccagaagcgttaatgtctggcttctgataaagcgggccatgttaagggcggtt
ttttc
ctgtttggtcacttgatgcctccgtgtaaggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaaccccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgcgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttttcaccagtgagacgggcaacagctgattgcccttcacgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggtcccgctaacagcgcgatttgctgatgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttttcccgcgtttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
ataccc
gcgaaaggttttgcgccattcgatggtgtcaacgtaaatgcatgccgcttcgccttcgcgcgcgaattgcaagct
gatcc
```

Figure 9 (Cont.)

```
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgtttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGCGgccggccgatcctcgagagctcccgggCTGCAGcctgttctggaaaaccgggctgctcagggcgat
attac
tgcaccggcggtgctcgccgtttaacgggtgatcagactgccgctctgcgtgattctcttagcgataaacctgc
aaaaa
atattattttgctgattggcgatgggatgggggactcggaaattactgccgcacgtaattatgccgaaggtgcgg
gcggc
tttttaaaggtatagatgccttaccgcttaccgggcaatacactcactatgcgctgaataaaaaaaccggcaaa
ccgga
ctacgtcaccgactcggctgcatcagcaaccgcctggtcaaccggtgtcaaaacctataacggcgcgctgggcgt
cgata
ttcacgaaaaagatcacccaacgattctggaaatggcaaaagccgcaggtctggcgaccggtaacgtttctaccg
cagag
ttgcaggatgccacgcccgctgcgctggtggcacatgtgacctcgcgcaaatgctacggtccgagcgcgaccagt
gaaaa
atgtccgggtaacgctctggaaaaaggcggaaaaggatcgattaccgaacagctgcttaacgctcgtgccgacgt
tacgc
ttggcggcggcgcaaaaacctttgctgaaacggcaaccgctggtgaatggcagggaaaaacgctgcgtgaacagg
cacag
gcgcgtggttatcagttggtgagcgatgctgcctcactgaattcggtgacggaagcgaatcagcaaaaacccctg
cttgg
cctgtttgctgacggcaatatgccagtgcgctggctaggaccgaaagcaacgtaCCACGGcaatatcgataagcc
cgcag
tcacctgtacgccaaatccgcaacgtaatgacagtgtaccaaccctggcgcagatgaccgacaaagccattgaat
tgttg
agtaaaaatgagaaaggcttttcctgcaagttgaaggtgcgtcaatcgataaacaggatcatgctgcgaatcct
tgtgg
gcaaattggcgagacggtcgatctcgatgaagccgtacaacgggcgctggaattcgctaaaaaggagggtaacac
gctgg
tcatagtcaccgctgatcacgccacgccagccagattgttgcgccggataccaaagctccgggcctcacccagg
cgcta
aataccaaagatggcgcagtgatggtgatgagttacgggaactccgaagaggattcacaagaacataccggcagt
cagtt
gcgtattgcggcgtatggccgcatgccgccaatgttgttggactgaccgaccagaccgatctcttctacaccat
gaaag
ccgctctggggctgaaaCATCATCATCACCATCACGGGAGCtaatAAGCTTggctgttttggcggatgagagaag
atttt
cagcctgatacagattaaatcagaacgcagaagcggtctgataaaacagaatttgcctggcggcagtagcgcggt
ggtcc
cacctgacccatgccgaactcagaagtgaaacgccgtagcgccgatggtagtgtggggtctcccatgcgagag
taggg
aactgccaggcatcaaataaaacgaaaggctcagtcgaaagactgggcctttcgttttatctgttgtttgtcggt
gaacg
ctctcctgagtaggacaaatccgccgggagcggatttgaacgttgcgaagcaacggcccggaggaccctggcggg
cagga
cgcccgccataaactgccaggcatcaaattaagcagaaggccatcctgacggatggccttttgcgtttctacaa
actct
t
``` p55/MCS1 (SEQ ID NO:92)

Figure 9 (Cont.)

ttgtttatttttctaaatacattcaaatatgtatccgctcatgagacaataaccctgataaatgcttcaataata
ttgaa
aaaggaagagtatgagtattcaacatttccgtgtcgcccttattcccttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgcccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgatt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc

Figure 9 (Cont.)

```
gcgtccagctcgttgagtttctccagaagcgttaatgtctggcttctgataaagcgggccatgttaagggcggtt
ttttc
ctgtttggtcacttgatgcctccgtgtaaggggaatttctgttcatgggggtaatgataccgatgaaacgagag
aggat
gctcacgatacggggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttttcaccagtgagacgggcaacagctgattgcccttcaccgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagccact
gacgc
gttgcgcgagaagattgtgcaccgcgctttacaggcttcgacgcgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttccgcgtttcgcagaaacgtggctggcctggttcaccacgcgggaaacggtctgataagagacaccgg
catac
tctgcgacatcgtataacgttactggtttcacattcaccaccctgaattgactctcttccggcgctatcatgcc
atacc
gcgaaaggttttgcgccattcgatggtgtcaacgtaaatgcatgccgcttcgccttcgcgcgcgaattgcaagct
gatcc
```

Figure 9 (Cont.)

```
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCgtctcctcaaaCCGCGGaCTCGAGgcGGCCcagccGGCCatggccGCTAGCGCGGCCG
CTCTA
GAttAAGCTTggctgttttggcggatgagagaagattttcagcctgatacagattaaatcagaacgcagaagcgg
tctga
taaaacagaatttgcctggcggcagtagcgcggtggtcccacctgacccatgccgaactcagaagtgaaacgcc
gtagc
gccgatggtagtgtggggtctcccatgcgagagtagggaactgccaggcatcaaataaaacgaaaggctcagtc
gaaag
actggcctttcgtttatctgttgtttgtcggtgaacgctctcctgagtaggacaaatccgccgggagcggatt
tgaac
gttgcgaagcaacggcccggaggaccctggcgggcaggacgcccgccataaactgccaggcatcaaattaagcag
aaggc
catcctgacggatggcctttttgcgtttctacaaactctt P55Flag/RBS/35 (SEQ ID NO:93)

ttgtttatttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
cttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
```

Figure 9 (Cont.)

```
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
aaagcgccacgctcccgaagggagaaaggcggacaggtatccggtaagcggcagggtcggaacaggagagcgca
cgagg
gagcttccaggggaaacgcctggtatctttatagtcctgtcgggtttcgccacctctgacttgagcgtcgatt
ttgtg
atgctcgtcaggggggcggagcctatggaaaaacgccagcaacgcggccttttacggttcctggcctttgctg
gcctt
ttgctcacatgttctttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacaccgctgacgcgcctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaaggggaatttctgttcatggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaaccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
```

Figure 9 (Cont.)

```
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactccgttctggataatgttttttgcgccgacatcataac
ggttc
tggcaaatatrctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGCccaGGTcACCgtctcctcaaaCCGCGGAGAGTGTgcaggtGATTACAAAGACGATGACGATAAGTAAT
AAacA
GGAAacagaaGtccatATGAAATACCTATTGCCTACGGCAGCCGCTGGATTGTTATTACTCGCGGCCcagccGGC
Catgg
ccGCTAGCGCGGCCGCTCTAGATTAAGCTTggctgttttggcggatgagagaagattttcagcctgatacagatt
aaatc
agaacgcagaagcggtctgataaaacagaatttgcctggcggcagtagcgcggtggtcccacctgacccatgcc
gaact
cagaagtgaaacgccgtagcgccgatggtagtgtggggtctcccatgcgagagtagggaactgccaggcatcaa
ataaa
acgaaaggctcagtcgaaagactgggcctttcgttttatctgttgtttgtcggtgaacgctctcctgagtaggac
aaatc
cgccgggagcggatttgaacgttgcgaagcaacggcccggaggaccctggcgggcaggacgcccgccataaactg
ccagg
catcaaattaagcagaaggccatcctgacggatggcctttttgcgtttctacaaactctt
```

P55Flag/RBS/35cmyc6HisGS (SEQ ID NO:94)

```
ttgtttatttttctaaatacattcaaatatgtatccgctcatgagacaataaccctgataaatgcttcaataata
ttgaa
aaaggaagagtatgagtattcaacatttccgtgtcgcccttattccctttttgcggcatttgccttcctgttt
ttgct
cacccagaaacgctggtgaaagtaaaagatgctgaagatcagttgggtgcacgagtgggttacatcgaactggat
ctcaa
```

Figure 9 (Cont.)

```
cagcggtaagatccttgagagtttctgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattgtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggaaacgcctggtatctttatagtcctgtcgggtttcgccacctctgacttgagcgtcgattt
ttgtg
atgctcgtcaggggggcggagcctatggaaaaacgccagcaacgcggccttttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtatttctc
cttac
gcatctgtgcggtatttcacaccgcatatatggtgcactctcagtacaatctgctctgatgccgcatagttaagc
cagta
tacactccgctatcgctacgtgactgggtcatggctgcgcccgacacccgccaacaccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
```

Figure 9 (Cont.)

```
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccgaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
ctttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
```

Figure 9 (Cont.)

```
CCATGGcccaGGTcACCgtgtcctcaaaCCGCGGAGAGTGTgcaggtGATTACAAAGACGATGACGATAAGTAAT
AAacA
GGAAacagaaGtccatATGAAATACCTATTGCCTACGGCAGCCGCTGGATTGTTATTACTCGCGGCCcagccGGC
Catgg
ccGCTAGCGCGGCCGCAGAACAAAAACTCATCTCAGAAGAGGATCTGAATGGGGCCGTACATCACCACCATCATC
ATGGG
AGCTAAGCTTggctgttttggcggatgagagaagatttt cagcctgatacagattaaatcagaacgcagaagcgg
tctga
taaaacagaatttgcctggcggcagtagcgcggtggtcccacctgaccccatgccgaactcagaagtgaaacgcc
gtagc
gccgatggtagtgtgggtctcccatgcgagagtagggaactgccaggcatcaaataaaacgaaaggctcagtc
gaaag
actgggcctttcgttttatctgttgtttgtcggtgaacgctctcctgagtaggacaaatccgccgggagcggatt
tgaac
gttgcgaagcaacggcccggaggaccctggcgggcaggacgcccgccataaactgccaggcatcaaattaagcag
aaggc
catcctgacggatggcctttttgcgtttctacaaactctt pHCH2CH3γ1-TAG (SEQ ID NO:95)

ttgtttattttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggttttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
```

Figure 9 (Cont.)

aacggggggttcgtgcacacagcccagcttggagcgaacgacctacaccgaactgagatacctacagcgtgagcattgag
aaagcgccacgcttcccgaagggagaaaggcggacaggtatccggtaagcggcaggtcggaacaggagagcgcacgagg
gagcttccaggggaaacgcctggtatctttatagtcctgtcgggtttcgccacctctgacttgagcgtcgattttgtg
atgctcgtcaggggcggagcctatggaaaaacgccagcaacgcggccttttacggttcctggccttttgctggcctt
ttgctcacatgttctttcctgcgttatccctgattctgtggataacgtattaccgcctttgagtgagctgataccgct
cgccgcagccgaacgaccgagcgcagcgagtcagtgagcgaggaagcggaagagcgcctgatgcggtattttctccttac
gcatctgtgcggtatttcacaccgcatatatggtgcactctcagtacaatctgctctgatgccgcatagttaagccagta
tacactccgctatcgctacgtgactgggtcatggctgcgcccgacaccgccaacacccgctgacgcgcctgacgggc
ttgtctgctcccggcatccgcttacagacaagctgtgaccgtctccgggagctgcatgtgtcagaggttttcaccgtcat
caccgaaacgcgcgaggcagctgcggtaaagctcatcagcgtggtcgtgaagcgattcacagatgtctgcctgttcatcc
gcgtccagctcgttgagtttctccagaagcgttaatgtctggcttctgataaagcgggccatgttaagggcggttttttc
ctgtttggtcacttgatgcctccgtgtaaggggaatttctgttcatgggggtaatgataccgatgaaacgagaggat
gctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccag
cagcatcctgcgatgcagatccggaacataatggtgcagggcgctgacttccgcgtttccagactttacgaaacacggaa
accgaagaccattcatgttgttgctcaggtcgcagacgttttgcagcagcagtcgcttcacgttcgctcgcgtatcggtg
attcattctgctaaccagtaaggcaacccgccagcctagccgggtcctcaacgacaggagcacgatcatgcgcaccgt
ggccaggacccaacgctgcccgagatgcgccgcgtgcggctgctggagatggcggacgcgatggatatgttctgccaagg
gttggtttgcgcattcacagttctccgcaagaattgattggctccaattcttggagtggtgaatccgttagcgaggtgcc
gccggcttccattcaggtcgaggtggcccggctccatgcaccgcgacgcaacgcggggaggcagacaaggtataggcgg
cgcctacaatccatgccaacccgttccatgtgctcgccgaggcggcataaatcgccgtgacgatcagcggtccagtgatc
gaagttaggctggtaagagccgcgagcgatccttgaagctgtccctgatggtcgtcatctacctgcctggacagcatggc
ctgcaacgcgggcatccgatgccgccggaagcgagaagaatcataatggggaaggccatccagcctcgcgtcgcgaacg
ccagcaagacgtagcccagcgcgtcggccagcttgcaattcgcgctaacttacattaattgcgttgcgctcactcccgc
tttccagtcgggaaacctgtcgtgccagctgcattaatgaatcggccaacgcgcggggagaggcggtttgcgtattgggc
gccagggtggttttcttttcaccagtgagacgggcaacagctgattgcccttcaccgcctggccctgagagagtgcag
caagcggtccacgctggtttgccccagcaggcgaaaatcctgtttgatggtggttgacggcgggatataacatgagctgt
cttcggtatcgtcgtatcccactaccgagatatccgcaccaacgcgcagcccggactcggtaatggcgcgcattgcgccc
agcgccatctgatcgttggcaaccagcatcgcagtgggaacgatgccctcattcagcatttgcatggtttgttgaaaacc

Figure 9 (Cont.)

```
ggacatggcactccagtcgccttcccgttccgctatcggctgaatttgattgcgagtgagatatttatgccagcc
agcca
gacgcagacgcgccgagacagaacttaatggTccogctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
ctttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCgtctcctcaGACAAAACTCACACATGCCCACCGTGCCCAgcacctgaactcctggggg
gaccg
tcagtcttcctcttcccccaaacccaaggacaccctcatgatctcccggacccctgaggtcacatgcgtggtg
gtgga
cgtgagccacgaagaccctgaggtcaagttcaactggtacgtggacggcgtggaggtgcataatgccaagacaaa
gccgc
gggaggagcagtacaacagcacgtaccgggtggtcagcgtcctcaccgtcctgcaccaggactggctgaatggca
aggag
tacaagtgcaaggtctccaacaaagccctcccagcccccatcgagaaaaccatctccaaagccaaaGGGCAGCCC
CGAGA
ACCACAGGTGTACACCCTGCCCCCATCCCGGGATGAGCTGACCAAGAACCAGGTCAGCCTGACCTGCCTGGTCAA
AGGCT
TCTATCCCAGCGACATCGCCGTGGAGTGGGAGAGCAATGGGCAGCCGGAGAACAACTACAAGACCACGCCTCCCG
TGCTG
GACTCCGACGGCTCCTTCTTCCTCTACAGCAAGCTCACCGTGGACAAGAGCAGGTGGCAGCAGGGGAACGTCTTC
TCATG
CTCCGTGATGCATGAGGCTCTGCACAACCACTACACGCAGAAGAGCCTCTCCCTGTCTCCGGGTAAAGCGGCCGC
AGAAC
AAAAACTCATCTCAGAAGAGGATCTGAATGGGGCCGTACATCACCACCATCATCATGGGAGCTAAGCTTggctgt
tttgg
cggatgagagaagattttcagcctgatacagattaaatcagaacgcagaagcggtctgataaaacagaatttgcc
tggcg
gcagtagcgcggtggtcccacctgaccccatgccgaactcagaagtgaaacgccgtagcgccgatggtagtgtgg
ggtct
ccccatgcgagagtagggaactgccaggcatcaaataaaacgaaaggctcagtcgaaagactgggcctttcgttt
tatct
gttgtttgtcggtgaacgctctcctgagtaggacaaatccgccgggagcggatttgaacgttgcgaagcaacggc
ccgga
ggaccctggcgggcaggacgcccgccataaactgccaggcatcaaattaagcagaaggccatcctgacggatggc
ctttt
```

Figure 9 (Cont.)

tgcgtttctacaaactctt pHCH2CH3γ1 (SEQ ID NO:96)

ttgtttattttttctaaatacattcaaatatgtatccgctcatgagacaataaccctgataaatgcttcaataatattgaa
aaaggaagagtatgagtattcaacatttccgtgtcgccttattccttttttgcggcatttttgccttcctgttttttgct
cacccagaaacgctggtgaaagtaaaagatgctgaagatcagttgggtgcacgagtgggttacatcgaactggatctcaa
cagcggtaagatccttgagagttttcgccccgaagaacgttttccaatgatgagcacttttaaagttctgctatgtggcg
cggtattatcccgtgttgacgccgggcaagagcaactcggtcgccgcatacactattctcagaatgacttggttgagtac
tcaccagtcacagaaaagcatcttacggatggcatgacagtaagagaattatgcagtgctgccataaccatgagtgataa
cactgcggccaacttacttctgacaacgatcggaggaccgaaggagctaaccgcttttttgcacaacatggggatcatg
taactcgccttgatcgttgggaaccggagctgaatgaagccataccaaacgacgagcgtgacaccacgatgcctgtagca
atggcaacaacgttgcgcaaactattaactggcgaactacttactctagcttcccggcaacaattaatagactggatgga
ggcggataaagttgcaggaccacttctgcgctcggcccttccggctggctggtttattgctgataaatctggagccggtg
agcgtgggtctcgcggtatcattgcagcactggggccagatggtaagccctcccgtatcgtagttatctacacgacggg
agtcaggcaactatggatgaacgaaatagacagatcgctgagataggtgcctcactgattaagcattggtaactgtcaga
ccaagtttactcatatatactttagattgatttaaaacttcatttttaatttaaaaggatctaggtgaagatccttttg
ataatctcatgaccaaaatcccttaacgtgagttttcgttccactgagcgtcagacccgtagaaaagatcaaaggatct
tcttgagatcctttttttctgcgcgtaatctgctgcttgcaaacaaaaaaaccaccgctaccagcggtggtttgttgcc
ggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggct
gctgccagtggcgataagtcgtgtcttaccgggttggactcaagacgatagttaccggataaggcgcagcggtcgggctg
aacgggggttcgtgcacacagcccagcttggagcgaacgacctacaccgaactgagatacctacagcgtgagcattgag
aaagcgccacgcttcccgaagggagaaaggcggacaggtatccggtaagcggcagggtcggaacaggagagcgcacgagg
gagcttccaggggaaacgcctggtatctttatagtcctgtcgggtttcgccacctctgacttgagcgtcgatttttgtg
atgctcgtcaggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctccttac
gcatctgtgcggtatttcacaccgcatatatggtgcactctcagtacaatctgctctgatgccgcatagttaagccagta
tacactccgctatcgctacgtgactgggtcatggctgcgccccgacacccgccaacaccgctgacgcgccctgacgggc

Figure 9 (Cont.)

```
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaaggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggaccaacgctgccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttttcttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtacgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
```

Figure 9 (Cont.)

tctgcgacatcgtataacgttactggtttcacattcaccaccctgaattgactctcttccgggcgctatcatgccatacc
gcgaaaggttttgcgccattcgatggtgtcaacgtaaatgcatgccgcttcgccttcgcgcgcgaattgcaagctgatcc
ggagcttatcgactgcacggtgcaccaatgcttctggcgtcaggcagccatcggaagctgtggtatggctgtgcaggtcg
taaatcactgcataattcgtgtcgctcaaggcgcactcccgttctggataatgttttttgcgccgacatcataacggttc
tggcaaatattctgaaatgagctgttgacaattaatcatcggctcgtataatgtgtggaattgtgagcggataacaattt
cacacaggaaacaGAATTCcatATGAAATACCTATTACCAACAGCAGCAGCTGGGTTATTATTGCTCGCTGCGCAGCCGG
CCATGGcccaGGTcACCgtctcctcaGACAAAACTCACACATGCCCACCGTGCCCAgcacctgaactcctgggggaccg
tcagtcttcctcttcccccaaaacccaaggacaccctcatgatctcccggacccctgaggtcacatgcgtggtggtgga
cgtgagccacgaagaccctgaggtcaagttcaactggtacgtggacggcgtggaggtgcataatgccaagacaaagccgc
gggaggagcagtacaacagcacgtaccgggtggtcagcgtcctcaccgtcctgcaccaggactggctgaatggcaggag
tacaagtgcaaggtctccaacaaagccctcccagcccccatcgagaaaaccatctccaaagccaaaGGGCAGCCCCGAGA
ACCACAGGTGTACACCCTGCCCCCATCCCGGGATGAGCTGACCAAGAACCAGGTCAGCCTGACCTGCCTGGTCAAAGGCT
TCTATCCCAGCGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTGTCTCCGGGTAAATAAGCTTgctgt
tttggcggatgagagaagattttcagcctgatacagattaaatcagaacgcagaagcggtctgataaaacagaattgcc
tggcggcagtagcgcggtggtcccacctgacccatgccgaactcagaagtgaaacgccgtagcgccgatggtagtgtgg
ggtctcccatgcgagagtagggaactgccaggcatcaaataaaacgaaaggctcagtcgaaagactgggcctttcgttt
tatctgttgtttgtcggtgaacgctctcctgagtaggacaaatccgccgggagcggatttgaacgttgcgaagcaacggc
ccggaggaccctggcgggcaggacgcccgccataaactgccaggcatcaaattaagcagaaggccatcctgacggatggc
cttttgcgtttctacaaactctt P55CKFlag/RBS/35cmyc6HisGS (SEQ ID NO:97)

ttgtttatttttctaaatacattcaaatatgtatccgctcatgagacaataaccctgataaatgcttcaataatattgaa
aaaggaagagtatgagtattcaacatttccgtgtcgcccttattccctttttttgcggcattttgccttcctgttttttgct
cacccagaaacgctggtgaaagtaaaagatgctgaagatcagttgggtgcacgagtgggttacatcgaactggatctcaa
cagcggtaagatccttgagagttttcgccccgaagaacgttttccaatgatgagcacttttaaagttctgctatgtggcg
cggtattatcccgtgttgacgccgggcaagagcaactcggtcgccgcatacactattctcagaatgacttggttgagtac
tcaccagtcacagaaaagcatcttacggatggcatgacagtaagagaattatgcagtgctgccataaccatgagtgataa

Figure 9 (Cont.)

```
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacaccgccaacaccgctgacgcgcctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaatcactcagggtcaatgccagcgcttcgttaatacagatgtaggtgttccacaggta
gccag
cagcatctgcgatgcagatccggaacataatggtgcagggcgctgacttccgcgtttccagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
```

Figure 9 (Cont.)

```
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgccttcaccgcctggccctgagagt
tgcag
caagcggtccacgctggtttgcccagcaggcgaaaatcctgtttgatggtggttgacggcgggatataacatga
gctgt
cttcggtatcgtcgtatcccactaccgagatatccgccaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccacectgaattgactctcttccggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
```

Figure 9 (Cont.)

```
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTgcaggtGATTACAAAGACGATGACGATAAGTAATAAacAGGAAacaga
aGtcc
atATGAAATACCTATTGCCTACGGCAGCCGCTGGATTGTTATTACTCGCGGCCcagccGGCCatggccGCTAGCG
CGGCC
GCAGAACAAAAACTCATCTCAGAAGAGGATCTGAATGGGGCCGTACATCACCACCATCATCATGGGAGCTAAGCT
Tggct
gttttggcggatgagagaagattttcagcctgatacagattaaatcagaacgcagaagcggtctgataaaacaga
atttg
cctggcggcagtagcgcggtggtcccacctgacccatgccgaactcagaagtgaaacgccgtagcgccgatggt
agtgt
ggggtctccccatgcgagagtagggaactgccaggcatcaaataaaacgaaaggctcagtcgaaagactgggcct
ttcgt
tttatctgttgtttgtcggtgaacgctctcctgagtaggacaaatccgccgggagcggatttgaacgttgcgaag
caacg
gcccggaggaccctggcgggcaggacgcccgccataaactgccaggcatcaaattaagcagaaggccatcctgac
ggatg
gccttttgcgtttctacaaactctt pCKCH1γ1-TAG (SEQ ID NO:98)

ttgtttattttctaaatacattcaaatatgtatccgctcatgagacaataaccctgataaatgcttcaataata
ttgaa
aaaggaagagtatgagtattcaacatttccgtgtcgcccttattccctttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
```

Figure 9 (Cont.)

```
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggaaacgcctggtatctttatagtcctgtcgggtttcgccacctctgacttgagcgtcgattt
ttgtg
atgctcgtcaggggggcggagcctatggaaaaacgccagcaacgcggccttttacggttcctggccttttgctg
gcctt
ttgctcacatgttctttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtatttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacaccgccaacaccgctgacgcgccctga
cgggc
ttgtctgctccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttcagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgccagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttcttttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
```

Figure 9 (Cont.)

agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTGcaggtGATTACAAAGACGATGACGATAAGTAATAAacaggaAacaga
aGtcc
atATGAAATACCTATTGCCTACGGCAGCCGCTGGATTGTTATTACTCGCGGCCcagcCGGCCATGGCCGCTAGCA
CCAAG
GGCCCATCGGTCTTCCCCCTGGCACCCTCCTCCAAGAGCACCTCTGGGGGCACAGCGGCCCTGGGCTGCCTGGTC
AAGGA
CTACTTCCCCGAACCGGTGACGGTGTCGTGGAACTCAGGCGCCCTGACCAGCGGCGTGCACACCTTCCCGGCTGT
CCTAC
AGTCCTCAGGACTCTACTCCCTCAgcagcGTAGTGACCGTGCCCTCCAGCAGCTTGGGCACCCAGACCTACATCT
GCAAC
GTGAATCACAAGCCCAGCAACACCAAGGTGGACAAGAAAGTTGAGCCCAAATCTTGTGCGGCCGCAGAACAAAAA
CTCAT
CTCAGAAGAGGATCTGAATGGGGCCGTACATCACCACCATCATCATGGGAGCTAAGCTTggctgttttggcggat
gagag
aagatttttcagcctgatacagattaaatcagaacgcagaagcggtctgataaaacagaatttgcctggcggcagt
agcgc
ggtggtcccacctgacccatgccgaactcagaagtgaaacgccgtagcgccgatggtagtgtggggtctcccca
tgcga
gagtagggaactgccaggcatcaaataaaacgaaaggctcagtcgaaagactgggcctttcgttttatctgttgt
ttgtc

Figure 9 (Cont.)

```
ggtgaacgctctcctgagtaggacaaatccgccgggagcggatttgaacgttgcgaagcaacggcccggaggacc
ctggc
gggcaggacgcccgccataaactgccaggcatcaaattaagcagaaggccatcctgacggatggccttttttgcgt
ttcta
caaactctt
``` pCKCH1Hy1-TAG (SEQ ID NO:99)

```
ttgtttattttctaaatacattcaaatatgtatccgctcatgagacaataaccctgataaatgcttcaataata
ttgaa
aaaggaagagtatgagtattcaacatttccgtgtcgcccttattccctttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagacccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
```

Figure 9 (Cont.)

gcatctgtgcggtatttcacaccgcatatatggtgcactctcagtacaatctgctctgatgccgcatagttaagccagta
tacactccgctatcgctacgtgactgggtcatggctgcgcccgacacccgccaacacccgctgacgcgccctgacgggc
ttgtctgctcccggcatccgcttacagacaagctgtgaccgtctccgggagctgcatgtgtcagaggttttcaccgtcat
caccgaaacgcgcgaggcagctgcggtaaagctcatcagcgtggtcgtgaagcgattcacagatgtctgcctgttcatcc
gcgtccagctcgttgagtttctccagaagcgttaatgtctggcttctgataaagcgggccatgttaagggcggttttttc
ctgtttggtcacttgatgcctccgtgtaaggggaatttctgttcatgggggtaatgataccgatgaaacgagagaggat
gctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccag
cagcatcctgcgatgcagatccggaacataatggtgcagggcgctgacttccgcgtttccagactttacgaaacacggaa
accgaagaccattcatgttgttgctcaggtcgcagacgttttgcagcagcagtcgcttcacgttcgctcgcgtatcggtg
attcattctgctaaccagtaaggcaacccgccagcctagccgggtcctcaacgacaggagcacgatcatgcgcacccgt
ggccaggacccaacgctgcccgagatgcgccgcgtgcggctgctggagatggcggacgcgatggatatgttctgccaagg
gttggtttgcgcattcacagttctccgcaagaattgattggctccaattcttggagtggtgaatccgttagcgaggtgcc
gccggcttccattcaggtcgaggtggcccggctccatgcaccgcgacgcaacgcggggaggcagacaaggtataggcgg
cgcctacaatccatgccaacccgttccatgtgctcgccgaggcggcataaatcgccgtgacgatcagcggtccagtgatc
gaagttaggctggtaagagccgcgagcgatccttgaagctgtccctgatggtcgtcatctacctgctggacagcatggc
ctgcaacgcgggcatcccgatgccgccggaagcgagaagaatcataatggggaaggccatccagcctcgcgtcgcgaacg
ccagcaagacgtagcccagcgcgtcggccagcttgcaattcgcgctaacttacattaattgcgttgcgctcactgcccgc
tttccagtcgggaaacctgtcgtgccagctgcattaatgaatcggccaacgcgcggggagaggcggtttgcgtatgggc
gccagggtggttttctttcaccagtgagacgggcaacagctgattgcccttcaccgcctggccctgagagagttgcag
caagcggtccacgctggtttgcccagcaggcgaaaatcctgtttgatggtggttgacggcgggatataacatgagctgt
cttcggtatcgtcgtatcccactaccgagatatccgcaccaacgcgcagcccggactcggtaatggcgcgcattgcgccc
agcgccatctgatcgttggcaaccagcatcgcagtgggaacgatgccctcattcagcatttgcatggtttgttgaaacc
ggacatggcactccagtcgccttcccgttccgctatcggctgaatttgattgcgagtgagatatttatgccagccagcca
gacgcagacgcgccgagacagaacttaatggTccgctaacagcgcgatttgctgAtgacccaatgcgaccagatgctcc
acgcccagtcgcgtaccgtcttcatgggagaaaataatactgttgatgggtgtctggtcagagacatcaagaataacgc
cggaacattagtgcaggcagcttccacagcaatggcatcctggtcatccagcggatagttaatgatcagcccactgacgc
gttgcgcgagaagattgtgcaccgccgctttacaggcttcgacgccgcttcgttctaccatcgacaccaccacgctggca
cccagttgatcggcgcgagatttaatcgccgcgacaatttgcgacggcgcgtgcagggccagactggaggtggcaacgcc

Figure 9 (Cont.)

```
aatcagcaacgactgtttgcccgccagttgttgtgccacgcggttgggaatgtaattcagctccgccatcgccgc
ttcca
cttttccccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTgcaggtGATTACAAAGACGATGACGATAAGTAATAAacAGGAAacaga
aGtcc
atATGAAATACCTATTGCCTACGGCAGCCGCTGGATTGTTATTACTCGCGGCCcagcCGGCCATGGCCGCTAGCA
CCAAG
GGCCCATCGGTCTTCCCCCTGGCACCCTCCTCCAAGAGCACCTCTGGGGGCACAGCGGCCCTGGGCTGCCTGGTC
AAGGA
CTACTTCCCCGAACCGGTGACGGTGTCGTGGAACTCAGGCGCCCTGACCAGCGGCGTGCACACCTTCCCGGCTGT
CCTAC
AGTCCTCAGGACTCTACTCCCTCAGCAGCGTAGTGACCGTGCCCTCCAGCAGCTTGGGCACCCAGACCTACATCT
GCAAC
GTGAATCACAAGCCCAGCAACACCAAGGTGGACAAGAAAGTTGAGCCCAAATCTTGTGACAAAACTCACACATGC
CCACC
GTGCCCAGCGGCCGCAGAACAAAAACTCATCTCAGAAGAGGATCTGAATGGGGCCGTACATCACCACCATCATCA
TGGGA
GCTAAGCTTggctgttttggcggatgagagaagatttttcagcctgatacagattaaatcagaacgcagaagcggt
ctgat
aaaacagaatttgcctggcggcagtagcgcggtggtcccacctgaccccatgccgaactcagaagtgaaacgccg
tagcg
ccgatggtagtgtggggtctccccatgcgagagtagggaactgccaggcatcaaataaaacgaaaggctcagtcg
aaaga
ctgggcctttcgttttatctgttgtttgtcggtgaacgctctcctgagtaggacaaatccgccgggagcggattt
gaacg
ttgcgaagcaacggcccggaggaccctggcggcaggacgcccgccataaactgccaggcatcaaattaagcaga
aggcc
atcctgacggatggcctttttgcgtttctacaaactctt
``` pCKCH1γ1 (SEQ ID NO:100)

```
ttgtttattttctaaatacattcaaatatgtatccgctcatgagacaataaccctgataaatgcttcaataata
ttgaa
aaaggaagagtatgagtattcaacatttccgtgtcgcccttattcccttttttgcggcattttgccttcctgttt
ttgct
```

Figure 9 (Cont.)

```
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactgggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcatttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactcttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacgggggttcgtgcacacagcccagcttggagcgaacgacctacaccgaactgagatacctacagcgtgagca
ttgag
aaagcgccacgcttcccgaagggagaaaggcggacaggtatccggtaagcggcagggtcggaacaggagagcgca
cgagg
gagcttccaggggggaaacgcctggtatctttatagtcctgtcgggtttcgccacctctgacttgagcgtcgattt
ttgtg
atgctcgtcaggggggcggagcctatggaaaaacgccagcaacgcggcctttttacggttcctggccttttgctg
gcctt
ttgctcacatgttctttcctgcgttatcccctgattctgtggataaccgtattaccgcctttgagtgagctgata
ccgct
cgccgcagccgaacgaccgagcgcagcgagtcagtgagcgaggaagcggaagagcgcctgatgcggtatttctc
cttac
gcatctgtgcggtatttcacaccgcatatatggtgcactctcagtacaatctgctctgatgccgcatagttaagc
cagta
tacactccgctatcgctacgtgactgggtcatggctgcgccccgacacccgccaacacccgctgacgcgccctga
cgggc
ttgtctgctcccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaattctgttcatgggggtaatgataccgatgaaacgagag
aggat
gctcacgatacgggttactgatgatgaacatgcccggttactggaacgttgtgagggtaaacaactggcggtatg
gatgc
```

Figure 9 (Cont.)

ggcgggaccagagaaaaatcactcagggtcaatgccagcgcttcgttaatacagatgtaggtgttccacagggtagccag cagcatcctgcgatgcagatccggaacataatggtgcagggcgctgacttccgcgtttccagactttacgaaacacggaa accgaagaccattcatgttgttgctcaggtcgcagacgttttgcagcagcagtcgcttcacgttcgctcgcgtatcggtg attcattctgctaaccagtaaggcaaccccgccagcctagccgggtcctcaacgacaggagcacgatcatgcgcacccgt ggccaggacccaacgctgcccgagatgcgccgcgtgcggctgctggagatggcggacgcgatggatatgttctgccaagg gttggtttgcgcattcacagttctccgcaagaattgattggctccaattcttggagtggtgaatccgttagcgaggtgcc gccggcttccattcaggtcgaggtggccggctccatgcaccgcgacgcaacgcggggaggcagacaaggtataggggcgg cgcctacaatccatgccaacccgttccatgtgctcgccgaggcggcataaatcgccgtgacgatcagcggtccagtgatc gaagttaggctggtaagagccgcgagcgatccttgaagctgtccctgatggtcgtcatctacctgcctggacagcatggc ctgcaacgcgggcatcccgatgccgccggaagcgagaagaatcataatggggaaggccatccagcctcgcgtcgcgaacg ccagcaagacgtagcccagcgcgtcggccagcttgcaattcgcgctaacttacattaattgcgttgcgctcactgcccgc tttccagtcgggaaacctgtcgtgccagctgcattaatgaatcggccaacgcgcggggagaggcggtttgcgtattgggc gccagggtggttttctttcaccagtgagacgggcaacagctgattgcccttcaccgcctggccctgagagagttgcag caagcggtccacgctggtttgccccagcaggcgaaaatcctgtttgatggtggttgacggcgggatataacatgagctgt cttcggtatcgtcgtatcccactaccgagatatccgcaccaacgcgcagcccggactcggtaatggcgcgcattgcgccc agcgccatctgatcgttggcaaccagcatcgcagtgggaacgatgccctcattcagcatttgcatggtttgttgaaaacc ggacatggcactccagtcgccttcccgttccgctatcggctgaatttgattgcgagtgagatatttatgccagccagcca gacgcagacgcgccgagacagaacttaatggTccgctaacagcgcgatttgctgAtgacccaatgcgaccagatgctcc acgcccagtcgcgtaccgtcttcatgggagaaaataatactgttgatgggtgtctggtcagagacatcaagaaataacgc cggaacattagtgcaggcagcttccacagcaatggcatcctggtcatccagcggatagttaatgatcagcccactgacgc gttgcgcgagaagattgtgcaccgccgctttacaggcttcgacgccgcttcgttctaccatcgacaccaccacgctggca cccagttgatcggcgcgagatttaatcgccgcgacaatttgcgacggcgcgtgcagggccagactggaggtggcaacgcc aatcagcaacgactgtttgcccgccagttgttgtgccacgcggttgggaatgtaattcagctccgccatcgccgcttcca ctttttcccgcgtttccgcagaaacgtggctggctggttcaccacgcgggaaacggtctgataagagacaccggcatac tctgcgacatcgtataacgttactggtttcacattcaccaccctgaattgactctcttccgggcgctatcatgccatacc gcgaaggttttgcgccattcgatggtgtcaacgtaaatgcatgccgcttcgccttcgcgcgcgaattgcaagctgatcc ggagcttatcgactgcacggtgcaccaatgcttctggcgtcaggcagccatcggaagctgtggtatggctgtgcaggtcg taaatcactgcataattcgtgtcgctcaaggcgcactcccgttctggataatgttttttgcgccgacatcataacggttc tggcaaatattctgaaatgagctgttgacaattaatcatcggctcgtataatgtgtggaattgtgagcggataacaattt

Figure 9 (Cont.)

```
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTTAATAAaCAGGAAacagaaGtccatATGAAATACCTATTGCCTACGGC
AGCCG
CTGGATTGTTATTACTCGCGGCCcagcCGGCCATGGCCGCTAGCACCAAGGGCCCATCGGTCTTCCCCCTGGCAC
CCTCC
TCCAAGAGCACCTCTGGGGGCACAGCGGCCCTGGGCTGCCTGGTCAAGGACTACTTCCCCGAACCGGTGACGGTG
TCGTG
GAACTCAGGCGCCCTGACCAGCGGCGTGCACACCTTCCCGGCTGTCCTACAGTCCTCAGGACTCTACTCCCTCAg
cagcG
TAGTGACCGTGCCCTCCAGCAGCTTGGGCACCCAGACCTACATCTGCAACGTGAATCACAAGCCCAGCAACACCA
AGGTG
GACAAGAAAGTTGAGCCCAAATCTTGTTAAGCTTggctgttttggcggatgagagaagattttcagcctgataca
gatta
aatcagaacgcagaagcggtctgataaaacagaatttgcctggcggcagtagcgcggtggtcccacctgacccca
tgccg
aactcagaagtgaaacgccgtagcgccgatggtagtgtggggtctccccatgcgagagtagggaactgccaggca
tcaaa
taaaacgaaaggctcagtcgaaagactgggcctttcgttttatctgttgtttgtcggtgaacgctctcctgagta
ggaca
aatccgccgggagcggatttgaacgttgcgaagcaacggcccggaggacectggcgggcaggacgccgccataa
actgc
caggcatcaaattaagcagaaggccatcctgacggatggccttttttgcgtttctacaaactctt pCKCH1Hy1 (SEQ ID NO:101)

ttgtttattttttctaaatacattcaaatatgtatccgctcatgagacaataaccctgataaatgcttcaataata
ttgaa
aaaggaagagtatgagtattcaacatttccgtgtcgcccttattccctttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcactttTaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactgggccagatggtaagccctcccgtatcgtagttatctacacga
cgggg
```

Figure 9 (Cont.)

agtcaggcaactatggatgaacgaaatagacagatcgctgagataggtgcctcactgattaagcattggtaactgtcaga
ccaagtttactcatatatactttagattgatttaaaacttcatttttaatttaaaaggatctaggtgaagatcctttttg
ataatctcatgaccaaaatcccttaacgtgagttttcgttccactgagcgtcagacccgtagaaagatcaaaggatct
tcttgagatccttttttctgcgcgtaatctgctgcttgcaaacaaaaaaaccaccgctaccagcggtggtttgtttgcc
ggatcaagagctaccaactcttttccgaaggtaactggcttcagcagagcgcagataccaaatactgtccttctagtgt
agccgtagttaggccaccacttcaagaactctgtagcaccgcctacatacctcgctctgctaatcctgttaccagtggct
gctgccagtggcgataagtcgtgtcttaccgggttggactcaagacgatagttaccggataaggcgcagcggtcgggctg
aacgggggttcgtgcacacagcccagcttggagcgaacgacctacaccgaactgagatacctacagcgtgagcattgag
aaagcgccacgcttcccgaagggagaaaggcggacaggtatccggtaagcggcagggtcggaacaggagagcgcacgagg
gagcttccaggggggaaacgcctggtatctttatagtcctgtcgggtttcgccacctctgacttgagcgtcgatttttgtg
atgctcgtcaggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtatttctccttac
gcatctgtgcggtatttcacaccgcatatatggtgcactctcagtacaatctgctctgatgccgcatagttaagccagta
tacactccgctatcgctacgtgactgggtcatggctgcgccccgacacccgccaacacccgctgacgcgccctgacgggc
ttgtctgctcccggcatccgcttacagacaagctgtgaccgtctccgggagctgcatgtgtcagaggttttcaccgtcat
caccgaaacgcgcgaggcagctgcggtaaagctcatcagcgtggtcgtgaagcgattcacagatgtctgcctgttcatcc
gcgtccagctcgttgagtttctccagaagcgttaatgtctggcttctgataaagcgggccatgttaagggcggttttttc
ctgtttggtcacttgatgcctccgtgtaagggggaatttctgttcatgggggtaatgataccgatgaaacgagagaggat
gctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccag
cagcatcctgcgatgcagatccggaacataatggtgcagggcgctgacttccgcgtttccagactttacgaaacacggaa
accgaagaccattcatgttgttgctcaggtcgcagacgttttgcagcagcagtcgcttcacgttcgctcgcgtatcggtg
attcattctgctaaccagtaaggcaacccgccagcctagccgggtcctcaacgacaggagcacgatcatgcgcacccgt
ggccaggacccaacgctgcccgagatgcgccgcgtgcggctgctggagatggcggacgcgatggatatgttctgccaagg
gttggtttgcgcattcacagttctccgcaagaattgattggctccaattcttggagtggtgaatccgttagcgaggtgcc
gccggcttccattcaggtcgaggtggcccggctccatgcaccgcgacgcaacgcggggaggcagacaaggtatagggcgg
cgcctacaatccatgccaacccgttccatgtgctcgccgaggcggcataaatcgccgtgacgatcagcggtccagtgatc
gaagttaggctggtaagagccgcgagcgatccttgaagctgtccctgatggtcgtcatctacctgcctggacagcatggc

Figure 9 (Cont.)

ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttttcttttcaccagtgagacgggcaacagctgattgcccttcaccgcctggccctgagagagt
tgcag
caagcggtccacgctggtttgcccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
gacgcagacgcgccgagacagaacttaatggTcccgctaacagcgcgatttgctgAtgacccaatgcgaccagat
gctcc
acgcccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGgCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTTAATAAacAGGAAacagaaGtccatATGAAATACCTATTGCCTACGGC
AGCCG
CTGGATTGTTATTACTCGCGGCCcagcCGGCCATGGCCGCTAGCACCAAGGGCCCATCGGTCTTCCCCCTGGCAC
CCTCC
TCCAAGAGCACCTCTGGGGGCACAGCGGCCCTGGGCTGCCTGGTCAAGGACTACTTCCCCGAACCGGTGACGGTG
TCGTG
GAACTCAGGCGCCCTGACCAGCGGCGTGCACACCTTCCCGGCTGTCCTACAGTCCTCAGGACTCTACTCCCTCAG
CAGCG

Figure 9 (Cont.)

```
TAGTGACCGTGCCCTCCAGCAGCTTGGGCACCCAGACCTACATCTGCAACGTGAATCACAAGCCCAGCAACACCA
AGGTG
GACAAGAAAGTTGAGCCCAAATCTTGTGACAAAACTCACACATGCCCACCGTGCCCATAAGCTTggctgttttgg
cggat
gagagaagattttcagcctgatacagattaaatcagaacgcagaagcggtctgataaaacagaatttgcctggcg
gcagt
agcgcggtggtcccacctgacccatgccgaactcagaagtgaaacgccgtagcgccgatggtagtgtggggtct
cccca
tgcgagagtagggaactgccaggcatcaaataaaacgaaaggctcagtcgaaagactgggcctttcgttttatct
gttgt
ttgtcggtgaacgctctcctgagtaggacaaatccgccgggagcggatttgaacgttgcgaagcaacggcccgga
ggacc
ctggcgggcaggacgcccgccataaactgccaggcatcaaattaagcagaaggccatcctgacggatggccttt
tgcgt
ttctacaaactctt
``` pMabγ1* (SEQ ID NO:102)

```
ttgtttattttttctaaatacattcaaatatgtatccgctcatgagacaataaccctgataaatgcttcaataata
ttgaa
aaggaagagtatgagtattcaacatttccgtgtcgcccttattcccttttttgcggcattttgccttcctgttt
ttgct
cacccagaaacgctggtgaaagtaaaagatgctgaagatcagttgggtgcacgagtgggttacatcgaactggat
ctcaa
cagcggtaagatccttgagagttttcgccccgaagaacgttttccaatgatgagcacttttaaagttctgctatg
tggcg
cggtattatcccgtgttgacgccgggcaagagcaactcggtcgccgcatacactattctcagaatgacttggttg
agtac
tcaccagtcacagaaaagcatcttacggatggcatgacagtaagagaattatgcagtgctgccataaccatgagt
gataa
cactgcggccaacttacttctgacaacgatcggaggaccgaaggagctaaccgcttttttgcacaacatggggga
tcatg
taactcgccttgatcgttgggaaccggagctgaatgaagccataccaaacgacgagcgtgacaccacgatgcctg
tagca
atggcaacaacgttgcgcaaactattaactggcgaactacttactctagcttcccggcaacaattaatagactgg
atgga
ggcggataaagttgcaggaccacttctgcgctcggcccttccggctggctggtttattgctgataaatctggagc
cggtg
agcgtgggtctcgcggtatcattgcagcactggggccagatggtaagccctcccgtatcgtagttatctacacga
cgggg
agtcaggcaactatggatgaacgaaatagacagatcgctgagataggtgcctcactgattaagcattggtaactg
tcaga
ccaagtttactcatatatactttagattgatttaaaacttcattttttaatttaaaaggatctaggtgaagatcct
ttttg
ataatctcatgaccaaaatcccttaacgtgagttttcgttccactgagcgtcagaccccgtagaaaagatcaaag
gatct
tcttgagatcctttttttctgcgcgtaatctgctgcttgcaaacaaaaaaaccaccgctaccagcggtggtttgt
ttgcc
ggatcaagagctaccaactctttttccgaaggtaactggcttcagcagagcgcagataccaaatactgtccttct
agtgt
agccgtagttaggccaccacttcaagaactctgtagcaccgcctacatacctcgctctgctaatcctgttaccag
tggct
gctgccagtggcgataagtcgtgtcttaccgggttggactcaagacgatagttaccggataaggcgcagcggtcg
ggctg
aacggggggttcgtgcacacagcccagcttggagcgaacgacctacaccgaactgagatacctacagcgtgagca
ttgag
```

Figure 9 (Cont.)

```
aaagcgccacgcttcccgaagggagaaaggcggacaggtatccggtaagcggcagggtcggaacaggagagcgca
cgagg
gagcttccagggggaaacgcctggtatctttatagtcctgtcgggtttcgccacctctgacttgagcgtcgattt
ttgtg
atgctcgtcagggggcggagcctatggaaaaacgccagcaacgcggccttttacggttcctggccttttgctg
gcctt
ttgctcacatgttctttcctgcgttatccctgattctgtggataaccgtattaccgcctttgagtgagctgata
ccgct
cgccgcagccgaacgaccgagcgcagcgagtcagtgagcgaggaagcggaagagcgcctgatgcggtattttctc
cttac
gcatctgtgcggtatttcacaccgcatatatggtgcactctcagtacaatctgctctgatgccgcatagttaagc
cagta
tacactccgctatcgctacgtgactgggtcatggctgcgcccgacacccgccaacaccgctgacgcgcctga
cgggc
ttgtctgctccggcatccgcttacagacaagctgtgaccgtctccgggagctgcatgtgtcagaggttttcacc
gtcat
caccgaaacgcgcgaggcagctgcggtaaagctcatcagcgtggtcgtgaagcgattcacagatgtctgcctgtt
catcc
gcgtccagctcgttgagtttctccagaagcgttaatgtctggcttctgataaagcgggccatgttaagggcggtt
ttttc
ctgtttggtcacttgatgcctccgtgtaagggggaatttctgttcatgggggtaatgataccgatgaaacgagag
aggat
gctcacgatacgggttactgatgatgaacatgcccggttactggaacgttgtgagggtaaacaactggcggtatg
gatgc
ggcgggaccagagaaaaatcactcagggtcaatgccagcgcttcgttaatacagatgtaggtgttccacagggta
gccag
cagcatcctgcgatgcagatccggaacataatggtgcagggcgctgacttccgcgtttcagactttacgaaaca
cggaa
accgaagaccattcatgttgttgctcaggtcgcagacgttttgcagcagcagtcgcttcacgttcgctcgcgtat
cggtg
attcattctgctaaccagtaaggcaacccgcagcctagccgggtcctcaacgacaggagcacgatcatgcgca
cccgt
ggccaggacccaacgctgcccgagatgcgccgcgtgcggctgctggagatggcggacgcgatggatatgttctgc
caagg
gttggtttgcgcattcacagttctccgcaagaattgattggctccaattcttggagtggtgaatccgttagcgag
gtgcc
gccggcttccattcaggtcgaggtggcccggctccatgcaccgcgacgcaacgcggggaggcagacaaggtatag
ggcgg
cgcctacaatccatgccaacccgttccatgtgctcgccgaggcggcataaatcgccgtgacgatcagcggtccag
tgatc
gaagttaggctggtaagagccgcgagcgatccttgaagctgtccctgatggtcgtcatctacctgcctggacagc
atggc
ctgcaacgcgggcatcccgatgccgccggaagcgagaagaatcataatggggaaggccatccagcctcgcgtcgc
gaacg
ccagcaagacgtagcccagcgcgtcggccagcttgcaattcgcgctaacttacattaattgcgttgcgctcactg
cccgc
tttccagtcgggaaacctgtcgtgccagctgcattaatgaatcggccaacgcgcggggagaggcggtttgcgtat
tgggc
gccagggtggttttctttcaccagtgagacgggcaacagctgattgcccttcaccgcctggccctgagagagt
tgcag
caagcggtccacgctggtttgccccagcaggcgaaaatcctgtttgatggtggttgacggcgggatataacatga
gctgt
cttcggtatcgtcgtatcccactaccgagatatccgcaccaacgcgcagcccggactcggtaatggcgcgcattg
cgccc
agcgccatctgatcgttggcaaccagcatcgcagtgggaacgatgccctcattcagcatttgcatggtttgttga
aaacc
ggacatggcactccagtcgccttcccgttccgctatcggctgaatttgattgcgagtgagatatttatgccagcc
agcca
```

Figure 9 (Cont.)

```
gacgcagacgcgccgagacagaacttaatggTcccgctaacagcgcgatttgctgAtgacccaatgcgaccagat
gctcc
acgccagtcgcgtaccgtcttcatgggagaaaataatactgttgatgggtgtctggtcagagacatcaagaaat
aacgc
cggaacattagtgcaggcagcttccacagcaatggcatcctggtcatccagcggatagttaatgatcagcccact
gacgc
gttgcgcgagaagattgtgcaccgccgctttacaggcttcgacgccgcttcgttctaccatcgacaccaccacgc
tggca
cccagttgatcggcgcgagatttaatcgccgcgacaatttgcgacggcgcgtgcagggccagactggaggtggca
acgcc
aatcagcaacgactgtttgcccgccagttgttgtgccacgcggttgggaatgtaattcagctccgccatcgccgc
ttcca
cttttcccgcgttttcgcagaaacgtggctggcctggttcaccacgcgggaaacggtctgataagagacaccgg
catac
tctgcgacatcgtataacgttactggtttcacattcaccaccctgaattgactctcttccgggcgctatcatgcc
atacc
gcgaaaggttttgcgccattcgatggtgtcaacgtaaatgcatgccgcttcgccttcgcgcgcgaattgcaagct
gatcc
ggagcttatcgactgcacggtgcaccaatgcttctggcgtcaggcagccatcggaagctgtggtatggctgtgca
ggtcg
taaatcactgcataattcgtgtcgctcaaggcgcactcccgttctggataatgttttttgcgccgacatcataac
ggttc
tggcaaatattctgaaatgagctgttgacaattaatcatcggctcgtataatgtgtggaattgtgagcggataac
aattt
cacacaggaaacaGAATTCcatATGAAATACCTATTACCAACAGCAGCAGCTGGGTTATTATTGCTCGCTGCGCA
GCCGG
CCATGGcccaGGTcACCGTCTCCTCAGGTACCGTGGCTGCACCATCTGTCTTCATCTTCCCGCCATCTGATGAGC
AGTTG
AAATCTGGAACTGCCTCTGTTGTGTGCCTGCTGAATAACTTCTATCCCAGAGAGGCCAAAGTACAGTGGAAGGTG
GATAA
CGCCCTCCAATCGGGTAACTCCCAGGAGAGTGTCACAGAGCAGGACAGCAAGGACAGCACCTACAGCCTCAGCAG
CACCC
TGACGCTGAGCAAAGCAGACTACGAGAAACACAAAGTCTACGCCTGCGAAGTCACCCATCAGGGCCTGAGCTCGC
CGGTG
ACAAAGAGCTTCAACCGCGGAGAGTGTTAATAAaCAGGAAacagaaGtccatATGAAATACCTATTGCCTACGGC
AGCCG
CTGGATTGTTATTACTCGCGGCCcagcCGGCCATGGCCGCTAGCACCAAGGGCCCatcggtcttcccctggcac
cctcc
tccaagagcacctctgggggcacagcggccctgggctgcctggtcaaggactacttccccgaaccggtgacggtg
tcgtg
gaactcaggcgccctgaccagcggcgtgcacaccttcccggctgtcctacagtcctcaggactctactccctcag
cagcg
tggtgaccgtgccctccagcagcttgggcacccagacctacatctgcaacgtgaatcacaagcccagcaacacca
aggtg
gacaagaaagttGAGCCCAAATCTTGTGACAAAACTCACACATGCCCACCGTGCCCAgcacctgaactcctgggg
ggacc
gtcagtcttcctcttccccccaaaacccaaggacaccctcatgatctcccggacccctgaggtcacatgcgtggt
ggtgg
acgtgagccacgaagaccctgaggtcaagttcaactggtacgtggacggcgtggaggtgcataatgccaagacaa
agccg
cgggaggagcagtacaacagcacgtaccgggtggtcagcgtcctcaccgtcctgcaccaggactggctgaatggc
aagga
gtacaagtgcaaggtctccaacaaagccctcccagcccccatcgagaaaaccatctccaaagccaaaGGGCAGCC
CCGAG
AACCACAGGTGTACACCCTGCCCCCATCCCGGGATGAGCTGACCAAGAACCAGGTCAGCCTGACCTGCCTGGTCA
AAGGC
TTCTATCCCAGCGACATCGCCGTGGAGTGGGAGAGCAATGGGCAGCCGGAGAACAACTACAAGACCACGCCTCCC
GTGCT
```

Figure 9 (Cont.)

GGACTCCGACGGCTCCTTCTTCCTCTACAGCAAGCTCACCGTGGACAAGAGCAGGTGGCAGCAGGGGAACGTCTT
CTCAT
GCTCCGTGATGCATGAGGCTCTGCACAACCACTACACGCAGAAGAGCCTCTCCCTGTCTCCGGGTAAATAAGCTT
ggctg
ttttggcggatgagagaagattttcagcctgatacagattaaatcagaacgcagaagcggtctgataaaacagaa
tttgc
ctggcggcagtagcgcggtggtcccacctgacccatgccgaactcagaagtgaaacgccgtagcgccgatggta
gtgtg
gggtctccccatgcgagagtagggaactgccaggcatcaaataaaacgaaaggctcagtcgaaagactgggcctt
tcgtt
ttatctgttgtttgtcggtgaacgctctcctgagtaggacaaatccgccgggagcggatttgaacgttgcgaagc
aacgg
cccggaggaccctggcgggcaggacgcccgccataaactgccaggcatcaaattaagcagaaggccatcctgacg
gatgg
ccttttgcgtttctacaaactctt

FIGURE 11 p55PhoA6HisGS/N⁻

SEQ ID N° 89

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aagagctaa ccgctttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagaccccg tagaaaagat caaaggatct cttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca gggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg tatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggggag
3421 aggcggtttg cgtattgggc gccagggtgg ttttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttgc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg ggcccgctaa cagcgcgatt tgctggtgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggcggc cgatcctcga gagctcccgg gctgcagccc
4921 tgttctggaa aaccgggctg ctcagggcga tattactgca cccggcggtg ctcgccgttt
4981 aacgggtgat cagactgccg ctctgcgtga ttctcttagc gataaacctg caaaaaatat
5041 tatttttgctg attggcgatg ggatggggga ctcggaaatt actgccgcac gtaattatgc
5101 cgaaggtcg ggcgcttttt ttaaaggtat agatgcctta ccgcttaccg ggcaatacac
5161 tcactatgcg ctgaataaaa aaaccggcaa accggactac gtcaccgact cggctgcatc
5221 agcaaccgcc tggtcaaccg gtgtcaaaac ctataacggc gcgctgggcg tcgatattca
5281 cgaaaaagat cacccaacga ttctggaaat ggcaaaagcc gcaggtctgg cgaccggtaa
5341 cgtttctacc gcagagttgc aggatgccac gcccgctgcg ctggtggcac atgtgacctc
5401 gcgcaaatgc tacgtccga gcgcgaccag tgaaaaatgt ccgggtaacg ctctggaaaa
5461 aggcggaaaa ggatcgatta ccgaacagct gcttaacgct cgtgccgacg ttacgcttgg
5521 cggcggcgca aaacctttg ctgaaacggc aaccgctggt gaatggcagg gaaaaacgct
5581 gcgtgaacag gcacaggcgc gtggttatca gttggtgagc gatgctgcct cactgaattc
5641 ggtgacggaa gcgaatcagc aaaaacccct gcttggcctg tttgctgacg gcaatatgcc
5701 agtgcgctgg ctaggaccga aagcaacgta ccacggcaat atcgataagc ccgcagtcac
5761 ctgtacgcca aatccgcaac gtaatgacag tgtaccaacc ctggcgcaga tgaccgacaa
5821 agccattgaa ttgttgagta aaaatgagaa aggcttttc ctgcaagttg aaggtgcgtc
5881 aatcgataaa caggatcatg ctgcgaatcc ttgtgggcaa attggcgaga cggtcgatct
5941 cgatgaagcc gtacaacggg cgctggaatt cgctaaaaag gagggtaaca cgctggtcat
6001 agtcaccgct gatcacgccc acgccagcca gattgttgcg ccggatacca agctccggg
6061 cctcacccag gcgctaaata ccaaagatgg cgcagtgatg gtgatgagtt acgggaactc
6121 cgaagaggat tcacaagaac ataccggcag tcagttgcgt attgcggcgt atggcccgca
6181 tgccgccaat gttgttggac tgaccgacca gaccgatctc ttctacacca tgaaagccgc
6241 tctgggctg aaacatcatc atcaccatca cggagctaa taagcttctg ttttggcgga
6301 tgagagaaga ttttcagcct gatacagatt aaatcagaac gcagaagcgg tctgataaaa
6361 cagaatttgc ctggcggcag tagcgcggtg gtcccacctg acccatgcc gaactcagaa
6421 gtgaaacgcc gtagcgccga tggtagtgtg gggtctcccc atgcgagagt agggaactgc
6481 caggcatcaa ataaaacgaa aggctcagtc gaaagactgg gcctttcgtt ttatctgttg
```

Figure 11 (Contd.)

```
6541 tttgtcggtg aacgctctcc tgagtaggac aaatccgccg ggagcggatt tgaacgttgc
6601 gaagcaacgg cccggaggac cctggcgggc aggacgcccg ccataaactg ccaggcatca
6661 aattaagcag aaggccatcc tgacggatgg ccttttgcg tttctacaaa ctctt
``` p55PhoA6HisGS/NAB⁻

SEQ ID N° 90

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc tcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg ataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagaccccg tagaaagat caaggatct tcttgagatc cttttttct
1141 gcgcgtaatc tgctgcttgc aaacaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttcttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaattc tgttcatggg gtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag tgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat cgcacccgt ggcaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggcggc cgatcctcga gagctcccgg gctgcagccc
4921 tgttctggaa aaccgggctg ctcagggcga tattactgca cccggcggtg ctcgccgttt
4981 aacgggtgat cagactgccg ctctgcgtga ttctcttagc gataaacctg caaaaaatat
5041 tatttgctg attggcgatg ggatggggga ctcggaaatt actgccgcac gtaattatgc
5101 cgaaggtgcg ggcggctttt ttaaaggtat agatgcctta ccgcttaccg ggcaatacac
5161 tcactatgcg ctgaataaaa aaaccggcaa accggactac gtcaccgact cggctgcatc
5221 agcaaccgcc tggtcaaccg gtgtcaaaac ctataacggc gcgctgggcg tcgatattca
5281 cgaaaaagat cacccaacga ttctggaaat ggcaaaagcc gcaggtctgg cgaccggtaa
5341 cgtttctacc gcagagttgc aggatgccac gcccgctgcg ctggtggcac atgtgacctc
5401 gcgcaaatgc tacggtccga gcgcgaccag tgaaaaatgt ccgggtaacg ctctggaaaa
5461 aggcggaaaa ggatcgatta ccgaacagct gcttaacgct cgtgccgacg ttacgcttgg
5521 cggcggcgca aaaaccttg ctgaaacggc aaccgctggt gaatggcagg gaaaaacgct
5581 gcgtgaacag gcacaggcgc gtggttatca gttggtgagc gatgctgcct cactgaattc
5641 ggtgacggaa gcgaatcagc aaaaacccct gcttggcctg tttgctgacg caatatgcc
5701 agtgcgctgg ctaggaccga aagcaacgta ccacggcaat atcgataagc ccgcagtcac
5761 ctgtacgcca aatccgcaac gtaatgacag tgtaccaacc ctggcgcaga tgaccgacaa
5821 agccattgaa ttgttgagta aaaatgagaa aggcttttc ctgcaagttg aaggtgcgtc
5881 aatcgataaa caggatcatg ctgcgaatcc ttgtgggcaa attggcgaga cggtcgatct
5941 cgatgaagcc gtacaacggg cgctgaatt cgctaaaaag gagggtaaca cgctggtcat
6001 agtcaccgct gatcacgccc acgccagcca gattgttgcg ccggatacca aagctccggg
6061 cctcacccag gcgctaaata ccaaagatgg cgcagtgatg gtgatgagtt acgggaactc
6121 cgaagaggat tcacaagaac ataccggcag tcagttgcgt attgcggcgt atggcccgca
6181 tgccgccaat gttgttggac tgaccgacca gaccgatctc ttctacacca tgaaagccgc
6241 tctgggcctg aaacatcatc atcaccatca cgggagctaa taagcttctg ttttggcgga
6301 tgagagaaga ttttcagcct gatacagatt aaatcagaac gcagaagcgg tctgataaaa
6361 cagaatttgc ctggcggcag tagcgcggtg gtcccacctg accccatgcc gaactcagaa
6421 gtgaaacgcc gtagcgccga tggtagtgtg gggtctcccc atgcgagagt agggaactgc
6481 caggcatcaa ataaaacgaa aggctcagtc gaaagactgg gcctttcgtt ttatctgttg
```

Figure 11 (Contd.)

```
6541 tttgtcggtg aacgctctcc tgagtaggac aaatccgccg ggagcggatt tgaacgttgc
6601 gaagcaacgg cccggaggac cctggcgggc aggacgcccg ccataaactg ccaggcatca
6661 aattaagcag aaggccatcc tgacggatgg ccttttgcg tttctacaaa ctctt
``` p55/PhoA6HisGS⁻/NAB⁻

SEQ ID N° 91
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg ataggtgc ctcactgatt aagcattggt aactgtcaga
 961 ccaagtttac tcatatatac tttagattga tttaaaactt catttttaat ttaaaggat
1021 ctaggtgaag atcctttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatgaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt tgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg ctccaattc ttggagtggt
2941 gaatccgtta gcgaggtgcc gccggcttcc attcaggtcg aggtggcccg ctccatgca
3001 ccgcgacgca acgcggggag gcagacaagg tataggggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaatcc tgtttgatgg tggttgacgg cgggatataa catgagctgt
3601 cttcggtatc gtcgtatcc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggcggc cggccgatcc tcgagagctc ccgggctgca
4921 gccctgttct ggaaaaccgg gctgctcagg gcgatattac tgcaccccggc ggtgctcgcc
4981 gtttaacggg tgatcagact gccgctctgc gtgattctct tagcgataaa cctgcaaaaa
5041 atattatttt gctgattggc gatgggatgg gggactcgga aattactgcc gcacgtaatt
5101 atgccgaagg tgcgggcggc tttttttaaag gtatagatgc cttaccgctt accgggcaat
5161 acactcacta tgcgctgaat aaaaaaaccg gcaaaccgga ctacgtcacc gactcggctg
5221 catcagcaac cgcctggtca accggtgtca aaacctataa cggcgcgctg ggcgtcgata
5281 ttcacgaaaa agatcaccca acgattctgg aaatggcaaa agccgcaggt ctggcgaccg
5341 gtaacgtttc taccgcagag ttgcaggatg ccacgcccgc tgcgctggtg gcacatgtga
5401 cctcgcgcaa atgctacggt ccgagcgcga ccagtgaaaa atgtccgggt aacgctctgg
5461 aaaaggcgg aaaaggatcg attaccgaac agctgcttaa cgctcgtgcc gacgttacgc
5521 ttggcggcgg cgcaaaaacc tttgctgaaa cggcaaccgc tggtgaatgg cagggaaaaa
5581 cgctgcgtga acaggcacag gcgcgtggtt atcagttggt gagcgatgct gcctcactga
5641 attcggtgac ggaagcgaat cagcaaaaac ccctgcttgg cctgtttgct gacggcaata
5701 tgccagtgcg ctggctagga ccgaaagcaa cgtaccacgg caatatcgat aagcccgcag
5761 tcacctgtac gccaaatccg caacgtaatg acagtgtacc aaccctggcg cagatgaccg
5821 acaaagccat tgaattgttg agtaaaaatg agaaggctt tttcctgcaa gttgaaggtg
5881 cgtcaatcga taaacaggat catgctgcga atccttgtgg gcaaattggc gagacggtcg
5941 atctcgatga agccgtacaa cgggcgctgg aattcgctaa aaggagggt aacacgctgg
6001 tcatagtcac cgctgatcac gcccacgcca gccagattgt tgcgccggat accaaagctc
6061 cgggcctcac ccaggcgcta aataccaaag atggcgcagt gatggtgatg agttacggga
6121 actccgaaga ggattcacaa gaacataccg gcagtcagtt gcgtattgcg gcgtatggcc
6181 cgcatgccgc caatgttgtt ggactgaccg accagaccga tctcttctac accatgaaag
6241 ccgctctggg gctgaaacat catcatcacc atcacgggag ctaataagct tggctgtttt
6301 ggcggatgag agaagatttt cagcctgata cagattaaat cagaacgcag aagcggtctg
6361 ataaaacaga atttgcctgg cggcagtagc gcggtggtcc cacctgaccc catgccgaac
6421 tcagaagtga aacgccgtag cgccgatggt agtgtggggt ctccccatgc gagagtaggg
6481 aactgccagg catcaaataa aacgaaaggc tcagtcgaaa gactgggcct ttcgttttat
```

Figure 11 (Contd.)

```
6541 ctgttgtttg tcggtgaacg ctctcctgag taggacaaat ccgccgggag cggatttgaa
6601 cgttgcgaag caacggcccg gaggaccctg gcgggcagga cgcccgccat aaactgccag
6661 gcatcaaatt aagcagaagg ccatcctgac ggatggcctt tttgcgtttc tacaaactct
6721 t
``` p55/MCS1

SEQ ID N° 92

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagacccg tagaaaagat caaggatct tcttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatgaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag tgttccaca gggtagccag cagcatcctg cgatgcagat
2581 ccggaacata atggtgcagg gcgctgactt ccgcgtttcc agactttacg aaacacgaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
```

Figure 11 (Contd.)

```
3001 ccgcgacgca acgcggggag gcagacaagg tataggqcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatgcccca ggtcaccgtc tcctcaaacc gcggactcga
4921 ggcggcccag ccggccatgg ccgctagcgc ggccgctcta gattaagctt ggctgttttg
4981 gcggatgaga gaagattttc agcctgatac agattaaatc agaacgcaga agcggtctga
5041 taaaacagaa tttgcctggc ggcagtagcg cggtggtccc acctgacccc atgccgaact
5101 cagaagtgaa acgccgtagc gccgatggta gtgtggggtc tccccatgcg agagtaggga
5161 actgccaggc atcaaataaa acgaaaggct cagtcgaaag actgggcctt tcgttttatc
5221 tgttgtttgt cggtgaacgc tctcctgagt aggacaaatc cgccgggagc ggatttgaac
5281 gttgcgaagc aacggcccgg aggaccctgg cgggcaggac gcccgccata aactgccagg
5341 catcaaatta agcagaaggc catcctgacg gatggccttt ttgcgtttct acaaactctt
```

P55Flag/RBS/35

SEQ ID N° 93

```
  1 ttgtttattt ttctaaatac attcaaatat gtatccgctc atgagacaat aaccctgata
 61 aatgcttcaa taatattgaa aaaggaagag tatgagtatt caacatttcc gtgtcgccct
121 tattcccttt tttgcggcat tttgccttcc tgttttgct cacccagaaa cgctggtgaa
181 agtaaaagat gctgaagatc agttgggtgc acgagtgggt tacatcgaac tggatctcaa
241 cagcggtaag atccttgaga gttttcgccc cgaagaacgt tttccaatga tgagcacttt
301 taaagttctg ctatgtggcg cggtattatc ccgtgttgac gccgggcaag agcaactcgg
361 tcgccgcata cactattctc agaatgactt ggttgagtac tcaccagtca cagaaaagca
421 tcttacggat ggcatgacag taagagaatt atgcagtgct gccataacca tgagtgataa
481 cactgcggcc aacttacttc tgacaacgat cggaggaccg aaggagctaa ccgcttttt
541 gcacaacatg ggggatcatg taactcgcct tgatcgttgg gaaccggagc tgaatgaagc
601 cataccaaac gacgagcgtg acaccacgat gcctgtagca atggcaacaa cgttgcgcaa
661 actattaact ggcgaactac ttactctagc ttcccggcaa caattaatag actggatgga
721 ggcggataaa gttgcaggac cacttctgcg ctcggccctt ccggctggct ggtttattgc
781 tgataaatct ggagccggtg agcgtgggtc tcgcggtatc attgcagcac tggggccaga
```

Figure 11 (Contd.)

```
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc cggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
```

Figure 11 (Contd.)

```
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaaacc gcggagagtg
4921 tgcaggtgat tacaaagacg atgacgataa gtaataaaca ggaaacagaa gtccatatga
4981 aataccatt gcctacggca gccgctggat tgttattact cgcggcccag ccggccatgg
5041 ccgctagcgc ggccgctcta gattaagctt ggctgttttg gcggatgaga aagattttc
5101 agcctgatac agattaaatc agaacgcaga agcggtctga taaaacagaa tttgcctggc
5161 ggcagtagcg cggtggtccc acctgacccc atgccgaact cagaagtgaa acgccgtagc
5221 gccgatggta gtgtggggtc tccccatgcg agagtaggga actgccaggc atcaaataaa
5281 acgaaaggct cagtcgaaag actgggcctt tcgttttatc tgttgtttgt cggtgaacgc
5341 tctcctgagt aggacaaatc cgccgggagc ggatttgaac gttgcgaagc aacggcccgg
5401 aggaccctgg cgggcaggac gcccgccata aactgccagg catcaaatta agcagaaggc
5461 catcctgacg gatggccttt ttgcgtttct acaaactctt
```

SEQ ID N° 109
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattccctt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagacccg tagaaagat caaggatct tcttgagatc ctttttttct
1141 gcgcgtaatc tgctgcttgc aaacaaaaa accaccgcta ccagcggtgg tttgtttgcc
1201 ggatcaagag ctaccaactc tttttccgaa ggtaactggc ttcagcagag cgcagatacc
1261 aaatactgt cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gattttttgtg
1681 atgctcgtca ggggggcgga gcctatgaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatagt tggtcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
```

Figure 11 (Contd.)

```
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatgca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaaacc gcggagagtg
4921 tgcaggtgat tacaaagacg atgacgataa gtaataaaca ggaaacagaa gtccatatga
4981 aatatctttt acctacggca gccgcaggtt tgttgttact cgcggccag ccggccatgg
5041 ccgctagcgc ggccgctcta gattaagctt ggctgttttg gcggatgaga gaagattttc
5101 agcctgatac agattaaatc agaacgcaga gcggtctga taaaacagaa tttgcctggc
5161 ggcagtagcg cggtggtccc acctgacccc atgccgaact cagaagtgaa acgccgtagc
5221 gccgatggta gtgtgggtc tccccatgcg agagtaggga actgccaggc atcaaataaa
5281 acgaaaggct cagtcgaaag actgggcctt tcgttttatc tgttgtttgt cggtgaacgc
5341 tctcctgagt aggacaaatc cgccgggagc ggatttgaac gttgcgaagc aacgcccgg
5401 aggaccctgg cgggcaggac gcccgccata aactgccagg catcaaatta agcagaaggc
5461 catcctgacg gatggccttt ttgcgtttct acaaactctt
```

P55Flag/RBS/35cmyc6HisGS

Figure 11 (Contd.)

SEQ ID N° 94

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc gaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aagagctaa ccgcttttt
 541 gcacaacatg ggggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag gggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg tcgtcatct
3181 acctgcctgg acagcatggc ctgcaacgcg gcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact acattaatt gcgttgcgct cactgcccgc
```

Figure 11 (Contd.)

```
3361 tttccagtcg ggaaacctgt cgtgccagct gcattaatga atcggccaac gcgcggggag
3421 aggcggtttg cgtattgggc gccagggtgg tttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgtttttcga gaaacgtgc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctggttatt
4861 attgctcgct gcgcagccgg ccatgcccca ggtcaccgtc tcctcaaacc gcggagagtg
4921 tgcaggtgat tacaaagacg atgacgataa gtaataaaca ggaaacagaa gtccatatga
4981 aataccatt gcctacggca gccgctggat tgttattact cgcggccag ccggccatgg
5041 ccgctagcgc ggccgcagaa caaaaactca tctcagaaga ggatctgaat ggggccgtac
5101 atcaccacca tcatcatggg agctaagctt ggctgttttg gcggatgaga gaagattttc
5161 agcctgatac agattaaatc agaacgcaga agcggtctga taaaacagaa tttgcctggc
5221 ggcagtagcg cggtggtccc acctgacccc atgccgaact cagaagtgaa acgccgtagc
5281 gccgatggta gtgtggggtc tccccatgcg agagtaggga actgccaggc atcaaataaa
5341 acgaaaggct cagtcgaaag actgggcctt tcgttttatc tgttgtttgt cggtgaacgc
5401 tctcctgagt aggacaaatc cgccgggagc ggatttgaac gttgcgaagc aacggcccgg
5461 aggaccctgg cgggcaggac gcccgccata aactgccagg catcaaatta agcagaaggc
5521 catcctgacg gatggccttt ttgcgtttct acaaactctt
```

SEQ ID N° 110

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt cattttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc cttttttct
```

Figure 11 (Contd.)

```
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gattttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
```

Figure 11 (Contd.)

```
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaaacc gcggagagtg
4921 tgcaggtgat tacaaagacg atgacgataa gtaataaaca ggaaacagaa gtccatatga
4981 aatatctttt acctacggca gccgcaggtt tgttgttact cgcggcccag ccggccatgg
5041 ccgctagcgc ggccgcagaa caaaaactca tctcagaaga ggatctgaat ggggccgtac
5101 atcaccacca tcatcatggg agctaagctt ggctgttttg gcggatgaga aagattttc
5161 agcctgatac agattaaatc agaacgcaga agcggtctga taaacagaa tttgcctggc
5221 ggcagtagcg cggtggtccc acctgacccc atgccgaact cagaagtgaa acgccgtagc
5281 gccgatggta gtgtggggtc tccccatgcg agagtaggga actgccaggc atcaaataaa
5341 acgaaaggct cagtcgaaag actgggcctt tcgttttatc tgttgtttgt cggtgaacgc
5401 tctcctgagt aggacaaatc cgccgggagc ggatttgaac gttgcgaagc aacggcccgg
5461 aggacctgg cgggcaggac gcccgccata aactgccagg catcaaatta agcagaaggc
5521 catcctgacg gatggccttt ttgcgtttct acaaactctt
``` pHCH2CH3γ1-TAG

SEQ ID N° 95

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
```

Figure 11 (Contd.)

```
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcagaca aaactcacac
4921 atgcccaccg tgcccagcac ctgaactcct ggggggaccg tcagtcttcc tcttcccccc
4981 aaaacccaag gacaccctca tgatctcccg gacccctgag gtcacatgcg tggtggtgga
5041 cgtgagccac gaagaccctg aggtcaagtt caactggtac gtggacggcg tggaggtgca
5101 taatgccaag acaaagccgc gggaggagca gtacaacagc acgtaccggg tggtcagcgt
5161 cctcaccgtc ctgcaccagg actggctgaa tggcaaggag tacaagtgca aggtctccaa
5221 caaagcctc ccagccccca tcgagaaaac catctccaaa gccaagggc agccccgaga
5281 accacaggtg tacaccctgc cccatcccg ggatgagctg accaagaacc aggtcagcct
5341 gacctgcctg gtcaaaggct tctatcccag cgacatcgcc gtggagtggg agagcaatgg
5401 gcagccggag aacaactaca agaccacgcc tcccgtgctg gactccgacg gctccttctt
5461 cctctacagc aagctcaccg tggacaagag caggtggcag caggggaacg tcttctcatg
5521 ctccgtgatg catgaggctc tgcacaacca ctacacgcag aagagcctct ccctgtctcc
5581 gggtaaagcg gccgcagaac aaaaactcat ctcagaagag gatctgaatg gggccgtaca
5641 tcaccaccat catcatggga gctaagcttg gctgttttgg cggatgagag aagattttca
```

Figure 11 (Contd.)

```
5701 gcctgataca gattaaatca gaacgcagaa gcggtctgat aaaacagaat ttgcctggcg
5761 gcagtagcgc ggtggtccca cctgacccca tgccgaactc agaagtgaaa cgccgtagcg
5821 ccgatggtag tgtggggtct ccccatgcga gagtagggaa ctgccaggca tcaaataaaa
5881 cgaaaggctc agtcgaaaga ctgggccttt cgttttatct gttgtttgtc ggtgaacgct
5941 ctcctgagta ggacaaatcc gccgggagcg gatttgaacg ttgcgaagca acggcccgga
6001 ggaccctggc gggcaggacg cccgccataa actgccaggc atcaaattaa gcagaaggcc
6061 atcctgacgg atggccttt tgcgtttcta caaactctt
``` pHCH2CH3γ1

SEQ ID N° 96

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcaccccgt ggccaggacc caacgctgcc
```

Figure 11 (Contd.)

```
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattca atatgaaata cctattacca acagcagcag ctgggttatt
4861 attgctcgct gcgcagccgg ccatggccca ggtcaccgtc tcctcagaca aaactcacac
4921 atgccaccg tgcccagcac ctgaactcct gggggaccg tcagtcttcc tcttcccccc
4981 aaaacccaag gacaccctca tgatctcccg gacccctgag gtcacatgcg tggtggtgga
5041 cgtgagccac gaagaccctg aggtcaagtt caactggtac gtggacggcg tggaggtgca
5101 taatgccaag acaaagccgc gggaggagca gtacaacagc acgtaccggg tggtcagcgt
5161 cctcaccgtc ctgcaccagg actggctgaa tggcaaggag tacaagtgca aggtctccaa
5221 caaagccctc ccagccccca tcgagaaaac catctccaaa gccaagggc agccccgaga
5281 accacaggtg tacaccctgc ccccatcccg ggatgagctg accaagaacc aggtcagcct
5341 gacctgcctg gtcaaaggct tctatcccag cgacatcgcc gtggagtggg agagcaatgg
5401 gcagccggag aacaactaca agaccacgcc tcccgtgctg gactccgacg gctccttctt
5461 cctctacagc aagctcaccg tggacaagag caggtggcag caggggaacg tcttctcatg
5521 ctccgtgatg catgaggctc tgcacaacca ctacgcag aagagcctct ccctgtctcc
5581 gggtaaataa gcttggctgt tttggcggat gagagaagat tttcagcctg atacagatta
5641 aatcagaacg cagaagcggt ctgataaaac agaatttgcc tggcggcagt agcgcggtgg
5701 tcccacctga ccccatgccg aactcagaag tgaaacgccg tagcgccgat ggtagtgtgg
5761 ggtctcccca tgcgagagta gggaactgcc aggcatcaaa taaaacgaaa ggctcagtcg
5821 aaagactggg cctttcgttt tatctgttgt ttgtcggtga acgctctcct gagtaggaca
5881 aatccgccgg gagcggattt gaacgttgcg aagcaacggc ccggaggacc ctggcgggca
5941 ggacgcccgc cataaactgc caggcatcaa attaagcaga aggccatcct gacggatggc
6001 cttttgcgt ttctacaaac tctt
```

P55CKFlag/RBS/35cmyc6HisGS

SEQ ID N° 97

Figure 11 (Contd.)

```
   1 ttgtttattt ttctaaatac attcaaatat gtatccgctc atgagacaat aaccctgata
  61 aatgcttcaa taatattgaa aaggaagag tatgagtatt caacatttcc gtgtcgcct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atccttttg ataatctcat gaccaaaatc ccttaacgtg agttttcgtt
1081 ccactgagcg tcagacccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg aacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggtttttc ctgtttggtc acttgatgcc
2341 tccgtgtaag gggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtgcccg gctccatgca
3001 ccgcgacgca acgcggggag gcagacaagg tatagggcgg cgcctacaat ccatgccaac
3061 ccgttccatg tgctcgccga gcggcataa atcgccgtga cgatcagcgg tccagtgatc
3121 gaagttaggc tggtaagagc cgcgagcgat ccttgaagct gtccctgatg tcgtcatct
3181 acctgcctgg acagcatggc ctgcaacgcg gcatcccga tgccgccgga agcgagaaga
3241 atcataatgg gaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg ttttctttt caccagtgag acgggcaaca
```

Figure 11 (Contd.)

```
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tgcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatgcccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgtgca ggtgattaca aagacgatga cgataagtaa taaacaggaa acagaagtcc
5281 atatgaaata cctattgcct acggcagccg ctggattgtt attactcgcg gcccagccgg
5341 ccatggccgc tagcgcggcc gcagaacaaa aactcatctc agaagaggat ctgaatgggg
5401 ccgtacatca ccaccatcat catgggagct aagcttggct gttttggcgg atgagagaag
5461 attttcagcc tgatacagat taaatcgaaa cgcagaagcg gtctgataaa acagaatttg
5521 cctggcggca gtagcgcggt ggtcccacct gacccccatgc cgaactcaga agtgaaacgc
5581 cgtagcgccg atggtagtgt ggggtctccc catgcgagag tagggaactg ccaggcatca
5641 aataaaacga aaggctcagt cgaaagactg ggcctttcgt tttatctgtt gtttgtcggt
5701 gaacgctctc ctgagtagga caaatccgcc gggagcggat ttgaacgttg cgaagcaacg
5761 gcccggagga ccctggcggg caggacgccc gccataaact gccaggcatc aaattaagca
5821 gaaggccatc ctgacggatg gcctttttgc gtttctacaa actctt
```

SEQ ID N° 111
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
```

Figure 11 (Contd.)

```
 961 ccaagtttac tcatatatac tttagattga tttaaaactt cattttaat ttaaaggat
1021 ctaggtgaag atccttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggttcg ccacctctga cttgagcgtc gatttttgtg
1681 atgctcgtca gggggcgga gcctatggaa aaacgccagc aacgcggcct ttttacggtt
1741 cctgccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggtttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg tttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacgcgcg gtgcaggcc agactggagg tggcaacgcc aatcagcaac gactgtttgc
4261 ccgccagttg ttgtgccacg cggttgggaa tgtaattcag ctccgccatc gccgcttcca
4321 cttttccccg cgttttcgca gaaacgtggc tggcctggtt caccacgcgg gaaacggtct
4381 gataagagac accggcatac tctgcgacat cgtataacgt tactggtttc acattcacca
```

Figure 11 (Contd.)

```
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgtgca ggtgattaca agacgatga cgataagtaa taaacaggaa acagaagtcc
5281 atatgaaata tcttttacct acggcagccg caggtttgtt gttactcgcg gcccagccgg
5341 ccatggccgc tagcgcggcc gcagaacaaa aactcatctc agaagaggat ctgaatgggg
5401 ccgtacatca ccaccatcat catgggagct aagcttggct gttttggcgg atgagagaag
5461 attttcagcc tgatacgata taaatcagaa cgcagaagcg gtctgataaa acagaatttg
5521 cctggcggca gtagcgcggt ggtcccacct gacccatgc cgaactcaga agtgaaacgc
5581 cgtagcgccg atggtagtgt ggggtctccc catgcgagag tagggaactg ccaggcatca
5641 aataaaacga aaggctcagt cgaaagactg ggcctttcgt tttatctgtt gtttgtcggt
5701 gaacgctctc ctgagtagga caaatccgcc gggagcggat ttgaacgttg cgaagcaacg
5761 gcccgaggga ccctggcggg caggacgccc gccataaact gccaggcatc aaattaagca
5821 gaaggccatc ctgacggatg cctttttgc gtttctacaa actctt
``` pCKCH1γ1-TAG

SEQ ID N° 98

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg gggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaagat caaggatct cttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatgaa aaacgccagc aacgcggcct ttttacggtt
1741 cctggccttt tgctggcctt ttgctcacat gttctttcct gcgttatccc ctgattctgt
```

Figure 11 (Contd.)

```
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg ctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagctatc gactgacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgtgca ggtgattaca aagacgatga cgataagtaa taaacaggaa acagaagtcc
```

Figure 11 (Contd.)

```
      5281 atatgaaata cctattgcct acggcagccg ctggattgtt attactcgcg gcccagccgg
      5341 ccatggccgc tagcaccaag ggcccatcgg tcttcccect ggcaccctcc tccaagagca
      5401 cctctggggg cacagcggcc ctgggctgcc tggtcaagga ctacttcccc gaaccggtga
      5461 cggtgtcgtg gaactcaggc gccctgacca gcggcgtgca caccttcccg gctgtcctac
      5521 agtcctcagg actctactcc ctcagcagcg tagtgaccgt gccctccagc agcttgggca
      5581 cccagaccta catctgcaac gtgaatcaca agcccagcaa caccaaggtg gacaagaaag
      5641 ttgagcccaa atcttgtgcg gccgcagaac aaaaactcat ctcagaagag gatctgaatg
      5701 gggccgtaca tcaccaccat catcatggga gctaagcttg gctgttttgg cggatgagag
      5761 aagattttca gcctgataca gattaaatca gaacgcagaa gcggtctgat aaaacagaat
      5821 ttgcctggcg gcagtagcgc ggtggtccca cctgacccca tgccgaactc agaagtgaaa
      5881 cgccgtagcg ccgatggtag tgtggggtct ccccatgcga gagtagggaa ctgccaggca
      5941 tcaaataaaa cgaaaggctc agtcgaaaga ctgggccttt cgttttatct gttgtttgtc
      6001 ggtgaacgct ctcctgagta ggacaaatcc gccgggagcg gatttgaacg ttgcgaagca
      6061 acggcccgga ggaccctggc gggcaggacg cccgccataa actgccaggc atcaaattaa
      6121 gcagaaggcc atcctgacgg atggccttt tgcgtttcta caaactctt SEQ ID N° 112
         1 ttgtttattt ttctaaatac attcaaatat gtatccgctc atgagacaat aaccctgata
        61 aatgcttcaa taatattgaa aaggaagag tatgagtatt caacatttcc gtgtcgccct
       121 tattccettt tttgcggcat tttgccttcc tgttttgct cacccagaaa cgctggtgaa
       181 agtaaaagat gctgaagatc agttgggtgc acgagtgggt tacatcgaac tggatctcaa
       241 cagcggtaag atccttgaga gttttcgccc cgaagaacgt tttccaatga tgagcacttt
       301 taaagttctg ctatgtggcg cggtattatc ccgtgttgac gccgggcaag agcaactcgg
       361 tcgccgcata cactattctc agaatgactt ggttgagtac tcaccagtca cagaaaagca
       421 tcttacggat ggcatgacag taagagaatt atgcagtgct gccataacca tgagtgataa
       481 cactgcggcc aacttacttc tgacaacgat cggaggaccg aaggagctaa ccgcttttt
       541 gcacaacatg ggggatcatg taactcgcct tgatcgttgg gaaccggagc tgaatgaagc
       601 cataccaaac gacgagcgtg acaccacgat gcctgtagca atggcaacaa cgttgcgcaa
       661 actattaact ggcgaactac ttactctagc ttcccggcaa caattaatag actggatgga
       721 ggcggataaa gttgcaggac cacttctgcg ctcggccctt ccggctggct ggtttattgc
       781 tgataaatct ggagccggtg agcgtgggtc tcgcggtatc attgcagcac tggggccaga
       841 tggtaagccc tcccgtatcg tagttatcta cacgacgggg agtcaggcaa ctatgatga
       901 acgaaataga cagatcgctg agataggtgc ctcactgatt aagcattggt aactgtcaga
       961 ccaagtttac tcatatatac tttagattga tttaaaactt catttttaat ttaaaaggat
      1021 ctaggtgaag atccttttg ataatctcat gaccaaaatc ccttaacgtg agttttcgtt
      1081 ccactgagcg tcagaccccg tagaaaagat caaaggatct cttgagatc ctttttttct
      1141 gcgcgtaatc tgctgcttgc aaacaaaaa accaccgcta ccagcggtgg tttgtttgcc
      1201 ggatcaagag ctaccaactc tttttccgaa ggtaactggc ttcagcagag cgcagatacc
      1261 aaatactgtc cttctagtgt agccgtagtt aggccaccac ttcaagaact ctgtagcacc
      1321 gcctacatac ctcgctctgc taatcctgtt accagtggct gctgccagtg gcgataagtc
      1381 gtgtcttacc gggttggact caagacgata gttaccggat aaggcgcagc ggtcgggctg
      1441 aacgggggt tcgtgcacac agcccagctt ggagcgaacg acctacaccg aactgagata
      1501 cctacagcgt gagcattgag aaagcgccac gcttcccgaa gggagaaagg cggacaggta
      1561 tccggtaagc ggcagggtcg gaacaggaga gcgcacgagg gagcttccag gggaaacgc
      1621 ctggtatctt tatagtcctg tcgggtttcg ccacctctga cttgagcgtc gatttttgtg
      1681 atgctcgtca gggggcgga gcctatggaa aaacgccagc aacgcggcct ttttacggtt
      1741 cctggccttt tgctggcctt ttgctcacat gttctttcct gcgttatccc ctgattctgt
      1801 ggataaccgt attaccgcct ttgagtgagc tgataccgct cgccgcagcc gaacgaccga
      1861 gcgcagcgag tcagtgagcg aggaagcgga agagcgcctg atgcggtatt ttctccttac
      1921 gcatctgtgc ggtatttcac accgcatata tggtgcactc tcagtacaat ctgctctgat
      1981 gccgcatagt taagccagta tacactccgc tatcgctacg tgactgggtc atggctgcgc
      2041 cccgacaccc gccaacaccc gctgacgcgc cctgacgggc ttgtctgctc ccggcatccg
      2101 cttacagaca agctgtgacc gtctccggga gctgcatgtg tcagaggttt tcaccgtcat
      2161 caccgaaacg cgcgaggcag ctgcggtaaa gctcatcagc gtggtcgtga agcgattcac
      2221 agatgtctgc ctgttcatcc gcgtccagct cgttgagttt ctccagaagc gttaatgtct
      2281 ggcttctgat aaagcgggcc atgttaaggg cggttttttc ctgtttggtc acttgatgcc
      2341 tccgtgtaag ggggaatttc tgttcatggg gtaatgata ccgatgaaac gagagaggat
      2401 gctcacgata cgggttactg atgatgaaca tgcccggtta ctggaacgtt gtgagggtaa
```

Figure 11 (Contd.)

```
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttccttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaagtcta
5161 cgcctgcgaa gtcacccatc agggcctgag ctcgccggtg acaaagagct tcaaccgcgg
5221 agagtgtgca ggtgattaca agacgatga cgataagtaa taaacaggaa acagaagtcc
5281 atatgaaata tcttttacct acggcagccg caggtttgtt gttactgcg gccagccgg
5341 ccatggccgc tagcaccaag ggcccatcgg tcttccccct ggcacctcc tccaagagca
5401 cctctggggg cacagcggcc ctgggctgcc tggtcaagga ctacttcccc gaaccggtga
5461 cggtgtcgtg gaactcaggc gccctgacca gcggcgtgca caccttcccg gctgtcctac
5521 agtcctcagg actctactcc ctcagcagcg tagtgaccgt gccctccagc agcttgggca
5581 cccagaccta catctgcaac gtgaatcaca agcccagcaa caccaaggtg gacaagaaag
5641 ttgagcccaa atcttgtgcg gccgcagaac aaaaactcat ctcagaagag gatctgaatg
5701 gggccgtaca tcaccaccat catcatggga gctaagcttg gctgttttgg cggatgagag
5761 aagattttca gcctgataca gattaaatca gaacgcagaa gcggtctgat aaaacagaat
5821 ttgcctggcg gcagtagcgc ggtggtccca cctgacccca tgccgaactc agaagtgaaa
5881 cgccgtagcg ccgatggtag tgtggggtct ccccatgcga gagtagggaa ctgccaggca
```

Figure 11 (Contd.)

```
5941 tcaaataaaa cgaaaggctc agtcgaaaga ctgggccttt cgttttatct gttgtttgtc
6001 ggtgaacgct ctcctgagta ggacaaatcc gccgggagcg gatttgaacg ttgcgaagca
6061 acggcccgga ggaccctggc gggcaggacg cccgccataa actgccaggc atcaaattaa
6121 gcagaaggcc atcctgacgg atggcctttt tgcgtttcta caaactctt
``` pCKCH1Hγ1-TAG

SEQ ID N° 99

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt caccgtcat
2161 caccgaaacg cgcgaggcag ctgcggtaaa gctcatcagc gtggtcgtga gcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcaggtc aatgccagcg
2521 cttcgttaat acagatgtag gtgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
```

Figure 11 (Contd.)

```
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttttcttttt caccagtgag acggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttccccg cgtttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca aagacgatga cgataagtaa taaacaggaa acagaagtcc
5281 atatgaaata cctattgcct acggcagccg ctggattgtt attactcgcg gcccagccgg
5341 ccatggccgc tagcaccaag ggcccatcgg tcttccccct ggcaccctcc tccaagagca
5401 cctctggggg cacagcggcc ctgggctgcc tggtcaagga ctacttcccc gaaccggtga
5461 cggtgtcgtg gaactcaggc gccctgacca gcggcgtgca caccttcccg gctgtcctac
5521 agtcctcagg actctactcc ctcagcagcg tagtgaccgt gccctccagc agcttgggca
5581 cccagaccta catctgcaac gtgaatcaca agcccagcaa caccaaggtg gacaagaaag
5641 ttgagcccaa atcttgtgac aaaactcaca catgcccacc gtgcccagca gcgcagaac
5701 aaaaactcat ctcagaagag gatctgaatg gggccgtaca tcaccaccat catcatggga
5761 gctaagcttg gctgttttgg cggatgagag aagattttca gcctgataca gattaaatca
5821 gaacgcagaa gcggtctgat aaaacagaat ttgcctggcg gcagtagcgc ggtggtccca
5881 cctgacccca tgccgaactc agaagtgaaa cgccgtagcg ccgatggtag tgtgggtct
5941 ccccatgcga gagtagggaa ctgccaggca tcaaataaaa cgaaaggctc agtcgaaaga
6001 ctgggccttt cgttttatct gttgtttgtc ggtgaacgct ctcctgagta ggacaaatcc
6061 gccgggagcg gatttgaacg ttgcgaagca acggcccgga ggacctggc gggcaggacg
6121 cccgccataa actgccaggc atcaaattaa gcagaaggcc atcctgacgg atggcctttt
6181 tgcgtttcta caaactctt
```

SEQ ID N° 113

```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
```

Figure 11 (Contd.)

```
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg ataggtgc ctcactgatt aagcattggt aactgtcaga
 961 ccaagtttac tcatatatac tttagattga tttaaaactt cattttaat ttaaaaggat
1021 ctaggtgaag atccttttg ataatctcat gaccaaaatc ccttaacgtg agttttcgtt
1081 ccactgagcg tcagacccg tagaaaagat caaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg ttttctttt caccagtgag acggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
```

Figure 11 (Contd.)

```
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tgcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgtgca ggtgattaca aagacgatga cgataagtaa taaacaggaa acagaagtcc
5281 atatgaaata tcttttacct acggcagccg caggtttgtt gttactgcg cccagccgg
5341 ccatggccgc tagcaccaag ggcccatcgg tcttccccct ggcaccctcc tccaagagca
5401 cctctggggg cacagcggcc ctgggctgcc tggtcaagga ctacttcccc gaaccggtga
5461 cggtgtcgtg gaactcaggc gccctgacca gcggcgtgca caccttcccg gctgtcctac
5521 agtcctcagg actctactcc ctcagcagcg tagtgaccgt gccctccagc agcttgggca
5581 cccagaccta catctgcaac gtgaatcaca agcccagcaa caccaaggtg gacaagaaag
5641 ttgagcccaa atcttgtgac aaaactcaca catgcccacc gtgcccagcg gccgcagaac
5701 aaaaactcat ctcagaagag gatctgaatg gggccgtaca tcaccaccat catcatggga
5761 gctaagcttg gctgttttgg cggatgagag aagattttca gcctgataca gattaaatca
5821 gaacgcagaa gcggtctgat aaaacagaat ttgcctggcg cagtagcgc ggtggtccca
5881 cctgacccca tgccgaactc agaagtgaaa cgccgtagcg ccgatggtag tgtgggtct
5941 ccccatgcga gagtagggaa ctgccaggca tcaaataaaa cgaaaggctc agtcgaaaga
6001 ctgggccttt cgttttatct gttgtttgtc ggtgaacgct ctcctgagta ggacaaatcc
6061 gccgggagcg gatttgaacg ttgcgaagca acgcccgga ggacctggc gggcaggacg
6121 cccgccataa actgccaggc atcaaattaa gcagaaggcc atcctgacgg atggccttt
6181 tgcgtttcta caaactctt
``` pCKCH1γ1

SEQ ID N° 100
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgtttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
```

Figure 11 (Contd.)

```
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atccttttg ataatctcat gaccaaaatc ccttaacgtg agttttcgtt
1081 ccactgagcg tcagaccccg tagaaaagat caaaggatct tcttgagatc cttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct tgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc cggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact acattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccgactcgg
3661 taatggcgcg cattcgcgcc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
```

Figure 11 (Contd.)

```
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttccccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatgtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct caaccgcgg
5221 agagtgttaa taaacaggaa acagaagtcc atatgaaata cctattgcct acggcagccg
5281 ctggattgtt attactcgcg gcccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca cacctttccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgttaa gcttggctgt
5641 tttggcggat gagagaagat tttcagcctg atacagatta aatcagaacg cagaagcggt
5701 ctgataaaac agaatttgcc tggcggcagt agcgcggtgg tcccacctga ccccatgccg
5761 aactcagaag tgaaacgccg tagcgccgat ggtagtgtgg ggtctcccca tgcgagagta
5821 gggaactgcc aggcatcaaa taaaacgaaa ggctcagtcg aaagactggg cctttcgttt
5881 tatctgttgt ttgtcggtga acgctctcct gagtaggaca aatccgccgg gagcggattt
5941 gaacgttgcg aagcaacggc ccggaggacc ctggcgggca ggacgcccgc cataaactgc
6001 caggcatcaa attaagcaga aggccatcct gacggatggc ctttttgcgt ttctacaaac
6061 tctt
```

SEQ ID N° 114
```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc tttttccgaa ggtaactggc ttcagcagag cgcagatacc
```

Figure 11 (Contd.)

```
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttcttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 ctttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
```

Figure 11 (Contd.)

```
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata tcttttacct acggcagccg
5281 caggtttgtt gttactcgcg gcccagccgg ccatggccgc tagcaccaag ggcccatcgg
5341 tcttccccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttcccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgttaa gcttggctgt
5641 tttggcggat gagagaagat tttcagcctg atacagatta aatcagaacg cagaagcggt
5701 ctgataaaac agaatttgcc tggcggcagt agcgcggtgg tcccacctga ccccatgccg
5761 aactcagaag tgaaacgccg tagcgccgat ggtagtgtgg ggtctcccca tgcgagagta
5821 gggaactgcc aggcatcaaa taaaacgaaa ggctcagtcg aaagactggg cctttcgttt
5881 tatctgttgt ttgtcggtga acgctctcct gagtaggaca aatccgccgg agcggattt
5941 gaacgttgcg aagcaacggc ccggaggacc ctggcgggca ggacgcccgc cataaactgc
6001 caggcatcaa attaagcaga aggccatcct gacggatggc cttttttgcgt ttctacaaac
6061 tctt
``` pcKcH1Hγ1

SEQ ID N° 101

```
   1 ttgtttattt ttctaaatac attcaaatat gtatccgctc atgagacaat aaccctgata
  61 aatgcttcaa taatattgaa aaaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgac aaggagctaa ccgcttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaggat
1021 ctaggtgaag atccttttg ataatctcat gaccaaaatc ccttaacgtg agttttcgtt
1081 ccactgagcg tcagaccccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatgaa aaacgccagc aacgcggcct ttttacggtt
1741 cctggccttt tgctggcctt ttgctcacat gttctttcct gcgttatccc ctgattctgt
```

Figure 11 (Contd.)

```
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctgaacgtt gtgagggtaa
2461 acaactggcg gtatggatgc ggcgggacca gagaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttttccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc cctcaggta ccgtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata cctattgcct acggcagccg
```

Figure 11 (Contd.)

```
5281 ctggattgtt attactcgcg gcccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttcccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgtgac aaaactcaca
5641 catgcccacc gtgcccataa gcttggctgt tttggcggat gagagaagat tttcagcctg
5701 atacagatta aatcagaacg cagaagcggt ctgataaaac agaatttgcc tggcggcagt
5761 agcgcggtgg tcccacctga ccccatgccg aactcagaag tgaaacgccg tagcgccgat
5821 ggtagtgtgg ggtctcccca tgcgagagta gggaactgcc aggcatcaaa taaaacgaaa
5881 ggctcagtcg aaagactggg cctttcgttt tatctgttgt ttgtcggtga acgctctcct
5941 gagtaggaca aatccgccgg gagcggattt gaacgttgcg aagcaacggc ccggaggacc
6001 ctggcgggca ggacgccgc cataaactgc caggcatcaa attaagcaga aggccatcct
6061 gacgatggc ctttttgcgt ttctacaaac tctt SEQ ID N° 115
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgctttttt
 541 gcacaacatg ggggatcatg taactcgcct tgatcgttgg gaaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacggga gtcaggcaa ctatgatga
 901 acgaaataga cagatcgctg agataggtgc ctcactgatt aagcattggt aactgtcaga
 961 ccaagtttac tcatatatac tttagattga tttaaaactt cattttttaat ttaaaaggat
1021 ctaggtgaag atcctttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaa accaccgcta ccagcggtgg tttgtttgcc
1201 ggatcaagag ctaccaactc tttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacgggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga gcgattcac
2221 agatgtctgc ctgttcatcc gcgtccagct cgttgagttt ctccagaagc gttaatgtct
2281 ggcttctgat aaagcgggcc atgttaaggg cggtttttc ctgtttggtc acttgatgcc
2341 tccgtgtaag ggggaatttc tgttcatggg gtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
```

Figure 11 (Contd.)

```
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat cgccacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccaggtggt ttttcttttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata tctttttacct acggcagccg
5281 caggtttgtt gttactcgcg gcccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttcccg gctgtcctac agtcctcagg actctactcc ctcagcagcg
5521 tagtgaccgt gccctccagc agcttgggca cccagaccta catctgcaac gtgaatcaca
5581 agcccagcaa caccaaggtg gacaagaaag ttgagcccaa atcttgtgac aaaactcaca
5641 catgcccacc gtgcccataa gcttggctgt tttgggggat gagagaagat tttcagcctg
5701 atacagatta aatcagaacg cagaagcggt ctgataaaac agaatttgcc tggcggcagt
5761 agcgcggtgg tcccacctga ccccatgccg aactcagaag tgaaacgccg tagcgccgat
5821 ggtagtgtgg ggtctcccca tgcgagagta gggaactgcc aggcatcaaa taaaacgaaa
5881 ggctcagtcg aaagactggg cctttcgttt tatctgttgt ttgtcggtga acgctctcct
5941 gagtaggaca aatccgccgg gagcggattt gaacgttgcg aagcaacggc ccggaggacc
```

Figure 11 (Contd.)

```
6001 ctggcgggca ggacgcccgc cataaactgc caggcatcaa attaagcaga aggccatcct
6061 gacggatggc cttttgcgt ttctacaaac tctt
``` pMabγ1*

SEQ ID N° 102
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aaggagctaa ccgcttttt
 541 gcacaacatg ggggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat ttaaaaggat
1021 ctaggtgaag atcctttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca ggggggcgga gcctatggaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga gagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg tatggatgc ggcgggacca gagaaaaatc actcagggtc aatgccagcg
2521 cttcgttaat acagatgtag tgttccaca gggtagccag cagcatcctg cgatgcagat
2581 ccggaacata atggtgcagg cgctgactt ccgcgtttcc agactttacg aaacacggaa
2641 accgaagacc attcatgttg ttgctcaggt cgcagacgtt ttgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc aacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
```

Figure 11 (Contd.)

```
3061 ccgttccatg tgctcgccga ggcggcataa atcgccgtga cgatcagcgg tccagtgatc
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcggggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaggtt ttgcgccatt
4501 cgatggtgtc aacgtaaatg catgccgctt cgccttcgcg gcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgtttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcaggta ccgtggctgc
4921 accatctgtc ttcatcttcc cgccatctga tgagcagttg aaatctggaa ctgcctctgt
4981 tgtgtgcctg ctgaataact tctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata cctattgcct acggcagccg
5281 ctggattgtt attactcgcg gcccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttcccg gctgtcctac agtcctcagg actctactcc ctcagcagcg
5521 tggtgaccgt gccctccagc agcttgggca cccagaccta catctgcaac gtgaatcaca
5581 agcccagcaa caccaaggtg gacaagaaag ttgagcccaa atcttgtgac aaaactcaca
5641 catgcccacc gtgcccagca cctgaactcc tggggggacc gtcagtcttc ctcttccccc
5701 caaacccaa ggacaccctc atgatctccc ggacccctga ggtcacatgc gtggtggtgg
5761 acgtgagcca cgaagaccct gaggtcaagt tcaactggta cgtggacggc gtggaggtgc
5821 ataatgccaa gacaaagccg cgggaggagc agtacaacag cacgtaccgg gtggtcagcg
5881 tcctcaccgt cctgcaccag gactggctga atggcaagga gtacaagtgc aaggtctcca
5941 acaaagccct cccagccccc atcgagaaaa ccatctccaa agccaaaggg cagccccgag
6001 aaccacaggt gtacaccctg cccccatccc gggatgagct gaccaagaac caggtcagcc
6061 tgacctgcct ggtcaaaggc ttctatccca gcgacatcgc cgtggagtgg gagagcaatg
6121 ggcagccgga gaacaactac aagaccacgc ctcccgtgct ggactccgac ggctccttct
6181 tcctctacag caagctcacc gtggacaaga gcaggtggca gcagggaac gtcttctcat
6241 gctccgtgat gcatgaggct ctgcacaacc actacacgca gaagagcctc tccctgtctc
6301 cgggtaaata gcttggctg ttttggcgga tgagagaaga ttttcagcct gatacagatt
6361 aaatcagaac gcagaagcgg tctgataaaa cagaatttgc ctggcggcag tagcgcggtg
6421 gtcccacctg acccatgcc gaactcagaa gtgaaacgcc gtagcgccga tggtagtgtg
6481 gggtctcccc atgcgagagt agggaactgc caggcatcaa ataaaacgaa aggctcagtc
```

Figure 11 (Contd.)

```
6541 gaaagactgg gcctttcgtt ttatctgttg tttgtcggtg aacgctctcc tgagtaggac
6601 aaatccgccg ggagcggatt tgaacgttgc gaagcaacgg cccggaggac cctggcgggc
6661 aggacgcccg ccataaactg ccaggcatca aattaagcag aaggccatcc tgacggatgg
6721 ccttttttgcg tttctacaaa ctctt
```

SEQ ID N° 116
```
   1 ttgtttattt ttctaaatac attcaaatat gtatccgctc atgagacaat aaccctgata
  61 aatgcttcaa taatattgaa aaggaagag tatgagtatt caacatttcc gtgtcgccct
 121 tattcccttt tttgcggcat tttgccttcc tgttttttgct cacccagaaa cgctggtgaa
 181 agtaaaagat gctgaagatc agttgggtgc acgagtgggt tacatcgaac tggatctcaa
 241 cagcggtaag atccttgaga gttttcgccc cgaagaacgt tttccaatga tgagcacttt
 301 taaagttctg ctatgtggcg cggtattatc ccgtgttgac gccgggcaag agcaactcgg
 361 tcgccgcata cactattctc agaatgactt ggttgagtac tcaccagtca cagaaaagca
 421 tcttacggat ggcatgacag taagagaatt atgcagtgct gccataacca tgagtgataa
 481 cactgcggcc aacttacttc tgacaacgat cggaggaccg aagagctaa ccgcttttt
 541 gcacaacatg ggggatcatg taactcgcct tgatcgttgg aaccggagc tgaatgaagc
 601 cataccaaac gacgagcgtg acaccacgat gcctgtagca atggcaacaa cgttgcgcaa
 661 actattaact ggcgaactac ttactctagc ttcccggcaa caattaatag actggatgga
 721 ggcggataaa gttgcaggac cacttctgcg ctcggccctt ccggctggct ggtttattgc
 781 tgataaatct ggagccggtg agcgtgggtc tcgcggtatc attgcagcac tggggccaga
 841 tggtaagccc tcccgtatcg tagttatcta cacgacgggg agtcaggcaa ctatggatga
 901 acgaaataga cagatcgctg agataggtgc ctcactgatt aagcattggt aactgtcaga
 961 ccaagtttac tcatatatac tttagattga tttaaaactt catttttaat taaaaggat
1021 ctaggtgaag atcctttttg ataatctcat gaccaaaatc ccttaacgtg agttttcgtt
1081 ccactgagcg tcagacccg tagaaaagat caaaggatct tcttgagatc ctttttttct
1141 gcgcgtaatc tgctgcttgc aaacaaaaaa accaccgcta ccagcggtgg tttgtttgcc
1201 ggatcaagag ctaccaactc ttttccgaa ggtaactggc ttcagcagag cgcagatacc
1261 aaatactgtc cttctagtgt agccgtagtt aggccaccac ttcaagaact ctgtagcacc
1321 gcctacatac ctcgctctgc taatcctgtt accagtggct gctgccagtg gcgataagtc
1381 gtgtcttacc gggttggact caagacgata gttaccggat aaggcgcagc ggtcgggctg
1441 aacggggggt tcgtgcacac agcccagctt ggagcgaacg acctacaccg aactgagata
1501 cctacagcgt gagcattgag aaagcgccac gcttcccgaa gggagaaagg cggacaggta
1561 tccggtaagc ggcagggtcg gaacaggaga gcgcacgagg gagcttccag ggggaaacgc
1621 ctggtatctt tatagtcctg tcgggtttcg ccacctctga cttgagcgtc gatttttgtg
1681 atgctcgtca gggggcgga gcctatgaa aaacgccagc aacgcggcct ttttacggtt
1741 cctggccttt tgctggcctt ttgctcacat gttctttcct gcgttatccc ctgattctgt
1801 ggataaccgt attaccgcct ttgagtgagc tgataccgct cgccgcagcc gaacgaccga
1861 gcgcagcgag tcagtgagcg aggaagcgga agagcgcctg atgcggtatt ttctccttac
1921 gcatctgtgc ggtatttcac accgcatata tggtgcactc tcagtacaat ctgctctgat
1981 gccgcatagt taagccagta tacactccgc tatcgctacg tgactgggtc atggctgcgc
2041 cccgacaccc gccaacaccc gctgacgcgc cctgacgggc ttgtctgctc ccggcatccg
2101 cttacagaca agctgtgacc gtctccggga gctgcatgtg tcagaggttt tcaccgtcat
2161 caccgaaacg cgcgaggcag ctgcggtaaa gctcatcagc gtggtcgtga agcgattcac
2221 agatgtctgc ctgttcatcc gcgtccagct cgttgagttt ctccagaagc gttaatgtct
2281 ggcttctgat aaagcgggcc atgttaaggg cggttttttc ctgtttggtc acttgatgcc
2341 tccgtgtaag ggggaatttc tgttcatggg ggtaatgata ccgatgaaac gagagaggat
2401 gctcacgata cgggttactg atgatgaaca tgcccggtta ctggaacgtt gtgagggtaa
2461 acaactggcg gtatggatgc ggcgggacca gagaaaaatc actcagggtc aatgccagcg
2521 cttcgttaat acagatgtag gtgttccaca gggtagccag cagcatcctg cgatgcagat
2581 ccggaacata atggtgcagg gcgctgactt ccgcgtttcc agactttacg aaacacggaa
2641 accgaagacc attcatgttg ttgctcaggt cgcagacgtt tgcagcagc agtcgcttca
2701 cgttcgctcg cgtatcggtg attcattctg ctaaccagta aggcaacccc gccagcctag
2761 ccgggtcctc aacgacagga gcacgatcat gcgcacccgt ggccaggacc caacgctgcc
2821 cgagatgcgc cgcgtgcggc tgctggagat ggcggacgcg atggatatgt tctgccaagg
2881 gttggtttgc gcattcacag ttctccgcaa gaattgattg gctccaattc ttggagtggt
2941 gaatccgtta gcgaggtgcc gccggcttcc attcaggtcg aggtggcccg gctccatgca
3001 ccgcgacgca acgcggggag gcagacaagg tatagggcgg cgcctacaat ccatgccaac
3061 ccgttccatg tgctcgccga ggcggcataa atcgccgtga cgatcagcgg tccagtgatc
```

Figure 11 (Contd.)

```
3121 gaagttaggc tggtaagagc cgcgagcgat ccttgaagct gtccctgatg gtcgtcatct
3181 acctgcctgg acagcatggc ctgcaacgcg ggcatcccga tgccgccgga agcgagaaga
3241 atcataatgg ggaaggccat ccagcctcgc gtcgcgaacg ccagcaagac gtagcccagc
3301 gcgtcggcca gcttgcaatt cgcgctaact tacattaatt gcgttgcgct cactgcccgc
3361 tttccagtcg ggaaacctgt cgtgccagct gcattaatga atcggccaac gcgcgggag
3421 aggcggtttg cgtattgggc gccagggtgg ttttctttt caccagtgag acgggcaaca
3481 gctgattgcc cttcaccgcc tggccctgag agagttgcag caagcggtcc acgctggttt
3541 gccccagcag gcgaaaatcc tgtttgatgg tggttgacgg cgggatataa catgagctgt
3601 cttcggtatc gtcgtatccc actaccgaga tatccgcacc aacgcgcagc ccggactcgg
3661 taatggcgcg cattgcgccc agcgccatct gatcgttggc aaccagcatc gcagtgggaa
3721 cgatgccctc attcagcatt tgcatggttt gttgaaaacc ggacatggca ctccagtcgc
3781 cttcccgttc cgctatcggc tgaatttgat tgcgagtgag atatttatgc cagccagcca
3841 gacgcagacg cgccgagaca gaacttaatg gtcccgctaa cagcgcgatt tgctgatgac
3901 ccaatgcgac cagatgctcc acgcccagtc gcgtaccgtc ttcatgggag aaaataatac
3961 tgttgatggg tgtctggtca gagacatcaa gaaataacgc cggaacatta gtgcaggcag
4021 cttccacagc aatggcatcc tggtcatcca gcggatagtt aatgatcagc ccactgacgc
4081 gttgcgcgag aagattgtgc accgccgctt tacaggcttc gacgccgctt cgttctacca
4141 tcgacaccac cacgctggca cccagttgat cggcgcgaga tttaatcgcc gcgacaattt
4201 gcgacggcgc gtgcagggcc agactggagg tggcaacgcc aatcagcaac gactgtttgc
4261 ccgccagttg ttgtgccacg cggttgggaa tgtaattcag ctccgccatc gccgcttcca
4321 cttttcccg cgttttcgca gaacgtggc tggcctggtt caccacgcgg gaaacggtct
4381 gataagagac accggcatac tctgcgacat cgtataacgt tactggtttc acattcacca
4441 ccctgaattg actctcttcc gggcgctatc atgccatacc gcgaaaggtt ttgcgccatt
4501 cgatggtgtc aacgtaaatg catgccgctt cgccttcgcg cgcgaattgc aagctgatcc
4561 ggagcttatc gactgcacgg tgcaccaatg cttctggcgt caggcagcca tcggaagctg
4621 tggtatggct gtgcaggtcg taaatcactg cataattcgt gtcgctcaag gcgcactccc
4681 gttctggata atgttttttg cgccgacatc ataacggttc tggcaaatat tctgaaatga
4741 gctgttgaca attaatcatc ggctcgtata atgtgtggaa ttgtgagcgg ataacaattt
4801 cacacaggaa acagaattcc atatgaaata cctattacca acagcagcag ctgggttatt
4861 attgctcgct gcgcagccgg ccatggccca ggtcaccgtc tcctcacgta cggtggctgc
4921 accatctgtc ttcatcttcc cgccatctga tgagcagttg aaatctggaa ctgcctctgt
4981 tgtgtgcctg ctgaataact ctatcccag agaggccaaa gtacagtgga aggtggataa
5041 cgccctccaa tcgggtaact cccaggagag tgtcacagag caggacagca aggacagcac
5101 ctacagcctc agcagcaccc tgacgctgag caaagcagac tacgagaaac acaaagtcta
5161 cgcctgcgaa gtcacccatc agggcctgag ctcgccggtg acaaagagct tcaaccgcgg
5221 agagtgttaa taaacaggaa acagaagtcc atatgaaata tctttacct acggcagccg
5281 caggtttgtt gttactgcgc gcccagccgg ccatggccgc tagcaccaag ggcccatcgg
5341 tcttcccct ggcaccctcc tccaagagca cctctggggg cacagcggcc ctgggctgcc
5401 tggtcaagga ctacttcccc gaaccggtga cggtgtcgtg gaactcaggc gccctgacca
5461 gcggcgtgca caccttcccg gctgtcctac agtcctcagg actctactcc ctcagcagcg
5521 tggtgaccgt gccctccagc agcttgggca cccagaccta catctgcaac gtgaatcaca
5581 agcccagcaa caccaaggtg gacaagaaag ttgagcccaa atcttgtgac aaaactcaca
5641 catgcccacc gtgcccagca cctgaactcc tggggggacc gtcagtcttc ctcttccccc
5701 caaaacccaa ggacaccctc atgatctccc ggacccctga ggtcacatgc gtggtggtgg
5761 acgtgagcca cgaagaccct gaggtcaagt tcaactggta cgtggacggc gtggaggtgc
5821 ataatgccaa gacaaagccg cgggaggagc agtacaacag cacgtaccgg gtggtcagcg
5881 tcctcaccgt cctgcaccag gactggctga atggcaagga gtacaagtgc aaggtctcca
5941 acaaagccct cccagccccc atcgagaaaa ccatctccaa agccaagggg cagccccgag
6001 aaccacaggt gtacaccctg cccccatccc gggatgagct gaccaagaac caggtcagcc
6061 tgacctgcct ggtcaaaggc ttctatccca gcgacatcgc cgtggagtgg gagagcaatg
6121 ggcagccgga gaacaactac aagaccacgc ctcccgtgct ggactccgac ggctccttct
6181 tcctctacag caagctcacc gtggacaaga gcaggtggca gcagggaac gtcttctcat
6241 gctccgtgat gcatgaggct ctgcacaacc actacacgca gaagagcctc tccctgtctc
6301 cgggtaaata gcttggctg ttttggcgga tgagagaaga ttttcagcct gatacagatt
6361 aaatcagaac gcagaagcgg tctgataaaa cagaatttgc ctggcggcag tagcgcggtg
6421 gtcccacctg acccatgcc gaactcagaa gtgaaacgcc gtagcgccga tggtagtgtg
6481 gggtctcccc atgcgagagt agggaactgc caggcatcaa ataaaacgaa aggctcagtc
6541 gaaagactgg gcctttcgtt ttatctgttg tttgtcggtg aacgctctcc tgagtaggac
```

Figure 11 (Contd.)

```
6601 aaatccgccg ggagcggatt tgaacgttgc gaagcaacgg cccggaggac cctggcgggc
6661 aggacgcccg ccataaactg ccaggcatca aattaagcag aaggccatcc tgacggatgg
6721 cctttttgcg tttctacaaa ctctt
```

Type (HCH2CH3)2:
VHH-HCH2CH3
(cloning of VHH in the plasmids
pHC2CH3γ1-TAG or pHCH2CH3γ1)
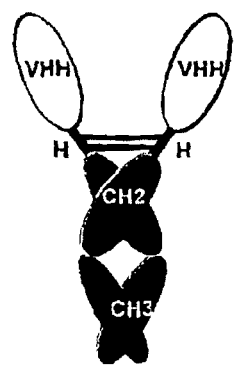
| Combinations: | | |
|---|---|---|
| VHH | A | A |
| Formats: | | |
| A2 = monospecific, bivalent | | |
Type mAb*
VHH1-CL/VHH2-CH1HCH2CH3 γ1
(cloning of VHH in the plasmid
pCkCH1CH2CH3γ1)
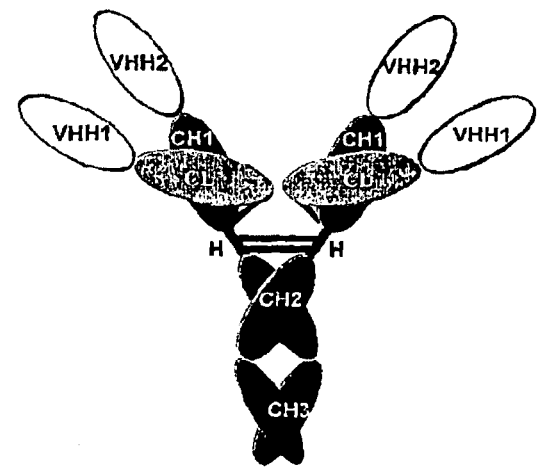
| Combinations: | | |
|---|---|---|
| VHH1 | Ax2 | Ax2 |
| VHH2 | Ax2 | Bx2 |
| Formats: | | |
| A4 = monospecific, tetravalent
A2B2 = bispecific or biepitopic, bivalent | | |
Figure 12B

PRODUCTION OF ANTIBODY FORMATS AND IMMUNOLOGICAL APPLICATIONS OF SAID FORMATS

CROSS-REFERENCE TO RELATED APPLICATIONS

This application is a continuation of U.S. patent application Ser. No. 11/818,218, filed Jun. 13, 2007, which is a continuation of PCT Serial No. PCT/FR2005/003151, filed Dec. 15, 2005, which claims priority to French Application Serial No. 04/13433, filed Dec. 16, 2004. The entire text of the aforementioned applications is incorporated herein by reference in its entirety.

BACKGROUND AND SUMMARY

The invention relates to the production of antibody formats and their immunological applications, more specifically in immunotherapy and immunodiagnostic. The inventors call to mind that antibody molecules are immunoglobulins (Ig) belonging to 5 classes: IgM, IgG, IgD, IgE and IgA. In general, these molecules comprise a heavy chain (H) and a light chain (L) that is either the kappa chain (κ), or the lambda chain (λ).

Each class of immunoglobulins comprises a specific type of H chain: μ chain for IgM, γ for IgG, δ for IgD, ε for IgE and α for IgA. Each chain is formed by domains, each with an inner disulphide bond. An L chain has two domains and an H chain has 4 domains. The sequence of the domain comprising the amine end of each chain is variable (VH and VL regions), that of other domains is constant (CH1, CH2 and CH3 of the H chain, and CL of the L chain). The variable regions V comprise regions of hypervariable sequences called CDR together determining the complementarity.

In the H chains, the first two domains (VH-CH1) are followed by a hinge region. In an immunoglobulin, the L chain is connected to the H chain by a disulphide bond to form a heterodimer. This heterodimer is connected to the same heterodimer by several disulphide bonds at the hinge region to form the immunoglobulin. By splitting with a protease at the level of the hinge, we obtain two fragments: fragment Fab (antigen binding domain, comprising the VL-CL and VH-CH1 domains) and fragment Fc (effector domain, comprising domains $(CH2-CH3)_2$).

The invention more specifically refers to antibody fragments and different antibody formats created from these fragments, in particular formats of chimerised or humanised, multispecific and/or multivalent antibodies. The "antibody formats" as referred to in the invention correspond to different combinations of domains and regions of the types mentioned above.

By "chimerised antibody", the inventors refer to a VH domain of animal origin fused to constant regions of human immunoglobulin. By "humanized antibody", the inventors refer to a human VH domain on which hypervariable regions (CDRs) are grafted from a VH of animal origin, fused to constant regions of a human Ig.

These antibodies recognise the epitopes of targets corresponding to a given molecule. These epitopes may differ, and belong to different targets or the same target. Thereby "bispecific antibody" refers to a format with two different VH binding two different targets; "biepitopic antibody" refers to a format with two different VH binding two different epitopes on the same target. The "valence" corresponds to the number of times the same VH is found on the fragment considered.

The recognition specificity of antibodies to reach a determined target has been used for the diagnosis and treatment of different diseases and, in particular in oncology, where the target may be an antigen associated with a tumour, a growth factor receptor, an oncogene product or a muted "tumour suppressor" gene, or even a molecule linked to angiogenesis or a molecule also expressed on non-tumoural cells, but absent from progenitor cells (as in the case of CD20).

After over 20 years of experimental work, the immuno-targeting of tumours by monoclonal antibodies is currently developing considerably. Thereby, the results of the different clinical studies have recently demonstrated the therapeutic possibilities of certain antibodies and have led to their approval by the FDA and the granting of a European AMM.

This progression is largely due to the use of so-called "second generation" recombinant antibodies: humanised antibodies, such as Herceptine, an anti-HER2/Neu antibody used in association with chemotherapy in certain breast carcinomas; and chimeric antibodies such as Rituximab, an anti-CD20 antibody used in the treatment of follicular 8-cell lymphomas.

Through gene engineering, it is possible to "graft" the variable or hypervariable regions of mouse antibodies on human Ig molecules. New techniques can now be used to obtain fully human antibodies either by selection of variable human domains expressed on phages (so-called "Phage display" technique), or by using transgenic mice producing human antibodies.

Moreover, the concept of bispecific antibodies has been used to stimulate the immune system and thereby favour the contact between the tumoural target cell and an effector cell. It consists in constructing an antibody endowed with a double specificity. This antibody should be able to bind a molecule produced at the surface of tumoural cells (such as CEA, HER2/Neu, GD2, etc.) and a molecule expressed at the surface of effector cells of the immunity, NK cells, killer T lymphocytes or CTL, polynuclear neutrophils, monocytes and macrophages (such as Fc receptors, etc.). A variant of this strategy consists of constructing an antibody linking a molecule produced at the surface of the tumoural cell and a molecule presenting direct or indirect properties of cytotoxicity (radio-element, toxin, prodrug).

Until now, most of the bispecific antibodies were developed by biochemically coupling 2 fragments of antibodies. However, this technique is rarely developed on an industrial scale. Several bispecific antibodies have been genetically developed, such as bispecific antibodies of the scFv type ("diabodies"). Unfortunately, they remain difficult to produce in *E. coli* in soluble form and they also are not very effective in terms of ADCC.

Within the search for candidate antibodies to generate antibody formats for immunotherapy and in particular to obtain multi-specific antibodies, the inventors directed their work towards specific antibodies, without a light chain, identified in the Camelidae (camel, dromedary, llama) (Hamers-Casterman et al., 1993).

Variable domains of heavy single chain antibodies from Camelidae (VHH), specifically recognising a type of antigen, were selected from immunised animals and were used to develop different formats of chimerised or humanised antibodies that may be produced from plasmid constructions. It turned out that the different formats were compatible to enable the production of any other VHH or humanised VHH, or human VH.

The invention aims at providing antibody formats comprising a part of the totality of VHH or humanised VHH, or human VH domains with properties to recognise the searched for targets and epitopes. It also aims at providing a method for the production of these different constructions. According to another aspect, the invention aims at immunotherapeutic and immunodiagnostic applications of the different formats provided. The invention also relates to antibody formats including a part or the totality of the VHH domains of Camelidae, in particular llamas and/or human VH, fused to constant regions of human antibodies.

According to a first means of achievement of the invention, the antibody formats are of Fab type and are characterised by the association of two identical or different VHH domains or two human VH domains, or two human VH domains on which are grafted the CDRs of the VHH, one of the domains being fused to the constant region Cκ or Cλ of a human immunoglobulin, the other to the constant region CH1 from a human immunoglobulin.

According to a second means of achievement of the invention, the antibody formats are of the Fab' type and are characterised by the association of two identical or different VHH domains or two human VH domains, or two human VH domains on which are grafted the CDRs of the VHH, one of the domains being fused to the constant region Cκ or Cλ of a human immunoglobulin, the other to the constant region CH1 followed by a hinge region H from a human immunoglobulin. These chimerised or humanised antibody formats are of monospecific/bivalent, bispecific/monovalent and biepitopic/monovalent types.

According to a third means of achievement of the invention, the antibody formats are of F(ab')$_2$ type and are characterised by the association of two formats of Fab' type as defined above. These chimerised or humanised antibody formats have a hinge region H, from a human immunoglobulin and allow for monospecific/tetravalent, bispecific/bivalent and biepitopic/bivalent combinations.

According to a fourth means of achievement of the invention, the antibody formats are of F(ab')$_2$ type and are characterised by the association of two Fab' obtained by reduction of formats of the above F(ab')$_2$ type. These chimerised or humanised antibody formats have a hinge region H from a human immunoglobulin and allow for monospecific/tetravalent to tetraspecifique/monovalent or tetraepitopic/monovalent combinations, including all of the intermediate possibilities.

According to a fifth means of achievement of the invention, the antibody formats are of (HCH2CH3)$_2$ type (H, representing the hinge region of a human immunoglobulin, CH2 and CH3, representing the second and third constant domain of a heavy chain from a human Ig, and are characterised by the association of two identical VHH or human VH, or two human VH on which are grafted the hypervariable regions of the VHH, each being fused at the region H-CH2-CH3 of a human Ig. These chimerised or humanised antibody formats allow for monospecific/bivalent combinations.

According to a sixth means of achievement of the invention, the antibody formats are of mAb* type (this type refers to variable domains of origin replaced by all or part of the VHH or humanised VHH or human VH domains, fused to constant regions of human antibodies) and are characterised by the association of two identical or different VHH or two human VH, or two human VH on which are grafter hypervariable regions of VHH, one being fused to the Cκ or human Cλ region, the other to the CH1-H-CH2-CH3 region of a human Ig. These chimerised or humanised antibody formats allow for monospecific/tetravalent and bispecific/bivalent and biepitopic/bivalent combinations.

In these different formats, the immunoglobulin is an IgG, corresponding to a human isoform IgG1, IgG2, IgG3 or IgG4, or a human IgA corresponding to an isoform IgA1, IgA2, or any other human Ig. The VHH may be replaced by human VH or humanised VHH by the grafting of CDRs from VHH on human VH.

In the examples of the above means of achievement of the invention, the VHH correspond to or comprise fragments of Camelidae VHH antibodies, in particular from llamas. In particular, it involves characteristic fragments in that it consists of a part or the totality of anti-carcinoembryonic antigen (anti-CEA in abbreviated form) or anti-receptor FcγRIII (anti-CD16 in abbreviated form) fragments.

The anti-CEA antibody fragments more specifically comprise an amino acid sequence selected from the group consisting of the sequences SEQ ID NO:77, SEQ ID NO:78, SEQ ID NO:79, SEQ ID NO:80 and SEQ ID NO:105. The anti-CD16 antibody fragments in a preferred manner comprise an amino acid sequence selected from the group consisting of the sequences SEQ ID NO:73, SEQ ID NO:74, SEQ ID NO:75, SEQ ID NO:76, SEQ ID NO:103 and SEQ ID NO:104. These fragments form new products and in this way also come into the scope of the invention.

The invention also includes the CDRs of these VHH fragments. The invention also includes a method for the production of chimerised or humanised, multispecific and/or multivalent antibodies for immunotherapy or immunodiagnostics, characterised in that it comprises the use of antibody formats defined above. The invention specifically aims at a method of said formats comprising anti-CEA and anti-CD16 Camelidae VHH, in particular llama VHH. More specifically, it refers to variable domains of anti-CEA and anti-CD16 VHH advantageously produced according to a protocol comprising: the immunisation of Camelidae, in particular of llamas with, as immunogen, a CEA or a CD 16; the purification of B lymphocytes obtained from blood; the construction of a VHH bank; and the isolation of VHH from the bank.

The construction of the bank comprises: the extraction of whole RNA from B lymphocytes; the reverse transcription of RNA to obtain the corresponding cDNA; the amplification by PCR of genes coding for the variable regions of single heavy chain anti-CD 16 and anti-CEA antibodies; and the ligation of VHH DNA fragments obtained by cutting, by enzymes, of DNA amplified with a phagemid. The VHH are isolated from banks by the phage display technique and are purified.

Said variable domains of anti-CEA and anti-CD16 VHH are advantageously produced according to a protocol comprising: the immunisation of Camelidae, in particular llamas with, as immunogen, a CEA or a CD16; the purification of B lymphocytes recovered from blood; the construction of a VHH bank; and the isolation of VHH from the bank.

In an advantageous manner, the construction of the bank comprises: the extraction of whole RNA from B lymphocytes; the reverse transcription of RNA to obtain the corresponding cDNA; the amplification by PCR of genes coding for the variable regions of single heavy chain anti-CD16 and anti-CEA antibodies; and the ligation of fragments of DNA VHH, obtained by cutting by enzymes of amplified DNA with a phagemid. The VHH are isolated from banks by the phage display technique and are purified. The different VHH have been validated in terms of specificity and affinity as illustrated by the examples.

According to the invention, the genes of the selected VHH are then introduced in expression vectors, in particular plasmids, to produce different chimerised multispecific and/ or multivalent (anti-CEA/anti-CD16) antibodies, able to bind with tumoral cells expressing the CEA at their surface and recruit the effector cells from the immune system (monocytes, macrophages, NK, polynuclear neutrophils, et al.) that express CD16.

The invention also refers to expression vectors of the antibody formats defined above. It more specifically refers to expression vectors, in particular plasmids containing, between two unique sites of restriction enzymes, the promoters, the signal sequences, the nucleotide sequences able to code for the VHH domains defined above, and the constant regions of a human Ig, or for human VH domains, the CDRs regions of a VHH, and the constant regions of a human Ig.

The plasmids according to the invention are able to express high quantities of the antibody formats defined above, in soluble forms in bacteria and the regions coding for the antibody domains may easily be transferred to other systems of prokaryotic or even eukaryotic expression.

The invention therefore refers to plasmids pCκCH1γ1-TAG (SEQ ID NO:98 and SEQ ID NO:112) and pCκCH1γ1 (SEQ ID NO:100 and SEQ ID NO:114) allowing for the production of antibodies of Fab type according to a first means of achievement of the antibody formats defined above. These plasmids are more specifically characterised by the insertion of nucleotide sequences coding for the light region Cκ, and the constant heavy region CH1 of an Ig in the plasmid p55Flag/RBS/35cmyc6HisGS (SEQ ID NO:94 and SEQ ID NO:110).

The invention also refers to the plasmids pCκCH1Hγ1-TAG (SEQ ID NO:99 and SEQ ID NO:113) and pCκCH1Hγ1 (SEQ ID NO:101 and SEQ ID NO:115) allowing for the production of antibodies of Fab' and F(ab')$_2$ type according to a second, third and fourth means of achievement of the antibody formats defined above. These plasmids are more specifically characterised by the insertion of nucleotide sequences coding for the heavy chain CH1 and the hinge region (H) of an Ig in p55CκFlag/RBS/35cmyc6HisGS (SEQ ID NO:97 and SEQ ID NO:111).

The invention also refers to the plasmids pHCH2CH3γ1-TAG (SEQ ID NO:95) and pHCH2CH3γ1 (SEQ ID NO:96) allowing for the production of antibodies of (HCH2CH3)$_2$ type according to a fifth means of achievement of the antibody formats defined above. These plasmids are more specifically characterised by the insertion of nucleotide sequences coding for the hinge region (H) and the constant regions CH2 and CH3 of an Ig in p55Flag/RBS/35cmyc6HisGS.

The invention also refers to plasmid pMabγI* (SEQ ID NO:102 and SEQ ID NO:116) allowing for the production of antibodies of mAb* type according to a sixth means of achievement of the invention. This plasmid is more specifically characterised by the insertion of nucleotide sequences coding for the constant heavy region CH1, the hinge region and the constant regions CH2 and CH3 of an Ig in pCκCH1γ1-TAG.

The diagrams of these plasmids are illustrated in FIG. 10B and their nucleotide sequences in FIG. 11. The intermediate plasmids used for the construction of the above plasmids also fall within the scope of the invention. More specifically, it involves plasmids p55PhoA6HisGS/N (SEQ ID NO:89), p55PhoA6HisGS/NAB' (SEQ ID NO:90), p55/MCS1 (SEQ ID NO:92), p55Fiag/RBS/35 (SEQ ID NO:93 and SEQ ID NO:109), p55Flag/RBS/35cmyc6HisGS (SEQ ID NO:94 and SEQ ID NO:110) and p55CKFlag/RBS/35cmyc6HisGS (SEQ ID NO:97 and SEQ ID NO:111) constructed to develop the plasmids defined above. The domains CH1, CH2, CH3, H of an Ig in these plasmids belong to IgG1, IgG2, IgG3 or IgG4, or even IgA, or any other Ig.

The genes coding for the VHH or the human VH are introduced between the unique sites in the different plasmids. These genes may be replaced by genes coding for humanised VHH by grafting of CDRs of VHH on human VH. More generally, the plasmids used according to the invention may be designed to contain nucleotide sequences coding for VHH other than anti-CEA or anti-CD16 VHH, or for other human VH, or for other humanised VHH, able to bind on any molecule.

The invention also refers to plasmid p55PhoA6HisGS/NAB (SEQ ID NO:91) characterised in that it comprises the nucleotide sequences to produce human VH domains fused to alkaline phosphatase according to the diagram in FIGS. 10A and 11.

A method to select the variable human fragments of heavy chains of immunoglobulins (VH) and isolate the best produced and best secreted clones has been developed. Advantageously, these human VH are used as a matrix to graft the CDR from previously selected VHH in order to humanise the variable regions.

The antibody formats defined above are of great interest in immunotherapy and immunodiagnostics. They are able to recognise different molecules or bind two different epitopes on the same molecule, and also provide access to new epitopes that are not recognised by the conventional antibodies. They may also be humanised, which opens the way to advantageous prospects, to have antibodies of low immunogenicity after injection in man. The fact that they are obtained in a soluble form is an additional characteristic of interest for these antibodies. Their applications in immunodiagnostics and immunotherapy are also part of the invention.

BRIEF DESCRIPTION OF DRAWINGS

Other characteristics and advantages of the invention will be provided in the following examples in which reference is made to FIGS. 1 to 13, that respectively represent:

FIG. 1, the amino acid (SEQ ID NOs:73 to 76, 103 and 104) sequences of 4 clones of anti-CD16 VHH and the amino acid (SEQ ID NOs:77 to 80 and 105) sequences of 4 anti-CEA clones isolated according to the invention;

FIG. 2, the nucleotide (SEQ ID NOs:81 to 84, 106 and 107) sequences of 4 clones of anti-CD16 VHH and the nucleotide (SEQ ID NOs:85 to 88 and 108) sequences of 4 anti-CEA clones isolated according to the invention;

FIG. 6, the results of competition tests by ELISA between 2 anti-CD16 VHH and monoclonal anti-CD 16 antibodies;

FIG. 8, the activation results of CD16A by 2 anti-CD16 VHH, and by the bispecific anti-CEA 17/anti-CD16 c21 antibody of type F(ab')$_2$;

FIG. 9, the results of cell lysis by NK cells activated by the bi-specific antibodies;

FIG. 11, the plasmid sequences of the invention;

FIGS. 12A and 12B, antibody formats of type Fab, Fab', F(ab')$_2$, (HCH2CH3)$_2$ and mAb*;

DETAILED DESCRIPTION

Figure 3:
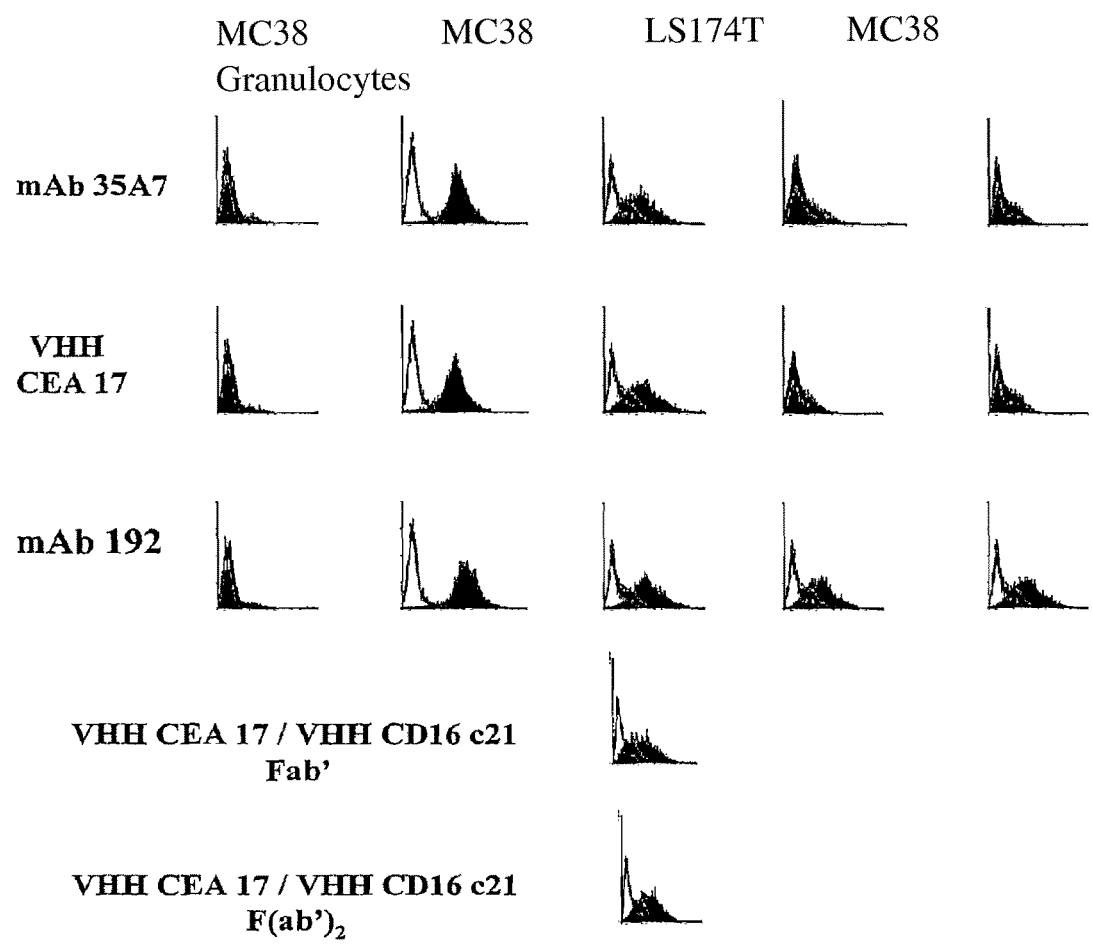
FIG. 3, the results by FACS demonstrating the specificity of 8 VHH analysed, and the corresponding bispecific antibodies.

The following examples are provided by way of illustration and do not limit the extent of the present invention. Other advantages and characteristics of the invention will emerge in the light of the following examples.

Example 1

Immunisation of Llamas, Titration of Serums and Purification of B Lymphocytes

A female llama was immunised with the extracellular region of human recombinant (CD16B) receptor FcγRIIIB (described in: Teillaud C et al., 1993). REF. A male llama was immunised with the extracellular region of the human recombinant carcinoembryonary antigen (CEA) (described in: Terskikh et al., 1993, and in patent: Terskikh A et al., 1993). REF The animals were immunised every month with 500 µg of each immunogen. 100 ml of blood was taken 15 days after each immunisation. For each sample taken, the serums and the purified antibodies (IgG1, 2 and 3) were titrated to detect the presence of antibodies against the different immunogens. The B lymphocytes were then purified on Ficoll gradient (histopaque-1077, Sigma-Aldrich), then washed twice with PBS.

Construction of VHH Banks: Purification of Whole RNA, Reverse Transcription, PCR1, PCR2 and Cloning in Phagemid pHen1.

Construction of VHH Banks:

Purification of Whole RNA:

The whole RNA of the B lymphocytes is extracted according to the method using guanidium isothiocyanate (Chomczynski and Sacchi, 1987) REF. After phenol/chloroform extractions in an acid medium, the whole RNA is precipitated with ethanol. The quality of the RNA and the quantification are evaluated on 1% agarose gel. They are then converted into cDNA by reverse transcription.

Reverse transcription and PCR: Sequences SEQ ID NOs:1 to 9 of the oligonucleotides used:

3' CH2FORTA4
SEQ ID NO. 1: CGCCATCAAGGTACCAGTTGA

3'CH2-2
SEQ ID NO: 2: GGTACGTGCTGTTGAACTGTTCC

3' RC-IgG2
SEQ ID NO: 3: GGAGCTGGGGTCTTCGCTGTGGTGCG

3' RC-IgG3
SEQ ID NO: 4: TGGTTGTGGTTTTGGTGTCTTGGGTT

5'VH1-Sfi
SEQ ID NO: 5:
CATGCCATGACTCGCGGCCCAGCCGGCCATGGCCCAGGTGCAGCTGGTGC

AGTCTGG

5'VH2-Sfi
SEQ ID NO: 6:
CATGCCATGACTCGCGGCCCAGCCGGCCATGGCCCAGGTCACCTTGAAGG

AGTCTGG

5'VH3-Sfi
SEQ ID NO: 7:
CATGCCATGACTCGCGGCCCAGCCGGCCATGGCCGAGGTGCAGCTGGTGG

AGTTGG

5'VH4-Sfi
SEQ ID NO: 8:
CATGCCATGACTCGCGGCCCAGCCGGCCATGGCCCAGGTGCAGCTGCAGG

AGTCGGG

3'VHH-Not
SEQ ID NO: 9:
CACGATTCTGCGGCCGCTGAGGAGAC(AG)GTGACCTGGGTCC

Five µg of whole RNA are hybridised with 1 pmole of oligonucleotide 3' CH2FORTA4 (Arbabi Ghahroudi et al., 1997) REF or CH2-2 specific to the CH2 domain of the heavy single chain IgG of llama reverse transcribed with 150 U of superscript II (BRL) for 30 min at 50° C. The specific oligonucleotides of the hinge regions of IgG 2 and 3, 3' RC-IgG2 and 3' RC-IgG3, may also be used. The single strand cDNA are purified on beads (BioMag® Carboxyl Terminator, Polyscience Inc.) and eluted with 17 µl of 10 mM Tris-acetate pH 7.8.

PCR1 conditions: Four µl of cDNA are amplified by PCR with 0.5 U of Dynazyme Extend DNA polymerase (Finnzymes), 10 pmoles of the same primer 3' CH2FORTA4 or CH2-2 and 10 pmoles of 4 primers 5' VH1-4-Sfi specific to the VH domain of human IgG, in a volume of 50 µl. (94° C., 3 min; 94° C., 1 min; 60° C., 1 min; 72° C., 1 min; 37 cycles then 72° C., 10 min). Three fragments of DNA are amplified: one fragment of about 900 bp coding for the VH-CH1-CH2 domains of IgG1; and two fragments of about 600 bp coding for the VHH-CH2 domain of IgG2 and 3.

PCR2 conditions: The 600 bp fragments are purified on 1% agarose gel ("Qiaquick gel extraction" kit, Qiagen) then amplified by PCR with 1 U of Deep Vent (Biolabs) and 10 pmoles of 4 primers 5'VH 1-4-Sfi specific for the VH domain of human IgG and 10 pmoles of primer 3' VHH-NotI. (94° C., 3 min; 94° C., 45 sec; 65° C., 45 sec; 72° C., 45 sec; 15 cycles, then 94° C., 45 sec; 60° C., 45 sec; 72° C., 45 sec; 15 further cycles, then 72° C., 10 min).

Fragments of about 400 bp coding for the VHH are purified on 1% agarose gel ("Qiaquick gel extraction" kit, Qiagen) assembled and precipitated with ethanol. They are then cut by restriction enzymes NcoI and NotI, or BglI and NotI (Biolabs) to be cloned in phagemid pHen1 (Hoogenboom et al., 1991) REF at sites NcoI and NotI or SfiI and NotI.

Preparation of the vector: Twenty µg of phagemid pHen1 are digested in a 300 µl volume with 50 U of SfiI in the presence of BSA, at 50° C., 16 h; or with 50 U of NcoI in the presence of BSA, at 37° C., 16 h. The linearized phagemid is purified on 0.7% agarose gel ("Qiaquick gel extraction" kit, Qiagen). The eluted DNA is then cut by 50 U of NotI at 37° C. in a volume of 200 µl, 16 h. The enzyme is destroyed by heat for 15 min at 65° C. and the DNA is extracted with phenol/chloroform and precipitated by ethanol. The cut pHen1 is controlled on 0.7% agarose gel, quantified and adjusted to 200 ng/µl.

Preparation of the VHH DNA fragments: Five µg of VHH fragments are cut in a volume of 300 µl with 50 U of BgII and NotI in the presence of BSA, at 37° C., 16 h; or with 50

U of NcoI and NotI in the presence of BSA, at 37° C., 16 h. The enzymes are denatured at 65° C., 15 min; the DNA is then extracted with phenol/chloroform and precipitated with ethanol in the presence of 10 µg of glycogen (Roche). The VHH fragments cut by NcoI and NotI are purified on 1% agarose gel and then controlled on 2% agarose gel, quantified and adjusted at 100 ng/µl.

Ligation: One hundred and fifty ng of pHen1 digested by SfiI and NotI are ligated with 60 ng of VHH fragment digested by BgII and NotI in a volume of 20 µl with 2000 U of T4 DNA ligase (Biolabs) at 16° C., 17 h.

The ligase is inactivated at 65° C., 15 min, and the ligation product is cut by 20 U of XhoI (Biolabs) to eliminate the non-ligated residual vector, 37° C., 4 h. Six ligations are thereby made. The ligation products are then collected in 2 tubes and extracted with phenol/chloroform, precipitated in the presence of 10 µg of glycogen and taken up in 2×18 µl ultrapure $H_2O$. Two µl are used by electroporation.

The VHH bank from the male llama (ref.: 080101) represents $5.4 \times 10^6$ clones and the VHH bank from the female llama (ref.: 010301) $10^6$ clones.

Isolation of the VHH from the Banks by Phage-Display Technology.

Selection of Anti-CEA and Anti-CD16 VHH:

The different VHH are isolated by the phage-display technique.

Production of phage banks: Ten µl of stock from bank 080101 or 010301 (TG1 cells transformed with phagemids) are inoculated in 50 ml of (2TY, 100 µg/ml of ampicillin, 2% glucose) and incubated at 37° C. until the $OD_{600}$ is equal to 0.5. Five ml of culture are then infected with 5 ml of M13KO7 at $10^{13}$ pfu/ml, 30 min, 37° C., without stirring. After centrifugation, the phage sediment is taken up in 25 ml of (2TY, 100 µg/ml of ampicillin, 25 µg/ml kanamycin). The culture is incubated 16 h at 30° C. with stirring. The phages are then precipitated with 1/5 vol of 2.5 M NaCl/20% PEG 6000 and concentrated 25 times in PBS.

VHH selection: Two hundred µl of beads coated with streptavidin (Dynabeads M-280, Dynal) are equilibrated with 1 ml of 2% milk/PBS for 45 min at ambient temperature with stirring on a wheel. $10^{12}$ phages from the above production are also equilibrated with 2% milk/PBS in a final volume of 500 µl for 60 min at ambient temperature with stirring on a wheel.

The beads are compacted with a magnet, re-suspended with 250 µl of 2% milk/PBS and incubated with 200 µl of biotinylated antigen for 30 min at ambient temperature on a wheel. 150, 75 and 25 nM final of biotinyl antigen are used on the $1^{st}$, $2^{nd}$ and $3^{rd}$ rotation, respectively.

To 450 µl of beads/antigen-biotin are added the 500 µl of phages for 3 h at ambient temperature with stirring on a wheel. The beads/antigen-biotin/phages mixture is washed 5 times with 800 µl of 4% milk-PBS and then transferred to a new Eppendorf tube. Five other washings are carried out with 800 µl of PBS-0.1% Tween and the mixture is then transferred to another Eppendorf tube. Finally, 5 washings are carried out with 800 µl of PBS.

The antibody phages bound on the beads/antigen-biotin are re-suspended with 200 µl of PBS and incubated 30 min at 37° C., without stirring, with 1 ml of TG1 rendered competent for the binding of phages to pili (competent cells: from a culture of TG1 in 2YT overnight, a 1/100 dilution is made and 50 ml of 2YT is inoculated at 37° C. while stirring until the $OD_{600}$ is close to 0.5). At each selection, the phages are counted and amplified for another round of selection.

Counting of the selections: 1 µl dilutions are made of TG1 cells transfected with the phages (see above) of $10^{-2}$ to $10^{-5}$ with 2YT. One, 10 and 100 µl of each dilution are spread on a Petri dish (2YT/ampicillin 100 µg/ml/2% glucose). The dishes are incubated for 16 h at 30° C.

Spreading of the selection for the isolation of the colonies: Centrifuge the 5 ml of TG1 transfected for 10 min at 3000 g to concentrate the cells and pick up the sediment with 1 ml of 2YT. Two hundred and fifty µl are used per Petri dish (12 cm×12 cm) (2TY/ampicillin 100 µg/ml/2% glucose) and are incubated for 16 h at 30° C.

The following VHH were isolated using this method: four anti-CEA VHH (clones: 3, 17, 25, 43) and four anti-CD16 VHH (clones: c13, c21, c28, c72) were obtained whose amino acid and nucleotide sequences are indicated in FIGS. 1 and 2.

Recloning, Production and Purification of VHH and Bispecific Antibodies.

VHH Cloning:

The VHH were cloned in plasmid p55PhoA6HisGS/NAB (construction described in section 1.3.6, see FIGS. 10A and 11) between the SfiI and HindIII restriction sites.

PCR Conditions:

Fifty ng of VHH were amplified by PCR with 1 U of Deep Vent (Biolabs), 10 pmoles of primers 5' pJF-VH3-Sfi and 3' cmyc-6His/HindIII in a final volume of 50 µl. (94° C., 3 min; 94° C., 45 sec; 52° C., 45 sec; 72° C., 45 sec; 30 cycles then, 72° C., 5 min).

The following oligonucleotide sequences SEQ ID NO: 10 and SEQ ID NO: 11 are used:

```
5' pJF-VH3-Sfi
SEQ ID NO: 10:
CTTTACTATTCTCACGGCCATGGCGGCCGAGGTGCAGCTGGTGG

3'cmyc-6His/HindIII
SEQ ID NO: 11:
CCGCGCGCGCCAAGACCCAAGCTTGGGCTA(GA)TG(GA)TG(GA)

TG(GA)TG(GA)TG(GA)TGTGCGGCCCCATTCAGATC
```

The PCR products are purified on 1% agarose gel ("Qiaquick gel extraction" kit, Qiagen) and cut with 20 U of BgII and 20 U of HindIII (Biolabs) 16 h at 37° C. Ten µg of p55PhoA/NAB are first cut with 50 U of SfiI 16 h at 50° C., then with 20 U of HindIII 12 h at 37° C. The digestion products (vector and PCR fragments) are precipitated in ethanol. The DNA are re-suspended in 20 µl of $H_2O$ and quantified on 90.7% agarose gel.

The ligation is carried out with 200 U of T4 DNA ligase (50 ng of p55PhoA/NAB cut by SfiI and HindIII and 10 ng of PCR fragment cut by BgII and HindIII in a volume of 20 µl, 16 h at 16° C. After the inactivation of the T4 DNA ligase 15 min at 65° C., the non-recombinant vector is eliminated by enzyme digestion with 10 U of XhoI, 2 h at 37° C. After transformation of the ligation and analysis of several recombinant colonies, the VHH of interest are produced in *E. coli*.

Production of VHH:

An isolated colony is inoculated in 3 ml of 2YT/ampicillin 100 µg/ml/2% glucose and incubated at 37° C. with stirring. Fifty ml of 2YT/ampicillin 100 µg/ml/2% glucose are then seeded with a dilution of the above culture and incubated for 16 h at 30° C. with stirring. Four hundred ml of 2YT/ampicillin 100 µg/ml are inoculated with the equivalent of 0.1 units $OD_{600}$, and incubated at 30° C. with stirring, until the $OD_{600}$ is 0.5 to 0.7. The culture is then induced with 400 µl of IPTG (isopropyl-β-D-thiogalactopyranoside) 0.1 mM final and cultivated at 30° C. for 16 h.

Production of Bispecific Antibodies:

An isolated colony, derived from a transformation of plasmids carried out in the E. coli strain DH5a, is inoculated in 3 ml of 2YT/ampicillin 100 µg/ml/2% glucose and incubated at 30° C. with stirring. Fifty ml of LB/ampicillin 100 µg/ml/2% glucose are then seeded with a dilution of the previous culture and incubated for 16 h at 30° C. with stirring. Four hundred ml of LB/ampicillin 100 µg/ml are inoculated with the equivalent of 0.1 units $OD_{600}$, and incubated at 30° C. with stirring for 2.5 h, then the culture is incubated at 20° C. with stirring, until the $OD_{600}$ is 0.5 to 0.7. The culture is then induced with 400 µl of IPTG (isopropyl-β-D-thiogalactopyranoside) 0.1 mM final, cultivated at 20° C. for 72 h.

Extraction of the Soluble Fraction of the Periplasma:

The cultures used to produce the VHH or the bispecific antibodies are centrifuged at 4200 g, 4° C., 40 min. The sediment is taken up in 4 ml of glacial TES (0.2 M Tris-HCl pH 8.0; 0.5 mM EDTA; 0.5 M sucrose). 160 µl of lysozyme (10 mg/ml in TES, freshly prepared) is then added and then 24 ml of cold TES diluted to 1/2 in $H_2O$. The mixture is incubated for 30 min in ice.

After centrifugation at 4200 g, 4° C., 40 min, the supernatant is recovered (corresponding to the periplasmic fraction) and 150 µl of DNAse (10 mg/ml) and 5 mM final of $MgCl_2$ are added, 30 min at ambient temperature. The solution is dialysed for 16 h against the equilibrium buffer (50 mM sodium acetate, 0.1M NaCl pH 7.0).

Purification of the VHH:

The column (BD TALON™ Metal affinity, BD Biosciences Clontech) is equilibrated with the equilibration buffer (50 mM sodium acetate, 0.1M NaCl pH 7.0). The periplasmic fraction is deposited on the column. After washing the column with 5 volumes of equilibration buffer, the VHH is eluted by pH gradient or imidazole (gradient between the equilibration buffer pH 7.0 and the 50 mM sodium acetate solution pH 5.0 or the 200 mM imidazole solution). Each fraction is controlled on a SDS/PAGE gel (15% acrylamide) after colouration with Coomassie blue. The fractions of interest are assembled and dialysed against PBS. The VHH is concentrated on membrane (Amicon Ultra 5000MWCO, Millipore) and assayed with Lowry's colorimetric method using the Biorad Protein Assay kit.

Purification of the Bispecific Antibodies:

The bispecific antibodies are purified from the soluble fraction of the periplasma (refer to extraction of the soluble fraction of the periplasma) in two steps. First on a BD TALON column (refer to VHH purification) and then on a protein G (HiTrap protein G 5 ml, Amersham biosciences).

The "Hi Trap protein G" column is equilibrated in PBS (NaCl 137 mM, KCl 2.67 mM, $Na_2HPO_4$ 1.2 mM, $KH_2PO_4$ 1.76 mM pH 7.4). The proteins eluted on the BD TALON column and dialysed on PBS are deposited on the protein G. After washing the column with 5 volumes of PBS, the bispecific antibody is eluted with 0.1 M glycine pH 2.7 then buffered with 1 M hepes pH 8. After control on SDS/PAGE gel (10% acrylamide), the bispecific antibody is dialysed in 0.1×PBS, frozen at −80° C. and lyophilised to be concentrated ten times. Finally, the $F(ab')_2$ is separated from the Fab' on a Tricorn Superdex 200 10/300 GL column (Amersham Biosciences) equilibrated in PBS.

Functional Characterisation of the VHH and Bispecific Antibodies by ELISA, Biacore, Immunofluorescence (Flow Cytometry, FACS) and by Activation Tests of CD16.

Characterisation of Anti-CEA and Anti-CD16 Antibodies by ELISA:

ELISA of phages-VHH: Five µg/ml of biotinylated antigen (CEA or CD16) are bound on a streptavidin plate (BioBind Assembly Streptavidin Coated, ThermoLabsystems) previously saturated with 2% milk-PBS. $5\times10^{10}$ phages-antibodies are put in contact with the antigen. The antigen/antibody binding is detected by an ELISA comprising a monoclonal antibody directed against protein P8 of the phage (HRP/anti-M13 monoclonal conjugate, Pharmacia). The addition of the substrate, 10 mg ABTS (2,2'-azino bis (3-ethylbenzo-thiazoline-6-sulphonic acid, diammonium salt)) to 20 ml of detection buffer (18 ml PBS, 1 ml 1 M citric acid, 1 ml 1 M sodium citrate, 10 ml 30% $H_2O_2$), are used to read the reaction at 405 nm (Tecan).

ELISA of the VHH:

Five µg/ml of biotinylated antibody are binded on a streptavidin plate (BioBind Assembly Streptavidin Coated, ThermoLabsystems) previously saturated in 2% milk-PBS. Each VHH (range from 0.001 µg/ml to 1 µg/ml) is bound to the adsorbed antigen in the microwells. The binding is detected with a monoclonal antibody directed against the c-myc label (Santa Cruz Biotechnology, Inc) diluted to 1/1000 and a goat polyclonal antibody directed against the IgG of mice coupled with peroxidase diluted to 1/5000 (ref 55556, ICN) in the presence of ABTS (2,2'-Azino-di-(3-ethylbenzthiazoline sulphonate)diammonium salt, Roche).

ELISA of the Bispecific Antibodies:

Ten µg/ml of antigen (rhCD16 or rhCEA) are passively coated on a MaxiSorp plate (Nunc). After saturation of the plate in PBS/4% milk, the bispecific antibody ($F(ab')_2$, Fab', Fab) (range from 800 to 0.4 nM) is bound to the antigen adsorbed in the microwells. The binding is detected:

with a monoclonal antibody directed against the Flag tag (anti-Flag M2 mAb, Sigma) diluted to 1/5000 and a goat monoclonal antibody directed against mouse IgG coupled with alkaline phosphatase diluted to 1/5000 (ref 115-055-003, Jackson Immunoresearch) in the presence of DNPP (disodium 4-nitrophenyl phosphate hexahydrate); or with a monoclonal antibody directed against the c-myc tag (Santa Cruz Biotechnology) diluted to 1/500 and a goat polyclonal antibody directed against mouse IgG coupled with alkaline phosphatase diluted to 1/5000 (ref 115-055-003, Jackson Immunoresearch) in the presence of DNPP; or with a goat polyclonal antibody directed against the light human kappa chain coupled with alkaline phosphatase diluted to 1/500 (ref 2060-04, SouthernBiotech) in the presence of DNPP.

Demonstration of the accessibility of VHH CEA 17 when the VHH CD16 c21 is bound to rhCD16 adsorbed in the microwells with biotinylated rhCEA and streptavidin coupled with alkaline phosphatase diluted to 1/500 (DAKO, cat D0396).

Affinity Constants for the Anti-CEA and Anti-CD16 Antibodies by Biacore:

BIACORE uses the principle of surface plasmon resonance (SPR) to monitor, in real time, the interactions between molecules without their labelling. One of the partners in the interaction is covalently immobilised on a biosensor while the other is injected in a continuous flow. The principle of detection by SPR allows the changes in the mass to be monitored at the surface of the biosensor due to the formation and then the dissociation of the molecular complexes. The response, quantified in resonance units (RU) is a direct indication of the rate of binding of the analyte by the measurement of the variation of the refraction index. The recorded signal (a sensorgram) is processed mathematically to obtain the association speed, $k_a$, dissociation speed $k_d$ constants and the association $K_A$ ($K_A$=$k_a$/kd) and dissociation $K_D$ (KD=kd/ka) constants at equilibrium.

The interactions between the CEA or the CD16 and the VHH (that have a c-myc tag recognised by the monoclonal antibody 9E10, Santa Cruz Biotechnology, Inc) were studied on a BIACORE 3000 equipped with a CM5 biosensor on which the monoclonal antibody 9E10 was covalently immobilized following the standard coupling procedure by the amines proposed by BIACORE (activation by NHS/EDC). The VHH (in buffer: 10 mM HEPES; 150 mM NaCl; 3 mM EDTA; 0.005% surfactant P20) is then injected and then a range of CEA or CD16 is injected on the VHH immobilised on the 9E10. In parallel, the injections are carried out on a control channel that has been subjected to the same coupling chemistry without the injection of protein. The affinities of the VHH are indicated in Table 1 below. Equivalent affinities are obtained from the different formats of bispecific antibodies.

TABLE 1

| VHH | ka × 10$^5$ (1/Ms) | kd × 10$^{-3}$ (1/s) | KA × 10$^7$ (1/M) | KD × 10$^{-9}$ (M) |
| --- | --- | --- | --- | --- |
| Anti-CEA 3 | 1.24 ± 0.014 | 1.68 ± 0.002 | 7.38 | 13.6 |
| Anti-CEA 17 | 1.56 ± 0.014 | 1.3 ± 0.002 | 12 | 8.3 |
| Anti-CEA 25 | 1.13 ± 0.014 | 3.6 ± 0.004 | 3.15 | 31.7 |
| Anti-CEA 43 | 1.78 ± 0.019 | 1.83 ± 0.002 | 9.72 | 10.3 |
| Anti-CD16 c13 | 0.53 ± 0.07 | 5.67 ± 0.02 | 0.94 | 100.6 |
| Anti-CD16 c21 | 2.86 ± 0.02 | 2.79 ± 0.006 | 10.3 | 9.7 |
| Anti-CD16 c28 | 0.42 ± 0.03 | 3.45 ± 0.006 | 1.22 | 81.9 |
| Anti-CD16 c72 | 0.39 ± 0.02 | 3.7 ± 0.006 | 1.06 | 94.6 |

Analysis by FACS of the Specificity of Anti-CEA and Anti-CD16 VHH and the Corresponding Bispecific Antibodies.

Specificity for CEA: (for Effective Immunotargeting, it is Important that the Anti-CEA Antibodies do not Recognise the NCA, a Molecule that is Very Homologous to the CEA that is Expressed at the Surface of the Granulocytes.)

The detection of the antigen-antibody bond is carried out on the non-transfected line MC38 (cell line of a murine colon cancer), the lines transfected with the CEA (MC38/CEA$^+$) or the NCA (MC38/NCA$^+$), the human tumoural line LS174T (cell line of human colon adenocarcinoma expressing the CEA at its surface) and the granulocytes that express the NCA at their surface.

The granulocytes are extracted from fresh blood in the presence of heparin, on Ficoll gradient at two densities (Histopaque 1119 and 1077). The granulocytes are found at the interface of two Histopaques.

Antibodies used for the binding to the cells:
35A7, anti-CEA monoclonal antibody (specific for CEA).
192, anti-CEA monoclonal antibody (that crosses with the NCA).
7.5.4 and 3G8 anti-CD16 monoclonal antibody.
anti-CD16 VHH (c13, c21, c28, c72).
anti-CEA VHH (3, 17, 25, 43).
anti-CEA/anti-CD16 bispecific antibodies constructed from the 8 VHH isolated.

Antibodies used for the detection:
9E10, mouse anti-cmyc monoclonal antibody (200 µg/ml, used at 1/10$^{th}$) binding at the c-myc label of the purified VHH.
AP326F, sheep polyclonal antibody anti-IgG of mouse coupled with FITC (Silenus, used at 1/100$^{th}$).
0.5×10$^6$ cells are used per test. The VHH and monoclonal antibodies are diluted in 100 µl of PBS-1% BSA.

0.5×10$^6$ cells (autofluorescence measurement of the cells).
0.5×10$^6$ cells+anti-IgG of mouse-FITC 20 µg/ml.
0.5×10$^6$ cells+anti-9E10 20 µg/ml, then anti-IgG of mouse-FITC 20 µg/ml.
0.5×10$^6$ cells+VHH anti-CEA or anti-CD16 1 to 5 µg/ml, then 9E10 20 µg/ml, then anti-IgG of mouse-FITC 20 µg/ml.
0.5×10$^6$ cells+monoclonal antibody (35A7, 192, 7.5.4) 20 µg/ml, then anti-IgG of mouse-FITC 20 µg/ml.

At each step, the samples are incubated for 45 min, 4° C., in the dark. Between each reaction, a washing is carried out with 2 ml of PBS/1% BSA. At the last step, the cells are taken up with 0.5 ml of PBS.

The results by FACS demonstrate the specificity of the 4 anti-CEA VHH analysed and the anti-CEA/anti-CD16 bispecific antibodies in Fab, Fab' and F(ab')$_2$ form. They are CEA specific and do not cross with the NCA. One example is illustrated in FIG. 3. In this example, the monoclonal antibodies of reference mAb 35A7 and 192 do not bond on the MC38 cells that do not express CEA but on the MC38 CEA$^+$, and LS174T CEA$^+$ cells that express CEA on their surface. The mAb 192 also bonds on the MC38 NCA$^+$ cells and granulocytes that express NCA on their surface. CEA 17 VHH only bonds cells that express CEA on their surface. Equivalent results are obtained with other anti-CEA VHH antibodies (clones 3, 25 and 43). The CEA 17/VHH CD16 c21 VHH bispecific antibody is specific to tumoural cells both in Fab' and F(ab')$_2$ form. Equivalent results are obtained with other anti-CEA/anti-CD16 bispecific antibodies in Fab, Fab' and F(ab')$_2$ form (deriving 8 anti-CEA and anti-CD16 VHH).

Specificity for CD16:
For the effective recognition of the effector cells in the immune system, the anti-CD16 antibodies selected from CD16B should also recognise CD16A. In addition, they should not present a cross-over reaction with CD32 (RFcγIIA and RFcγIIB).

Experiments are carried out with Jurkat cells (cells from a human T lymphoma line; ATCC TIB-152) transfected or not with the gene coding for CD16A (stable line expressing CD16A at their surface; Vivier et al., 1992), granulocytes expressing CD16B, K562 cells that only express CD32A and IIA 6hullB1 cells that only express CD32B.

Antibodies used for the binding to cells:
3G8, anti-CD16 monoclonal antibody (human RFcγIIiA/IIIB), anti-site antibody recognising a conformational epitope and blocking the bond of the IgG to CD16A and CD16B.
7.5.4, anti-CD16 monoclonal antibody (human RFcγIIIA/IIIB), antibody recognising a linear epitope, localised outside the binding site of IgG of CD16 and only weakly affecting this bond at high concentrations in competition tests (Vely et al., 1997).
AT10 anti-CD32 monoclonal antibody (human RFcγIIA/IIB).
IV.3, anti-CD32 monoclonal antibody (human RFcγIIA).
anti-CD16 VHH (c13, c21, c28, c72).
anti-CEA VHH (3, 17, 25, 43).
35A7, anti-CEA monoclonal antibody.
192, anti-NCA monoclonal antibody (that crosses with CEA).
anti-CEA/anti-CD16 bispecific antibodies constructed from 8 isolated VHH.

Antibodies used for detection:
9E10, mouse anti-cmyc monoclonal antibody (200 µg/ml, used at 1/10th) binding at the c-myc label of the purified VHH.

Fab'2 of a goat antibody anti-IgG of mouse coupled with FITC (F(ab')$_2$/FITC) used at 20 µg/ml (Jackson Immunoresearch Lab. Inc., 115-096-003).

0.5×10$^6$ cells are used per test. The VHH and monoclonal antibodies are diluted in 100 µl of PBS-1% BSA.

0.5×10$^6$ cells (autofluorescence measurement of the cells)
0.5×10$^6$ cells+(F(ab')$_2$/FITC) 20 µg/ml
0.5×10$^6$ cells+anti-9E10 20 µg/ml, then (F(ab')$_2$/FITC) 20 µg/ml
0.5×10$^6$ cells+VHH 1 at 5 µg/ml, then 9E10 20 µg/ml, then (F(ab')$_2$/FITC) 20 µg/ml
0.5×10$^6$ cells+monoclonal antibodies (35A7, 192, 3G8, 7.5.4, AT10, N.3) 20 µg/ml, then (F(ab')$_2$/FITC) 20 µg/ml.
At each step, the samples are incubated for 45 min, 4° C., in the dark. Between each reaction, a washing is carried out with 2 ml of PBS/1% BSA. At the last step, the cells are taken up with 0.5 ml of PBS.

Figure 4:
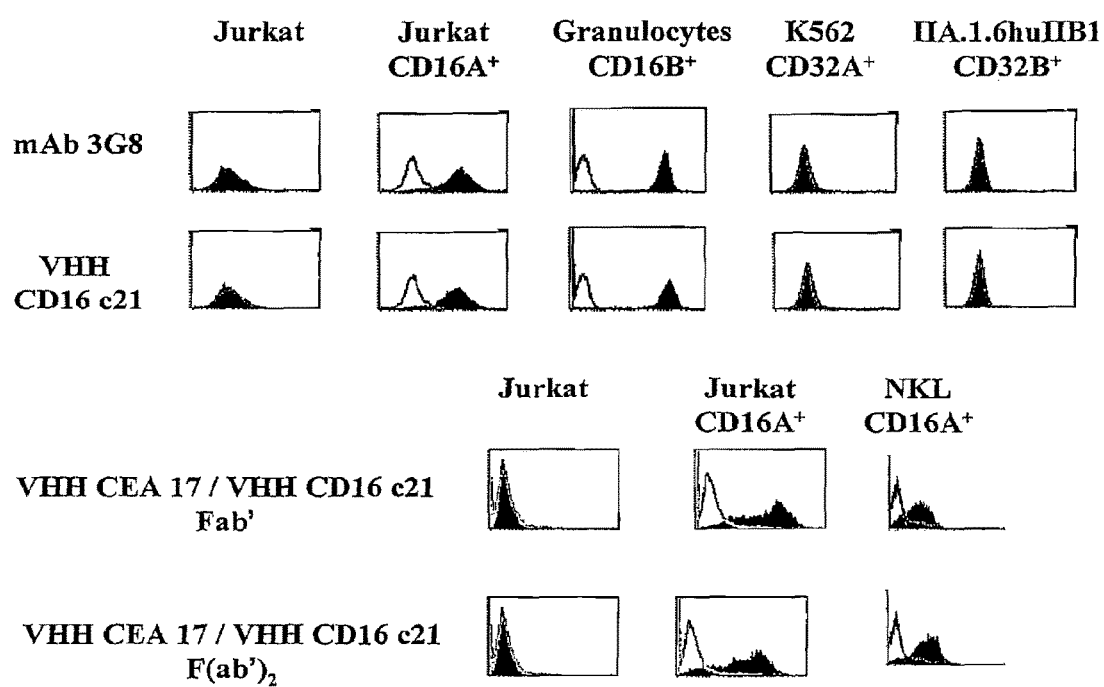
FIG. 4, the results by FACS demonstrating the specificity of 8 VHH analysed, and the corresponding bispecific antibodies.

The results by FACS demonstrate the specificity of the 4 anti-CD16 VHH analysed and the anti-CEA/anti-CD16 bispecific antibodies in Fab, Fab' and F(ab')$_2$ form. They are CD16 specific and do not cross with CD32. One example is illustrated in FIG. 4. In this example, the reference monoclonal antibody mAb 3G8 does not bind on the Jurkat cells, K562 CD32A$^+$ and IIA.1.6hullB1 CD32B$^+$ that do not express CD16 but on the Jurkat CD 16A$^+$ cells, and the granulocytes that express CD16 on their surface. CD16 c21 VHH does not bind on cells that express CD16 on their surface. Equivalent results are obtained with other anti-CD16 VHH antibodies (clones: c13, c28 and c72). The bispecific antibody VHH CEA 17/VHH CD16 c21 is specific in Jurkat CD16A+ and NKL cells both in Fab' and F(ab')$_2$ form. Equivalent results are obtained with other anti-CEA/anti-CD16 bispecific antibodies in Fab, Fab' and F(ab')$_2$ form (deriving 8 anti-CEA and anti-CD16 VHH).

FACS Analysis of the Accessibility of Bispecific Antibodies on Cells:
The Accessibility of Anti-CD16 VHH Domain:

5×10$^5$ LS174T cells are incubated for 30 min, in PBS-1% BSA in ice, in the presence of Fab, Fab' or F(ab')$_2$, (range from 10 µg/ml to 0.1 µg/ml). The cells are washed in PBS-BSA 1%. The binding of rhCD16 (µg/ml) on the anti-CD16 VHH domain of the different fragments of antibody is then detected, in two steps, by incubating monoclonal antibody 7.5.4 or 3G8 (3 µg/ml) with the cells for 30 min, in ice then by incubating the cells with goat F(ab')$_2$ anti-IgG of mouse (H+L) marked with FITC (Jackson Immunoresearch Laboratory, cat: 115-096-003), for 30 min in ice. After several washings, the immunofluorescence is analysed by flow cytometry with a FACScalibur 4C4 (Becton Dickinson) using the Cell Quest Pro programme.

The Accessibility of the Anti-CEA VHH Domain:

5×10$^5$ Jurkat CD16A$^+$ cells are incubated for 30 min, in PBS-BSA 1% in ice, in the presence of Fab, Fab' or F(ab')$_2$, (range from 10 µg/ml to 0.1 g/ml). The cells are washed in PBS-1% BSA. The binding of the rhCEA (10 µg/ml) on the anti-CEA VHH domain of the Fab, Fab' or F(ab')$_2$, is then detected, in two steps, by incubating monoclonal antibody 192 (3 µg/ml) with the cells for 30 min, in ice, and then by incubating the cells with goat F(ab')$_2$ anti-IgG of mouse (H+L) marked with FITC (Jackson Immunoresearch Laboratory, cat: 115-096-003), for 30 min in ice. After several washings, the immunofluorescence is analysed by flow cytometry with a FACScalibur 4C4 (Becton Dickinson) using the Cell Quest Pro programme.

Figure 5:
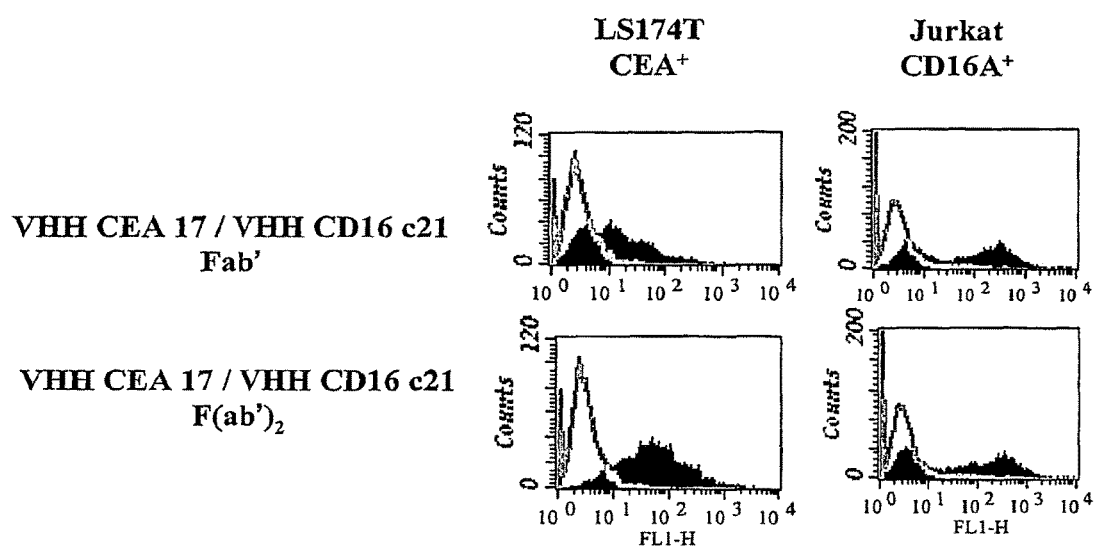
FIG. 5, the results by FACS demonstrating the accessibility on the cells of bispecific antibodies.

One example is illustrated in FIG. 5. The bispecific antibody VHH CEA 17/VHH CD16 c21 binds both with the LS174T and Jurkat CD16A$^+$ cells. Equivalent results are obtained with the other anti-CEA/anti-CD16 bispecific antibodies in Fab, Fab' and F(ab')$_2$ form (deriving 8 anti-CEA and anti-CD16 VHH).

Competition Test Between the Anti-CD16 VHH and the Monoclonal Antibody 3 GB and 7.5.4:
ELISA:

Five µg/ml of biotinyl VHH (c21, c28) are bound per well in a plate adsorbed with streptavidin (BioBind Assembly Streptavidin Coated, ThermoLabsystems) previously saturated in 2% milk-PBS. The CD16B with a concentration ranging from 0.07 to 20 µg/ml is then added. Secondly, the monoclonal antibody (3G8 or 7.5.4) at a constant concentration of 5 µg/ml is added. The CD16B-monoclonal antibody binding is detected with a goat F(ab')$_2$ anti-IgG of mouse coupled with alkaline phosphatase (Southern Biotechnology, 1030-04) in the presence of p-nitrophenylphosphatase (Sigma, N9389).

The competition curves in ELISA are demonstrated in FIG. 6. The CD16 c21 VHH is shifted by monoclonal antibody 7.5.4. The CD16 c28 VHH is shifted by monoclonal antibody 3G8.

Indirect Immunofluorescence (FACS):

5×10$^5$ Jurkat-CD16A cells are incubated for 30 min, in PBS-5% BSA in ice, in the presence of CD16 c21 or c28 VHH (1 to 100 µg/ml). The cells are then incubated with 0.1 µg/ml of 3G8 or 1 µg/ml of 7.5.4 for 30 min in the same conditions, then washed in PBS-5% BSA. The binding of 3G8 or 7.5.4 is then detected by incubating the cells with the F(ab')$_2$ of a goat antibody anti-IgG of mouse (H+L) marked with FITC (Jackson ImmunoResearch Laboratories Inc., West Grove, Pa., USA, cat No.: 115-096-003) for 30 min in ice. After several washings, the immunofluorescence is analysed by flow cytometry with a FACScalibur 4CA (Becton Dickinson, Mountain View, Calif., USA) using the Cell Quest Pro programme.

Figure 7:
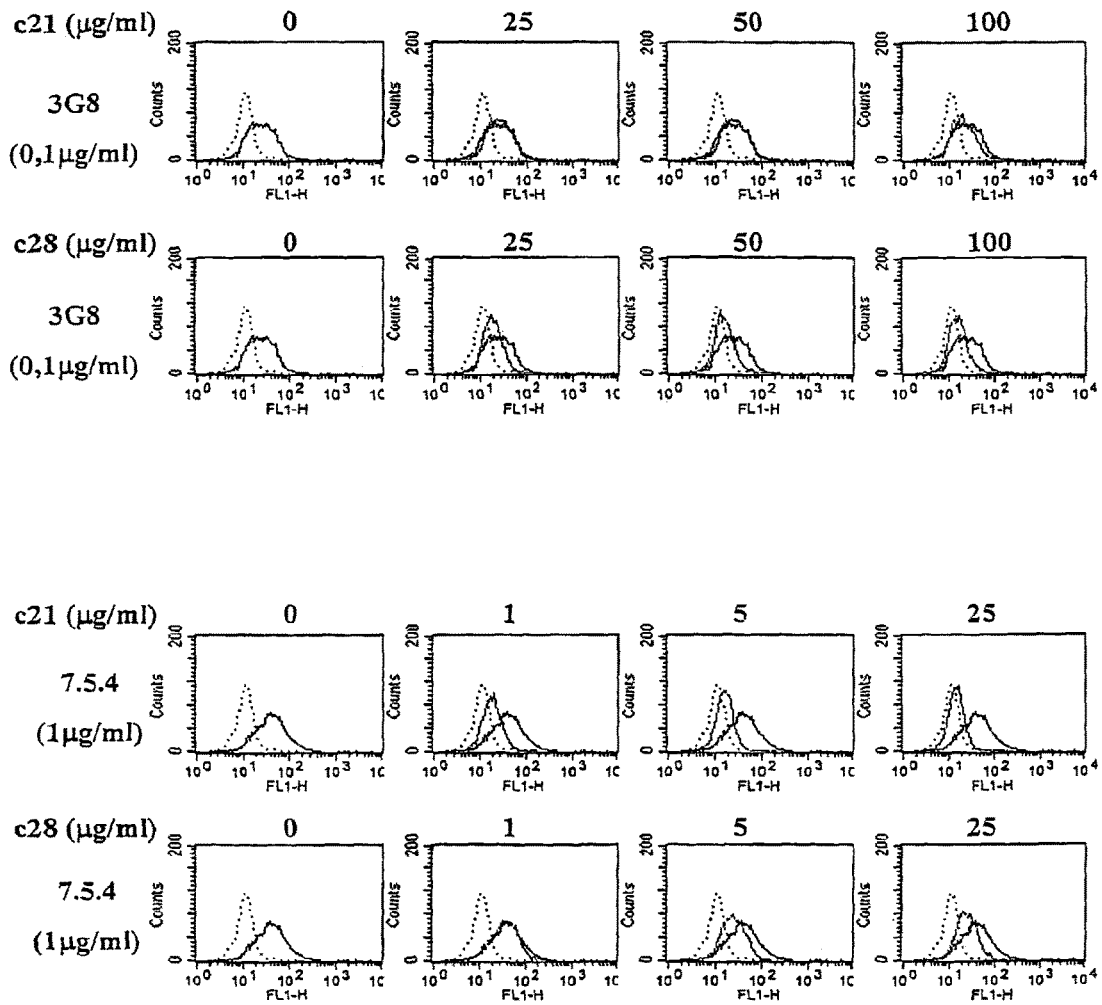
FIG. 7, the competition profiles on cells by FACS of 2 anti-CD16 VHH and the monoclonal anti-CD 16 antibodies.

The competition profiles on cells are provided in FIG. 7. CD16 c21 VHH is shifted by monoclonal antibody 7.5.4. CD16 c28 VHH is shifted by monoclonal antibody 3G8. A high dose of CD16 c28 VHH is also shifted by mAb 7.5.4.

Activation by the Anti-CD16 VHH and by the Bispecific Antibodies of Jurkat CD16$^+$ Cells:

The experiments are carried out with Jurkat cells (ATCC TIB-152) transfected with the gene that codes CD16A. The cells are cultivated in RPMI 1640 complemented with 10% FCS, 100 U/ml penicillin, 100 µg/ml streptomycin, 2 mM L-glutamine, 0.5 mg/ml G418.

5×10$^5$ cells are then incubated for 18 h in microplate wells (250 µl of RPMI containing 10% FCS, 1% PS, 0.5 mg/ml G418). Ten ng/ml of phorbol myristate acetate (PMA) (concentration not per se inducing the production and secretion of IL2, but necessary as a "second signal" for this production) are then added, followed by the addition of 0.01 to 0.1 µg/ml of biotinylated VHH and 10 µg/ml of streptavidin (enabling the bridging of the VHH) or non-biotinylated bispecific antibodies.

The human IL2 produced in the cell supernatants is measured by ELISA using antibodies from the R&D kit (Duoset Human IL2; reference: DY202) and streptavidin coupled with alkaline phosphatase (DAKO, D0396) in the presence of p-nitrophenylphosphate (Sigma, cat 104-405).

The results of the activation of CD16A (production and secretion of interleukin 2) are provided in FIG. 8. The two anti-CD16 c21 and c28 VHH activate the production of IL2 of Jurkat CD16A$^+$ cells. Higher quantities of c28 are required to obtain an induction of the production and the secretion of IL2 similar to that induced by the c21. The anti-CEA 17/anti-CD16 c21 bispecific antibody in form F(ab')2 also activates the production of IL2 if the Jurkat cells express CD16A at their surface in the absence of bridging via the streptavidin. Equivalent results are obtained from other anti-CD16 VHH and anti-CEA/anti-CD16 bispecific antibodies.

Lysis of Tumoural Cells by NKL Cells in the Presence of Bispecific Antibody:

For the cytotoxicity test of the NK cells, NKL cells are used as the cell lines (Robertson et al, 1996 (12)) obtained from leukemia with large granulocytic lymphocytes, whose functional properties are similar to that of the NK and whose expression of CD16 was first verified by flow cytometry. The target cells used are very NK sensitive HeLa cells obtained from a human leukemia, NK sensitive cells from murine colon C15.4.3 AP (MC38), and MC38 cells transfected with human CEA that are naturally NK resistant.

The target cells in culture are put into suspension (by tryptic reaction for the HeLa cells, mechanically for the MC38 and NKL cells) and counted using Trypan blue in a Malassay cell. Two thousand cells per well are incubated in 100 µl with 3.7×10$^6$ Bq of $^{51}$Cr and the different antibody formats (200, 100 or 50 µg/ml) 1 h at 37° C. The cells are then washed several times to eliminate the $^{51}$Cr remaining in the medium as well as the non-bound antibodies. The NKL cells in suspension are counted and added to the target cells with an effector/target ratio ranging from 60:1 to 0.2:1. After incubation for 4 h at 37° C., the radioactivity of the Cr released in the medium is counted using a γ counter. Examples showing the cell lysis obtained with the anti-CEA 17/anti-CD16 c21 and anti-CEA 17/anti-CD16 c28 bispecific antibodies in Fab' and F(ab')$_2$ form are represented in FIG. 9.

Construction of Different Plasmids (Refer to FIGS. 10A, 10B, 11, 12A and 12B).

All of the non detailed protocols are described in Sambrook, Fritsch and Maniatis, Molecular Cloning: A Laboratory Manual, 2nd ed, Cold Spring Harbor Laboratory Press, 1989.

The digestions with the restriction enzymes are carried out according to the supplier's recommendations.

Genes of human origin inserted: The genes coding for regions Cκ, CH1, H, CH2 and CH3 respectively correspond to: the domains of genes coding for the constant region of a light kappa chain of human immunoglobulin, for the first constant region, for the hinge region, for the second constant region and for the third constant region of a heavy chain of human immunoglobulin IgG1. These genes were obtained by RT-PCR from an LFB pouch (Laboratoire français du Fractionnement et des Biotechnologies). This material is subject to the legal authorisations and may be used for the experiments described.

The sequence of each plasmid is carried out on ABI 310 sequencer by using the oligonucleotides:

```
EcoRI-90 of sequence SEQ ID NO: 12:
GCGCCGACATCATAACGGTTCTGGC

HindIII + 88 of sequence SEQ ID NO: 13:
CGCTACTGCCGCCAGGC
```

Figure 10A:
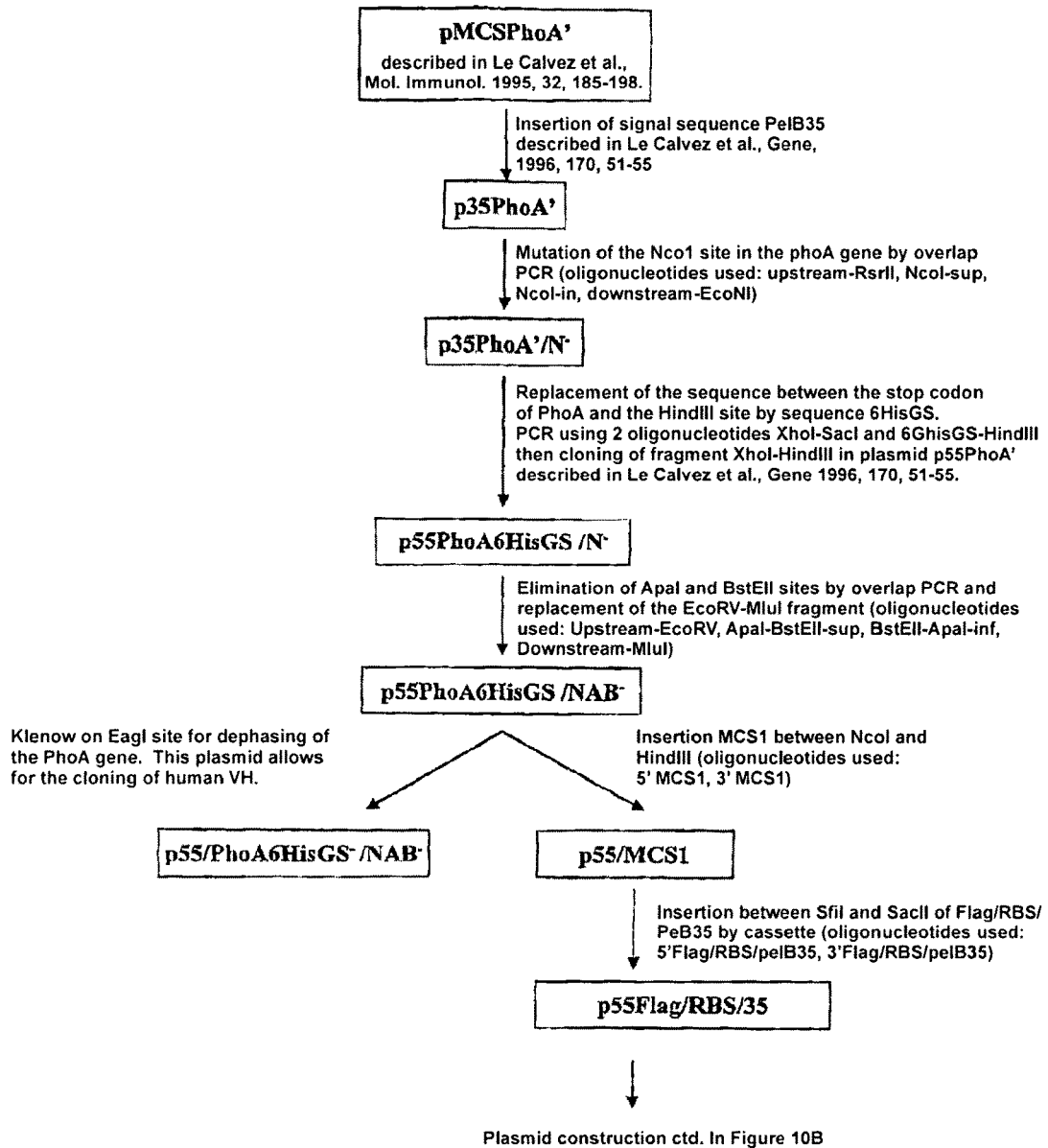
FIGS. 10A and 10B, plasmid constructions according to the invention.

All of the vectors are designed to allow for the introduction, between 2 unique sites of restriction enzymes, of: different promoters, different signal sequences of type PeIB (or other), different RBS sequences, any VHH or humanised VHH domain, any Cλ. domain, or domains CH1, H, CH2 and CH3 of any type of immunoglobulin.

pMCSPhoA' (FIG. 10A)

The construction of this plasmid is described in Le Calvez et al. (1995). REF. This plasmid codes for the mature form of the Alkaline Phosphatase (PhoA) starting at the sixth residue (Proline).

p35PhoA' (FIG. 10A)

The construction of this plasmid is described in Le Calvez (1996). A gene fragment (formed by degenerated oligonucleotides on the third base of codons 2 to 14 coding for the signal sequence of PeIB) is inserted between the NdeI and EagI sites of plasmid pMCSPhoA'. The clones (1 to 60) presenting the best alkaline phosphatase activity were then selected.

p35PhoA'/N$^-$ (FIGS. 10A and 11)

Suppression of the NcoI site in the phoA gene. An overlap PCR is carried out from pMCSPhoA' with the oligonucleotides: upstream-RsrII, NcoI-sup, NcoI-inf and downstream-EcoNI. Sequences SEQ ID NOs:14 to 17 of the oligonucleotides used:

```
upstream-RsrII
SEQ ID NO: 14: GGCACATGTGACCTCGCGC

NcoI-sup
SEQ ID NO: 15: GCAACGTACCACGGCAATATCG

NcoI-inf
SEQ ID NO: 16: CGATATTGCCGTGGTACGTTGC downstream-EcoNI
SEQ IDNO: 17: GCCATCTTTGGTATTTAGCGCC
```

Conditions for PCR 1 and PCR 2:

One µl of plasmid (5 ng), 10 pmoles of each oligonucleotide (upstream-RsrII and NcoI-inf for PCR 1 and NcoI-sup and downstream-EcoNI for PCR 2), 0.5 U Dynazyme (94° C., 3 min; 94° C., 45 s; 60° C., 45 s; 72° C., 45 s; for 25 cycles then 72° C., 10 min) in a final volume of 50 µl. The PCR products are purified from a 2% agarose gel (Qiagen Kit extraction gel, final volume 50 µl).

Conditions for the Overlapping PCR 3:

One µl of each of PCR 1 and 2 and 0.5 U Deep Vent, in a final volume of 50 µl. After 5 cycles (94° C., 3 min; 94° C., 1 min; 60° C., 1 min; 72° C., 1.5 min) 10 pmoles of each oligonucleotide are added (upstream-RsrII and downstream-EcoNI) and the PCR is continued for 35 cycles then 72° C., 10 min. The product of the PCR 3 is purified, from a 2% agarose gel (Qiagen Kit extraction gel, final volume 50 µl). The sequence of the PCR fragment is carried out on sequencer ABI 310 using oligo 5' EcoRI-90.

Cloning of the PCR 3 Fragment in Plasmid p35PhoA':

Thirty-five µl of PCR 3 fragment and 5 µl (2.5 µg) of p35PhoA' are digested by 10 U of RsrII and EcoNI. After 16 h of incubation, the enzymes are destroyed for 10 min at 65° C. Each DNA is then precipitated and resuspended with 20 µl of H$_2$O. The ligation is carried out for 16 h at 16° C. with 5 µl of PCR fragment, 0.5 µl of vector and 3 U Weiss of T4 DNA ligase Biolabs in a final volume of 10 µl. Competent TG1 bacteria (CaCl$_2$ technique) are transformed with 5 µl of ligation.

p55PhoA6HisGS/N$^-$ (FIGS. 10A and 11)

Insertion of the 6Histidine-Gly-Ser motif. A PCR is carried out from p35PhoA'/N$^-$ using oligonucleotides XhoI-SacI and 6HisGS/HindIII. Sequences SEQ ID NOs: 18 and 19 of the oligonucleotides used:

```
XhoI-SacI
SEQ ID NO: 18: CCATGGCGGCCGATCCTCGAGAG

6HisGS/HindIII
SEQ ID NO: 19:
CATGCAGTCCCAAGCTTATTAGCTCCCGTGATGGTGATGAT

GATGTTTCAGCCCCAGA GCGGCTTTC
```

PCR Conditions:

A PCR is carried out with 5 ng of p35PhoA'/N⁻ vector, 10 pmoles of each oligonucleotide and 0.5 U Dynazyme (94° C., 3 min; 94° C., 1 min; 70° C., 1 min; 72° C., 1 min; 35 cycles then 72° C., 10 min) in a final volume of 50 µl. The PCR product is purified from a 1% agarose gel (Qiagen Kit extraction gel, final volume 50 µl).

Cloning of Fragment XhoI-HindIII:

Twenty µl of the PCR fragment and 5 µl (2.5 µg) of p55PhoA' vector (Le Calvez et al. Gene 1996, 170, 51-55) are digested by 10 U of XhoI and HindIII in the presence of BSA. After 16 h of incubation, the enzymes are destroyed for 10 min at 65° C. Each DNA is then precipitated and resuspended with 20 µl of H₂O. The ligation is carried out for 16 h at 16° C. with 5 µl of PCR fragment, 0.5 µl of vector and 3 U Weiss of T4 DNA ligase Biolabs in a final volume of 10 µl. Competent TG1 bacteria (CaCl₂ technique) are transformed with 5 µl of ligation product.

p55PhoA6HisGS/NAB⁻ (FIGS. 10A and 11)

Suppression of sites ApaI and BstEII of p55PhoA6HisGS/N⁻. One overlap PCR is carried out from p55PhoA6HisGS/N⁻ with the oligonucleotides: upstream-EcoRV, ApaI-BstEII-sup, BstEII-ApaI-inf and downstream:—MluI. Sequences SEQ ID NOs:20 to 23 of the oligonucleotides used:

```
upstream-EcoRV
SEQ ID NO: 20: CATGAGCTGTCTTCGGTATC

ApaI-BstEII-sup
SEQ ID NO: 21:
TAATGGTCCCGCTAACAGCGCGATTTGCTGATGACCCA

BstEII-ApaI-inf
SEQ ID NO: 22:
TGGGTCATCAGCAAATCGCGCTGTTAGCGGGACCATTA downstream-MluI
SEQ ID NO: 23: GAACGAAGCGGCGTCGAAG
```

PCR 1 and PCR 2 Conditions:

One µl (5 ng) of plasmid p55PhoA6HisGS/N⁻, 10 pmoles of each oligonucleotide (upstream-EcoRV and BstEII-ApaI-inf for PCR 1 and ApaI-BstEII-sup and downstream-MluI for PCR 2), 0.5 U Dynazyme (94° C., 3 min; 94° C., 45 s; 60° C., 45 s; 72° C., 45 s; 25 cycles then 72° C., 10 min. The PCR products are purified from a 2% agarose gel (Qiagen Kit extraction gel, final volume 50 µl).

Conditions for the Overlap PCR 3:

One µl of each of PCR 1 and 2 and 0.5 U Deep Vent, in a final volume of 50 µl. After 5 cycles (94° C., 3 min; 94° C., 1 min; 60° C., 1 min; 72° C., 1.5 min) 10 pmoles of each oligonucleotide are added (upstream-EcoRV and downstream-MluI) and the PCR is continued for 35 cycles then 72° C., 10 min. The PCR 3 product is purified from a 2% agarose gel (Qiagen Kit extraction gel, final volume 50 µl). The sequence of the PCR fragment is carried out on ABI 310 sequencer using oligo 5' EcoRI-90.

Cloning of the PCR 3 Fragment in the p55PhoA6HisGS/N⁻ Plasmid:

Thirty-five µl of PCR 3 fragment and 5 µl (2.5 µg) of p55PhoA6HisGS/N⁻ are digested by 10 U of EcoRV and MluI. After 16 h of incubation, the enzymes are destroyed for 10 min at 65° C. Each DNA is then precipitated and resuspended with 20 µl of H₂O. The ligation is carried out for 16 h at 16° C. with 5 µl of PCR fragment, 0.5 µl of vector and 3 U Weiss of T4 DNA ligase Biolabs in a final volume of 10 µl. Competent TG1 bacteria (CaCl₂ technique) are transformed with 5 µl of ligation product.

p55PhoA6HisGS⁻/NAS⁻ (FIGS. 10A and 11)

Phase shift of the PhoA gene at the EagI site. This phase shift creates a single FseI site. Five µl (2.5 µg) of p55PhoA6HisGS/NAB⁻ are digested by 10 U of EagI. After 16 h of incubation, the enzyme is destroyed for 10 min at 65° C. The reaction mixture is then precipitated and resuspended with 20 µl of H₂O. An equimolar mixture of dGTP and dCTP (33 µM final) and 2.5 U of Klenow fragment exo (Biolabs) are added in a final volume of 50 µl, 15 min at 25° C. The reaction is stopped with 2 µl of EDTA at 500 mM, 20 min at 75° C. The reaction mixture is precipitated in ethanol, resuspended with 5 µl of H₂O and ligated with 3 U Weiss of T4 DNA ligase Biolabs in a final volume of 10 µl. Competent TG1 bacteria (CaCl₂ technique) are transformed with 5 µl of ligation. This plasmid allows for the cloning and selection of the best secreted fragments of human antibody VH.

p55/MCS1 (FIGS. 10A and 11)

Insertion of MCS1 in p55PhoA6HisGS/NAB⁻ between the NcoI and HindIII sites using the paired oligonucleotides 5' MCS1 and 3' MCS1. Sequences SEQ ID NOs:24 and 25 of the oligonucleotides used:

```
5' MCS1
SEQ ID NO: 24:
CATGGCCCAGGTCACCGTCTCCTCAAACCGCGGACTCGAGGCGGCCCAGC

CGGCCAT GGCCGCTAGCGCGGCCGCTCTAGATTA

3' MCS1
SEQ ID NO: 25:
AGCTTAATCTAGAGCGGCCGCGCTAGCGGCCATGGCCGGCTGGGCCGCCT

CGAGTCCG CGGTTTGAGGAGACGGTGACCTGGGC
```

Five µl (2.5 µg) of p55PhoA6HisGS/NAB⁻ vector are digested for 16 h by 10 U of each NcoI and HindIII enzyme. Ten pmoles of each of the oligonucleotides 5' MCS1 and 3' MCS1 are incubated for 5 min at 80° C.; the solution is then slowly reduced to ambient temperature. Ligate 5 µl of vector with 1.2 µl of the hybrid cassette (5' MCS1+3' MCS1) in the presence of 3 U Weiss of T4 DNA ligase Biolabs 1 h at ambient temperature. The ligase is destroyed by incubating for 10 min at 65° C. A reaction mixture (2 h) of 90 µl, containing, 10 U of EagI is added to destroy the original vector. This mixture is precipitated with ethanol and resuspended with 10 µl of H₂O. Competent TG1 bacteria (CaCl₂ technique) are transformed with 5 µl of mixture.

p55Flag/RBS/35 (FIGS. 10A and 11)

Insertion of the Flag/RBS/PelB35 motif in p55/MCS1 between the SfiI and Sac2 sites using the paired oligonucleotides 5' Flag/RBS/35-sup and 3' Flag/RBS/35-inf. Sequences SEQ ID NOs:26 and 27 of the oligonucleotides used:

5' Flag/RBS/35-sup
SEQ ID NO: 26:
GGAGAGTGTGCAGGTGATTACAAAGACGATGACGATAAGTAATAAACAGG

AAACAGAAGTCCATATGAAATACCTATTGCCTACGGCAGCCGCTGGATTG

TTATTACTCGCGGCCCAGC

SEQ ID NO: 117:
GGAGAGTGTGCAGGTGATTACAAAGACGATGACGATAAGTAATAAACAGG

AAACAGAAGTCCATATGAAATATCTTTTACCTACGGCAGCCGCAGGTTTG

TTGTTACTCGCGGCCCAGC

3' Flag/RBS/35-inf
SEQ ID NO: 27:
GGGCCGCGAGTAATAACAATCCAGCGGCTGCCGTAGGCAATAGGTATTTC

ATATGGACTTCTGTTTCCTGTTTATTACTTATCGTCATCGTCTTTGTAAT

CACCTGCACACTCTCCGC

SEQ ID NO: 118:
GGGCCGCGAGTAACAACAAACCTGCGGCTGCCGTAGGTAAAAGATATTTC

ATATGGACTTCTGTTTCCTGTTTATTACTTATCGTCATCGTCTTTGTAAT

CACCTGCACACTCTCCGC

Figure 10B:
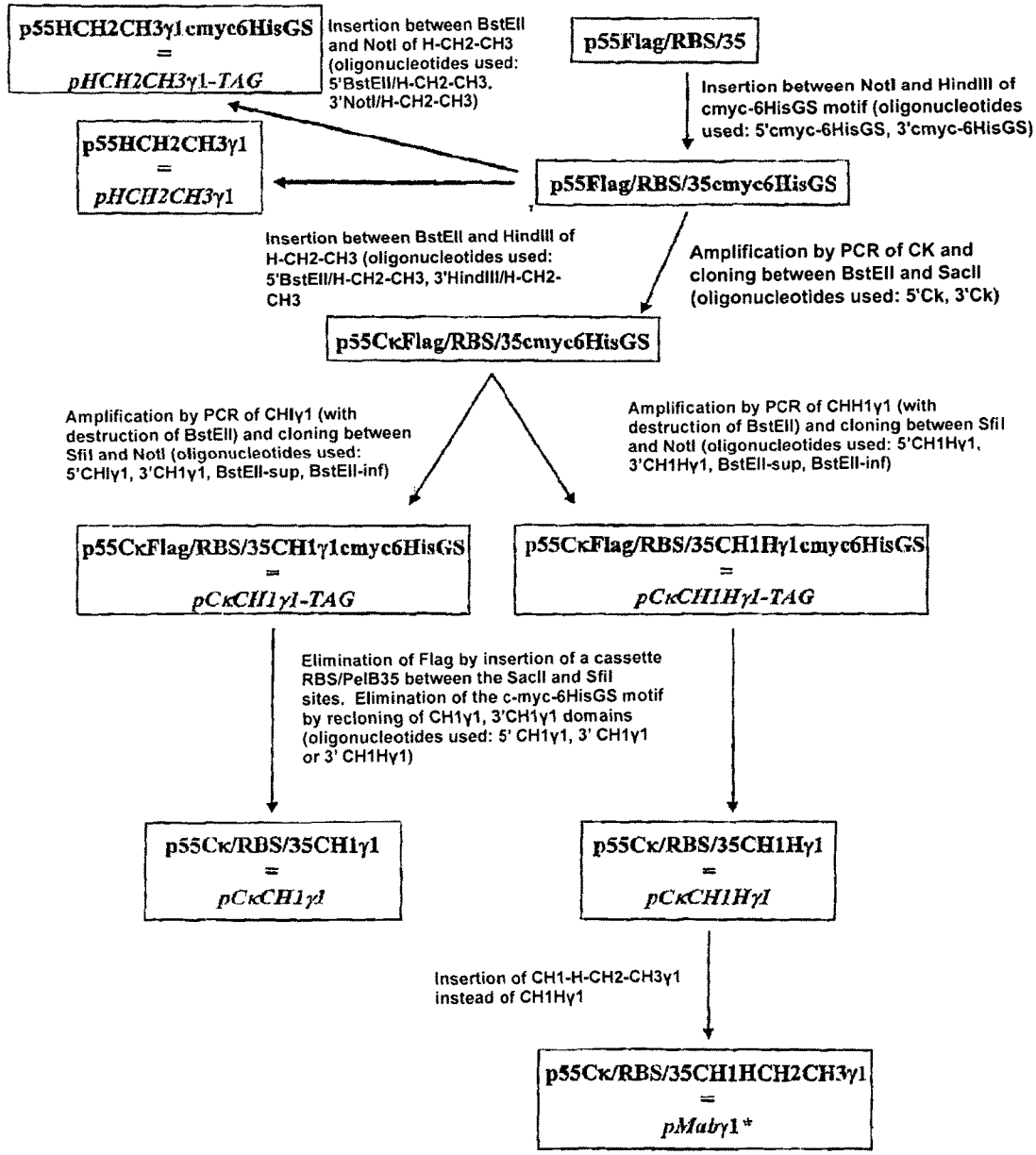

The cloning is carried out exactly according to the conditions previously described for the insertion of MCS1. After ligation, the reaction mixture is digested by 10 U of XhoI enzyme.

p55Flag/RBS/35cmyc6HisGS (FIGS. 10B and 11)

Insertion of the c-myc-6HisGS motif in p55Flag/RBS/35 between the NotI and HindIII sites using the paired oligonucleotides 5' c-myc-6HisGS and 3' c-myc-6HisGS. Sequences SEQ ID NOs:28 and 29 of the oligonucleotides used:

5' c-myc-6HisGS
SEQ ID NO: 28:
GGCCGCAGAACAAAAACTCATCTCAGAAGAGGATCTGAATGGGGCCGTAC

ATCACCACC ATCACCATGGGAGCTA

3' c-myc-6HisGS
SEQ ID NO: 29:
AGCTTAGCTCCCATGGTGATGGTGGTGATGTACGGCCCCATTCAGATCCT

CTTCTGAGA TGAGTTTTTGTTCTGC

The cloning is carried out exactly according to the conditions previously described for the insertion of MCS1. The ligation mixture is digested by 10 U of XbaI enzyme.

p55CκFlag/RBS/35cmyc6HisGS (FIGS. 10B and 11)

Insertion of the constant light Ckappa region of an immunoglobulin in p55Flag/RBS/35cmyc6HisGS. Sequences SEQ ID NOs:30 and 31 of the oligonucleotides used:

5' CK
SEQ ID NO: 30:
GGGGCCAGGGGACCCAGGTCACCGTCTCCTCAGGTACCGTGGCTGCACCA

TCTGTCTTC

SEQ ID NO: 119:
GGGGCCAGGGGACCCAGGTCACCGTCTCCTCACGTACGGTGGCTGCACCA

TCTGTCT TC

3' CK
SEQ ID NO: 31:
CGTCATCGTCTTTGTAATCACCTGCACACTCTCCGCGGTTGAAGCTCTTT

GTCACCG

Amplification of the Cκ Domain:

Human B lymphocytes are purified by Ficoll gradient from a pouch provided by LFB. The whole RNA is then prepared according to the protocol described in section 1.3.2.

Hybridisation:

One μl of whole DNA is preincubated with 1 pmole of oligonucleotide 3' Cκ for 10 min at 70° C. in a final volume of 8 μl. The temperature is slowly decreased (45 min) to 37° C.

Reverse Transcription:

Take 8 μl and add 0.5 μl of RNAsine (20 U), 3 μl of 5× buffer (SuperScriptII, Invitrogen), 1 μl DTT, 100 mM, 2 μl dNTP 10 mM and incubate for 10 min at 50° C. Then, 0.75 μl of SuperScript (150 U) are added and the incubation is continued for 30 min at 50° C. and 15 min at 70° C. The cDNA obtained is purified on beads (BioMag Carboxyl Terminated, Polysciences) according to the supplier's recommendations. The final elution is made with 15 μl of Tris-acetate 10 mM pH 7.8.

PCR 1 and 2 Conditions:

The PCR1 is carried out with 1 μl of cDNA, 10 pmoles of each oligonucleotide 5' Cκ and 3' Cκ, 0.5 U Dynazyme (94° C., 3 min; 94° C., 1 min; 60° C., 1 min; 72° C., 1.5 min; 30 cycles then 72° C., 10 min) in a final volume of 50 μl. The PCR2 is carried out from 1 μl of PCR1 using 0.5 U Deep-Vent, (94° C., 3 min; 94° C., 45 s; 60° C., 45 s; 72° C., 45 s; 25 cycles then 72° C., 5 min) in a final volume of 50 μl. The PCR product is purified from a 2% agarose gel (Qiagen Kit extraction gel, final volume 50 μl). The PCR fragment is sequenced, before cloning, on ABI310 with oligonucleotides 5' Cκ and 3' Cκ.

The cloning of the Cκ domain is carried out between sites BstEII and SacII of p55Flag/RBS/35cmyc6HisGS: 20 μl of PCR 2 fragment and 5 μl (2.5 rig) of p55Flag/RBS/35cmyc6HisGS are digested by 10 U of BstEII and SacII. After 16 h of incubation, the enzymes are destroyed for 10 min at 65° C. Each DNA is then precipitated and resuspended with 20 μl of H₂O. Ligation is carried out for 16 h at 16° C. with 5 μl of PCR 2 fragment, 0.5 μl of vector and 3 U Weiss of T4 DNA ligase Biolabs in a final volume of 10 μl. Competent TG1 bacteria (CaCl₂ technique) are transformed with 5 μl of ligate.

p55CκFlag/RBS/35CH1γ1cmyc6HisGS (pCκCH1 γt-TAG)

Insertion of the heavy constant region CH1 of an immunoglobulin of the IgG1 type in p55CκFlag/RBS/35cmyc6HisGS, Sequences SEQ ID NOs:32 to 35 of the oligonucleotides used:

5' CH1 γ1
SEQ ID NO: 32:
CTCGAGGCGGCCCAGCCGGCCATGGCCGCTAGCACCAAGGGCCCATCGG

3' CH1 γ1
SEQ ID NO: 33:
AAGCTTAATCTAGAGCGGCCGCACAAGATTTGGGCTCAACTTTC

BstEII-sup
SEQ ID NO: 34: CCCTCAGCAGCGTAGTGACCGTGCCCTCC

BstEII-inf
SEQ ID NO: 35: GGAGGGCACGGTCACTACGCTGCTGAGGG

The amplification of the CH1γ1 domain is carried out by overlapping PCR to destroy the BstEII site. The reverse transcription is carried out exactly as described above for the Cκ, but by using oligonucleotide 3' CH1γI. The PCR 1 after RT is carried out with 1 µl of cDNA, 10 pmoles of each oligonucleotide 5' CH1 γ1 and 3' CH1 γ1, 0.5 U of Dynazyme (94° C., 3 min; 94° C., 1 min; 60° C., 1 min; 72° C., 1.5 min; 30 cycles then 72° C., 10 min) in a final volume of 50 µl.

The PCR 2a is carried out from 1 µl of PCR 1, with oligonucleotides 5' CH1 γ1 and BstEII-inf using 0.5 U of Dynazyme (94° C., 3 min; 94° C., 45 s; 60° C., 45 s; 72° C., 45 s; 25 cycles then 72° C., 5 min) in a final volume of 50 µl. The PCR 2b is carried out from 1 µl of PCR 1, with oligonucleotides BstEII-sup and 3' CH1 γ1 using 0.5 U of Dynazyme (94° C., 3 min; 94° C., 45 s; 60° C., 45 s; 72° C., 45 s; 25 cycles then 72° C., 5 min) in a final volume of 50 µl.

The PCR 3 is carried out from one µl of each of PCR 2a and PCR 2b, with oligonucleotides 5' CH1γ1 and 3' CH1γ1, using 0.5 U of Deep-Vent (94° C., 3 min; 94° C., 45 s; 60° C., 45 s; 72° C., 45 s; 25 cycles then 72° C., 5 min) in a final volume of 50 µl. The product of PCR 3 is purified from a 2% agarose gel (Qiagen Kit extraction gel, final volume 50 µl). The sequence of the PCR 3 fragment is carried out on ABI 310 sequencer using oligonucleotides: 5' CH1γ1 and 3' CH1γ1.

Figure 12A:
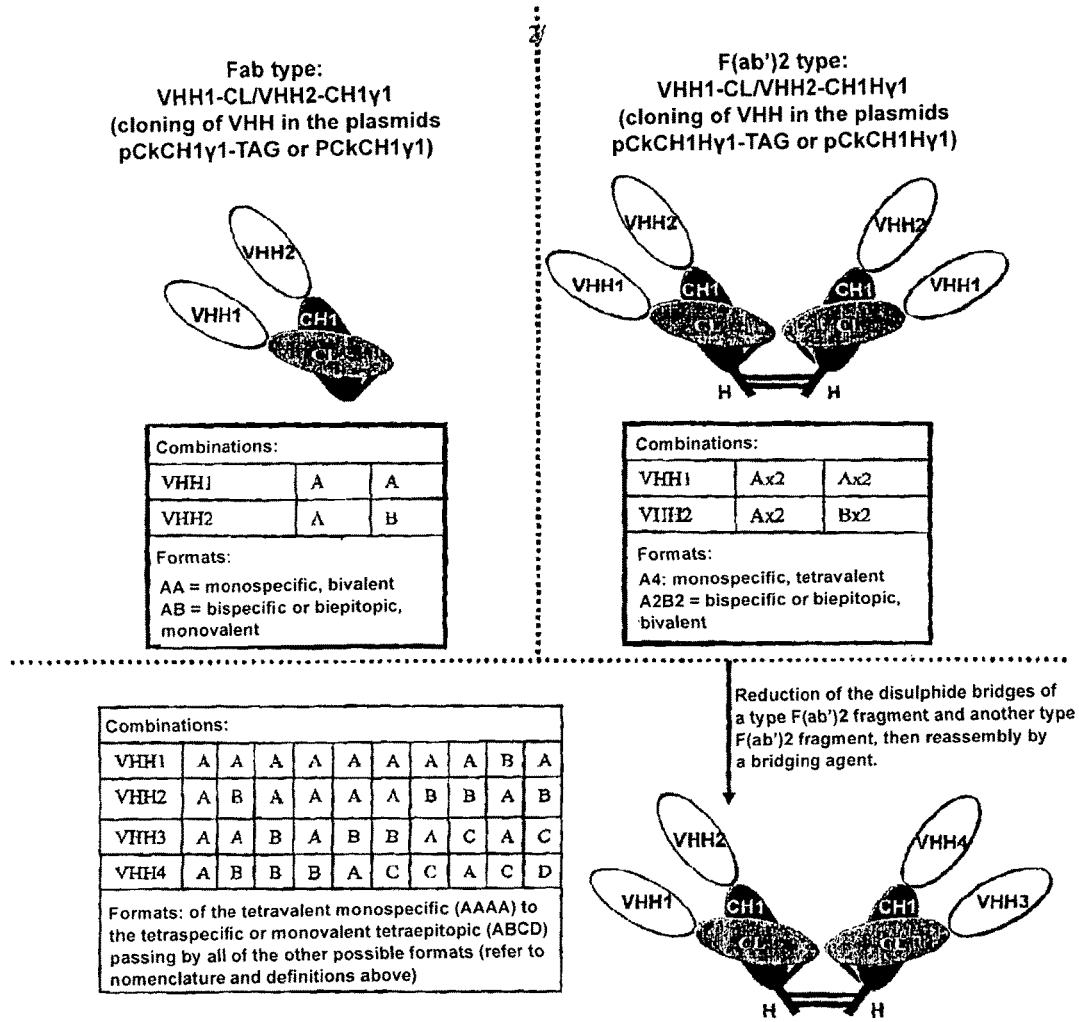

The cloning is carried out as described for the Cκ domain but between the SfiI and NotI sites of p55CκFlag/RBS/35cmyc6HisGS. The resulting plasmid is more commonly called: pCκCH1γ1-TAG; it allows for the production of antibody fragments of Fab type where each chain has a label (FIG. 12A).

p55CκFlag/RBS/35CH1Hγ1cmyc6HisGS (pC5κCH1Hγ1-TAG) (FIGS. 10B and 11)

Insertion of the heavy constant region CH1 and the hinge region (H) of an immunoglobulin of IgG1 type in p55CκFlag/RBS/35cmyc6HisGS. The PCR1, 2a, 2b and 3 are carried out exactly as for the amplification of the CHI domain described above by replacing oligonucleotide 3' Cγ1 by oligonucleotide 3' CH1Hγ1 whose sequence SEQ ID NO:36 is indicated below:

3' CH1Hγ1
SEQ ID NO: 36:
AAGCTTAATCTAGAGCGGCCGCTGGGCACGGTGGGCATGTGTGAGTTTTG

TCACAAGA TTTGGGCTCAACTTTC

The cloning is carried out as described for the CH1γ1 domain between the SfiI and NotI sites of p55CκFlag/RBS/35cmyc6HisGS. The resulting plasmid is commonly called: pCKCH1Hγ1-TAG, it allows for the production of antibody fragments of F(ab')₂ type where each chain has a label (FIG. 12A).

p55Cκ/RBS/35CH1γ1 (pCKCH1γ1) (FIGS. 10B and 11)

Elimination of the Flag and c-myc-6hisGS labels from plasmid p55CκFlag/RBS/35CH1γ1cmyc6HisGS by the replacement of the DNA fragment included between SacII and SfiI by a new cassette using the paired oligonucleotides 5' RBS/35-sup and 3' RBS/35-inf. Sequences SEQ ID NOs: 37 and 38 of the oligonucleotides used:

5' RBS/35-sup
SEQ ID NO: 37:
GGAGAGTGTTAATAAACAGGAAACAGAAGTCCATATGAAATACCTATTGC

CTACGGCA GCCGCTGGATTGTTATTACTCGCGGCCCAGC

SEQ ID NO: 120:
GGAGAGTGTTAATAAACAGGAAACAGAAGTCCATATGAAATATCTTTTAC

CTACGG CAGCCGCAGGTTTGTTGTTACTCGCGGCCCAGC

3' RBS/35-inf
SEQ ID NO: 38:
GGGCCGCGAGTAATAACAATCCAGCGGCTGCCGTAGGCAATAGGTATTTC

ATATGGA CTTCTGTTTCCTGTTTATTAACACTCTCCGC

SEQ ID NO: 121:
GGGCCGCGAGTAACAACAAACCTGCGGCTGCCGTAGGTAAAAGATATTTC

ATATGGAC TTCTGTTTCCTGTTTATTAACACTCTCCGC

The cloning is carried out exactly according to the conditions described for the insertion of MCS1. The resulting intermediate plasmid is called: p55Cκ/RBS/35CH1γ1cmyc6HisGS. The c-myc-6HisGS motif is removed by re-cloning the CH1γ1 domain in p55Cκ/RBS/35CH1γ1cmyc6HisGS.

One PCR is used by amplifying, from 5 ng of plasmid p55CκFlag/RBS/35CH1γ1cmyc6HisGS, the CH1γ1 domain with oligonucleotides 5' CH1γ1 and 3' CH1γ1-STOP. Sequence SEQ ID NO:39 of the oligonucleotide used:

3' CH1γ1-STOP
SEQ ID NO: 39:
CATGCAGTCCCAAGCTTAACAAGATTTGGGCTCAACTTTC

The cloning of the PCR fragment is carried out as described for the Cκ domain, but between the SfiI and HindIII sites of plasmid p55Cκ/RBS/35CH1γ1cmyc6HisGS. The resulting plasmid is commonly called: pCKCH1γ1; it allows for the production of antibody fragments of Fab type (FIG. 12A).

p55Cκ/RBS/35CH1Hγ1 (pCKCH1Hγ1) (FIGS. 10B and 11)

Elimination of the Flag and c-myc-6HisGS labels from the plasmid p55CκFlag/RBS/35CH1Hγ1cmyc6HisGS by replacement of the DNA fragment included between SacII and SfiI by a new cassette using the paired oligonucleotides 5'RBS/35-sup and 3' RBS/35-inf described above. The cloning is carried out exactly according to the conditions described for the insertion of MCS1. The resulting intermediate plasmid is called p55Cκ/RBS/35CH1Hγ1cmyc6HisGS. The c-myc-6HisGS motif is removed by re-cloning the CH1Hγ1 domain in p55Cκ/RBS/35CH1Hγ1 cmyc6HisGS.

One PCR is used by amplifying, from 5 ng of plasmid p55CκFlag/RBS/35CH1Hγ1cmyc6HisGS, the CH1Hγ1 domain with oligonucleotides 5' CH1γ1 and 3' CH1Hγ1-STOP. Sequence SEQ ID NO:40 of the oligonucleotide used:

3' CH1Hγ1-STOP
SEQ ID NO: 40:
CATGCAGTCCCAAGCTTATGGGCACGGTGGGCATGTGTG

The cloning of the PCR fragment is carried out between the SfiI and HindIII sites as described above, but from plasmid p55Cκ/RBS/35CH1Hγ1cmyc6HisGS. The resulting plasmid is commonly called: pCKCH1Hγ1, it allows for the production of antibody fragment of F(ab')₂ type (FIG. 12A).

p55Cκ/RBS/35CH1HCH2CH3γ1 (pMabγI*) (FIGS. 10B and 11)

Insertion of the constant heavy region CH1, of the hinge region (H) and the constant regions CH2 and CH3 of an immunoglobulin of IgG1 type in p55CκFlag/RBS/35CH1γ1cmyc6HisGS. The PCR1, 2a, 2b and 3 are carried out exactly as in the amplification of the CH1 domain described above by replacing oligonucleotide 3' CH1γ1 by oligonucleotide 3' HindIII/H-CH2-CH3: whose sequence SEQ ID NO.41 is indicated below:

```
3' HindIII/H-CH2-CH3
SEQ ID NO: 41:
CCGCCAAAACAGCCAAGCTTATTTACCCGGAGACAGGGAG
```

The cloning is carried out as described for the CH1γ domain between the SfiI and HindIII sites of p55CκFlag/RBS/35CH1γ1cmyc6HisGS. The resulting plasmid is more commonly called: pMAbγI*; it allows for the production of antibody fragments of mAb* type (FIG. 12B).

p55HCH2CH3γ1cmyc6HisGS (pHCH2CH3γ1-TAG) (FIGS. 10B and 11)

Insertion of the hinge region (H) and the constant regions CH2 and CH3 of an immunoglobulin of IgG1 type between the BstEII and NotI sites of p55Flag/RBS/35cmyc6HisGS. The reverse transcription is carried out exactly as described for Cκ, but by using oligonucleotide 3' NotI/H-CH2-CH3. Sequences SEQ ID NOs:42 and 43 of the oligonucleotides used:

```
5'BstE2/H-CH2-CH3
SEQ ID NO: 42:
CCGGCCATGGCCCAGGTCACCGTCTCCTCAGACAAAACTCACACATGCCC

3' NotI/H-CH2-CH3
SEQ ID NO: 43:
AAGCTTAATCTAGAGCGGCCGCTTTACCCGGAGACAGGGAG
```

The PCR after RT is carried out with 1 μl of cDNA, 10 pmoles of each oligonucleotide 5' BstE2/H-CH2-CH3 and 3' NotI/H-CH2-CH3, 0.5 U of Dynazyme (94° C., 3 min; 94° C., 1 min; 60° C., 1 min; 72° C., 1.5 min; 30 cycles then 72° C., 10 min) in a final volume of 50 μl. The resulting plasmid is more commonly called: pHCH2CH3γ1-TAG; it allows for the production of antibody fragments of (HCH2CH3)₂ type with a label at the end of CH3 (FIG. 12B).

p55HCH2CH3γ1 (pHCH2CH3γ1) (FIGS. 10B and 11)

Insertion of the hinge region (H) and constant regions CH2 and CH3 of an immunoglobulin of IgG1 type between the BstEII and HindIII sites of p55Flag/RBS/35cmyc6HisGS. The reverse transcription is carried out exactly as described for Cκ, but by using oligonucleotide 3' HindIII/H-CH2-CH3. Sequences SEQ ID NOs:44 and 45 of the oligonucleotides used:

```
5' BstE2/H-CH2-CH3
SEQ ID NO: 44:
CCGGCCATGGCCCAGGTCACCGTCTCCTCAGACAAAACT
CACACATGCCC

3' HindIII/H-CH2-CH3
SEQ ID NO: 45:
CCGCCAAAACAGCCAAGCTTATTTACCCGGAGACAGGGAG
```

The PCR after RT is carried out with 1 μl of cDNA, 10 pmoles each of oligonucleotides 5' BstE2/H-CH2-CH3 and 3' HindIII/H-CH2-CH3, 0.5 U of Dynazyme (94° C., 3 min; 94° C., 1 min; 60° C., 1 min; 72° C., 1.5 min; 30 cycles then 72° C., 10 min) in a final volume of 50 μl. The resulting plasmid is more commonly called: pHCH2CH3γ1; it allows for the production of antibody fragment of (HCH2CH3)₂ type (FIG. 12B).

Cloning of VHH

In the different formats, any VHH may be introduced between the unique sites: Upstream from Ck: between EcoRI and BstEII (or KpnI); Upstream from CH1: between SfiI and NheI; Upstream from H: EcoRI and BstEII. For this reason, we amplify the different VHH by PCR with the pairs of oligonucleotides 5' and 3' described below: Sequences SEQ ID NOs:46 to 52 of the oligonucleotides used:

```
5' EcoRI-PelB55-PelBPHen
SEQ ID NO: 46:
CGACACCGGAATTCCATATGAAATACCTATTACCAACAGCAGCAGCTGGG
TTATTATTGCTCGCTGCGCAGCCGGCCATGGCCGAGGTGCAGCTG

5'VH1-Sfi
SEQ ID NO: 47:
CATGCCATGACTCGCGGCCCAGCCGGCCATGGCCCAGGTGCAGCTGGTGC
AGTCTGG

5'VH2-Sfi
SEQ ID NO: 48:
CATGCCATGACTCGCGGCCCAGCCGGCCATGGCCCAGGTCACCTTGAAGG
AGTCTGG

5' VH3-Sfi
SEQ ID NO: 49:
CATGCCATGACTCGCGGCCCAGCCGGCCATGGCCGAGGTGCAGCTGGTGG
AGTCTGG

5'VH4-Sfi
SEQ ID NO: 50:
CATGCCATGACTCGCGGCCCAGCCGGCCATGGCCCAGGTGCA GCTGCAG
GAGTCGGG

3' BstEII/KpnI
SEQ ID NO: 51:
GGTGCAGCCACGGTACCTGAGGAGACGGTGACCTG

3' BstE2/NheI
SEQ ID NO: 52:
GGGCCCTTGGTGCTAGCTGAGGAGACGGTGACCTG
```

Production, Purification and Characterisation of Bio-Specific Antibodies.

Figure 13:
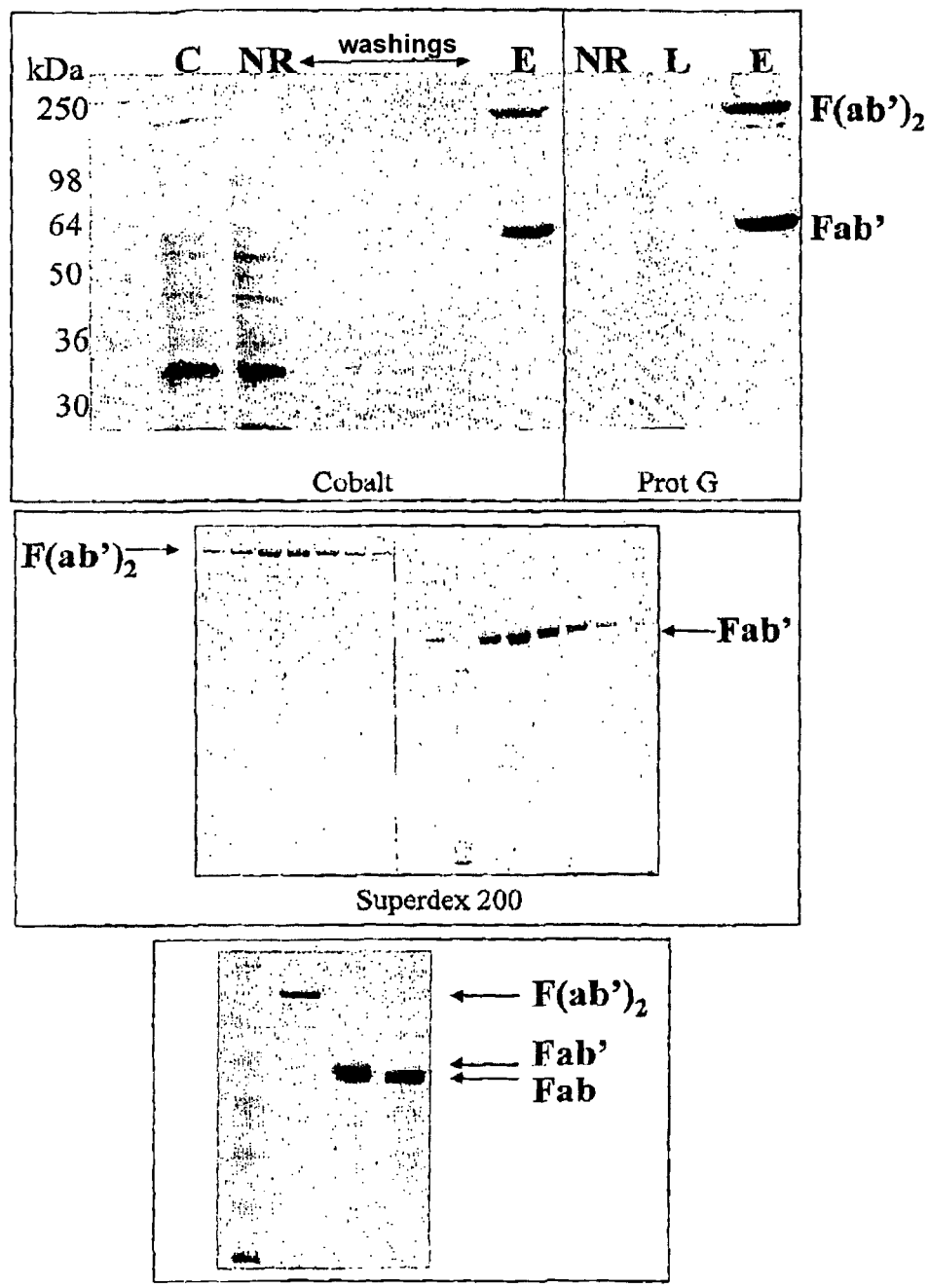
FIG. 13, electrophoresis gels of antibody fragments of type Fab, Fab' and F(ab')2 during different stages of their purification.

The production and purification of the different antibody fragments with the 6HisGS label are carried out as described above. For the purification of antibody fragments without label, the chromatography stage on base is replaced by an ion exchange column whose characteristics (anions or cations) depend on the characteristics of the antibody fragment. Electrophoresis gels are shown in FIG. 13. The Fab' and F(ab)₂ are purified on a•cobalt column and then on protein G. The different antibody fragments are then separated on Superdex 200 (or possibly Superdex 75).

Method to Isolate Human VH and Construction of Vectors.

The principle of the method consists of cloning human VH domains (isolated by RT-PCR from the LFB pouch) in plasmid p55PhoA6HisGS⁻/NAB⁻ (FIGS. 10A and 11). This plasmid has the gene coding for the alkaline phosphatase in a reading frame not allowing for its expression. The cloning of the VH restores the reading frame of the alkaline phosphatase and allows for the production of fused VH upstream from the alkaline phosphatase (bank for VH-PhoA cloned in TG1 bacteria). The different clones are then produced in 96-well microplates and the growth kinetics of the different clones is directly measured every 30 min (OD 620 nm) from the microplates. Thereby, the clones whose growth is not altered by the presence of VH are selected. The clones from the microplates are replicated and stored at −80° C. After 2 hours of induction at 37° C., or 16 hours of induction at 30° C., 24° C., or even 18° C., the growth is stopped and the phosphatase activity is directly measured from the supernatants in the culture medium. The phosphatase activity is then directly correlated with the number of bacteria found in each microplate well.

The alkaline phosphatase is only active if it is secreted in the bacterial periplasm, in dimer form with its disulphate bridges correctly formed. This approach allows for the selection of the clones producing the most fusion protein VH-PhoA secreted in the bacterial culture medium. It is thereby possible to select the VH that are correctly replicated and whose disulphide bridges are correctly formed, and therefore soluble. The selected VH are used as a matrix to exchange the CDR of human VH by the CDR from llama VHH previously described. The VH are chosen by selecting the VH whose amino acids at the CDR junctions are equivalent to those of the VHH.

RT-PCR and PCR Conditions.
Hybridisation:
One μl of whole RNA (purification described in section 1.3.2) is preincubated with 1 pmole of oligonucleotide (mixture of: 3' JH 1-4-5; 3' J 112; 3' JH3 and 3' JH6) for 10 min at 70° C. in a final volume of 8 μl. The temperature is slowly reduced (45 min) to 37° C.
Reverse Transcription:
Take 8 μl and add 0.5 μl of RNAsine (20 U), 3 μl of 5× buffer (SuperScriptII, Invitrogen), 1 μl on, 100 mM, 2 μl dNTP 10 mM and incubate for 10 min at 50° C. Then add 0.75 μl of SuperScript (150 U) and the incubation continues for 30 min at 50° C. and 15 min at 70° C. The cDNA obtained is purified on beads (BioMag Carboxyl Terminated, Polysciences) according to the supplier's recommendations. The final elution is made with 15 μl of 10 mM Tris-acetate pH 7.8.

The PCR1 is carried out with 1 μl of cDNA (obtained by RT-PCR), 10 pmoles of oligonucleotides 5' (0.625 pmole of each oligonucleotide 5' whose sequences are indicated below) and 3' (2.5 pmoles of each oligonucleotide 3' whose sequences are indicated below), 0.5 U of Dynazyme (95° C., 3 min; then 95° C., 1 min; 58° C., 1 min; 72° C., 1 min; for 35 cycles then 72° C., 10 min). The PCR products are deposited on a 2% agarose gel and the bands corresponding to the VH are purified (Qiagen Kit extraction gel). The PCR2 is carried out from 1 μl of PCR1 diluted to 1/1000th, the same quantity of oligonucleotides described above, 0.5 U Deep-Vent for a final volume of 50 μl. (94° C., 3 min; then 94° C., 1 min; 70° C., 1 min; 72° C., 1.5 min; for 40 cycles then 72° C., 10 min). The fragments are purified from 2% agarose gel as described above.

Sequences SEQ ID NO:53 to SEQ ID NO:72 of the oligonucleotides used:

```
5'VH1 a
SEQ ID NO: 53:
CG GCC CAG CCG GCC ATG GCC CAG GTG CAG CTG GTG CAG
TCT GG

5' VH1b
SEQ ID NO: 54:
CG GCC CAG CCG GCC ATG GCC CAG GT(CT) CAG CT(GT)
GTG CAG TCT GG

5' VH1c
SEQ ID NO: 55:
CG GCC CAG CCG GCC ATG GCC (CG)AG GTC CAG CTG GTA
CAG TCT GG

5' VH1d
SEQ ID NO: 56:
CG GCC CAG CCG GCC ATG GCC CA(GA) ATG CAG CTG GTG
CAG TCT GG

5' VH2a
SEQ ID NO: 57:
CG GCC CAG CCG GCC ATG GCC CAG GTC ACC TTG AAG GAG
TCT GG

5' VH2b
SEQ ID NO: 58:
CG GCC CAG CCG GCC ATG GCC CAG ATC ACC TTG AAG GAG
TCT GG

5' VH3a
SEQ ID NO: 59:
CG GCC CAG CCG GCC ATG GCC GAG GTG CAG CTG GTG GAG
TCT GG

5' VH3b
SEQ ID NO: 60:
CG GCC CAG CCG GCC ATG GCC GAA GTG CAG CTG GTG GAG
TCT GG

5' VH3c
SEQ ID NO: 61:
CG GCC CAG CCG GCC ATG GCC CAG GTG CAG CTG GTG GAG
TCT GG

5' VH3d
SEQ ID NO: 62:
CG GCC CAG CCG GCC ATG GCC GAG GTG CAG CTG GTG GAG
(AT)C(TC) (GC)G

5' VH4a
SEQ ID NO: 63:
CG GCC CAG CCG GCC ATG GCC CAG GTG CAG CTG CAG GAG
TCG GG

5' VH4b
SEQ ID NO: 64:
CG GCC CAG CCG GCC ATG GCC CAG CTG CAG CTG CAG GAG
TC(GC) GG

5' VH4c
SEQ ID NO: 65:
CG GCC CAG CCG GCC ATG GCC CAG GTG CAG CTA CAG CAG
TGG GG

5' VH5a
SEQ ID NO: 66:
CG GCC CAG CCG GCC ATG GCC GA(GA) GTG CAG CTG GTG
CAG TCT GG
```

```
5' VH6a
SEQ ID NO: 67:
CG GCC CAG CCG GCC ATG GCC CAG) GTA CAG CTG CAG

CAG TCA GG

5' VH7a
SEQ ID NO: 68:
CG GCC CAG CCG GCC ATG GCC CAG GTG CAG CTG GTG CAA

TCT GG

3' JH1-4-5
SEQ ID NO: 69:
GTC TAG ACG TCC CCC CGG GGA GGA GAC GGT GAC CAG GG

3' JH2
SEQ ID NO: 70:
GTC TAG ACG TCC CCC CGG GGA GGA GAC AGT GAC CAG GG

3' JH3
SEQ ID NO: 71:
GTC TAG ACG TCC CCC CGG GGA AGA GAC GGT GAC CAT TG

3' JH6
SEQ ID NO: 72:
GTC TAG ACG TCC CCC CGG GGA GGA GAC GGT GAC CGT GG
```

The different purified fragments of PCR are digested by 10 U of NcoI and XmaI and inserted in cloning vector p55/PhoA6HisGS⁻/NAB⁻ by ligation. The ligation mixture is digested by FseI before transformation of the bacteria. The transformation is carried out by electroporation with electrocompetent TG1 bacteria. The clones with an inserted VH domain restore the phosphatase activity (blue colonies).

Production in 96 or 384 Well Microplate:

Controls: negative medium control (2YT/ampicillin 100 µg/ml); negative control of vector p55/PhoA6HisGS⁻/NAB⁻; positive control of vector p55PhoA6HisGS/NAB⁻. Distribution of 150 or 40 µl of culture medium (2YT/ampicillin 100 µg/ml) per well (Nunclon Surface, Nunc). Each well is inoculated with an isolated blue colony with a toothpick or a cell pick (Qpix) and the plate is then sealed with a sterile adhesive sheet. Place for 16 h or at 37° C. or 30° C. in an IEMS Thermo plate incubator with stirring at 900 rpm and then make a replica of the "mother" microplate with a 96 or 384 well replicator in a microplate containing 150 or 40 µl of 2YT/ampicillin 100 µg/ml then seal with a sterile adhesive sheet. (After making the replica, add in the mother microplate 37.5 or 10 µl of 80% glycerol per well and store at 80° C.). After 3 h of culture (about OD 620 nm 0.5), induce for 16 h with 100 µM final of IPTG. The OD at 620 nm is measured at the end of induction.

Assay of the Alkaline Phosphatase Activity:

Take 10 µl of the whole culture (cells+culture medium) and 10 µl of culture supernatant (for this, centrifuge for 3 min at 910×g). To each sample, add 65 µl 10 mM Tris-HCl pH 8.0 and add 25 µl of PNPP (paranitrophenyl phosphate) at 1 mg/ml in (diethanolamine pH 9.8 (HCl); MgCl$_2$ 0.5 mM). After 30 min of reaction while stirring, measure the OD at 405 nm.

The alkaline phosphatase activity measured at 405 nm is corrected according to the number of cells (OD measurement 620 nm) contained in each well at the end of induction. Each phosphatase activity, of the clones expressing a VH fused to the alkaline phosphatase, is compared with that of the positive control (non-fused alkaline phosphatase produced by p55PhoA6HisGS/NAB⁻, SEQ. ID NO: 91). Only the clones with an activity equal or greater than the control are taken into account and sequenced with oligonucleotides 5' EcoRI-90 SEQ. ID NO: 12) and 3' inf-PstI+71 (sequence of oligonucleotide 3' inf-PstI+71: GTTAAACGGCGAG-CACCG, SEQ. ID NO: 122).

REFERENCES

1. Hamers-Casterman C, Atarhouch T, Muyldermans S, Robinson G, Hamers C, Sanga E B, Bendahinan N, Harriers R. Naturally occurring antibodies devoid of light chains. *Nature* 1993, 363:446-448.
2. Teillaud C, Galon J, Zilber M T, Mazieres N, Spagnoli R, Kurrle R, Fridman W H, Sautes C. Soluble CD16 binds peripheral blood mononuclear cells and inhibits pokeweed-nitrogen-induced responses. *Blood,* 1993, 82:3081-3090).
3. Terskikh, A, Mach, J P, and Pelegrin A. Marked increase in the secretion of a fully antigenic recombinant CEA obtained by deletion of its hydrophobic tail. *Mol Immunol,* 1993, 30:921-927.
4. Chomczynski P, Sacchi N. Single-step method of RNA isolation by acid guanidinium thiocyanate-phenol-chloroform extraction. *Anal Biochem,* 1987, 162:156-159.
5. Arbabi Ghahroudi M, Desmyter A, Wyns L, Hamers R, Muyldermans S. Selection and identification of single domain antibody fragments from camel heavy-chain antibodies. *FEBS Lett,* 1997, 414:521-526.
6. Vivier E, Rochet N, Ackerly M, Petrini J, Levine H, Daley J, Anderson P. Signaling function of reconstituted CD16: zeta: gamma receptor complex isoforms. *Int Immunol,* 1992, 4:1313-1323.
7. Vely F, Gruel N, Moncuit J, Cochet O, Rouard H, Dard S, Galon J, Sautes C, Fridman W H, Teillaud J-L. A new set of monoclonal antibodies against human FcgammaRII (CD32) and FcgammaRIII (CD16): characterization and use in various assays. *Hybridoma,* 1997, 16:519-528.
8. Le Calvez H, Fieschi J, Green J M, Marchesi N, Chauveau J, Saty D. Paratope characterisation by structural modelling of two anti-cortisol single-chain variable fragments produced in *E. coli. Mol. Immunol,* 1995, 32: 185-198.
9. Le Calvez H, Green J M, Baty D. Increased efficiency of alkaline phosphatase production levels in *Escherichia coli* using a degenerate PeIB signal sequence. *Gene,* 1996, 170:51-55.

What is claimed:

1. Antibody formats wherein said antibody formats are of Fab type and comprise, in association, two different VHH domains wherein a first VHH domain is directly fused to a constant Cκ or human Cλ domain, and a second VHH domain is directly fused to a CH1 domain of an immunoglobulin.

2. Antibody formats wherein said antibody formats are of Fab type and comprise, in association, two different VHH domains wherein a first VHH domain is directly fused to a constant Cκ or human Cλ domain, and a second VHH domain is directly fused to a CH1 domain of an immunoglobulin, and wherein the immunoglobulin is an IgG corresponding to a human isoform IgG1, IgG2, IgG3 or IgG4 or a human IgA corresponding to an isoform IgA1 or IgA2.

3. Pharmaceutical compositions, comprising at least one antibody format according to claim 1.

* * * * *

SEQUENCE LISTING

```
<160> NUMBER OF SEQ ID NOS: 122

<210> SEQ ID NO 1
<211> LENGTH: 21
<212> TYPE: DNA
<213> ORGANISM: Artificial sequence
<220> FEATURE:
<223> OTHER INFORMATION: primer 3? CH2FORTA4
```

```
<400> SEQUENCE: 1
cgccatcaag gtaccagttg a                                              21

<210> SEQ ID NO 2
<211> LENGTH: 23
<212> TYPE: DNA
<213> ORGANISM: Artificial sequence
<220> FEATURE:
<223> OTHER INFORMATION: primer 3? CH2-2

<400> SEQUENCE: 2
ggtacgtgct gttgaactgt tcc                                            23

<210> SEQ ID NO 3
<211> LENGTH: 26
<212> TYPE: DNA
<213> ORGANISM: Artificial sequence
<220> FEATURE:
<223> OTHER INFORMATION: primer 3? RC-IgG2

<400> SEQUENCE: 3
ggagctgggg tcttcgctgt ggtgcg                                         26

<210> SEQ ID NO 4
<211> LENGTH: 57
<212> TYPE: DNA
<213> ORGANISM: Artificial sequence
<220> FEATURE:
<223> OTHER INFORMATION: primer 3? RC-IgG3

<400> SEQUENCE: 4
catgccatga ctcgcggccc agccggccat ggcccaggtg cagctggtgc agtctgg       57

<210> SEQ ID NO 5
<211> LENGTH: 26
<212> TYPE: DNA
<213> ORGANISM: Artificial sequence
<220> FEATURE:
<223> OTHER INFORMATION: primer 5? VH1-Sfi

<400> SEQUENCE: 5
tggttgtggt tttggtgtct tgggtt                                         26

<210> SEQ ID NO 6
<211> LENGTH: 57
<212> TYPE: DNA
<213> ORGANISM: Artificial sequence
<220> FEATURE:
<223> OTHER INFORMATION: primer 5? VH2-Sfi

<400> SEQUENCE: 6
catgccatga ctcgcggccc agccggccat ggcccaggtc accttgaagg agtctgg       57

<210> SEQ ID NO 7
<211> LENGTH: 57
<212> TYPE: DNA
<213> ORGANISM: Artificial sequence
<220> FEATURE:
<223> OTHER INFORMATION: primer 5?VH3-Sfi

<400> SEQUENCE: 7
catgccatga ctcgcggccc agccggccat ggccgaggtg cagctggtgg agtctgg       57

<210> SEQ ID NO 8
<211> LENGTH: 57
```

```
<212> TYPE: DNA
<213> ORGANISM: Artificial sequence
<220> FEATURE:
<223> OTHER INFORMATION: primer 5?VH4-Sfi

<400> SEQUENCE: 8
catgccatga ctcgcggccc agccggccat ggcccaggtg cagctgcagg agtcggg      57

<210> SEQ ID NO 9
<211> LENGTH: 41
<212> TYPE: DNA
<213> ORGANISM: Artificial sequence
<220> FEATURE:
<223> OTHER INFORMATION: primer 3?VHH-Not

<400> SEQUENCE: 9
cacgattctg cggccgctga ggagacaggt gacctgggtc c                       41

<210> SEQ ID NO 10
<211> LENGTH: 44
<212> TYPE: DNA
<213> ORGANISM: Artificial sequence
<220> FEATURE:
<223> OTHER INFORMATION: primer 5?pJF-VH3-Sfi

<400> SEQUENCE: 10
ctttactatt ctcacggcca tggcggccga ggtgcagctg gtgg                    44

<210> SEQ ID NO 11
<211> LENGTH: 72
<212> TYPE: DNA
<213> ORGANISM: Artificial sequence
<220> FEATURE:
<223> OTHER INFORMATION: primer 3'cmyc-6His/HindIII

<400> SEQUENCE: 11
ccgcgcgcgc caagacccaa gcttgggcta gatggatgga tggatggatg gatgtgcggc    60
cccattcaga tc                                                       72

<210> SEQ ID NO 12
<211> LENGTH: 25
<212> TYPE: DNA
<213> ORGANISM: Artificial sequence
<220> FEATURE:
<223> OTHER INFORMATION: primer EcoRI-90

<400> SEQUENCE: 12
gcgccgacat cataacggtt ctggc                                         25

<210> SEQ ID NO 13
<211> LENGTH: 17
<212> TYPE: DNA
<213> ORGANISM: Artificial sequence
<220> FEATURE:
<223> OTHER INFORMATION: primer HindIII+88

<400> SEQUENCE: 13
cgctactgcc gccaggc                                                  17

<210> SEQ ID NO 14
<211> LENGTH: 19
<212> TYPE: DNA
<213> ORGANISM: Artificial sequence
<220> FEATURE:
<223> OTHER INFORMATION: primer amont-RsrII
```

```
<400> SEQUENCE: 14
ggcacatgtg acctcgcgc                                              19

<210> SEQ ID NO 15
<211> LENGTH: 22
<212> TYPE: DNA
<213> ORGANISM: Artificial sequence
<220> FEATURE:
<223> OTHER INFORMATION: primer NcoI-sup

<400> SEQUENCE: 15
gcaacgtacc acggcaatat cg                                          22

<210> SEQ ID NO 16
<211> LENGTH: 22
<212> TYPE: DNA
<213> ORGANISM: Artificial sequence
<220> FEATURE:
<223> OTHER INFORMATION: primer NcoI-inf

<400> SEQUENCE: 16
cgatattgcc gtggtacgtt gc                                          22

<210> SEQ ID NO 17
<211> LENGTH: 22
<212> TYPE: DNA
<213> ORGANISM: Artificial sequence
<220> FEATURE:
<223> OTHER INFORMATION: primer aval-EcoNI

<400> SEQUENCE: 17
gccatctttg gtatttagcg cc                                          22

<210> SEQ ID NO 18
<211> LENGTH: 23
<212> TYPE: DNA
<213> ORGANISM: Artificial sequence
<220> FEATURE:
<223> OTHER INFORMATION: primer XhoI-SacI

<400> SEQUENCE: 18
ccatggcggc cgatcctcga gag                                         23

<210> SEQ ID NO 19
<211> LENGTH: 67
<212> TYPE: DNA
<213> ORGANISM: Artificial sequence
<220> FEATURE:
<223> OTHER INFORMATION: primer 6HisGS/HindIII

<400> SEQUENCE: 19
catgcagtcc caagcttatt agctcccgtg atggtgatga tgatgtttca gccccagagc    60
ggctttc                                                           67

<210> SEQ ID NO 20
<211> LENGTH: 20
<212> TYPE: DNA
<213> ORGANISM: Artificial sequence
<220> FEATURE:
<223> OTHER INFORMATION: primer amont-EcoRV

<400> SEQUENCE: 20
catgagctgt cttcggtatc                                             20
```

```
<210> SEQ ID NO 21
<211> LENGTH: 38
<212> TYPE: DNA
<213> ORGANISM: Artificial sequence
<220> FEATURE:
<223> OTHER INFORMATION: primer ApaI-BstEII-sup

<400> SEQUENCE: 21
taatggtccc gctaacagcg cgatttgctg atgaccca                              38

<210> SEQ ID NO 22
<211> LENGTH: 38
<212> TYPE: DNA
<213> ORGANISM: Artificial sequence
<220> FEATURE:
<223> OTHER INFORMATION: primer BstEII-ApaI-inf

<400> SEQUENCE: 22
tgggtcatca gcaaatcgcg ctgttagcgg gaccatta                              38

<210> SEQ ID NO 23
<211> LENGTH: 19
<212> TYPE: DNA
<213> ORGANISM: Artificial sequence
<220> FEATURE:
<223> OTHER INFORMATION: primer aval-MluI

<400> SEQUENCE: 23
gaacgaagcg gcgtcgaag                                                   19

<210> SEQ ID NO 24
<211> LENGTH: 84
<212> TYPE: DNA
<213> ORGANISM: Artificial sequence
<220> FEATURE:
<223> OTHER INFORMATION: linker 5' MCS1

<400> SEQUENCE: 24
catggcccag gtcaccgtct cctcaaaccg cggactcgag gcggcccagc cggccatggc     60
cgctagcgcg gccgctctag atta                                            84

<210> SEQ ID NO 25
<211> LENGTH: 84
<212> TYPE: DNA
<213> ORGANISM: Artificial sequence
<220> FEATURE:
<223> OTHER INFORMATION: linker 3' MCS1

<400> SEQUENCE: 25
agcttaatct agagcggccg cgctagcggc catggccggc tgggccgcct cgagtccgcg     60
gtttgaggag acggtgacct gggc                                            84

<210> SEQ ID NO 26
<211> LENGTH: 119
<212> TYPE: DNA
<213> ORGANISM: Artificial sequence
<220> FEATURE:
<223> OTHER INFORMATION: linker 5' flag/rbs/35-sup

<400> SEQUENCE: 26
ggagagtgtg caggtgatta caaagacgat gacgataagt aataaacagg aaacagaagt     60
ccatatgaaa tacctattgc ctacggcagc cgctggattg ttattactcg cggcccagc     119

<210> SEQ ID NO 27
```

```
<211> LENGTH: 118
<212> TYPE: DNA
<213> ORGANISM: Artificial sequence
<220> FEATURE:
<223> OTHER INFORMATION: linker 3'flag/RBS/35-inf

<400> SEQUENCE: 27
gggccgcgag taataacaat ccagcggctg ccgtaggcaa taggtatttc atatggactt    60
ctgtttcctg tttattactt atcgtcatcg tctttgtaat cacctgcaca ctctccgc   118

<210> SEQ ID NO 28
<211> LENGTH: 75
<212> TYPE: DNA
<213> ORGANISM: Artificial sequence
<220> FEATURE:
<223> OTHER INFORMATION: linker 5' c-myc-6HISGS

<400> SEQUENCE: 28
ggccgcagaa caaaaactca tctcagaaga ggatctgaat ggggccgtac atcaccacca    60
tcaccatggg agcta                                                    75

<210> SEQ ID NO 29
<211> LENGTH: 75
<212> TYPE: DNA
<213> ORGANISM: Artificial sequence
<220> FEATURE:
<223> OTHER INFORMATION: linker 3' c-myc-6HISGS

<400> SEQUENCE: 29
agcttagctc ccatggtgat ggtggtgatg tacggcccca ttcagatcct cttctgagat    60 gagttttttgt tctgc                                                   75

<210> SEQ ID NO 30
<211> LENGTH: 59
<212> TYPE: DNA
<213> ORGANISM: Artificial sequence
<220> FEATURE:
<223> OTHER INFORMATION: linker 5' Ck

<400> SEQUENCE: 30
ggggccaggg gacccaggtc accgtctcct caggtaccgt ggctgcacca tctgtcttc     59

<210> SEQ ID NO 31
<211> LENGTH: 57
<212> TYPE: DNA
<213> ORGANISM: Artificial sequence
<220> FEATURE:
<223> OTHER INFORMATION: linker 3'Ck

<400> SEQUENCE: 31
cgtcatcgtc tttgtaatca cctgcacact ctccgcggtt gaagctcttt gtcaccg       57

<210> SEQ ID NO 32
<211> LENGTH: 49
<212> TYPE: DNA
<213> ORGANISM: Artificial sequence
<220> FEATURE:
<223> OTHER INFORMATION: linker 5'CH1y1

<400> SEQUENCE: 32
ctcgaggcgg cccagccggc catggccgct agcaccaagg gcccatcgg                49

<210> SEQ ID NO 33
<211> LENGTH: 44
```

```
<212> TYPE: DNA
<213> ORGANISM: Artificial sequence
<220> FEATURE:
<223> OTHER INFORMATION: linker 3' CH1y1

<400> SEQUENCE: 33
aagcttaatc tagagcggcc gcacaagatt tgggctcaac tttc                44

<210> SEQ ID NO 34
<211> LENGTH: 29
<212> TYPE: DNA
<213> ORGANISM: Artificial sequence
<220> FEATURE:
<223> OTHER INFORMATION: linker BstEII-sup

<400> SEQUENCE: 34
ccctcagcag cgtagtgacc gtgccctcc                                 29

<210> SEQ ID NO 35
<211> LENGTH: 29
<212> TYPE: DNA
<213> ORGANISM: Artificial sequence
<220> FEATURE:
<223> OTHER INFORMATION: linker BstEII-inf

<400> SEQUENCE: 35
ggagggcacg gtcactacgc tgctgaggg                                 29

<210> SEQ ID NO 36
<211> LENGTH: 74
<212> TYPE: DNA
<213> ORGANISM: Artificial sequence
<220> FEATURE:
<223> OTHER INFORMATION: linker 3'CHHy1

<400> SEQUENCE: 36
aagcttaatc tagagcggcc gctgggcacg gtgggcatgt gtgagttttg tcacaagatt    60
tgggctcaac tttc                                                     74

<210> SEQ ID NO 37
<211> LENGTH: 89
<212> TYPE: DNA
<213> ORGANISM: Artificial sequence
<220> FEATURE:
<223> OTHER INFORMATION: linker 5'RBS/35-inf

<400> SEQUENCE: 37
ggagagtgtt aataaacagg aaacagaagt ccatatgaaa tacctattgc ctacggcagc    60
cgctggattg ttattactcg cggcccagc                                     89

<210> SEQ ID NO 38
<211> LENGTH: 88
<212> TYPE: DNA
<213> ORGANISM: Artificial sequence
<220> FEATURE:
<223> OTHER INFORMATION: linker 3'RBS/35-inf

<400> SEQUENCE: 38
gggccgcgag taataacaat ccagcggctg ccgtaggcaa taggtatttc atatggactt    60
ctgtttcctg tttattaaca ctctccgc                                      88

<210> SEQ ID NO 39
<211> LENGTH: 40
<212> TYPE: DNA
```

<213> ORGANISM: Artificial sequence
<220> FEATURE:
<223> OTHER INFORMATION: primer 3' CH1y1-STOP

<400> SEQUENCE: 39
catgcagtcc caagcttaac aagatttggg ctcaactttc          40

<210> SEQ ID NO 40
<211> LENGTH: 39
<212> TYPE: DNA
<213> ORGANISM: Artificial sequence
<220> FEATURE:
<223> OTHER INFORMATION: primer 3' CH1Hy1-STOP

<400> SEQUENCE: 40
catgcagtcc caagcttatg ggcacggtgg gcatgtgtg          39

<210> SEQ ID NO 41
<211> LENGTH: 40
<212> TYPE: DNA
<213> ORGANISM: Artificial sequence
<220> FEATURE:
<223> OTHER INFORMATION: primer 3' HINDIII/H-CH2-CH3

<400> SEQUENCE: 41
ccgccaaaac agccaagctt atttacccgg agacagggag          40

<210> SEQ ID NO 42
<211> LENGTH: 50
<212> TYPE: DNA
<213> ORGANISM: Artificial sequence
<220> FEATURE:
<223> OTHER INFORMATION: primer 5' BstE2/H-CH2-CH3

<400> SEQUENCE: 42
ccggccatgg cccaggtcac cgtctcctca gacaaaactc acacatgccc          50

<210> SEQ ID NO 43
<211> LENGTH: 41
<212> TYPE: DNA
<213> ORGANISM: Artificial sequence
<220> FEATURE:
<223> OTHER INFORMATION: primer 3'Not/H-CH2-CH3

<400> SEQUENCE: 43
aagcttaatc tagagcggcc gctttacccg gagacaggga g          41

<210> SEQ ID NO 44
<211> LENGTH: 50
<212> TYPE: DNA
<213> ORGANISM: Artificial sequence
<220> FEATURE:
<223> OTHER INFORMATION: primer 5' BstE2/H-CH2-CH3

<400> SEQUENCE: 44
ccggccatgg cccaggtcac cgtctcctca gacaaaactc acacatgccc          50

<210> SEQ ID NO 45
<211> LENGTH: 40
<212> TYPE: DNA
<213> ORGANISM: Artificial sequence
<220> FEATURE:
<223> OTHER INFORMATION: primer 3'HindIII/H-CH2-CH3

<400> SEQUENCE: 45
ccgccaaaac agccaagctt atttacccgg agacagggag          40

<210> SEQ ID NO 46
<211> LENGTH: 95
<212> TYPE: DNA
<213> ORGANISM: Artificial sequence
<220> FEATURE:
<223> OTHER INFORMATION: primer 5' EcoR1-PelB55-PelBPHen

<400> SEQUENCE: 46
cgacaccgga attccatatg aaatacctat taccaacagc agcagctggg ttattattgc      60
tcgctgcgca gccggccatg gccgaggtgc agctg      95

<210> SEQ ID NO 47
<211> LENGTH: 57
<212> TYPE: DNA
<213> ORGANISM: Artificial sequence
<220> FEATURE:
<223> OTHER INFORMATION: primer 5'VH1-Sfi

<400> SEQUENCE: 47
catgccatga ctcgcggccc agccggccat ggcccaggtg cagctggtgc agtctgg      57

<210> SEQ ID NO 48
<211> LENGTH: 57
<212> TYPE: DNA
<213> ORGANISM: Artificial sequence
<220> FEATURE:
<223> OTHER INFORMATION: primer 5'VH2-Sfi

<400> SEQUENCE: 48
catgccatga ctcgcggccc agccggccat ggcccaggtc accttgaagg agtctgg      57

<210> SEQ ID NO 49
<211> LENGTH: 57
<212> TYPE: DNA
<213> ORGANISM: Artificial sequence
<220> FEATURE:
<223> OTHER INFORMATION: primer 5'VH3-Sfi

<400> SEQUENCE: 49
catgccatga ctcgcggccc agccggccat ggccgaggtg cagctggtgg agtctgg      57

<210> SEQ ID NO 50
<211> LENGTH: 57
<212> TYPE: DNA
<213> ORGANISM: Artificial sequence
<220> FEATURE:
<223> OTHER INFORMATION: primer 5'VH4-Sfi

<400> SEQUENCE: 50
catgccatga ctcgcggccc agccggccat ggcccaggtg cagctgcagg agtcggg      57

<210> SEQ ID NO 51
<211> LENGTH: 35
<212> TYPE: DNA
<213> ORGANISM: Artificial sequence
<220> FEATURE:
<223> OTHER INFORMATION: primer 3' BstE2/KpnI

<400> SEQUENCE: 51
ggtgcagcca cggtacctga ggagacggtg acctg      35

<210> SEQ ID NO 52
<211> LENGTH: 35
<212> TYPE: DNA

```
<213> ORGANISM: Artificial sequence
<220> FEATURE:
<223> OTHER INFORMATION: primer 3' BstE2/NheI

<400> SEQUENCE: 52
gggcccttgg tgctagctga ggagacggtg acctg                          35

<210> SEQ ID NO 53
<211> LENGTH: 43
<212> TYPE: DNA
<213> ORGANISM: Artificial sequence
<220> FEATURE:
<223> OTHER INFORMATION: primer 5' VH1a

<400> SEQUENCE: 53
cggcccagcc ggccatggcc caggtgcagc tggtgcagtc tgg                 43

<210> SEQ ID NO 54
<211> LENGTH: 45
<212> TYPE: DNA
<213> ORGANISM: Artificial sequence
<220> FEATURE:
<223> OTHER INFORMATION: primer 5' VH1b

<400> SEQUENCE: 54
cggcccagcc ggccatggcc caggtctcag ctgtgtgcag tctgg               45

<210> SEQ ID NO 55
<211> LENGTH: 44
<212> TYPE: DNA
<213> ORGANISM: Artificial sequence
<220> FEATURE:
<223> OTHER INFORMATION: primer 5'VH1c

<400> SEQUENCE: 55
cggcccagcc ggccatggcc cgaggtccag ctggtacagt ctgg                44

<210> SEQ ID NO 56
<211> LENGTH: 44
<212> TYPE: DNA
<213> ORGANISM: Artificial sequence
<220> FEATURE:
<223> OTHER INFORMATION: primer 5'VH1d

<400> SEQUENCE: 56
cggcccagcc ggccatggcc cagaatgcag ctggtgcagt ctgg                44

<210> SEQ ID NO 57
<211> LENGTH: 43
<212> TYPE: DNA
<213> ORGANISM: Artificial sequence
<220> FEATURE:
<223> OTHER INFORMATION: primer 5'VH2a

<400> SEQUENCE: 57
cggcccagcc ggccatggcc caggtcacct tgaaggagtc tgg                 43

<210> SEQ ID NO 58
<211> LENGTH: 43
<212> TYPE: DNA
<213> ORGANISM: Artificial sequence
<220> FEATURE:
<223> OTHER INFORMATION: primer 5' VH2b

<400> SEQUENCE: 58
cggcccagcc ggccatggcc cagatcacct tgaaggagtc tgg                 43
```

<210> SEQ ID NO 59
<211> LENGTH: 43
<212> TYPE: DNA
<213> ORGANISM: Artificial sequence
<220> FEATURE:
<223> OTHER INFORMATION: primer 5'VH3a

<400> SEQUENCE: 59
cggcccagcc ggccatggcc gaggtgcagc tggtggagtc tgg        43

<210> SEQ ID NO 60
<211> LENGTH: 43
<212> TYPE: DNA
<213> ORGANISM: Artificial sequence
<220> FEATURE:
<223> OTHER INFORMATION: primer 5'VH3b

<400> SEQUENCE: 60
cggcccagcc ggccatggcc gaagtgcagc tggtggagtc tgg        43

<210> SEQ ID NO 61
<211> LENGTH: 43
<212> TYPE: DNA
<213> ORGANISM: Artificial sequence
<220> FEATURE:
<223> OTHER INFORMATION: primer 5'VH3c

<400> SEQUENCE: 61
cggcccagcc ggccatggcc caggtgcagc tggtggagtc tgg        43

<210> SEQ ID NO 62
<211> LENGTH: 46
<212> TYPE: DNA
<213> ORGANISM: Artificial sequence
<220> FEATURE:
<223> OTHER INFORMATION: primer 5'VH3d

<400> SEQUENCE: 62
cggcccagcc ggccatggcc gaggtgcagc tggtggagat ctcgcg     46

<210> SEQ ID NO 63
<211> LENGTH: 43
<212> TYPE: DNA
<213> ORGANISM: Artificial sequence
<220> FEATURE:
<223> OTHER INFORMATION: primer 5' VH4a

<400> SEQUENCE: 63
cggcccagcc ggccatggcc caggtgcagc tgcaggagtc ggg        43

<210> SEQ ID NO 64
<211> LENGTH: 44
<212> TYPE: DNA
<213> ORGANISM: Artificial sequence
<220> FEATURE:
<223> OTHER INFORMATION: primer 5'VH4b

<400> SEQUENCE: 64
cggcccagcc ggccatggcc cagctgcagc tgcaggagtc gcgg       44

<210> SEQ ID NO 65
<211> LENGTH: 43
<212> TYPE: DNA
<213> ORGANISM: Artificial sequence
<220> FEATURE:

```
<223> OTHER INFORMATION: primer 5' VH4c

<400> SEQUENCE: 65
cggcccagcc ggccatggcc caggtgcagc tacagcagtg ggg                    43

<210> SEQ ID NO 66
<211> LENGTH: 44
<212> TYPE: DNA
<213> ORGANISM: Artificial sequence
<220> FEATURE:
<223> OTHER INFORMATION: primer 5'VH5a

<400> SEQUENCE: 66
cggcccagcc ggccatggcc gagagtgcag ctggtgcagt ctgg                   44

<210> SEQ ID NO 67
<211> LENGTH: 43
<212> TYPE: DNA
<213> ORGANISM: Artificial sequence
<220> FEATURE:
<223> OTHER INFORMATION: primer 5'VH6a

<400> SEQUENCE: 67
cggcccagcc ggccatggcc caggtacagc tgcagcagtc agg                    43

<210> SEQ ID NO 68
<211> LENGTH: 43
<212> TYPE: DNA
<213> ORGANISM: Artificial sequence
<220> FEATURE:
<223> OTHER INFORMATION: primer 5'VH7a

<400> SEQUENCE: 68
cggcccagcc ggccatggcc caggtgcagc tggtgcaatc tgg                    43

<210> SEQ ID NO 69
<211> LENGTH: 38
<212> TYPE: DNA
<213> ORGANISM: Artificial sequence
<220> FEATURE:
<223> OTHER INFORMATION: primer 3' JH1-4-5

<400> SEQUENCE: 69
gtctagacgt cccccggggg aggagacggt gaccaggg                          38

<210> SEQ ID NO 70
<211> LENGTH: 38
<212> TYPE: DNA
<213> ORGANISM: Artificial sequence
<220> FEATURE:
<223> OTHER INFORMATION: primer 3'JH2

<400> SEQUENCE: 70
gtctagacgt cccccggggg aggagacagt gaccaggg                          38

<210> SEQ ID NO 71
<211> LENGTH: 38
<212> TYPE: DNA
<213> ORGANISM: Artificial sequence
<220> FEATURE:
<223> OTHER INFORMATION: primer 3'JH3

<400> SEQUENCE: 71
gtctagacgt cccccggggg aagagacggt gaccattg                          38
```

<210> SEQ ID NO 72
<211> LENGTH: 38
<212> TYPE: DNA
<213> ORGANISM: Artificial sequence
<220> FEATURE:
<223> OTHER INFORMATION: primer 3'JH6

<400> SEQUENCE: 72
gtctagacgt cccccgggg aggagacggt gaccgtgg                        38

<210> SEQ ID NO 73
<211> LENGTH: 126
<212> TYPE: PRT
<213> ORGANISM: Artificial sequence
<220> FEATURE:
<223> OTHER INFORMATION: CD 16 c13 amino acid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (109)..(113)
<223> OTHER INFORMATION: Unknown amino acid

<400> SEQUENCE: 73

Glu Val Gln Leu Val Gln Ser Gly Gly Gly Leu Val Gln Pro Gly Gly
1               5                   10                  15

Ser Leu Arg Leu Ser Cys Ser Phe Pro Gly Ser Ile Phe Ser Leu Thr
            20                  25                  30

Met Gly Xaa Xaa Xaa Trp Tyr Arg Gln Ala Pro Gly Lys Glu Arg Glu
        35                  40                  45

Leu Val Thr Ser Ala Thr Xaa Xaa Xaa Pro Gly Gly Asp Thr Asn Tyr
    50                  55                  60

Ala Asp Phe Val Lys Gly Arg Phe Thr Ile Ser Arg Asp Asn Ala Arg
65                  70                  75                  80

Ser Ile Ile Tyr Leu Gln Met Asn Ser Leu Lys Pro Glu Asp Thr Ala
                85                  90                  95

Val Tyr Tyr Cys Tyr Ala Arg Thr Arg Asn Trp Gly Xaa Xaa Xaa Xaa
            100                 105                 110

Xaa Thr Val Trp Gly Gln Gly Thr Gln Val Thr Val Ser Ser
        115                 120                 125

<210> SEQ ID NO 74
<211> LENGTH: 126
<212> TYPE: PRT
<213> ORGANISM: Artificial sequence
<220> FEATURE:
<223> OTHER INFORMATION: CD 16 c21 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (56)..(57)
<223> OTHER INFORMATION: Unknown amino acid

<400> SEQUENCE: 74

Glu Val Gln Leu Val Gln Ser Gly Gly Glu Leu Val Gln Ala Gly Gly
1               5                   10                  15

Ser Leu Arg Leu Ser Cys Ala Ala Ser Gly Leu Thr Phe Ser Ser Tyr

```
                 20                  25                  30
Asn Met Gly Xaa Xaa Trp Phe Arg Arg Ala Pro Gly Lys Glu Arg Glu
             35                  40                  45

Phe Val Ala Ser Ile Thr Trp Xaa Xaa Ser Gly Arg Asp Thr Phe Tyr
         50                  55                  60

Ala Asp Ser Val Lys Gly Arg Phe Thr Ile Ser Arg Asp Asn Ala Lys
 65                  70                  75                  80

Asn Thr Val Tyr Leu Gln Met Ser Ser Leu Lys Pro Glu Asp Thr Ala
                 85                  90                  95

Val Tyr Tyr Cys Ala Ala Asn Pro Trp Pro Val Ala Ala Pro Arg Ser
            100                 105                 110

Gly Thr Tyr Trp Gly Gln Gly Thr Gln Val Thr Val Ser Ser
            115                 120                 125

<210> SEQ ID NO 75
<211> LENGTH: 126
<212> TYPE: PRT
<213> ORGANISM: Artificial sequence
<220> FEATURE:
<223> OTHER INFORMATION: CD16 c28 aminoacid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (113)..(113)
<223> OTHER INFORMATION: Unknown amino acid

<400> SEQUENCE: 75

Glu Val Gln Leu Val Glu Ser Gly Gly Gly Leu Val Gln Pro Gly Glu
 1               5                  10                  15

Ser Leu Thr Leu Ser Cys Val Val Ala Gly Ser Ile Phe Ser Phe Ala
             20                  25                  30

Met Ser Xaa Xaa Xaa Trp Tyr Arg Gln Ala Pro Gly Lys Glu Arg Glu
             35                  40                  45

Leu Val Ala Arg Ile Gly Xaa Xaa Xaa Ser Asp Asp Arg Val Thr Tyr
         50                  55                  60

Ala Asp Ser Val Lys Gly Arg Phe Thr Ile Ser Arg Asp Asn Ile Lys
 65                  70                  75                  80

Arg Thr Ala Gly Leu Gln Met Asn Ser Leu Lys Pro Glu Asp Thr Ala
                 85                  90                  95

Val Tyr Tyr Cys Asn Ala Gln Thr Asp Leu Arg Asp Trp Thr Val Arg
            100                 105                 110

Xaa Glu Tyr Trp Gly Gln Gly Thr Gln Val Thr Val Ser Ser
            115                 120                 125

<210> SEQ ID NO 76
<211> LENGTH: 126
<212> TYPE: PRT
<213> ORGANISM: Artificial sequence
<220> FEATURE:
<223> OTHER INFORMATION: CD 16 c72 aminoacid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
```

```
<222> LOCATION: (55)..(57)
<223> OTHER INFORMATION: Unknown amino acid
<220> FEATURE:
<221> NAME/KEY: MISC_FEATURE
<222> LOCATION: (113)..(113)
<223> OTHER INFORMATION: Unknown amino acid

<400> SEQUENCE: 76

Glu Val Gln Leu Val Glu Ser Gly Gly Gly Leu Val Gln Pro Gly Gly
1               5                   10                  15

Ser Leu Thr Leu Ser Cys Val Ala Ala Gly Ser Ile Phe Thr Phe Ala
            20                  25                  30

Met Ser Xaa Xaa Xaa Trp Tyr Arg Gln Ala Pro Arg Lys Glu Arg Glu
        35                  40                  45

Leu Val Ala Arg Ile Gly Xaa Xaa Xaa Thr Asp Asp Glu Thr Met Tyr
    50                  55                  60

Lys Asp Ser Val Lys Gly Arg Phe Thr Ile Ser Arg Asp Asn Val Lys
65                  70                  75                  80

Arg Thr Ala Gly Leu Gln Met Asn Asn Leu Lys Pro Glu Asp Thr Ala
                85                  90                  95

Val Tyr Tyr Cys Asn Ala Arg Thr Asp Tyr Arg Asp Trp Thr Val Arg
            100                 105                 110

Xaa Glu Tyr Trp Gly Gln Gly Thr Gln Val Thr Val Ser Ser
        115                 120                 125

<210> SEQ ID NO 77
<211> LENGTH: 126
<212> TYPE: PRT
<213> ORGANISM: Artificial sequence
<220> FEATURE:
<223> OTHER INFORMATION: CEA 3 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (56)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 77

Glu Val Gln Leu Val Glu Ser Gly Gly Gly Leu Val Gln Ala Gly Gly
1               5                   10                  15

Ser Leu Arg Leu Ser Cys Thr Ser Ser Thr Val Thr Phe Thr Pro Tyr
            20                  25                  30

Gln Met Gly Xaa Xaa Trp Tyr Arg Gln Ala Pro Gly Lys Gln Arg Ala
        35                  40                  45

Leu Val Ala Asp Ile Ser Thr Xaa Xaa Gly Gly Ser Arg Thr Asn Tyr
    50                  55                  60

Ala Asp Phe Ala Lys Gly Arg Phe Thr Ile Ser Arg Asp Asp Val Lys
65                  70                  75                  80

Asn Thr Val Tyr Leu Gln Met Asn Asn Leu Lys Pro Glu Asp Thr Ala
                85                  90                  95

Val Tyr Tyr Cys Asn Thr Tyr Tyr Ala Met Ile Gly His Ala Xaa Xaa
            100                 105                 110

Xaa Arg Asn Trp Gly Gln Gly Thr Gln Val Thr Val Ser Ser
        115                 120                 125
```

<210> SEQ ID NO 78
<211> LENGTH: 126
<212> TYPE: PRT
<213> ORGANISM: Artificial sequence
<220> FEATURE:
<223> OTHER INFORMATION: CEA 17 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 78

Glu Val Gln Leu Val Glu Ser Gly Gly Gly Phe Val Gln Ala Gly Glu
1               5                   10                  15

Ser Leu Thr Leu Ser Cys Thr Ser Ser Thr Leu Thr Phe Thr Pro Tyr
            20                  25                  30

Arg Met Ala Xaa Xaa Trp Tyr Arg Gln Ala Pro Gly Lys Gln Arg Asp
        35                  40                  45

Leu Val Ala Asp Ile Ser Ser Gly Xaa Asp Gly Arg Thr Thr Asn Tyr
    50                  55                  60

Ala Asp Phe Ala Lys Gly Arg Phe Thr Ile Ser Arg Asp Asn Ile Lys
65                  70                  75                  80

Asn Thr Val Phe Leu Arg Met Thr Asn Leu Lys Pro Glu Asp Thr Ala
                85                  90                  95

Val Tyr Tyr Cys Asn Thr Phe Val Ser Phe Val Gly Ile Ala Xaa Xaa
            100                 105                 110

Xaa Arg Ser Trp Gly Gln Gly Thr Gln Val Thr Val Ser Ser
        115                 120                 125

<210> SEQ ID NO 79
<211> LENGTH: 126
<212> TYPE: PRT
<213> ORGANISM: Artificial sequence
<220> FEATURE:
<223> OTHER INFORMATION: CEA 25 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 79

Glu Val Gln Leu Val Glu Ser Gly Gly Gly Leu Val Gln Ala Gly Asp
1               5                   10                  15

Ser Leu Thr Leu Thr Cys Thr Ser Pro Thr Leu Thr Phe Thr Pro Tyr
            20                  25                  30

Arg Met Gly Xaa Xaa Trp Tyr Arg Gln Ala Pro Gly Lys Gln Arg Asp
        35                  40                  45

Leu Val Ala Asp Ile Ser Gly Gly Xaa Asp Gly Arg Thr Thr Asn Tyr
    50                  55                  60

Ala Asp Phe Ala Lys Gly Arg Phe Thr Ile Ser Arg Asp Asn Val Lys
65                  70                  75                  80

Asn Ala Val Tyr Leu Gln Met Asn Asn Leu Lys Pro Glu Asp Thr Ala
            85                  90                  95

Ile Tyr Tyr Cys Asn Thr Tyr Val Ala Ile Val Gly His Ala Xaa Xaa
            100                 105                 110

Xaa Arg Ser Trp Gly Gln Gly Thr Gln Val Thr Val Ser Ser
        115                 120                 125

<210> SEQ ID NO 80
<211> LENGTH: 126
<212> TYPE: PRT
<213> ORGANISM: Artificial sequence
<220> FEATURE:
<223> OTHER INFORMATION: CEA 43 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 80

Gln Val Gln Leu Gln Glu Ser Gly Gly Gly Leu Val Gln Ala Gly Gly
1               5                   10                  15

Ser Leu Thr Leu Ser Cys Thr Ser Ser Thr Leu Thr Phe Thr Pro Tyr
            20                  25                  30

Arg Met Gly Xaa Xaa Trp Tyr Arg Gln Thr Pro Gly Lys Gln Arg Asp
            35                  40                  45

Leu Val Ala Asp Ile Ser Pro Gly Xaa Asp Gly Ser Thr Lys Asn Tyr
50                  55                  60

Ala Gly Phe Ala Gln Gly Arg Phe Thr Ile Ser Arg Asp Asn Ile Lys
65                  70                  75                  80

Asn Thr Val Tyr Leu Gln Met Asn Asp Leu Lys Pro Glu Asp Thr Ala
            85                  90                  95

Val Tyr Tyr Cys Asn Thr Tyr Val Ala Phe Val Gly Arg Ala Xaa Xaa
            100                 105                 110

Xaa Arg Thr Trp Gly Gln Gly Thr Gln Val Thr Val Thr Ser
        115                 120                 125

<210> SEQ ID NO 81
<211> LENGTH: 345
<212> TYPE: DNA
<213> ORGANISM: Artificial sequence
<220> FEATURE:
<223> OTHER INFORMATION: CD16 cl3

<400> SEQUENCE: 81
gaggtgcagc tggtgcagtc tggggggaggc ttggtgcagc ctggggggtc tctgagactc      60
tcctgttcat tccctggaag catcttcagt ctcaccatgg ctggtaccg tcaggctcca      120 gggaaggagc gcgagttggt cacaagtgct actcctggtg gtgacacaaa ctatgcagac      180
ttcgtgaagg gccgattcac catctccaga gacaacgcca ggagcatcat atatctacaa      240
atgaatagcc tgaaacctga ggacacggcc gtctattatt gttatgcacg tacgaggaat      300

```
tggggtacgg tctggggcca ggggacccag gtcaccgtct cctca         345
```

<210> SEQ ID NO 82
<211> LENGTH: 366
<212> TYPE: DNA
<213> ORGANISM: Artificial sequence
<220> FEATURE:
<223> OTHER INFORMATION: CD16 c21

<400> SEQUENCE: 82

```
gaggtgcagc tggtgcagtc tggggggagag ttggtgcagg ctggggggctc tctgagactc    60
tcctgtgcag cctctggcct caccttcagt agctataaca tgggctggtt ccgccgggct   120
ccagggaagg agcgtgagtt tgtagcatct attacctgga gtggtcggga cacattctat   180
gcagactccg tgaagggccg attcaccatc tccagagaca cgccaagaa cactgtttat   240
ctgcaaatga gcagcctgaa acctgaggac acggccgttt attattgtgc tgcaaacccc   300
tggccagtgg cggcgccacg tagtggcacc tactggggcc aagggaccca ggtcaccgtc   360
tcctca                                                              366
```

<210> SEQ ID NO 83
<211> LENGTH: 357
<212> TYPE: DNA
<213> ORGANISM: Artificial sequence
<220> FEATURE:
<223> OTHER INFORMATION: anti CD16 nucleotide

<400> SEQUENCE: 83

```
gaggtgcagc tggtggagtc tgggggaggc ttagtgcagc ctggggagtc tctgacactc    60
tcctgtgtag ttgctggaag catcttcagc ttcgccatga gctggtatcg ccaggctcca   120
ggaaaagagc gcgaattggt cgcacgtatt ggttcggatg atcgggtaac gtacgcagat   180
tccgtgaagg gccgatttac catctccaga acaacatca gcgcacggc gggcctgcag   240
atgaacagcc tgaaacctga ggacacggcc gtctactact gcaatgccca aacagatttg   300
agggattgga ctgtgcgaga gtactgggc caggggaccc aggtcaccgt ctcctca       357
```

<210> SEQ ID NO 84
<211> LENGTH: 357
<212> TYPE: DNA
<213> ORGANISM: Artificial sequence
<220> FEATURE:
<223> OTHER INFORMATION: anti CD16 nucleotide

<400> SEQUENCE: 84

```
gaggtgcagc tggtggagtc tgggggaggc ttggtgcagc ctgggggggtc tctgacactc    60
tcctgtgttg ccgctggaag catcttcacc ttcgccatga gctggtaccg ccaggctcca   120
cgaaaagagc gcgaattggt cgcacgtatt ggtacggatg acgaaacaat gtacaaagac   180
tccgtgaagg gtcgattcac catctccaga acaacgtca gcgcacggc gggtctgcag   240
atgaacaacc tgaaacccga ggacacggcc gtctactact gcaatgcccg gacagattat   300
agggactgga ctgtccgtga gtactggggc caggggaccc aggtcaccgt ctcctca      357
```

<210> SEQ ID NO 85
<211> LENGTH: 357
<212> TYPE: DNA
<213> ORGANISM: Artificial sequence
<220> FEATURE:
<223> OTHER INFORMATION: VHH anti-cea cea3

<400> SEQUENCE: 85

```
gaggtgcagc tggtggagtc tggggaggc ttggtgcagg ctggggctc tctgagactc      60 tcctgtacca gctctacggt taccttcact ccgtatcaaa tgggctggta ccgccaggct    120
ccagggaagc agcgtgcttt ggtcgcagat attagtacgg gtggtagccg cacaaattat    180
gcggatttcg cgaagggccg attcaccatc tccagagacg acgttaagaa cacggtgtat    240
ctgcaaatga caacctgaa acctgaggac acggccgtct actactgtaa cacctactac     300
gcgatgatag ggcatgcgcg taattgggc caggggaccc aggtcactgt ctcctca        357
```

<210> SEQ ID NO 86
<211> LENGTH: 360
<212> TYPE: DNA
<213> ORGANISM: Artificial sequence
<220> FEATURE:
<223> OTHER INFORMATION: CEA 17

<400> SEQUENCE: 86

```
gaggtgcagc tggtggagtc tggggaggc ttcgtgcagg cggggaatc tctgacgctc      60 tcctgtacaa gttctacact gaccttcact ccgtatcgca tggcctggta ccgccaggct    120
ccagggaagc agcgtgattt agtcgcggat attagtagtg gtgatggtag gaccacaaac    180
tatgcggact tcgcgaaggg ccgattcacc atctccagag acaacatcaa gaacacggtc    240
tttctgcgaa tgactaacct gaaacctgag gacacggccg tctactactg taacaccttc    300
gtttcgtttg tggggattgc gcgttcttgg ggccagggga cccaggtcac tgtctcctca    360
```

<210> SEQ ID NO 87
<211> LENGTH: 360
<212> TYPE: DNA
<213> ORGANISM: Artificial sequence
<220> FEATURE:
<223> OTHER INFORMATION: CEA 25

<400> SEQUENCE: 87

```
gaggtgcagc tggtggagtc tggggaggc ttggtgcagg cggggactc tctgacactg      60 acctgtacaa gccctacact taccttcact ccgtatcgca tgggctggta ccgccaagct    120
ccagggaagc agcgtgattt ggtcgcagat attagtggtg gtgatggtcg taccacaaac    180
tatgcagact tcgcgaaggg ccgattcacc atctccagag acaacgtcaa gaacgcggtc    240
tatctgcaaa tgaacaacct gaaacctgaa gacacggcca tttattactg taacacctac    300
gtcgcgattg tgggccatgc gcgttcctgg ggccagggga cccaggtcac cgtctcctca    360
```

<210> SEQ ID NO 88
<211> LENGTH: 360
<212> TYPE: DNA
<213> ORGANISM: Artificial sequence
<220> FEATURE:
<223> OTHER INFORMATION: nucleotide CEA 43

<400> SEQUENCE: 88

```
caggtgcagc tgcaggagtc tggggaggc ttggtgcagg cggggggctc tctgacactc     60
tcctgcacaa gttctacact taccttcact ccgtatcgca tgggctggta ccgccagact    120
ccagggaagc agcgtgattt ggtcgcggac attagtcctg gtgatggtag taccaaaaat    180
tatgcaggct tcgcgcaggg ccgattcacc atctccagag acaacatcaa gaacacggtg    240
tatctgcaaa tgaacgacct gaaacctgag gacacggccg tctattactg caacacctac    300
gtcgcgtttg tggggcgtgc gcgtacttgg ggccagggga cccaggtcac tgtcacctca    360
```

<210> SEQ ID NO 89
<211> LENGTH: 6715
<212> TYPE: DNA
<213> ORGANISM: Artificial sequence
<220> FEATURE:
<223> OTHER INFORMATION: plasmid p55PhoA5HisGS/N-

<400> SEQUENCE: 89

```
ttgtttattt ttctaaatac attcaaatat gtatccgctc atgagacaat aaccctgata      60
aatgcttcaa taatattgaa aaaggaagag tatgagtatt caacatttcc gtgtcgccct     120
tattcccttt tttgcggcat tttgccttcc tgttttgct cacccagaaa cgctggtgaa      180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttttt   540
gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg cgataagtc    1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatgaa aacgccagc aacgcggcct ttttacggtt     1740
cctggccttt tgctggcctt tgctcacat gttctttcct gcgttatccc ctgattctgt    1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
```

```
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg ctccaattc ttggagtggt    2940 gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttttctttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg ggcccgctaa cagcgcgatt tgctggtgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320 cttttttccccg cgttttcgca gaaacgtggc tggcctggtt caccacgcgg gaaacggtct    4380
gataagagac accggcatac tctgcgacat cgtataacgt tactggtttc acattccacca    4440
```

```
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct cgcagccggc catggcggc cgatcctcga gagctcccgg gctgcagccc      4920
tgttctggaa aaccgggctg ctcagggcga tattactgca cccggcggtg ctcgccgttt    4980
aacgggtgat cagactgccg ctctgcgtga ttctcttagc gataaacctg caaaaaatat    5040
tattttgctg attggcgatg ggatggggga ctcggaaatt actgccgcac gtaattatgc    5100
cgaaggtgcg ggcggctttt ttaaaggtat agatgcctta ccgcttaccg ggcaatacac    5160
tcactatgcg ctgaataaaa aaaccggcaa accggactac gtcaccgact cggctgcatc    5220
agcaaccgcc tggtcaaccg gtgtcaaaac ctataacggc gcgctgggcg tcgatattca    5280
cgaaaaagat cacccaacga ttctggaaat ggcaaaagcc gcaggtctgg cgaccggtaa    5340
cgtttctacc gcagagttgc aggatgccac gcccgctgcg ctggtggcac atgtgacctc    5400
gcgcaaatgc tacggtccga gcgcgaccag tgaaaaatgt ccgggtaacg ctctggaaaa    5460
aggcggaaaa ggatcgatta ccgaacagct gcttaacgct cgtgccgacg ttacgcttgg    5520
cggcggcgca aaaacctttg ctgaaacggc aaccgctggt gaatggcagg aaaaacgct    5580
gcgtgaacag gcacaggcgc gtggttatca gttggtgagc gatgctgcct cactgaattc    5640
ggtgacggaa gcgaatcagc aaaaacccct gcttggcctg tttgctgacg caatatgcc    5700
agtgcgctgg ctaggaccga agcaacgta ccacggcaat atcgataagc cgcagtcac     5760
ctgtacgcca aatccgcaac gtaatgcacag tgtaccaacc ctggcgcaga tgaccgacaa    5820
agccattgaa ttgttgagta aaaatgagaa aggcttttc ctgcaagttg aaggtgcgtc     5880
aatcgataaa caggatcatg ctgcgaatcc ttgtgggcaa attggcgaga cggtcgatct    5940
cgatgaagcc gtacaacggg cgctggaatt cgctaaaaag gagggtaaca cgctggtcat    6000
agtcaccgct gatcacgccc acgcagcca gattgttgcg ccggataccaa aagctccggg    6060
cctcacccag gcgctaaata ccaaagatgg cgcagtgatg gtgatgagtt acgggaactc    6120
cgaagaggat tcacaagaac ataccggcag tcagttgcgt attgcggcgt atggcccgca    6180
tgccgccaat gttgttggac tgaccgacca gaccgatctc ttctacacca tgaaagccgc    6240
tctgggctg aaacatcatc atcaccatca cgggagctaa taagcttctg ttttggcgga    6300
tgagagaaga ttttcagcct gatacagatt aaatcagaac gcagaagcgg tctgataaaa    6360
cagaatttgc ctggcggcag tagcgcggtg gtcccacctg accccatgcc gaactcagaa    6420
gtgaaacgcc gtagcgccga tggtagtgtg gggtctcccc atgcgagagt agggaactgc    6480
caggcatcaa ataaaacgaa aggctcagtc gaaagactgg gcctttcgtt ttatctgttg    6540
tttgtcggtg aacgctctcc tgagtaggac aaatccgccg ggagcggatt tgaacgttgc    6600
gaagcaacgg cccggaggac cctggcgggc aggacgcccg ccataaactg ccaggcatca    6660
aattaagcag aaggccatcc tgacggatgg ccttttttgcg tttctacaaa ctctt         6715
```

<210> SEQ ID NO 90
<211> LENGTH: 6715

<212> TYPE: DNA
<213> ORGANISM: Artificial sequence
<220> FEATURE:
<223> OTHER INFORMATION: plasmid p55/PhoA6HisGS-/NAB-

<400> SEQUENCE: 90

```
ttgtttattt ttctaaatac attcaaatat gtatccgctc atgagacaat aaccctgata      60
aatgcttcaa taatattgaa aaaggaagag tatgagtatt caacatttcc gtgtcgccct     120
tattcccttt tttgcggcat tttgccttcc tgttttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttttt   540
gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg atataggtgc ctcactgatt aagcattggt aactgtcaga    960
ccaagtttac tcatatatac tttagattga tttaaaactt cattttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca gggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct tgagtgagc tgataccgct cgccgcagcc gaacgaccga    1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
```

```
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttctttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggt gtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttt ttgtgccacg cggttgggaa tgtaattcag ctccgccatc gccgcttcca   4320
cttttttccccg cgttttcgca gaaacgtggc tggcctggtt caccacgcgg gaaacggtct   4380
gataagagac accggcatac tctgcgacat cgtataacgt tactggtttc acattccacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
```

```
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct cgcagccgg ccatggcggc cgatcctcga gagctccgg gctgcagccc    4920 tgttctggaa aaccgggctg ctcagggcga tattactgca cccggcggtg ctcgccgttt    4980
aacgggtgat cagactgccg ctctgcgtga ttctcttagc gataaacctg caaaaaatat    5040
tattttgctg attggcgatg ggatggggga ctcggaaatt actgccgcac gtaattatgc    5100
cgaaggtgcg gcggctttt ttaaaggtat agatgcctta ccgcttaccg gcaatacac    5160 tcactatgcg ctgaataaaa aaccggcaa accggactac gtcaccgact cggctgcatc    5220
agcaaccgcc tggtcaaccg gtgtcaaaac ctataacggc gcgctgggcg tcgatattca    5280
cgaaaaagat cacccaacga ttctggaaat ggcaaaagcc gcaggtctgg cgaccggtaa    5340
cgtttctacc gcagagttgc aggatgccca gcccgctgcg ctggtggcac atgtgacctc    5400
gcgcaaatgc tacggtccga gcgcgaccag tgaaaaatgt ccgggtaacg ctctggaaaa    5460
aggcggaaaa ggatcgatta ccgaacagct gcttaacgct cgtgccgacg ttacgcttgg    5520
cggcggcgca aaacctttg ctgaaacggc aaccgctggt gaatggcagg aaaaacgct    5580 gcgtgaacag gcacaggcgc gtggttatca gttggtgagc gatgctgcct cactgaattc    5640
ggtgacggaa gcgaatcagc aaaaacccct gcttggcctg tttgctgacg gcaatatgcc    5700
agtgcgctgg ctaggaccga agcaacgta ccacggcaat atcgataagc ccgcagtcac    5760
ctgtacgcca atccgcaac gtaatgacag tgtaccaacc ctggcgcaga tgaccgacaa    5820
agccattgaa ttgttgagta aaaatgagaa aggcttttc ctgcaagttg aaggtgcgtc    5880
aatcgataaa caggatcatg ctgcgaatcc ttgtgggcaa attggcgaga cggtcgatct    5940
cgatgaagcc gtacaacggg cgctggaatt cgctaaaaag gagggtaaca cgctggtcat    6000
agtcaccgct gatcacgccc acgccagcca gattgttgcg ccggatacca agctccggg    6060 cctcacccag cgcgctaaata ccaaagatgg cgcagtgatg gtgatgagtt acgggaactc    6120
cgaagaggat tcaaagaac ataccggcag tcagttgcgt attgcggcgt atggcccgca    6180
tgccgccaat gttgttggac tgaccgacca gaccgatctc ttctacacca tgaaagccgc    6240
tctggggctg aaacatcatc atcaccatca cgggagctaa taagcttctg ttttggcgga    6300
tgagagaaga ttttcagcct gatacagatt aaatcagaac gcagaagcgg tctgataaaa    6360
cagaatttgc ctggcggcag tagcgcggtg gtcccacctg accccatgcc gaactcagaa    6420
gtgaaacgcc gtagcgccga tggtagtgtg gggtctcccc atgcgagagt agggaactgc    6480
caggcatcaa ataaaacgaa aggctcagtc gaaagactgg gcctttcgtt ttatctgttg    6540
tttgtcggtg aacgctctcc tgagtaggac aaatccgccg ggagcggatt tgaacgttgc    6600
gaagcaacgg cccggaggac cctggcgggc aggacgcccg ccataaactg ccaggcatca    6660
aattaagcag aaggccatcc tgacggatgg ccttttttgcg tttctacaaa ctctt         6715
```

<210> SEQ ID NO 91
<211> LENGTH: 6721
<212> TYPE: DNA
<213> ORGANISM: Artificial sequence
<220> FEATURE:

<223> OTHER INFORMATION: plasmid p55/PhoAHisGS-/NAB-

<400> SEQUENCE: 91

```
ttgtttatttt ttctaaatac attcaaatat gtatccgctc atgagacaat aaccctgata      60
aatgcttcaa taatattgaa aaaggaagag tatgagtatt caacatttcc gtgtcgccct     120
tattccctttt tttgcggcat tttgccttcc tgttttttgct cacccagaaa cgctggtgaa    180
agtaaaagat gctgaagatc agttgggtgc acgagtgggt tacatcgaac tggatctcaa     240
cagcggtaag atccttgaga gttttcgccc cgaagaacgt tttccaatga tgagcacttt     300
taaagttctg ctatgtggcg cggtattatc ccgtgttgac gccgggcaag agcaactcgg     360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttttt   540
gcacaacatg ggggatcatg taactcgcct tgatcgttgg gaaccggagc tgaatgaagc     600
cataccaaac gacgagcgtg acaccacgat gcctgtagca atggcaacaa cgttgcgcaa     660
actattaact ggcgaactac ttactctagc ttcccggcaa caattaatag actggatgga    720
ggcggataaa gttgcaggac cacttctgcg ctcggccctt ccggctggct ggtttattgc     780
tgataaatct ggagccggtg agcgtgggtc tcgcggtatc attgcagcac tggggccaga    840
tggtaagccc tcccgtatcg tagttatcta cacgacgggg agtcaggcaa ctatggatga     900
acgaaataga cagatcgctg agataggtgc ctcactgatt aagcattggt aactgtcaga    960
ccaagtttac tcatatatac tttagattga tttaaaactt catttttaat ttaaaaggat    1020
ctaggtgaag atccttttttg ataatctcat gaccaaaatc ccttaacgtg agttttcgtt    1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
aacggggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gatttttgtg    1680
atgctcgtca gggggggcgga gcctatggaa aaacgccagc aacgcggcct ttttacggtt    1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
```

```
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc aacgctgcc    2820 cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattccacca    4440 ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
```

| | |
|---|---|
| tggtatggct gtgcaggtcg taaatcactg cataattcgt gtcgctcaag gcgcactccc | 4680 |
| gttctggata atgttttttg cgccgacatc ataacggttc tggcaaatat tctgaaatga | 4740 |
| gctgttgaca attaatcatc ggctcgtata atgtgtggaa ttgtgagcgg ataacaattt | 4800 |
| cacacaggaa acagaattcc atatgaaata cctattacca acagcagcag ctgggttatt | 4860 |
| attgctcgct gcgcagccgg ccatggcggc cggccgatcc tcgagagctc ccgggctgca | 4920 |
| gccctgttct ggaaaaccgg gctgctcagg gcgatattac tgcacccggc ggtgctcgcc | 4980 |
| gtttaacggg tgatcagact gccgctctgc gtgattctct tagcgataaa cctgcaaaaa | 5040 |
| atattatttt gctgattggc gatgggatgg gggactcgga aattactgcc gcacgtaatt | 5100 |
| atgccgaagg tgcgggcggc tttttttaaag gtatagatgc cttaccgctt accgggcaat | 5160 |
| acactcacta tgcgctgaat aaaaaaaccg gcaaaccgga ctacgtcacc gactcggctg | 5220 |
| catcagcaac cgcctggtca accggtgtca aaacctataa cggcgcgctg ggcgtcgata | 5280 |
| ttcacgaaaa agatcaccca acgattctgg aaatggcaaa agccgcaggt ctggcgaccg | 5340 |
| gtaacgtttc taccgcagag ttgcaggatg ccacgcccgc tgcgctggtg gcacatgtga | 5400 |
| cctcgcgcaa atgctacggt ccgagcgcga ccagtgaaaa atgtccgggt aacgctctgg | 5460 |
| aaaaaggcgg aaaaggatcg attaccgaac agctgcttaa cgctcgtgcc gacgttacgc | 5520 |
| ttggcggcgg cgcaaaaacc tttgctgaaa cggcaaccgc tggtgaatgg cagggaaaaa | 5580 |
| cgctgcgtga acaggcacag gcgcgtggtt atcagttggt gagcgatgct gcctcactga | 5640 |
| attcggtgac ggaagcgaat cagcaaaaac ccctgcttgg cctgtttgct gacggcaata | 5700 |
| tgccagtgcg ctggctagga ccgaaagcaa cgtaccacgg caatatcgat aagcccgcag | 5760 |
| tcacctgtac gccaaatccg caacgtaatg acagtgtacc aaccctggcg cagatgaccg | 5820 |
| acaaagccat tgaattgttg agtaaaaatg agaaaggctt tttcctgcaa gttgaaggtg | 5880 |
| cgtcaatcga taaacaggat catgctgcga atccttgtgg gcaaattggc gagacggtcg | 5940 |
| atctcgatga agccgtacaa cgggcgctgg aattcgctaa aaaggagggt aacacgctgg | 6000 |
| tcatagtcac cgctgatcac gcccacgcca gccagattgt tgcgccggat accaaagctc | 6060 |
| cgggcctcac ccaggcgcta ataccaaaag atggcgcagt gatggtgatg agttacggga | 6120 |
| actccgaaga ggattcacaa gaacataccg gcagtcagtt gcgtattgcg gcgtatggcc | 6180 |
| cgcatgccgc caatgttgtt ggactgaccg accagaccga tctcttctac accatgaaag | 6240 |
| ccgctctggg gctgaaacat catcatcacc atcacggag ctaataagct tggctgtttt | 6300 |
| ggcggatgag agaagatttt cagcctgata cagattaaat cagaacgcag aagcggtctg | 6360 |
| ataaaacaga atttgcctgg cggcagtagc gcggtggtcc cacctgaccc catgccgaac | 6420 |
| tcagaagtga aacgccgtag cgccgatggt agtgtgggt ctccccatgc gagagtaggg | 6480 |
| aactgccagg catcaaataa aacgaaaggc tcagtcgaaa gactgggcct ttcgttttat | 6540 |
| ctgttgtttg tcggtgaacg ctctcctgag taggacaaat ccgccgggag cggatttgaa | 6600 |
| cgttgcgaag caacggcccg gagggaccctg gcgggcagga cgcccgccat aaactgccag | 6660 |
| gcatcaaatt aagcagaagg ccatcctgac ggatggcctt tttgcgtttc tacaaactct | 6720 |
| t | 6721 |

<210> SEQ ID NO 92
<211> LENGTH: 5400
<212> TYPE: DNA
<213> ORGANISM: Artificial sequence
<220> FEATURE:
<223> OTHER INFORMATION: plasmid p55/MCS1

<400> SEQUENCE: 92

```
ttgtttattt ttctaaatac attcaaatat gtatccgctc atgagacaat aaccctgata      60
aatgcttcaa taatattgaa aaaggaagag tatgagtatt caacatttcc gtgtcgccct     120
tattccctt tttgcggcat tttgccttcc tgttttgct cacccagaaa cgctggtgaa       180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540
gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt cattttaat ttaaaaggat    1020
ctaggtgaag atccttttg ataatctcat gaccaaaatc ccttaacgtg agttttcgtt    1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc ttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
aacggggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gatttttgtg    1680
atgctcgtca ggggggcgga gcctatggaa aaacgccagc aacgcggcct ttttacggtt    1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
```

```
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa     2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc aacgctgcc    2820 cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200 gcgacgcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
```

```
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaaacc gcggactcga    4920
ggcggcccag ccggccatgg ccgctagcgc ggccgctcta gattaagctt ggctgttttg    4980
gcggatgaga agatttttc agcctgatac agattaaatc agaacgcaga agcggtctga    5040
taaaacagaa tttgcctggc ggcagtagcg cggtggtccc acctgacccc atgccgaact    5100
cagaagtgaa acgccgtagc gccgatggta gtgtggggtc tccccatgcg agagtaggga    5160
actgccaggc atcaaataaa acgaaaggct cagtcgaaag actgggcctt tcgttttatc    5220
tgttgtttgt cggtgaacgc tctcctgagt aggacaaatc cgccgggagc ggatttgaac    5280
gttgcgaagc aacggcccgg aggaccctgg cgggcaggac gcccgccata aactgccagg    5340
catcaaatta gcagaaggc catcctgacg gatggccttt tgcgtttct acaaactctt      5400
```

<210> SEQ ID NO 93
<211> LENGTH: 5500
<212> TYPE: DNA
<213> ORGANISM: Artificial sequence
<220> FEATURE:
<223> OTHER INFORMATION: plasmid P55Flag/RBS/35

<400> SEQUENCE: 93

```
ttgtttattt ttctaaatac attcaaatat gtatccgctc atgagacaat aaccctgata      60
aatgcttcaa taatattgaa aaaggaagag tatgagtatt caacatttcc gtgtcgccct    120
tattcccttt tttgcggcat tttgccttcc tgtttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt    540 gcacaacatg gggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
```

```
gcctacatac ctcgctctgc taatcctgtt accagtggct gctgccagtg gcgataagtc   1380
gtgtcttacc gggttggact caagacgata gttaccggat aaggcgcagc ggtcgggctg   1440 aacgggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg aacaggaga gcgcacgagg gagcttccag ggggaaacgc   1620
ctggtatctt tatagtcctg tcgggtttcg ccacctctga cttgagcgtc gattttgtg    1680 atgctcgtca gggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggtttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag tgttccaca gggtagccag cagcatcctg cgatgcagat   2580
ccggaacata atggtgcagg gcgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg ctccaattc ttggagtggt    2940 gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttctttt caccagtgag acgggcaaca    3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
```

```
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaaacc gcggagagtg    4920
tgcaggtgat tacaaagacg atgacgataa gtaataaaca ggaaacagaa gtccatatga    4980
aatacctatt gcctacggca gccgctggat tgttattact cgcggcccag ccggccatgg    5040
ccgctagcgc ggccgctcta gattaagctt ggctgttttg gcggatgaga agattttc     5100 agcctgatac agattaaatc agaacgcaga agcggtctga taaaacagaa tttgcctggc    5160
ggcagtagcg cggtggtccc acctgacccc atgccgaact cagaagtgaa acgccgtagc    5220
gccgatggta gtgtggggtc tccccatgcg agagtaggga actgccaggc atcaaataaa    5280
acgaaaggct cagtcgaaag actgggcctt tcgttttatc tgttgtttgt cggtgaacgc    5340
tctcctgagt aggacaaatc cgccgggagc ggatttgaac gttgcgaagc aacggcccgg    5400
aggaccctgg cgggcaggac gcccgccata aactgccagg catcaaatta gcagaaggc    5460 catcctgacg gatggccttt ttgcgtttct acaaactctt                          5500
```

<210> SEQ ID NO 94
<211> LENGTH: 5560
<212> TYPE: DNA
<213> ORGANISM: Artificial sequence
<220> FEATURE:
<223> OTHER INFORMATION: plasmid P55/RBS/35cmyc6HisGS

<400> SEQUENCE: 94

```
ttgtttattt ttctaaatac attcaaatat gtatccgctc atgagacaat aaccctgata    60
aatgcttcaa taatattgaa aaaggaagag tatgagtatt caacatttcc gtgtcgccct    120
tattcccttt tttgcggcat tttgccttcc tgttttgct cacccagaaa cgctggtgaa     180
agtaaaagat gctgaagatc agttgggtgc acgagtgggt tacatcgaac tggatctcaa    240
```

```
cagcggtaag atccttgaga gttttcgccc cgaagaacgt tttccaatga tgagcacttt      300
taaagttctg ctatgtggcg cggtattatc ccgtgttgac gccgggcaag agcaactcgg      360
tcgccgcata cactattctc agaatgactt ggttgagtac tcaccagtca cagaaaagca      420
tcttacggat ggcatgacag taagagaatt atgcagtgct gccataacca tgagtgataa      480
cactgcggcc aacttacttc tgacaacgat cggaggaccg aaggagctaa ccgcttttt       540 gcacaacatg ggggatcatg taactcgcct tgatcgttgg gaaccggagc tgaatgaagc      600
cataccaaac gacgagcgtg acaccacgat gcctgtagca atggcaacaa cgttgcgcaa      660
actattaact ggcgaactac ttactctagc ttcccggcaa caattaatag actggatgga      720
ggcggataaa gttgcaggac cacttctgcg ctcggccctt ccggctggct ggtttattgc      780
tgataaatct ggagccggtg agcgtgggtc tcgcggtatc attgcagcac tggggccaga      840
tggtaagccc tcccgtatcg tagttatcta cacgacgggg agtcaggcaa ctatggatga      900
acgaaataga cagatcgctg ataggtgcc tcactgatt aagcattggt aactgtcaga       960
ccaagtttac tcatatatac tttagattga tttaaaactt cattttaat ttaaaaggat     1020 ctaggtgaag atccttttg ataatctcat gaccaaaatc ccttaacgtg agttttcgtt     1080
ccactgagcg tcagaccccg tagaaaagat caaaggatct tcttgagatc cttttttct     1140 gcgcgtaatc tgctgcttgc aaacaaaaaa accaccgcta ccagcggtgg tttgtttgcc     1200
ggatcaagag ctaccaactc ttttccgaa ggtaactggc ttcagcagag cgcagatacc     1260
aaatactgtc cttctagtgt agccgtagtt aggccaccac ttcaagaact ctgtagcacc     1320
gcctacatac ctcgctctgc taatcctgtt accagtggct gctgccagtg gcgataagtc     1380
gtgtcttacc gggttggact caagacgata gttaccggat aaggcgcagc ggtcgggctg     1440
aacggggggt tcgtgcacac agcccagctt ggagcgaacg acctacaccg aactgagata     1500
cctacagcgt gagcattgag aaagcgccac gcttcccgaa gggagaaagg cggacaggta     1560
tccggtaagc ggcagggtcg gaacaggaga gcgcacgagg gagcttccag ggggaaacgc     1620
ctggtatctt tatagtcctg tcgggtttcg ccacctctga cttgagcgtc gatttttgtg     1680
atgctcgtca gggggcgga gcctatggaa aaacgccagc aacgcggcct ttttacggtt     1740
cctggccttt tgctggcctt ttgctcacat gttctttcct gcgttatccc ctgattctgt     1800
ggataaccgt attaccgcct ttgagtgagc tgataccgct cgccgcagcc gaacgaccga     1860
gcgcagcgag tcagtgagcg aggaagcgga agagcgcctg atgcggtatt ttctccttac     1920
gcatctgtgc ggtatttcac accgcatata tggtgcactc tcagtacaat ctgctctgat     1980
gccgcatagt taagccagta tacactccgc tatcgctacg tgactgggtc atggctgcgc     2040
cccgacaccc gccaacaccc gctgacgcgc cctgacgggc ttgtctgctc ccggcatccg     2100
cttacagaca agctgtgacc gtctccggga gctgcatgtg tcagaggttt tcaccgtcat     2160
caccgaaacg cgcgaggcag ctgcggtaaa gctcatcagc gtggtcgtga agcgattcac     2220
agatgtctgc ctgttcatcc gcgtccagct cgttgagttt ctccagaagc gttaatgtct     2280
ggcttctgat aaagcgggcc atgttaaggg cggttttttc ctgtttggtc acttgatgcc     2340
tccgtgtaag ggggaatttc tgttcatggg ggtaatgata ccgatgaaac gagagaggat     2400
gctcacgata cgggttactg atgatgaaca tgcccggtta ctggaacgtt gtgagggtaa     2460
acaactggcg gtatggatgc ggcgggacca gagaaaaatc actcagggtc aatgccagcg     2520
cttcgttaat acagatgtag gtgttccaca gggtagccag cagcatcctg cgatgcagat     2580
ccggaacata atggtgcagg cgctgacttc cgcgtttcc agactttacg aaacacggaa     2640
```

```
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320 cttttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaaacc gcggagagtg    4920
tgcaggtgat tacaaagacg atgacgataa gtaataaaca ggaaacagaa gtccatatga    4980
```

| | |
|---|---|
| aatacctatt gcctacggca gccgctggat tgttattact cgcggcccag ccggccatgg | 5040 |
| ccgctagcgc ggccgcagaa caaaaactca tctcagaaga ggatctgaat ggggccgtac | 5100 |
| atcaccacca tcatcatggg agctaagctt ggctgttttg gcggatgaga aagatttttc | 5160 |
| agcctgatac agattaaatc agaacgcaga agcggtctga taaaacagaa tttgcctggc | 5220 |
| ggcagtagcg cggtggtccc acctgacccc atgccgaact cagaagtgaa acgccgtagc | 5280 |
| gccgatggta gtgtgggtc tccccatgcg agagtaggga actgccaggc atcaaataaa | 5340 |
| acgaaaggct cagtcgaaag actgggcctt tcgttttatc tgttgtttgt cggtgaacgc | 5400 |
| tctcctgagt aggacaaatc cgccgggagc ggatttgaac gttgcgaagc aacggcccgg | 5460 |
| aggaccctgg cgggcaggac gcccgccata aactgccagg catcaaatta agcagaaggc | 5520 |
| catcctgacg gatggccttt ttgcgtttct acaaactctt | 5560 |

<210> SEQ ID NO 95
<211> LENGTH: 6099
<212> TYPE: DNA
<213> ORGANISM: Artificial sequence
<220> FEATURE:
<223> OTHER INFORMATION: plasmid pHCH2CH3YI-TAG

<400> SEQUENCE: 95

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt cattttaat ttaaaaggat | 1020 |
| ctaggtgaag atccttttg ataatctcat gaccaaaatc ccttaacgtg agttttcgtt | 1080 |
| ccactgagcg tcagaccccg tagaaaagat caaaggatct tcttgagatc cttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg gcgataagtc | 1380 |
| gtgtcttacc gggttggact caagacgata gttaccggat aaggcgcagc ggtcgggctg | 1440 |
| aacggggggt tcgtgcacac agcccagctt ggagcgaacg acctacaccg aactgagata | 1500 |

-continued

```
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gattttgtg     1680 atgctcgtca gggggggcgga gcctatggaa aaacgccagc aacgcggcct ttttacggtt   1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgacttc cgcgtttcc agactttacg aaacacggaa     2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttctttt caccagtgag acgggcaaca     3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
```

```
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcagaca aaactcacac    4920
atgcccaccg tgcccagcac ctgaactcct ggggggaccg tcagtcttcc tcttccccc     4980 aaaacccaag gacaccctca tgatctcccg gacccctgag gtcacatgcg tggtggtgga    5040
cgtgagccac gaagaccctg aggtcaagtt caactggtac gtggacggcg tggaggtgca    5100
taatgccaag acaaagccgc gggaggagca gtacaacagc acgtaccggg tggtcagcgt    5160
cctcaccgtc ctgcaccagg actggctgaa tggcaaggag tacaagtgca aggtctccaa    5220
caaagccctc ccagccccca tcgagaaaac catctccaaa gccaaagggc agccccgaga    5280
accacaggtg tacaccctgc ccccatcccg ggatgagctg accaagaacc aggtcagcct    5340
gacctgcctg gtcaaaggct tctatcccag cgacatcgcc gtggagtggg agagcaatgg    5400
gcagccggag aacaactaca agaccacgcc tcccgtgctg gactccgacg gctccttctt    5460
cctctacagc aagctcaccg tggacaagag caggtggcag caggggaacg tcttctcatg    5520
ctccgtgatg catgaggctc tgcacaacca ctacacgcag aagagcctct ccctgtctcc    5580
gggtaaagcg gccgcagaac aaaaactcat ctcagaagag gatctgaatg gggccgtaca    5640
tcaccaccat catcatggga gctaagcttg gctgttttgg cggatgagag aagattttca    5700
gcctgataca gattaaatca gaacgcagaa gcggtctgat aaaacagaat ttgcctggcg    5760
gcagtagcgc ggtggtccca cctgacccca tgccgaactc agaagtgaaa cgccgtagcg    5820
ccgatggtag tgtggggtct ccccatgcga gagtagggaa ctgccaggca tcaaataaaa    5880
cgaaaggctc agtcgaaaga ctgggccttt cgttttatct gttgtttgtc ggtgaacgct    5940
ctcctgagta ggacaaatcc gccgggagcg gatttgaacg ttgcgaagca acggcccgga    6000
ggaccctggc gggcaggacg cccgccataa actgccaggc atcaaattaa gcagaaggcc    6060
atcctgacgg atggcctttt tgcgtttcta caaactcttt                          6099
```

<210> SEQ ID NO 96
<211> LENGTH: 6024

<212> TYPE: DNA
<213> ORGANISM: Artificial sequence
<220> FEATURE:
<223> OTHER INFORMATION: plasmid pHCH2CH3Y

<400> SEQUENCE: 96

| | | | | | |
|---|---|---|---|---|---|
| ttgtttattt | ttctaaatac | attcaaatat | gtatccgctc | atgagacaat | aaccctgata | 60 |
| aatgcttcaa | taatattgaa | aaaggaagag | tatgagtatt | caacatttcc | gtgtcgccct | 120 |
| tattcccttt | tttgcggcat | tttgccttcc | tgttttgct | cacccagaaa | cgctggtgaa | 180 |
| agtaaaagat | gctgaagatc | agttgggtgc | acagtgggt | tacatcgaac | tggatctcaa | 240 |
| cagcggtaag | atccttgaga | gttttcgccc | cgaagaacgt | tttccaatga | tgagcacttt | 300 |
| taaagttctg | ctatgtggcg | cggtattatc | ccgtgttgac | gccgggcaag | agcaactcgg | 360 |
| tcgccgcata | cactattctc | agaatgactt | ggttgagtac | tcaccagtca | cagaaaagca | 420 |
| tcttacggat | ggcatgacag | taagagaatt | atgcagtgct | gccataacca | tgagtgataa | 480 |
| cactgcggcc | aacttacttc | tgacaacgat | cggaggaccg | aaggagctaa | ccgcttttt | 540 |
| gcacaacatg | gggatcatg | taactcgcct | tgatcgttgg | gaaccggagc | tgaatgaagc | 600 |
| cataccaaac | gacgagcgtg | acaccacgat | gcctgtagca | atggcaacaa | cgttgcgcaa | 660 |
| actattaact | ggcgaactac | ttactctagc | ttcccggcaa | caattaatag | actggatgga | 720 |
| ggcggataaa | gttgcaggac | cacttctgcg | ctcggccctt | ccggctggct | ggtttattgc | 780 |
| tgataaatct | ggagccggtg | agcgtgggtc | tcgcggtatc | attgcagcac | tggggccaga | 840 |
| tggtaagccc | tcccgtatcg | tagttatcta | cacgacgggg | agtcaggcaa | ctatggatga | 900 |
| acgaaataga | cagatcgctg | agataggtgc | ctcactgatt | aagcattggt | aactgtcaga | 960 |
| ccaagtttac | tcatatatac | tttagattga | tttaaaactt | catttttaat | ttaaaaggat | 1020 |
| ctaggtgaag | atccttttg | ataatctcat | gaccaaaatc | ccttaacgtg | agttttcgtt | 1080 |
| ccactgagcg | tcagaccccg | tagaaaagat | caaaggatct | cttgagatc | ctttttttct | 1140 |
| gcgcgtaatc | tgctgcttgc | aaacaaaaaa | accaccgcta | ccagcggtgg | tttgtttgcc | 1200 |
| ggatcaagag | ctaccaactc | tttttccgaa | ggtaactggc | ttcagcagag | cgcagatacc | 1260 |
| aaatactgtc | cttctagtgt | agccgtagtt | aggccaccac | ttcaagaact | ctgtagcacc | 1320 |
| gcctacatac | ctcgctctgc | taatcctgtt | accagtggct | gctgccagtg | gcgataagtc | 1380 |
| gtgtcttacc | gggttggact | caagacgata | gttaccggat | aaggcgcagc | ggtcgggctg | 1440 |
| aacggggggt | tcgtgcacac | agcccagctt | ggagcgaacg | acctacaccg | aactgagata | 1500 |
| cctacagcgt | gagcattgag | aaagcgccac | gcttcccgaa | gggagaaagg | cggacaggta | 1560 |
| tccggtaagc | ggcagggtcg | gaacaggaga | gcgcacgagg | gagcttccag | ggggaaacgc | 1620 |
| ctggtatctt | tatagtcctg | tcgggtttcg | ccacctctga | cttgagcgtc | gatttttgtg | 1680 |
| atgctcgtca | ggggggcgga | gcctatggaa | aaacgccagc | aacgcggcct | ttttacggtt | 1740 |
| cctggccttt | tgctggcctt | ttgctcacat | gttctttcct | gcgttatccc | ctgattctgt | 1800 |
| ggataaccgt | attaccgcct | ttgagtgagc | tgataccgct | cgccgcagcc | gaacgaccga | 1860 |
| gcgcagcgag | tcagtgagcg | aggaagcgga | agagcgcctg | atgcggtatt | ttctccttac | 1920 |
| gcatctgtgc | ggtatttcac | accgcatata | tggtgcactc | tcagtacaat | ctgctctgat | 1980 |
| gccgcatagt | taagccagta | tacactccgc | tatcgctacg | tgactgggtc | atggctgcgc | 2040 |
| cccgacaccc | gccaacaccc | gctgacgcgc | cctgacgggc | ttgtctgctc | ccggcatccg | 2100 |
| cttacagaca | agctgtgacc | gtctccggga | gctgcatgtg | tcagaggttt | tcaccgtcat | 2160 |

```
caccgaaacg cgcgaggcag ctgcggtaaa gctcatcagc gtggtcgtga agcgattcac      2220
agatgtctgc ctgttcatcc gcgtccagct cgttgagttt ctccagaagc gttaatgtct      2280
ggcttctgat aaagcgggcc atgttaaggg cggttttttc ctgtttggtc acttgatgcc      2340
tccgtgtaag ggggaatttc tgttcatggg ggtaatgata ccgatgaaac gagagaggat      2400
gctcacgata cgggttactg atgatgaaca tgcccggtta ctggaacgtt gtgagggtaa      2460
acaactggcg gtatggatgc ggcgggacca gagaaaaatc actcagggtc aatgccagcg      2520
cttcgttaat acagatgtag gtgttccaca gggtagccag cagcatcctg cgatgcagat      2580
ccggaacata atggtgcagg cgctgacttc cgcgtttccc agactttacg aaacacggaa      2640
accgaagacc attcatgttg ttgctcaggt cgcagacgtt ttgcagcagc agtcgcttca      2700
cgttcgctcg cgtatcggtg attcattctg ctaaccagta aggcaacccc gccagcctag      2760
ccgggtcctc aacgacagga gcacgatcat gcgcacccgt ggccaggacc aacgctgcc       2820
cgagatgcgc cgcgtgcggc tgctggagat ggcggacgcg atggatatgt tctgccaagg      2880
gttggtttgc gcattcacag ttctccgcaa gaattgattg gctccaattc ttggagtggt      2940
gaatccgtta gcgaggtgcc gccggcttcc attcaggtcg aggtggcccg gctccatgca      3000
ccgcgacgca acgcggggag gcagacaagg tatagggcgg cgcctacaat ccatgccaac      3060
ccgttccatg tgctcgccga ggcggcataa atcgccgtga cgatcagcgg tccagtgatc      3120
gaagttaggc tggtaagagc cgcgagcgat ccttgaagct gtccctgatg gtcgtcatct      3180
acctgcctgg acagcatggc ctgcaacgcg ggcatcccga tgccgccgga agcgagaaga      3240
atcataatgg ggaaggccat ccagcctcgc gtcgcgaacg ccagcaagac gtagcccagc      3300
gcgtcggcca gcttgcaatt cgcgctaact tacattaatt gcgttgcgct cactgcccgc      3360
tttccagtcg ggaaacctgt cgtgccagct gcattaatga atcggccaac gcgcggggag      3420
aggcggtttg cgtattgggc gccagggtgg ttttctttt caccagtgag acgggcaaca      3480
gctgattgcc cttcaccgcc tggccctgag agagttgcag caagcggtcc acgctggttt      3540
gccccagcag gcgaaaatcc tgtttgatgg tggttgacgg cgggatataa catgagctgt      3600
cttcggtatc gtcgtatccc actaccgaga tatccgcacc aacgcgcagc ccggactcgg      3660
taatggcgcg cattgcgccc agcgccatct gatcgttggc aaccagcatc gcagtgggaa      3720
cgatgccctc attcagcatt tgcatggttt gttgaaaacc ggacatggca ctccagtcgc      3780
cttcccgttc cgctatcggc tgaatttgat tgcgagtgag atatttatgc cagccagcca      3840
gacgcagacg cgccgagaca gaacttaatg gtcccgctaa cagcgcgatt tgctgatgac      3900
ccaatgcgac cagatgctcc acgcccagtc gcgtaccgtc ttcatgggag aaaataatac      3960
tgttgatggt gtctggtcag agacatcaa gaaataacgc cggaacatta gtgcaggcag      4020
cttccacagc aatggcatcc tggtcatcca gcggatagtt aatgatcagc ccactgacgc      4080
gttgcgcgag aagattgtgc accgccgctt tacaggcttc gacgccgctt cgttctacca      4140
tcgacaccac cacgctggca cccagttgat cggcgcgaga tttaatcgcc gcgacaattt      4200
gcgacggcgc gtgcagggcc agactggagg tggcaacgcc aatcagcaac gactgtttgc      4260
ccgccagttt ttgtgccacg cggttgggaa tgtaattcag ctccgccatc gccgcttcca      4320
ctttttcccg cgttttcgca gaaacgtggc tggcctggtt caccacgcgg gaaacggtct      4380
gataagagac accggcatac tctgcgacat cgtataacgt tactggtttc acattcacca      4440
ccctgaattg actctcttcc gggcgctatc atgccatacc gcgaaaggtt ttgcgccatt      4500
cgatggtgtc aacgtaaatg catgccgctt cgccttcgcg cgcgaattgc aagctgatcc      4560
```

```
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcagaca aaactcacac    4920
atgcccaccg tgcccagcac ctgaactcct ggggggaccg tcagtcttcc tcttcccccc    4980
aaaacccaag gacaccctca tgatctcccg gaccctgag gtcacatgcg tggtggtgga    5040
cgtgagccac gaagaccctg aggtcaagtt caactggtac gtggacggcg tggaggtgca    5100
taatgccaag acaaagccgc gggaggagca gtacaacagc acgtaccggg tggtcagcgt    5160
cctcaccgtc ctgcaccagg actggctgaa tggcaaggag tacaagtgca aggtctccaa    5220
caaagccctc ccagccccca tcgagaaaac catctccaaa gccaaaggc agccccgaga    5280 accacaggtg tacaccctgc ccccatcccg ggatgagctg accaagaacc aggtcagcct    5340
gacctgcctg gtcaaaggct tctatcccag cgacatcgcc gtggagtggg agagcaatgg    5400
gcagccggag aacaactaca agaccacgcc tcccgtgctg gactccgacg gctccttctt    5460
cctctacagc aagctcaccg tggacaagag caggtggcag caggggaacg tcttctcatg    5520
ctccgtgatg catgaggctc tgcacaacca ctacacgcag aagagcctct ccctgtctcc    5580
gggtaaataa gcttggctgt tttggcggat gagagaagat tttcagcctg atacagatta    5640
aatcagaacg cagaagcggt ctgataaaac agaatttgcc tggcggcagt agcgcggtgg    5700
tcccacctga ccccatgccg aactcagaag tgaaacgccg tagcgccgat ggtagtgtgg    5760
ggtctcccca tgcgagagta gggaactgcc aggcatcaaa taaaacgaaa ggctcagtcg    5820
aaagactggg cctttcgttt tatctgttgt ttgtcggtga acgctctcct gagtaggaca    5880
aatccgccgg gagcggattt gaacgttgcg aagcaacggc ccggagggacc ctggcgggca    5940 ggacgcccgc cataaactgc caggcatcaa attaagcaga aggccatcct gacggatggc    6000 cttttttgcgt ttctacaaac tctt                                         6024
```

<210> SEQ ID NO 97
<211> LENGTH: 5866
<212> TYPE: DNA
<213> ORGANISM: Artificial sequence
<220> FEATURE:
<223> OTHER INFORMATION: plasmid p55/Flag/RBS/35cmyc6HisGS

<400> SEQUENCE: 97

```
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt    540
```

```
gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca gggggggcgga gcctatggaa aaacgccagc aacgcggcct ttttacggtt   1740
cctggccttt tgctggcctt tgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaattc tgttcatggg ggtaatgata ccgatgaaac gagagaggat   2400
gctcacgata cgggttactg atgatgaaca tgcccggtta ctggaacgtt gtgagggtaa   2460
acaactggcg gtatgatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat cgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
```

```
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg gcatcccga tgccgccgga agcgagaaga     3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttt caccagtgag acgggcaaca     3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200 gcgacgcgc gtgcagggcc agactggagg tggcaacgcc aatcagcaac gactgtttgc     4260
ccgccagttg ttgtgccacg cggttgggaa tgtaattcag ctccgccatc gccgcttcca    4320
ctttttcccg cgttttcgca gaaacgtggc tggcctggtt caccacgcgg gaaacggtct    4380
gataagagac accggcatac tctgcgacat cgtataacgt tactggtttc acattccaca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaggta ccgtggctgc    4920
accatctgtc ttcatcttcc cgccatctga tgagcagttg aaatctggaa ctgcctctgt    4980
tgtgtgcctg ctgaataact ctatcccag agaggccaaa gtacagtgga aggtggataa     5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220 agagtgtgca ggtgattaca agacgatga cgataagtaa taaacaggaa acagaagtcc    5280
```

| | |
|---|---:|
| atatgaaata cctattgcct acggcagccg ctggattgtt attactcgcg gcccagccgg | 5340 |
| ccatggccgc tagcgcggcc gcagaacaaa aactcatctc agaagaggat ctgaatgggg | 5400 |
| ccgtacatca ccaccatcat catgggagct aagcttggct gttttggcgg atgagagaag | 5460 |
| attttcagcc tgatacagat taaatcagaa cgcagaagcg gtctgataaa acagaatttg | 5520 |
| cctggcggca gtagcgcggt ggtcccacct gaccccatgc cgaactcaga agtgaaacgc | 5580 |
| cgtagcgccg atggtagtgt ggggtctccc catgcgagag tagggaactg ccaggcatca | 5640 |
| aataaaacga aaggctcagt cgaaagactg ggcctttcgt tttatctgtt gtttgtcggt | 5700 |
| gaacgctctc ctgagtagga caaatccgcc gggagcggat ttgaacgttg cgaagcaacg | 5760 |
| gcccggagga ccctggcggg caggacgccc gccataaact gccaggcatc aaattaagca | 5820 |
| gaaggccatc ctgacggatg ccttttttgc gtttctacaa actctt | 5866 |

<210> SEQ ID NO 98
<211> LENGTH: 6109
<212> TYPE: DNA
<213> ORGANISM: Artificial sequence
<220> FEATURE:
<223> OTHER INFORMATION: plasmid pcKCHlyl-TAG

<400> SEQUENCE: 98

| | |
|---|---:|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt catttttaat ttaaaaggat | 1020 |
| ctaggtgaag atcctttttg ataatctcat gaccaaaatc ccttaacgtg agttttcgtt | 1080 |
| ccactgagcg tcagaccccg tagaaaagat caaaggatct tcttgagatc ctttttttct | 1140 |
| gcgcgtaatc tgctgcttgc aaacaaaaaa accaccgcta ccagcggtgg tttgtttgcc | 1200 |
| ggatcaagag ctaccaactc ttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg gcgataagtc | 1380 |
| gtgtcttacc gggttggact caagacgata gttaccggat aaggcgcagc ggtcgggctg | 1440 |
| aacggggggt tcgtgcacac agcccagctt ggagcgaacg acctacaccg aactgagata | 1500 |

```
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gattttgtgt   1680
atgctcgtca ggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg gcgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggttttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttcttttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
```

```
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaggta ccgtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220
agagtgtgca ggtgattaca agacgatga cgataagtaa taaacaggaa acagaagtcc    5280
atatgaaata cctattgcct acggcagccg ctggattgtt attactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca agcccagcaa caccaaggtg gacaagaaag    5640
ttgagcccaa atcttgtgcg gccgcagaac aaaaactcat ctcagaagag gatctgaatg    5700
gggccgtaca tcaccaccat catcatggga gctaagcttg gctgttttgg cggatgagag    5760
aagattttca gcctgataca gattaaatca gaacgcagaa gcggtctgat aaaacagaat    5820
ttgcctggcg gcagtagcgc ggtggtccca cctgacccca tgccgaactc agaagtgaaa    5880
cgccgtagcg ccgatggtag tgtgggtct ccccatgcga gagtagggaa ctgccaggca    5940
tcaaataaaa cgaaaggctc agtcgaaaga ctgggccttt cgttttatct gttgtttgtc    6000
ggtgaacgct ctcctgagta ggacaaatcc gccgggagcg atttgaacg ttgcgaagca    6060
gcagaaggcc atcctgacgg atggcctttt tgcgtttcta caaactcttt    6109
```

<210> SEQ ID NO 99
<211> LENGTH: 6199

<212> TYPE: DNA
<213> ORGANISM: Artificial sequence
<220> FEATURE:
<223> OTHER INFORMATION: plasmid pcKCH1Hyl-TAG

<400> SEQUENCE: 99

| | | | | | |
|---|---|---|---|---|---|
| ttgtttattt | ttctaaatac | attcaaatat | gtatccgctc | atgagacaat | aaccctgata | 60 |
| aatgcttcaa | taatattgaa | aaaggaagag | tatgagtatt | caacatttcc | gtgtcgccct | 120 |
| tattcccttt | tttgcggcat | tttgccttcc | tgtttttgct | cacccagaaa | cgctggtgaa | 180 |
| agtaaaagat | gctgaagatc | agttgggtgc | acgagtgggt | tacatcgaac | tggatctcaa | 240 |
| cagcggtaag | atccttgaga | gttttcgccc | cgaagaacgt | tttccaatga | tgagcacttt | 300 |
| taaagttctg | ctatgtggcg | cggtattatc | ccgtgttgac | gccgggcaag | agcaactcgg | 360 |
| tcgccgcata | cactattctc | agaatgactt | ggttgagtac | tcaccagtca | cagaaaagca | 420 |
| tcttacggat | ggcatgacag | taagagaatt | atgcagtgct | gccataacca | tgagtgataa | 480 |
| cactgcggcc | aacttacttc | tgacaacgat | cggaggaccg | aaggagctaa | ccgcttttt | 540 |
| gcacaacatg | gggatcatg | taactcgcct | tgatcgttgg | gaaccggagc | tgaatgaagc | 600 |
| cataccaaac | gacgagcgtg | acaccacgat | gcctgtagca | atggcaacaa | cgttgcgcaa | 660 |
| actattaact | ggcgaactac | ttactctagc | ttcccggcaa | caattaatag | actggatgga | 720 |
| ggcggataaa | gttgcaggac | cacttctgcg | ctcggccctt | ccggctggct | ggtttattgc | 780 |
| tgataaatct | ggagccggtg | agcgtgggtc | tcgcggtatc | attgcagcac | tggggccaga | 840 |
| tggtaagccc | tcccgtatcg | tagttatcta | cacgacgggg | agtcaggcaa | ctatggatga | 900 |
| acgaaataga | cagatcgctg | agataggtgc | ctcactgatt | aagcattggt | aactgtcaga | 960 |
| ccaagtttac | tcatatatac | tttagattga | tttaaaactt | catttttaat | ttaaaaggat | 1020 |
| ctaggtgaag | atccttttg | ataatctcat | gaccaaaatc | ccttaacgtg | agttttcgtt | 1080 |
| ccactgagcg | tcagaccccg | tagaaaagat | caaaggatct | tcttgagatc | ctttttttct | 1140 |
| gcgcgtaatc | tgctgcttgc | aaacaaaaaa | accaccgcta | ccagcggtgg | tttgtttgcc | 1200 |
| ggatcaagag | ctaccaactc | ttttccgaa | ggtaactggc | ttcagcagag | cgcagatacc | 1260 |
| aaatactgtc | cttctagtgt | agccgtagtt | aggccaccac | ttcaagaact | ctgtagcacc | 1320 |
| gcctacatac | ctcgctctgc | taatcctgtt | accagtggct | gctgccagtg | gcgataagtc | 1380 |
| gtgtcttacc | gggttggact | caagacgata | gttaccggat | aaggcgcagc | ggtcgggctg | 1440 |
| aacggggggt | tcgtgcacac | agcccagctt | ggagcgaacg | acctacaccg | aactgagata | 1500 |
| cctacagcgt | gagcattgag | aaagcgccac | gcttcccgaa | gggagaaagg | cggacaggta | 1560 |
| tccggtaagc | ggcagggtcg | gaacaggaga | gcgcacgagg | gagcttccag | ggggaaacgc | 1620 |
| ctggtatctt | tatagtcctg | tcgggtttcg | ccacctctga | cttgagcgtc | gatttttgtg | 1680 |
| atgctcgtca | ggggggcgga | gcctatggaa | aaacgccagc | aacgcggcct | ttttacggtt | 1740 |
| cctggccttt | tgctggcctt | ttgctcacat | gttctttcct | gcgttatccc | ctgattctgt | 1800 |
| ggataaccgt | attaccgcct | ttgagtgagc | tgataccgct | cgccgcagcc | gaacgaccga | 1860 |
| gcgcagcgag | tcagtgagcg | aggaagcgga | agagcgcctg | atgcggtatt | ttctccttac | 1920 |
| gcatctgtgc | ggtatttcac | accgcatata | tggtgcactc | tcagtacaat | ctgctctgat | 1980 |
| gccgcatagt | taagccagta | tacactccgc | tatcgctacg | tgactgggtc | atggctgcgc | 2040 |
| cccgacaccc | gccaacaccc | gctgacgcgc | cctgacgggc | ttgtctgctc | ccggcatccg | 2100 |
| cttacagaca | agctgtgacc | gtctccggga | gctgcatgtg | tcagaggttt | tcaccgtcat | 2160 |

```
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg ctccaattc ttggagtggt   2940 gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttcttttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggt gtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttt ttgtgccacg cggttgggaa tgtaattcag ctccgccatc gccgcttcca   4320
ctttttcccg cgttttcgca gaaacgtggc tggcctggtt caccacgcgg gaaacggtct   4380
gataagagac accggcatac tctgcgacat cgtataacgt tactggtttc acattcacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
```

```
ggagcttatc gactgcacgg tgcaccaatg cttctggcgt caggcagcca tcggaagctg      4620
tggtatggct gtgcaggtcg taaatcactg cataattcgt gtcgctcaag gcgcactccc      4680
gttctggata atgtttttg cgccgacatc ataacggttc tggcaaatat tctgaaatga       4740
gctgttgaca attaatcatc ggctcgtata atgtgtggaa ttgtgagcgg ataacaattt      4800
cacacaggaa acagaattcc atatgaaata cctattacca acagcagcag ctgggttatt      4860
attgctcgct gcgcagccgg ccatggccca ggtcaccgtc tcctcaggta ccgtggctgc      4920
accatctgtc ttcatcttcc cgccatctga tgagcagttg aaatctggaa ctgcctctgt      4980
tgtgtgcctg ctgaataact tctatcccag agaggccaaa gtacagtgga aggtggataa      5040
cgccctccaa tcgggtaact cccaggagag tgtcacagag caggacagca aggacagcac      5100
ctacagcctc agcagcaccc tgacgctgag caaagcagac tacgagaaac acaaagtcta      5160
cgcctgcgaa gtcacccatc agggcctgag ctcgccggtg acaaagagct caaccgcgg      5220 agagtgtgca ggtgattaca agacgatga cgataagtaa taaacaggaa acagaagtcc       5280
atatgaaata cctattgcct acggcagccg ctggattgtt attactcgcg gcccagccgg      5340
ccatggccgc tagcaccaag ggcccatcgg tcttccccct ggcaccctcc tccaagagca      5400
cctctggggg cacagcggcc ctgggctgcc tggtcaagga ctacttcccc gaaccggtga      5460
cggtgtcgtg gaactcaggc gccctgacca gcggcgtgca caccttcccg gctgtcctac      5520
agtcctcagg actctactcc ctcagcagcg tagtgaccgt gccctccagc agcttgggca      5580
cccagaccta catctgcaac gtgaatcaca agcccagcaa caccaaggtg gacaagaaag      5640
ttgagcccaa atcttgtgac aaaactcaca catgcccacc gtgcccagcg ccgcagaac       5700 aaaaactcat ctcagaagag gatctgaatg gggccgtaca tcaccaccat catcatggga      5760
gctaagcttg gctgttttgg cggatgagag aagattttca gcctgataca gattaaatca      5820
gaacgcagaa gcggtctgat aaaacagaat ttgcctggcg gcagtagcgc ggtggtccca      5880
cctgacccca tgccgaactc agaagtgaaa cgccgtagcg ccgatggtag tgtggggtct      5940
ccccatgcga gagtagggaa ctgccaggca tcaaataaaa cgaaaggctc agtcgaaaga      6000
ctgggccttt cgttttatct gttgtttgtc ggtgaacgct ctcctgagta ggacaaatcc      6060
gccgggagcg gatttgaacg ttgcgaagca acggcccgga ggaccctggc gggcaggacg      6120
cccgccataa actgccaggc atcaaattaa gcagaaggcc atcctgacgg atggcctttt      6180
tgcgtttcta caaactctt                                                   6199
```

<210> SEQ ID NO 100
<211> LENGTH: 6064
<212> TYPE: DNA
<213> ORGANISM: Artificial sequence
<220> FEATURE:
<223> OTHER INFORMATION: plasmid pcKCH1yl

<400> SEQUENCE: 100

```
ttgtttattt ttctaaatac attcaaatat gtatccgctc atgagacaat aaccctgata       60
aatgcttcaa taatattgaa aaaggaagag tatgagtatt caacatttcc gtgtcgccct      120
tattcccttt tttgcggcat tttgccttcc tgttttgct cacccagaaa cgctggtgaa       180
agtaaaagat gctgaagatc agttgggtgc acagtgggt tacatcgaac tggatctcaa       240
cagcggtaag atccttgaga gttttcgccc cgaagaacgt tttccaatga tgagcacttt      300
taaagttctg ctatgtggcg cggtattatc ccgtgttgac gccgggcaag agcaactcgg      360
```

-continued

```
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540 gcacaacatg ggggatcatg taactcgcct tgatcgttgg aaccggagc tgaatgaagc     600 cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg ataggtgc ctcactgatt aagcattggt aactgtcaga     960
ccaagtttac tcatatatac tttagattga tttaaaactt cattttaat ttaaaaggat    1020 ctaggtgaag atccttttg ataatctcat gaccaaaatc ccttaacgtg agttttcgtt    1080
ccactgagcg tcagaccccg tagaaaagat caaaggatct tcttgagatc cttttttct    1140 gcgcgtaatc tgctgcttgc aaacaaaaaa accaccgcta ccagcggtgg tttgtttgcc    1200
ggatcaagag ctaccaactc ttttccgaa ggtaactggc ttcagcagag cgcagatacc     1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440 aacgggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gattttgtg     1680 atgctcgtca ggggggcgga gcctatggaa aaacgccagc aacgcggcct ttttacggtt    1740
cctggccttt tgctggcctt tgctcacat gttctttcct gcgttatccc ctgattctgt      1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa     2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
```

| | | | | |
|---|---|---|---|---|
| ccgggtcctc | aacgacagga | gcacgatcat | gcgcacccgt | ggccaggacc | caacgctgcc | 2820 |
| cgagatgcgc | cgcgtgcggc | tgctggagat | ggcggacgcg | atggatatgt | tctgccaagg | 2880 |
| gttggtttgc | gcattcacag | ttctccgcaa | gaattgattg | gctccaattc | ttggagtggt | 2940 |
| gaatccgtta | gcgaggtgcc | gccggcttcc | attcaggtcg | aggtggcccg | gctccatgca | 3000 |
| ccgcgacgca | acgcggggag | gcagacaagg | tatagggcgg | cgcctacaat | ccatgccaac | 3060 |
| ccgttccatg | tgctcgccga | ggcggcataa | atcgccgtga | cgatcagcgg | tccagtgatc | 3120 |
| gaagttaggc | tggtaagagc | cgcgagcgat | ccttgaagct | gtccctgatg | gtcgtcatct | 3180 |
| acctgcctgg | acagcatggc | ctgcaacgcg | ggcatcccga | tgccgccgga | agcgagaaga | 3240 |
| atcataatgg | ggaaggccat | ccagcctcgc | gtcgcgaacg | ccagcaagac | gtagcccagc | 3300 |
| gcgtcggcca | gcttgcaatt | cgcgctaact | tacattaatt | gcgttgcgct | cactgcccgc | 3360 |
| tttccagtcg | ggaaacctgt | cgtgccagct | gcattaatga | atcggccaac | gcgcggggag | 3420 |
| aggcggtttg | cgtattgggc | gccagggtgg | ttttctttt | caccagtgag | acgggcaaca | 3480 |
| gctgattgcc | cttcaccgcc | tggccctgag | agagttgcag | caagcggtcc | acgctggttt | 3540 |
| gccccagcag | gcgaaaatcc | tgtttgatgg | tggttgacgg | cgggatataa | catgagctgt | 3600 |
| cttcggtatc | gtcgtatccc | actaccgaga | tatccgcacc | aacgcgcagc | ccggactcgg | 3660 |
| taatggcgcg | cattgcgccc | agcgccatct | gatcgttggc | aaccagcatc | gcagtgggaa | 3720 |
| cgatgccctc | attcagcatt | tgcatggttt | gttgaaaacc | ggacatggca | ctccagtcgc | 3780 |
| cttcccgttc | cgctatcggc | tgaatttgat | tgcgagtgag | atatttatgc | cagccagcca | 3840 |
| gacgcagacg | cgccgagaca | gaacttaatg | gtcccgctaa | cagcgcgatt | tgctgatgac | 3900 |
| ccaatgcgac | cagatgctcc | acgcccagtc | gcgtaccgtc | ttcatgggag | aaaataatac | 3960 |
| tgttgatggg | tgtctggtca | gagacatcaa | gaaataacgc | cggaacatta | gtgcaggcag | 4020 |
| cttccacagc | aatggcatcc | tggtcatcca | gcggatagtt | aatgatcagc | ccactgacgc | 4080 |
| gttgcgcgag | aagattgtgc | accgccgctt | tacaggcttc | gacgccgctt | cgttctacca | 4140 |
| tcgacaccac | cacgctggca | cccagttgat | cggcgcgaga | tttaatcgcc | gcgacaattt | 4200 |
| gcgacggcgc | gtgcagggcc | agactggagg | tggcaacgcc | aatcagcaac | gactgtttgc | 4260 |
| ccgccagttg | ttgtgccacg | cggttgggaa | tgtaattcag | ctccgccatc | gccgcttcca | 4320 |
| cttttcccg | cgttttcgca | gaaacgtggc | tggcctggtt | caccacgcgg | gaaacggtct | 4380 |
| gataagagac | accggcatac | tctgcgacat | cgtataacgt | tactggtttc | acattcacca | 4440 |
| ccctgaattg | actctcttcc | gggcgctatc | atgccatacc | gcgaaaggtt | ttgcgccatt | 4500 |
| cgatggtgtc | aacgtaaatg | catgccgctt | cgccttcgcg | cgcgaattgc | aagctgatcc | 4560 |
| ggagcttatc | gactgcacgg | tgcaccaatg | cttctggcgt | caggcagcca | tcggaagctg | 4620 |
| tggtatggct | gtgcaggtcg | taaatcactg | cataattcgt | gtcgctcaag | gcgcactccc | 4680 |
| gttctgata | atgttttttg | cgccgacatc | ataacggttc | tggcaaatat | tctgaaatga | 4740 |
| gctgttgaca | attaatcatc | ggctcgtata | atgtgtggaa | ttgtgagcgg | ataacaattt | 4800 |
| cacacaggaa | acagaattcc | atatgaaata | cctattacca | acagcagcag | ctgggttatt | 4860 |
| attgctcgct | gcgcagccgg | ccatggccca | ggtcaccgtc | tcctcaggta | ccgtggctgc | 4920 |
| accatctgtc | ttcatcttcc | cgccatctga | tgagcagttg | aaatctggaa | ctgcctctgt | 4980 |
| tgtgtgcctg | ctgaataact | tctatcccag | agaggccaaa | gtacagtgga | aggtggataa | 5040 |
| cgccctccaa | tcgggtaact | cccaggagag | tgtcacagag | caggacagca | aggacagcac | 5100 |

| | |
|---|---|
| ctacagcctc agcagcaccc tgacgctgag caaagcagac tacgagaaac acaaagtcta | 5160 |
| cgcctgcgaa gtcacccatc agggcctgag ctcgccggtg acaaagagct tcaaccgcgg | 5220 |
| agagtgttaa taaacaggaa acagaagtcc atatgaaata cctattgcct acggcagccg | 5280 |
| ctggattgtt attactcgcg gcccagccgg ccatggccgc tagcaccaag ggcccatcgg | 5340 |
| tcttcccect ggcaccctcc tccaagagca cctctggggg cacagcggcc ctgggctgcc | 5400 |
| tggtcaagga ctacttcccc gaaccggtga cggtgtcgtg gaactcaggc gccctgacca | 5460 |
| gcggcgtgca caccttcccg gctgtcctac agtcctcagg actctactcc ctcagcagcg | 5520 |
| tagtgaccgt gccctccagc agcttgggca cccagaccta catctgcaac gtgaatcaca | 5580 |
| agcccagcaa caccaaggtg gacaagaaag ttgagcccaa atcttgttaa gcttggctgt | 5640 |
| tttggcggat gagagaagat tttcagcctg atacagatta aatcagaacg cagaagcggt | 5700 |
| ctgataaaac agaatttgcc tggcggcagt agcgcggtgg tcccacctga ccccatgccg | 5760 |
| aactcagaag tgaaacgccg tagcgccgat ggtagtgtgg ggtctcccca tgcgagagta | 5820 |
| gggaactgcc aggcatcaaa taaaacgaaa ggctcagtcg aaagactggg cctttcgttt | 5880 |
| tatctgttgt ttgtcggtga acgctctcct gagtaggaca atccgccgg gagcggattt | 5940 |
| gaacgttgcg aagcaacggc ccggaggacc ctggcgggca ggacgccgc cataaactgc | 6000 |
| caggcatcaa attaagcaga aggccatcct gacggatggc cttttgcgt tctacaaac | 6060 |
| tctt | 6064 |

<210> SEQ ID NO 101
<211> LENGTH: 6094
<212> TYPE: DNA
<213> ORGANISM: Artificial sequence
<220> FEATURE:
<223> OTHER INFORMATION: plasmid pcKCH1Hy1

<400> SEQUENCE: 101

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttgct cacccagaaa cgctggtgaa | 180 |
| agtaaaagat gctgaagatc agttgggtgc acagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg ggggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt cattttaat ttaaaaggat | 1020 |
| ctaggtgaag atcctttttg ataatctcat gaccaaaatc ccttaacgtg agttttcgtt | 1080 |

```
ccactgagcg tcagaccccg tagaaaagat caaaggatct tcttgagatc cttttttct    1140
gcgcgtaatc tgctgcttgc aaacaaaaaa accaccgcta ccagcggtgg tttgtttgcc    1200
ggatcaagag ctaccaactc ttttttccgaa ggtaactggc ttcagcagag cgcagatacc   1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
aacggggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg aacaggaga gcgcacgagg gagcttccag ggggaaacgc     1620
ctggtatctt tatagtcctg tcgggtttcg ccacctctga cttgagcgtc gattttttgtg   1680
atgctcgtca gggggcgga gcctatggaa aaacgccagc aacgcggcct ttttacggtt     1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa     2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tataggcgg cgcctacaat ccatgccaac     3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
```

```
aggcggtttg cgtattgggc gccagggtgg tttttctttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacgcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttcccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcaggta ccgtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct tcaaccgcgg    5220
agagtgttaa taaacaggaa acagaagtcc atatgaaata cctattgcct acggcagccg    5280
ctggattgtt attactcgcg gcccagccgg ccatggccgc tagcaccaag ggcccatcgg    5340
tcttccccct ggcaccctcc tccaagagca cctctggggg cacagcggcc ctgggctgcc    5400
tggtcaagga ctacttcccc gaaccggtga cggtgtcgtg gaactcaggc gccctgacca    5460
gcggcgtgca caccttcccg gctgtcctac agtcctcagg actctactcc ctcagcagcg    5520
tagtgaccgt gccctccagc agcttgggca cccagaccta catctgcaac gtgaatcaca    5580
agcccagcaa caccaaggtg gacaagaaag ttgagcccaa atcttgtgac aaaactcaca    5640
catgcccacc gtgcccataa gcttggctgt tttggcggat gagagaagat tttcagcctg    5700
atacagatta aatcagaacg cagaagcggt ctgataaaac agaatttgcc tggcggcagt    5760
agcgcggtgg tcccacctga ccccatgccg aactcagaag tgaaacgccg tagcgccgat    5820
```

```
ggtagtgtgg ggtctcccca tgcgagagta gggaactgcc aggcatcaaa taaaacgaaa    5880
ggctcagtcg aaagactggg cctttcgttt tatctgttgt ttgtcggtga acgctctcct    5940
gagtaggaca aatccgccgg gagcggattt gaacgttgcg aagcaacggc ccggaggacc    6000
ctggcgggca ggacgcccgc cataaactgc caggcatcaa attaagcaga aggccatcct    6060
gacggatggc cttttgcgt ttctacaaac tctt                                 6094
```

<210> SEQ ID NO 102
<211> LENGTH: 6745
<212> TYPE: DNA
<213> ORGANISM: Artificial sequence
<220> FEATURE:
<223> OTHER INFORMATION: plasmid pMaby1

<400> SEQUENCE: 102

```
ttgtttattt ttctaaatac attcaaatat gtatccgctc atgagacaat aaccctgata      60
aatgcttcaa taatattgaa aaaggaagag tatgagtatt caacatttcc gtgtcgccct    120
tattcccttt tttgcggcat tttgccttcc tgttttgct cacccagaaa cgctggtgaa     180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgctttttt    540
gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atccttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
```

-continued

```
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatgcgatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgacttc cgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttctttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
```

-continued

| | | | | |
|---|---|---|---|---|
| tcgacaccac | cacgctggca | cccagttgat | cggcgcgaga | tttaatcgcc | gcgacaattt | 4200 |
| gcgacggcgc | gtgcagggcc | agactggagg | tggcaacgcc | aatcagcaac | gactgtttgc | 4260 |
| ccgccagttg | ttgtgccacg | cggttgggaa | tgtaattcag | ctccgccatc | gccgcttcca | 4320 |
| cttttcccg | cgttttcgca | gaaacgtggc | tggcctggtt | caccacgcgg | gaaacggtct | 4380 |
| gataagagac | accggcatac | tctgcgacat | cgtataacgt | tactggtttc | acattcacca | 4440 |
| ccctgaattg | actctcttcc | gggcgctatc | atgccatacc | gcgaaaggtt | ttgcgccatt | 4500 |
| cgatggtgtc | aacgtaaatg | catgccgctt | cgccttcgcg | cgcgaattgc | aagctgatcc | 4560 |
| ggagcttatc | gactgcacgg | tgcaccaatg | cttctggcgt | caggcagcca | tcggaagctg | 4620 |
| tggtatggct | gtgcaggtcg | taaatcactg | cataattcgt | gtcgctcaag | gcgcactccc | 4680 |
| gttctggata | tgttttttg | cgccgacatc | ataacggttc | tggcaaatat | tctgaaatga | 4740 |
| gctgttgaca | attaatcatc | ggctcgtata | atgtgtggaa | ttgtgagcgg | ataacaattt | 4800 |
| cacacaggaa | acagaattcc | atatgaaata | cctattacca | acagcagcag | ctgggttatt | 4860 |
| attgctcgct | gcgcagccgg | ccatggccca | ggtcaccgtc | tcctcaggta | ccgtggctgc | 4920 |
| accatctgtc | ttcatcttcc | cgccatctga | tgagcagttg | aaatctggaa | ctgcctctgt | 4980 |
| tgtgtgcctg | ctgaataact | tctatcccag | agaggccaaa | gtacagtgga | aggtggataa | 5040 |
| cgccctccaa | tcgggtaact | cccaggagag | tgtcacagag | caggacagca | aggacagcac | 5100 |
| ctacagcctc | agcagcaccc | tgacgctgag | caaagcagac | tacgagaaac | acaaagtcta | 5160 |
| cgcctgcgaa | gtcacccatc | agggcctgag | ctcgccggtg | acaaagagct | tcaaccgcgg | 5220 |
| agagtgttaa | taaacaggaa | acagaagtcc | atatgaaata | cctattgcct | acggcagccg | 5280 |
| ctggattgtt | attactcgcg | gcccagccgg | ccatggccgc | tagcaccaag | ggcccatcgg | 5340 |
| tcttccccct | ggcaccctcc | tccaagagca | cctctggggg | cacagcggcc | ctgggctgcc | 5400 |
| tggtcaagga | ctacttcccc | gaaccggtga | cggtgtcgtg | gaactcaggc | gccctgacca | 5460 |
| gcggcgtgca | caccttcccg | gctgtcctac | agtcctcagg | actctactcc | ctcagcagcg | 5520 |
| tggtgaccgt | gccctccagc | agcttgggca | cccagaccta | catctgcaac | gtgaatcaca | 5580 |
| agcccagcaa | caccaaggtg | gacaagaaag | ttgagcccaa | atcttgtgac | aaaactcaca | 5640 |
| catgcccacc | gtgcccagca | cctgaactcc | tggggggacc | gtcagtcttc | ctcttccccc | 5700 |
| caaaacccaa | ggacaccctc | atgatctccc | ggacccctga | ggtcacatgc | gtggtggtgg | 5760 |
| acgtgagcca | cgaagaccct | gaggtcaagt | tcaactggta | cgtggacggc | gtggaggtgc | 5820 |
| ataatgccaa | gacaaagccg | cgggaggagc | agtacaacag | cacgtaccgg | gtggtcagcg | 5880 |
| tcctcaccgt | cctgcaccag | gactggctga | atggcaagga | gtacaagtgc | aaggtctcca | 5940 |
| acaaagccct | cccagccccc | atcgagaaaa | ccatctccaa | agccaaaggg | cagccccgag | 6000 |
| aaccacaggt | gtacaccctg | cccccatccc | gggatgagct | gaccaagaac | caggtcagcc | 6060 |
| tgacctgcct | ggtcaaaggc | ttctatccca | gcgacatcgc | cgtggagtgg | gagagcaatg | 6120 |
| ggcagccgga | gaacaactac | aagaccacgc | ctcccgtgct | ggactccgac | ggctccttct | 6180 |
| tcctctacag | caagctcacc | gtggacaaga | gcaggtggca | gcagggggaac | gtcttctcat | 6240 |
| gctccgtgat | gcatgaggct | ctgcacaacc | actacacgca | gaagagcctc | tccctgtctc | 6300 |
| cgggtaaata | agcttggctg | ttttggcgga | tgagagaaga | ttttcagcct | gatacagatt | 6360 |
| aaatcagaac | gcagaagcgg | tctgataaaa | cagaatttgc | ctggcggcag | tagcgcggtg | 6420 |
| gtcccacctg | accccatgcc | gaactcagaa | gtgaaacgcc | gtagcgccga | tggtagtgtg | 6480 |

-continued

```
gggtctcccc atgcgagagt agggaactgc caggcatcaa ataaaacgaa aggctcagtc    6540
gaaagactgg gcctttcgtt ttatctgttg tttgtcggtg aacgctctcc tgagtaggac    6600
aaatccgccg ggagcggatt tgaacgttgc gaagcaacgg cccggaggac cctggcgggc    6660
aggacgcccg ccataaactg ccaggcatca aattaagcag aaggccatcc tgacggatgg    6720 ccttttttgcg tttctacaaa ctctt                                         6745
```

<210> SEQ ID NO 103
<211> LENGTH: 126
<212> TYPE: PRT
<213> ORGANISM: Artificial sequence
<220> FEATURE:
<223> OTHER INFORMATION: CD16 c13 aminoacid sequence
<220> FEATURE:
<221> NAME/KEY: MISC_FEATURE
<222> LOCATION: (35)..(37)
<223> OTHER INFORMATION: Unknown amino acid
<220> FEATURE:
<221> NAME/KEY: MISC_FEATURE
<222> LOCATION: (55)..(57)
<223> OTHER INFORMATION: Unknown amino acid
<220> FEATURE:
<221> NAME/KEY: MISC_FEATURE
<222> LOCATION: (109)..(113)
<223> OTHER INFORMATION: Unknown amino acid

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ser Phe Pro Gly Ser Ile Phe Ser Leu Thr
            20                  25                  30

Met Gly Xaa Xaa Xaa Trp Tyr Arg Gln Ala Pro Gly Lys Glu Arg Glu
        35                  40                  45

Leu Val Thr Ser Ala Thr Xaa Xaa Xaa Pro Gly Gly Asp Thr Asn Tyr
    50                  55                  60

Ala Asp Phe Val Lys Gly Arg Phe Thr Ile Ser Arg Asp Asn Ala Arg
65                  70                  75                  80

Ser Ile Ile Tyr Leu Gln Met Asn Ser Leu Lys Pro Glu Asp Thr Ala
                85                  90                  95

Val Tyr Tyr Cys Tyr Ala Arg Thr Arg Asn Trp Gly Xaa Xaa Xaa Xaa
            100                 105                 110

Xaa Thr Val Trp Gly Gln Gly Thr Gln Val Thr Val Ser Ser
        115                 120                 125

<210> SEQ ID NO 104
<211> LENGTH: 126
<212> TYPE: PRT
<213> ORGANISM: Artificial sequence
<220> FEATURE:
<223> OTHER INFORMATION: CD16 c21 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (56)..(57)
<223> OTHER INFORMATION: Unknown amino acid

<400> SEQUENCE: 104

Glu Val Gln Leu Val Glu Ser Gly Gly Glu Leu Val Gln Ala Gly Gly
1               5                   10                  15

Ser Leu Arg Leu Ser Cys Ala Ala Ser Gly Leu Thr Phe Ser Ser Tyr
            20                  25                  30

Asn Met Gly Xaa Xaa Trp Phe Arg Arg Ala Pro Gly Lys Glu Arg Glu
            35                  40                  45

Phe Val Ala Ser Ile Thr Trp Xaa Xaa Ser Gly Arg Asp Thr Phe Tyr
    50                  55                  60

Ala Asp Ser Val Lys Gly Arg Phe Thr Ile Ser Arg Asp Asn Ala Lys
65                  70                  75                  80

Asn Thr Val Tyr Leu Gln Met Ser Ser Leu Lys Pro Glu Asp Thr Ala
                85                  90                  95

Val Tyr Tyr Cys Ala Ala Asn Pro Trp Pro Val Ala Ala Pro Arg Ser
            100                 105                 110

Gly Thr Tyr Trp Gly Gln Gly Thr Gln Val Thr Val Ser Ser
            115                 120                 125

<210> SEQ ID NO 105
<211> LENGTH: 126
<212> TYPE: PRT
<213> ORGANISM: Artificial sequence
<220> FEATURE:
<223> OTHER INFORMATION: CEA 43 aminoacid sequence
<220> FEATURE:
<221> NAME/KEY: MISC_FEATURE
<222> LOCATION: (36)..(37)
<223> OTHER INFORMATION: Unknown amino acid
<220> FEATURE:
<221> NAME/KEY: MISC_FEATURE
<222> LOCATION: (57)..(57)
<223> OTHER INFORMATION: Unknown amino acid
<220> FEATURE:
<221> NAME/KEY: MISC_FEATURE
<222> LOCATION: (111)..(113)
<223> OTHER INFORMATION: Unknown amino acid

<400> SEQUENCE: 105

Glu Val Gln Leu Val Glu Ser Gly Gly Gly Leu Val Gln Ala Gly Gly
1               5                   10                  15

Ser Leu Thr Leu Ser Cys Thr Ser Ser Thr Leu Thr Phe Thr Pro Tyr
            20                  25                  30

Arg Met Gly Xaa Xaa Trp Tyr Arg Gln Thr Pro Gly Lys Gln Arg Asp
            35                  40                  45

Leu Val Ala Asp Ile Ser Pro Gly Xaa Asp Gly Ser Thr Lys Asn Tyr
    50                  55                  60

Ala Gly Phe Ala Gln Gly Arg Phe Thr Ile Ser Arg Asp Asn Ile Lys
65                  70                  75                  80

Asn Thr Val Tyr Leu Gln Met Asn Asp Leu Lys Pro Glu Asp Thr Ala
                85                  90                  95

Val Tyr Tyr Cys Asn Thr Tyr Val Ala Phe Val Gly Arg Ala Xaa Xaa
            100                 105                 110

Xaa Arg Thr Trp Gly Gln Gly Thr Gln Val Thr Val Thr Ser
            115                 120                 125

<210> SEQ ID NO 106
<211> LENGTH: 345
<212> TYPE: DNA
<213> ORGANISM: Artificial sequence
<220> FEATURE:
<223> OTHER INFORMATION: nucleotide CD16 c13

<400> SEQUENCE: 106
gaggtgcagc tggtggagtc tgggggaggc ttggtgcagc ctggggggtc tctgagactc      60
tcctgttcat tccctggaag catcttcagt ctcaccatgg gctggtaccg tcaggctcca     120

```
gggaaggagc gcgagttggt cacaagtgct actcctggtg gtgacacaaa ctatgcagac    180
ttcgtgaagg gccgattcac catctccaga gacaacgcca ggagcatcat atatctacaa    240
atgaatagcc tgaaacctga ggacacggcc gtctattatt gttatgcacg tacgaggaat    300
tggggtacgg tctggggcca ggggacccag gtcaccgtct cctca                    345

<210> SEQ ID NO 107
<211> LENGTH: 366
<212> TYPE: DNA
<213> ORGANISM: Artificial sequence
<220> FEATURE:
<223> OTHER INFORMATION: nucleotide CD16 c21

<400> SEQUENCE: 107
gaggtgcagc tggtggagtc tgggggagag ttggtgcagg ctgggggctc tctgagactc     60
tcctgtgcag cctctggcct caccttcagt agctataaca tgggctggtt ccgccgggct    120
ccagggaagg agcgtgagtt tgtagcatct attaccctgga gtggtcggga cacattctat    180
gcagactccg tgaagggccg attcaccatc tccagagaca cgccaagaa cactgtttat     240 ctgcaaatga gcagcctgaa acctgaggac acggccgttt attattgtgc tgcaaacccc    300
tggccagtgg cggcgccacg tagtggcacc tactggggcc aagggaccca ggtcaccgtc    360
tcctca                                                               366

<210> SEQ ID NO 108
<211> LENGTH: 360
<212> TYPE: DNA
<213> ORGANISM: Artificial sequence
<220> FEATURE:
<223> OTHER INFORMATION: nucleotide CEA 43

<400> SEQUENCE: 108
gaggtgcagc tggtggagtc tgggggaggc ttggtgcagg cggggggctc tctgacactc     60
tcctgcacaa gttctacact taccttcact ccgtatcgca tgggctggta ccgccagact    120
ccagggaagc agcgtgattt ggtcgcggac attagtcctg gtgatggtag taccaaaaat    180
tatgcaggct cgcgcaggg ccgattcacc atctccagag acaacatcaa gaacacggtg     240
tatctgcaaa tgaacgacct gaaacctgag gacacggccg tctattactg caacacctac    300
gtcgcgtttg tggggcgtgc gcgtacttgg ggccagggga cccaggtcac tgtcacctca    360

<210> SEQ ID NO 109
<211> LENGTH: 5500
<212> TYPE: DNA
<213> ORGANISM: Artificial sequence
<220> FEATURE:
<223> OTHER INFORMATION: plasmid p55Flag/RBS/35

<400> SEQUENCE: 109
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
```

```
cactgcggcc aacttacttc tgacaacgat cggaggaccg aaggagctaa ccgcttttt       540 gcacaacatg ggggatcatg taactcgcct tgatcgttgg gaaccggagc tgaatgaagc      600
cataccaaac gacgagcgtg acaccacgat gcctgtagca atggcaacaa cgttgcgcaa      660
actattaact ggcgaactac ttactctagc ttcccggcaa caattaatag actggatgga      720
ggcggataaa gttgcaggac cacttctgcg ctcggccctt ccggctggct ggtttattgc      780
tgataaatct ggagccggtg agcgtgggtc tcgcggtatc attgcagcac tggggccaga      840
tggtaagccc tcccgtatcg tagttatcta cacgacgggg agtcaggcaa ctatggatga      900
acgaaataga cagatcgctg agataggtgc ctcactgatt aagcattggt aactgtcaga      960
ccaagtttac tcatatatac tttagattga tttaaaactt cattttaat ttaaaaggat      1020 ctaggtgaag atccttttg ataatctcat gaccaaaatc ccttaacgtg agttttcgtt      1080
ccactgagcg tcagaccccg tagaaaagat caaaggatct tcttgagatc ctttttttct      1140
gcgcgtaatc tgctgcttgc aaacaaaaaa accaccgcta ccagcggtgg tttgtttgcc      1200
ggatcaagag ctaccaactc tttttccgaa ggtaactggc ttcagcagag cgcagatacc      1260
aaatactgtc cttctagtgt agccgtagtt aggccaccac ttcaagaact ctgtagcacc      1320
gcctacatac ctcgctctgc taatcctgtt accagtggct gctgccagtg gcgataagtc      1380
gtgtcttacc gggttggact caagacgata gttaccggat aaggcgcagc ggtcgggctg      1440
aacggggggt tcgtgcacac agcccagctt ggagcgaacg acctacaccg aactgagata      1500
cctacagcgt gagcattgag aaagcgccac gcttcccgaa gggagaaagg cggacaggta      1560
tccggtaagc ggcagggtcg aacaggaga gcgcacgagg gagcttccag ggggaaacgc       1620
ctggtatctt tatagtcctg tcgggtttcg ccacctctga cttgagcgtc gatttttgtg      1680
atgctcgtca gggggggcgga gcctatgaa aacgccagc aacgcggcct ttttacggtt      1740
cctggccttt tgctggcctt tgctcacat gttctttcct gcgttatccc ctgattctgt      1800
ggataaccgt attaccgcct tgagtgagc tgataccgct cgccgcagcc gaacgaccga      1860
gcgcagcgag tcagtgagcg aggaagcgga agagcgcctg atgcggtatt ttctccttac      1920
gcatctgtgc ggtatttcac accgcatata tggtgcactc tcagtacaat ctgctctgat      1980
gccgcatagt taagccagta tacactccgc tatcgctacg tgactgggtc atggctgcgc      2040
cccgacaccc gccaacaccc gctgacgcgc cctgacgggc ttgtctgctc ccggcatccg      2100
cttacagaca agctgtgacc gtctccggga gctgcatgtg tcagaggttt tcaccgtcat      2160
caccgaaacg cgcgaggcag ctgcggtaaa gctcatcagc gtggtcgtga agcgattcac      2220
agatgtctgc ctgttcatcc gcgtccagct cgttgagttt ctccagaagc gttaatgtct      2280
ggcttctgat aaagcgggcc atgttaaggg cggttttttc ctgtttggtc acttgatgcc      2340
tccgtgtaag ggggaatttc tgttcatggg ggtaatgata ccgatgaaac gagagaggat      2400
gctcacgata cgggttactg atgatgaaca tgcccggtta ctggaacgtt gtgagggtaa      2460
acaactggcg gtatggatgc ggcgggacca gagaaaaatc actcagggtc aatgccagcg      2520
cttcgttaat acagatgtag gtgttccaca gggtagccag cagcatcctg cgatgcagat      2580
ccggaacata atggtgcagg cgctgactt ccgcgtttcc agactttacg aaacacggaa      2640
accgaagacc attcatgttg ttgctcaggt cgcagacgtt ttgcagcagc agtcgcttca      2700
cgttcgctcg cgtatcggtg attcattctg ctaaccagta aggcaacccc gccagcctag      2760
ccgggtcctc aacgacagga gcacgatcat gcgcacccgt ggccaggacc caacgctgcc      2820
```

```
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg gcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttttcttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttt ttgtgccacg cggttgggaa tgtaattcag ctccgccatc gccgcttcca   4320
ctttttcccg cgttttcgca gaaacgtggc tggcctggtt caccacgcgg gaaacggtct   4380
gataagagac accggcatac tctgcgacat cgtataacgt tactggtttc acattccacca   4440 ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata atgttttttg cgccgacatc ataacggttc tggcaaatat tctgaaatga   4740
gctgttgaca attaatcatc ggctcgtata atgtgtggaa ttgtgagcgg ataacaattt   4800
cacacaggaa acagaattcc atatgaaata cctattacca acagcagcag ctgggttatt   4860
attgctcgct gcgcagccgg ccatggccca ggtcaccgtc tcctcaaacc gcggagagtg   4920
tgcaggtgat tacaaagacg atgacgataa gtaataaaca ggaaacagaa gtccatatga   4980
aatatctttt acctacggca gccgcaggtt tgttgttact cgcggcccag ccggccatgg   5040
ccgctagcgc ggccgctcta gattaagctt ggctgttttg gcggatgaga aagattttc   5100 agcctgatac agattaaatc agaacgcaga agcggtctga taaaacagaa tttgcctggc   5160
ggcagtagcg cggtggtccc acctgacccc atgccgaact cagaagtgaa acgccgtagc   5220
```

```
gccgatggta gtgtggggtc tccccatgcg agagtaggga actgccaggc atcaaataaa    5280
acgaaaggct cagtcgaaag actgggcctt tcgttttatc tgttgtttgt cggtgaacgc    5340
tctcctgagt aggacaaatc cgccgggagc ggatttgaac gttgcgaagc aacggcccgg    5400
aggaccctgg cgggcaggac gcccgccata aactgccagg catcaaatta agcagaaggc    5460
catcctgacg gatggccttt ttgcgtttct acaaactctt                          5500
```

<210> SEQ ID NO 110
<211> LENGTH: 5560
<212> TYPE: DNA
<213> ORGANISM: Artificial sequence
<220> FEATURE:
<223> OTHER INFORMATION: p55Flag/RBS/35cmyc6HisGS

<400> SEQUENCE: 110

```
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa     180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540 gcacaacatg gggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt cattttttaat ttaaaaggat   1020 ctaggtgaag atcctttttg ataatctcat gaccaaaatc ccttaacgtg agttttcgtt    1080
ccactgagcg tcagaccccg tagaaaagat caaaggatct tcttgagatc ctttttttct    1140
gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440
aacggggggt tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gatttttgtg    1680
atgctcgtca ggggggcgga gcctatgaa aaacgccagc aacgcggcct ttttacggtt    1740
```

```
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgacttc cgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt ctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttccttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
```

```
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttg ttgtgccacg cggttgggaa tgtaattcag ctccgccatc gccgcttcca   4320 cttttcccg cgttttcgca gaaacgtggc tggcctggtt caccacgcgg gaaacggtct    4380
gataagagac accggcatac tctgcgacat cgtataacgt tactggtttc acattcacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata tgttttttg cgccgacatc ataacggttc tggcaaatat tctgaaatga    4740
gctgttgaca attaatcatc ggctcgtata atgtgtggaa ttgtgagcgg ataacaattt   4800
cacacaggaa acagaattcc atatgaaata cctattacca acagcagcag ctgggttatt   4860
attgctcgct gcgcagccgg ccatggccca ggtcaccgtc tcctcaaacc gcggagagtg   4920
tgcaggtgat tacaaagacg atgacgataa gtaataaaca ggaaacagaa gtccatatga   4980
aatatctttt acctacggca gccgcaggtt tgttgttact cgcggcccag ccggccatgg   5040
ccgctagcgc ggccgcagaa caaaaactca tctcagaaga ggatctgaat ggggccgtac   5100
atcaccacca tcatcatggg agctaagctt ggctgttttg gcggatgaga aagattttc    5160 agcctgatac agattaaatc agaacgcaga agcggtctga taaaacagaa tttgcctggc   5220
ggcagtagcg cggtggtccc acctgacccc atgccgaact cagaagtgaa acgccgtagc   5280
gccgatggta gtgtggggtc tccccatgcg agagtaggga actgccaggc atcaaataaa   5340
acgaaaggct cagtcgaaag actgggcctt tcgttttatc tgttgtttgt cggtgaacgc   5400
tctcctgagt aggacaaatc cgccgggagc ggatttgaac gttgcgaagc aacggcccgg   5460
aggaccctgg cgggcaggac gcccgccata aactgccagg catcaaatta gcagaaggc    5520 catcctgacg gatggccttt ttgcgtttct acaaactctt                         5560
```

<210> SEQ ID NO 111
<211> LENGTH: 5866
<212> TYPE: DNA
<213> ORGANISM: Artificial sequence
<220> FEATURE:
<223> OTHER INFORMATION: plasmid p55Flag/RBS/35cmyc6HisGS

<400> SEQUENCE: 111

```
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa    180
agtaaaagat gctgaagatc agttgggtgc acgagtgggt tacatcgaac tggatctcaa   240
cagcggtaag atccttgaga gttttcgccc cgaagaacgt tttccaatga tgagcacttt   300
taaagttctg ctatgtggcg cggtattatc ccgtgttgac gccgggcaag agcaactcgg   360
tcgccgcata cactattctc agaatgactt ggttgagtac tcaccagtca cagaaaagca   420
tcttacggat ggcatgacag taagagaatt atgcagtgct gccataacca tgagtgataa   480
cactgcggcc aacttacttc tgacaacgat cggaggaccg aaggagctaa ccgcttttt    540 gcacaacatg ggggatcatg taactcgcct tgatcgttgg gaaccggagc tgaatgaagc   600
```

```
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg ataggtgc ctcactgatt aagcattggt aactgtcaga      960
ccaagtttac tcatatatac tttagattga tttaaaactt cattttaat ttaaaaggat    1020 ctaggtgaag atcctttttg ataatctcat gaccaaaatc ccttaacgtg agttttcgtt   1080
ccactgagcg tcagacccg tagaaaagat caaaggatct tcttgagatc cttttttct      1140 gcgcgtaatc tgctgcttgc aaacaaaaaa accaccgcta ccagcggtgg tttgtttgcc    1200
ggatcaagag ctaccaactc tttttccgaa ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440 aacgggggt tcgtgcacac agcccagctt ggagcgaacg acctacaccg aactgagata     1500
cctacagcgt gagcattgag aaagcgccac gcttcccgaa gggagaaagg cggacaggta    1560
tccggtaagc ggcagggtcg gaacaggaga gcgcacgagg gagcttccag ggggaaacgc    1620
ctggtatctt tatagtcctg tcgggtttcg ccacctctga cttgagcgtc gatttttgtg    1680
atgctcgtca ggggggcgga gcctatggaa aaacgccagc aacgcggcct ttttacggtt    1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggtttttc ctgtttggtc acttgatgcc     2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa      2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
```

-continued

| | |
|---|---|
| ccgcgacgca acgcggggag gcagacaagg tatagggcgg cgcctacaat ccatgccaac | 3060 |
| ccgttccatg tgctcgccga ggcggcataa atcgccgtga cgatcagcgg tccagtgatc | 3120 |
| gaagttaggc tggtaagagc cgcgagcgat ccttgaagct gtccctgatg gtcgtcatct | 3180 |
| acctgcctgg acagcatggc ctgcaacgcg ggcatcccga tgccgccgga agcgagaaga | 3240 |
| atcataatgg ggaaggccat ccagcctcgc gtcgcgaacg ccagcaagac gtagcccagc | 3300 |
| gcgtcggcca gcttgcaatt cgcgctaact tacattaatt gcgttgcgct cactgcccgc | 3360 |
| tttccagtcg ggaaacctgt cgtgccagct gcattaatga atcggccaac gcgcggggag | 3420 |
| aggcggtttg cgtattgggc gccagggtgg ttttcttt caccagtgag acgggcaaca | 3480 |
| gctgattgcc cttcaccgcc tggccctgag agagttgcag caagcggtcc acgctggttt | 3540 |
| gccccagcag gcgaaaatcc tgtttgatgg tggttgacgg cgggatataa catgagctgt | 3600 |
| cttcggtatc gtcgtatccc actaccgaga tatccgcacc aacgcgcagc ccggactcgg | 3660 |
| taatggcgcg cattgcgccc agcgccatct gatcgttggc aaccagcatc gcagtgggaa | 3720 |
| cgatgccctc attcagcatt tgcatggttt gttgaaaacc ggacatggca ctccagtcgc | 3780 |
| cttcccgttc cgctatcggc tgaatttgat tgcgagtgag atatttatgc cagccagcca | 3840 |
| gacgcagacg cgccgagaca gaacttaatg gtcccgctaa cagcgcgatt tgctgatgac | 3900 |
| ccaatgcgac cagatgctcc acgcccagtc gcgtaccgtc ttcatgggag aaaataatac | 3960 |
| tgttgatggg tgtctggtca gagacatcaa gaaataacgc cggaacatta gtgcaggcag | 4020 |
| cttccacagc aatggcatcc tggtcatcca gcggatagtt aatgatcagc ccactgacgc | 4080 |
| gttgcgcgag aagattgtgc accgccgctt tacaggcttc gacgccgctt cgttctacca | 4140 |
| tcgacaccac cacgctggca cccagttgat cggcgcgaga tttaatcgcc gcgacaattt | 4200 |
| gcgacggcgc gtgcagggcc agactggagg tggcaacgcc aatcagcaac gactgtttgc | 4260 |
| ccgccagttg ttgtgccacg cggttgggaa tgtaattcag ctccgccatc gccgcttcca | 4320 |
| cttttttccg cgttttcgca gaaacgtggc tggcctggtt caccacgcgg gaaacggtct | 4380 |
| gataagagac accggcatac tctgcgacat cgtataacgt tactggtttc acattcacca | 4440 |
| ccctgaattg actctcttcc gggcgctatc atgccatacc gcgaaaggtt ttgcgccatt | 4500 |
| cgatggtgtc aacgtaaatg catgccgctt cgccttcgcg cgcgaattgc aagctgatcc | 4560 |
| ggagcttatc gactgcacgg tgcaccaatg cttctggcgt caggcagcca tcggaagctg | 4620 |
| tggtatggct gtgcaggtcg taaatcactg cataattcgt gtcgctcaag gcgcactccc | 4680 |
| gttctggata atgttttttg cgccgacatc ataacggttc tggcaaatat tctgaaatga | 4740 |
| gctgttgaca attaatcatc ggctcgtata atgtgtggaa ttgtgagcgg ataacaattt | 4800 |
| cacacaggaa acagaattcc atatgaaata cctattacca acagcagcag ctgggttatt | 4860 |
| attgctcgct gcgcagccgg ccatggccca ggtcaccgtc tcctcacgta cggtggctgc | 4920 |
| accatctgtc ttcatcttcc cgccatctga tgagcagttg aaatctggaa ctgcctctgt | 4980 |
| tgtgtgcctg ctgaataact tctatcccag agaggccaaa gtacagtgga aggtggataa | 5040 |
| cgcccctcca atcgggtaact cccaggagag tgtcacagag caggacagca aggacagcac | 5100 |
| ctacagcctc agcagcaccc tgacgctgag caaagcagac tacgagaaac acaaagtcta | 5160 |
| cgcctgcgaa gtcacccatc agggcctgag ctcgccggtg acaaagagct tcaaccgcgg | 5220 |
| agagtgtgca ggtgattaca agacgatga cgataagtaa taaacaggaa acagaagtcc | 5280 |
| atatgaaata tcttttacct acggcagccg caggtttgtt gttactcgcg gcccagccgg | 5340 |

| | |
|---|---:|
| ccatggccgc tagcgcggcc gcagaacaaa aactcatctc agaagaggat ctgaatgggg | 5400 |
| ccgtacatca ccaccatcat catgggagct aagcttggct gttttggcgg atgagagaag | 5460 |
| attttcagcc tgatacagat taaatcagaa cgcagaagcg gtctgataaa acagaatttg | 5520 |
| cctggcggca gtagcgcggt ggtcccacct gaccccatgc cgaactcaga agtgaaacgc | 5580 |
| cgtagcgccg atggtagtgt ggggtctccc catgcgagag tagggaactg ccaggcatca | 5640 |
| aataaaacga aaggctcagt cgaaagactg ggcctttcgt tttatctgtt gtttgtcggt | 5700 |
| gaacgctctc ctgagtagga caaatccgcc gggagcggat ttgaacgttg cgaagcaacg | 5760 |
| gcccggagga ccctggcggg caggacgccc gccataaact gccaggcatc aaattaagca | 5820 |
| gaaggccatc ctgacggatg ccttttttgc gtttctacaa actctt | 5866 |

<210> SEQ ID NO 112
<211> LENGTH: 6169
<212> TYPE: DNA
<213> ORGANISM: Artificial sequence
<220> FEATURE:
<223> OTHER INFORMATION: plasmid pCkCH1y1-TAG

<400> SEQUENCE: 112

| | |
|---|---:|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg gggatcatg taactcgcct tgatcgttgg gaaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt cattttaat ttaaaaggat | 1020 |
| ctaggtgaag atccttttg ataatctcat gaccaaaatc ccttaacgtg agttttcgtt | 1080 |
| ccactgagcg tcagaccccg tagaaaagat caaaggatct tcttgagatc cttttttct | 1140 |
| gcgcgtaatc tgctgcttgc aaacaaaaaa accaccgcta ccagcggtgg tttgtttgcc | 1200 |
| ggatcaagag ctaccaactc tttttccgaa ggtaactggc ttcagcagag cgcagatacc | 1260 |
| aaatactgtc cttctagtgt agccgtagtt aggccaccac ttcaagaact ctgtagcacc | 1320 |
| gcctacatac ctcgctctgc taatcctgtt accagtggct gctgccagtg gcgataagtc | 1380 |
| gtgtcttacc gggttggact caagacgata gttaccggat aaggcgcagc ggtcgggctg | 1440 |
| aacggggggt tcgtgcacac agcccagctt ggagcgaacg acctacaccg aactgagata | 1500 |
| cctacagcgt gagcattgag aaagcgccac gcttcccgaa gggagaaagg cggacaggta | 1560 |

```
tccggtaagc ggcagggtcg gaacaggaga gcgcacgagg gagcttccag ggggaaacgc    1620
ctggtatctt tatagtcctg tcgggtttcg ccacctctga cttgagcgtc gattttttgtg   1680 atgctcgtca ggggggcgga gcctatggaa aaacgccagc aacgcggcct ttttacggtt    1740
cctggccttt tgctggcctt ttgctcacat gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca gctgtgaccg tctccgggag ctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttttcttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
```

```
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgtttcgca gaaacgtggc tggcctggtt caccacgcgg aaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgtttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220
agagtgtgca ggtgattaca agacgatga cgataagtaa taaacaggaa acagaagtcc    5280
atatgaaata tcttttacct acggcagccg caggtttgtt gttactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca gcccagcaa caccaaggtg acaagaaag    5640
ttgagcccaa atcttgtgcg ccgcagaac aaaaactcat ctcagaagag gatctgaatg    5700
gggccgtaca tcaccaccat catcatggga gctaagcttg gctgttttgg cggatgagag    5760
aagattttca gcctgataca gattaaatca gaacgcagaa gcggtctgat aaaacagaat    5820
ttgcctggcg gcagtagcgc ggtggtccca cctgaccca tgccgaactc agaagtgaaa    5880
cgccgtagcg ccgatggtag tgtggggtct ccccatgcga gagtagggaa ctgccaggca    5940
tcaaataaaa cgaaaggctc agtcgaaaga ctgggccttt cgttttatct gttgtttgtc    6000
ggtgaacgct ctcctgagta ggacaaatcc gccgggagcg gatttgaacg ttgcgaagca    6060
acggcccgga ggaccctggc gggcaggacg cccgccataa actgccaggc atcaaattaa    6120
gcagaaggcc atcctgacgg atggcctttt tgcgtttcta caaactctt                6169
```

<210> SEQ ID NO 113
<211> LENGTH: 6199

```
<212> TYPE: DNA
<213> ORGANISM: Artificial sequence
<220> FEATURE:
<223> OTHER INFORMATION: plasmid pCkCH1Hy1-TAG

<400> SEQUENCE: 113
ttgtttattt ttctaaatac attcaaatat gtatccgctc atgagacaat aaccctgata      60
aatgcttcaa taatattgaa aaaggaagag tatgagtatt caacatttcc gtgtcgccct     120
tattcccttt tttgcggcat tttgccttcc tgttttttgct cacccagaaa cgctggtgaa    180
agtaaaagat gctgaagatc agttgggtgc acagtgggt tacatcgaac tggatctcaa     240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540
gcacaacatg gggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt cattttaat ttaaaaggat    1020
ctaggtgaag atcctttttg ataatctcat gaccaaaatc ccttaacgtg agttttcgtt    1080
ccactgagcg tcagacccccg tagaaaagat caaaggatct cttgagatc cttttttct    1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
```

```
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg gcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttttt caccagtgag acgggcaaca    3480
gctgattgcc cttcaccgcc tggccctgag agagttgcag caagcggtcc acgctggttt    3540
gccccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggt gtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttt ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattccacca   4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
```

-continued

```
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata atgtttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220 agagtgtgca ggtgattaca aagacgatga cgataagtaa taaacaggaa acagaagtcc    5280
atatgaaata tcttttacct acggcagccg caggtttgtt gttactcgcg gcccagccgg    5340
ccatggccgc tagcaccaag ggcccatcgg tcttccccct ggcaccctcc tccaagagca    5400
cctctggggg cacagcggcc ctgggctgcc tggtcaagga ctacttcccc gaaccggtga    5460
cggtgtcgtg gaactcaggc gccctgacca gcggcgtgca caccttcccg gctgtcctac    5520
agtcctcagg actctactcc ctcagcagcg tagtgaccgt gccctccagc agcttgggca    5580
cccagaccta catctgcaac gtgaatcaca agcccagcaa caccaaggtg gacaagaaag    5640
ttgagcccaa atcttgtgac aaaactcaca catgcccacc gtgcccagcg ccgcagaac    5700 aaaaactcat ctcagaagag gatctgaatg gggccgtaca tcaccaccat catcatggga    5760
gctaagcttg gctgttttgg cggatgagag aagattttca gcctgataca gattaaatca    5820
gaacgcagaa gcggtctgat aaaacagaat ttgcctggcg gcagtagcgc ggtggtccca    5880
cctgacccca tgccgaactc agaagtgaaa cgccgtagcg ccgatggtag tgtggggtct    5940
ccccatgcga gagtagggaa ctgccaggca tcaaataaaa cgaaaggctc agtcgaaaga    6000
ctgggccttt cgttttatct gttgtttgtc ggtgaacgct ctcctgagta ggacaaatcc    6060
gccgggagcg gatttgaacg ttgcgaagca acggcccgga ggaccctggc gggcaggacg    6120
cccgccataa actgccaggc atcaaattaa gcagaaggcc atcctgacgg atggcctttt    6180
tgcgtttcta caaactctt                                                 6199
```

<210> SEQ ID NO 114
<211> LENGTH: 6064
<212> TYPE: DNA
<213> ORGANISM: Artificial sequence
<220> FEATURE:
<223> OTHER INFORMATION: plasmid pCkCH1y1

<400> SEQUENCE: 114

```
ttgtttattt ttctaaatac attcaaatat gtatccgctc atgagacaat aaccctgata     60
aatgcttcaa taatattgaa aaaggaagag tatgagtatt caacatttcc gtgtcgccct    120
tattcccttt tttgcggcat tttgccttcc tgttttgct cacccagaaa cgctggtgaa    180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
```

-continued

```
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt    540 gcacaacatg ggggatcatg taactcgcct tgatcgttgg gaaccggagc tgaatgaagc    600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg ataggtgc ctcactgatt aagcattggt aactgtcaga    960
ccaagtttac tcatatatac tttagattga tttaaaactt catttttaat ttaaaaggat   1020
ctaggtgaag atccttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca gggggggcgga gcctatggaa aaacgccagc aacgcggcct ttttacggtt   1740
cctggccttt tgctggcctt tgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
```

```
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tatagggcgg cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
aggcggtttg cgtattgggc gccagggtgg ttttcttttt caccagtgag acgggcaaca    3480
gctgattgcc cttcaccgcc tggccctgag agagttgcag caagcggtcc acgctggttt    3540 gcccagcag gcgaaaatcc tgtttgatgg tggttgacgg cgggatataa catgagctgt    3600
cttcggtatc gtcgtatccc actaccgaga tatccgcacc aacgcgcagc ccggactcgg    3660
taatggcgcg cattgcgccc agcgccatct gatcgttggc aaccagcatc gcagtgggaa    3720
cgatgccctc attcagcatt tgcatggttt gttgaaaacc ggacatggca ctccagtcgc    3780
cttcccgttc cgctatcggc tgaatttgat tgcgagtgag atatttatgc cagccagcca    3840
gacgcagacg cgccgagaca gaacttaatg gtcccgctaa cagcgcgatt tgctgatgac    3900
ccaatgcgac cagatgctcc acgcccagtc gcgtaccgtc ttcatgggag aaaataatac    3960
tgttgatggg tgtctggtca gagacatcaa gaaataacgc cggaacatta gtgcaggcag    4020
cttccacagc aatggcatcc tggtcatcca gcggatagtt aatgatcagc ccactgacgc    4080
gttgcgcgag aagattgtgc accgccgctt tacaggcttc gacgccgctt cgttctacca    4140
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttttccg cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact tctatcccag agaggccaaa gtacagtgga aggtggataa    5040
cgccctccaa tcgggtaact cccaggagag tgtcacagag caggacagca aggacagcac    5100
```

| | |
|---|---|
| ctacagcctc agcagcaccc tgacgctgag caaagcagac tacgagaaac acaaagtcta | 5160 |
| cgcctgcgaa gtcacccatc agggcctgag ctcgccggtg acaaagagct tcaaccgcgg | 5220 |
| agagtgttaa taaacaggaa acagaagtcc atatgaaata tcttttacct acggcagccg | 5280 |
| caggtttgtt gttactcgcg gcccagccgg ccatggccgc tagcaccaag ggcccatcgg | 5340 |
| tcttccccct ggcaccctcc tccaagagca cctctggggg cacagcggcc ctgggctgcc | 5400 |
| tggtcaagga ctacttcccc gaaccggtga cggtgtcgtg gaactcaggc gccctgacca | 5460 |
| gcggcgtgca caccttcccg gctgtcctac agtcctcagg actctactcc ctcagcagcg | 5520 |
| tagtgaccgt gccctccagc agcttgggca cccagaccta catctgcaac gtgaatcaca | 5580 |
| agcccagcaa caccaaggtg gacaagaaag ttgagcccaa atcttgttaa gcttggctgt | 5640 |
| tttggcggat gagagaagat tttcagcctg atacagatta aatcagaacg cagaagcggt | 5700 |
| ctgataaaac agaatttgcc tggcggcagt agcgcggtgg tcccacctga ccccatgccg | 5760 |
| aactcagaag tgaaacgccg tagcgccgat ggtagtgtgg ggtctcccca tgcgagagta | 5820 |
| gggaactgcc aggcatcaaa taaaacgaaa ggctcagtcg aaagactggg cctttcgttt | 5880 |
| tatctgttgt ttgtcggtga acgctctcct gagtaggaca atccgccgg gagcggattt | 5940 |
| gaacgttgcg aagcaacggc ccggaggacc ctggcgggca ggacgccgc cataaactgc | 6000 |
| caggcatcaa attaagcaga aggccatcct gacggatggc cttttgcgt tctacaaac | 6060 |
| tctt | 6064 |

<210> SEQ ID NO 115
<211> LENGTH: 6094
<212> TYPE: DNA
<213> ORGANISM: Artificial sequence
<220> FEATURE:
<223> OTHER INFORMATION: plasmid pCkCH1Hy1

<400> SEQUENCE: 115

| | |
|---|---|
| ttgtttattt ttctaaatac attcaaatat gtatccgctc atgagacaat aaccctgata | 60 |
| aatgcttcaa taatattgaa aaaggaagag tatgagtatt caacatttcc gtgtcgccct | 120 |
| tattcccttt tttgcggcat tttgccttcc tgttttgct cacccagaaa cgctggtgaa | 180 |
| agtaaaagat gctgaagatc agttgggtgc acgagtgggt tacatcgaac tggatctcaa | 240 |
| cagcggtaag atccttgaga gttttcgccc cgaagaacgt tttccaatga tgagcacttt | 300 |
| taaagttctg ctatgtggcg cggtattatc ccgtgttgac gccgggcaag agcaactcgg | 360 |
| tcgccgcata cactattctc agaatgactt ggttgagtac tcaccagtca cagaaaagca | 420 |
| tcttacggat ggcatgacag taagagaatt atgcagtgct gccataacca tgagtgataa | 480 |
| cactgcggcc aacttacttc tgacaacgat cggaggaccg aaggagctaa ccgcttttt | 540 |
| gcacaacatg gggatcatg taactcgcct tgatcgttgg aaccggagc tgaatgaagc | 600 |
| cataccaaac gacgagcgtg acaccacgat gcctgtagca atggcaacaa cgttgcgcaa | 660 |
| actattaact ggcgaactac ttactctagc ttcccggcaa caattaatag actggatgga | 720 |
| ggcggataaa gttgcaggac cacttctgcg ctcggccctt ccggctggct ggtttattgc | 780 |
| tgataaatct ggagccggtg agcgtgggtc tcgcggtatc attgcagcac tggggccaga | 840 |
| tggtaagccc tcccgtatcg tagttatcta cacgacgggg agtcaggcaa ctatggatga | 900 |
| acgaaataga cagatcgctg agataggtgc ctcactgatt aagcattggt aactgtcaga | 960 |
| ccaagtttac tcatatatac tttagattga tttaaaactt cattttaat ttaaaaggat | 1020 |
| ctaggtgaag atcctttttg ataatctcat gaccaaaatc ccttaacgtg agttttcgtt | 1080 |

```
ccactgagcg tcagaccccg tagaaaagat caaaggatct tcttgagatc cttttttttct    1140 gcgcgtaatc tgctgcttgc aaacaaaaaa accaccgcta ccagcggtgg tttgtttgcc    1200
ggatcaagag ctaccaactc ttttccgaa  ggtaactggc ttcagcagag cgcagatacc    1260
aaatactgtc cttctagtgt agccgtagtt aggccaccac ttcaagaact ctgtagcacc    1320
gcctacatac ctcgctctgc taatcctgtt accagtggct gctgccagtg gcgataagtc    1380
gtgtcttacc gggttggact caagacgata gttaccggat aaggcgcagc ggtcgggctg    1440 aacgggggt  tcgtgcacac agcccagctt ggagcgaacg acctacaccg aactgagata    1500
cctacagcgt gagcattgag aaagcgccac gcttcccgaa gggagaaagg cggacaggta    1560
tccggtaagc ggcagggtcg aacaggaga  gcgcacgagg gagcttccag ggggaaacgc    1620
ctggtatctt tatagtcctg tcgggtttcg ccacctctga cttgagcgtc gattttttgtg   1680 atgctcgtca gggggcgga  gcctatggaa aaacgccagc aacgcggcct ttttacggtt    1740
cctggccttt tgctggcctt tgctcacat  gttctttcct gcgttatccc ctgattctgt    1800
ggataaccgt attaccgcct ttgagtgagc tgataccgct cgccgcagcc gaacgaccga    1860
gcgcagcgag tcagtgagcg aggaagcgga agagcgcctg atgcggtatt ttctccttac    1920
gcatctgtgc ggtatttcac accgcatata tggtgcactc tcagtacaat ctgctctgat    1980
gccgcatagt taagccagta tacactccgc tatcgctacg tgactgggtc atggctgcgc    2040
cccgacaccc gccaacaccc gctgacgcgc cctgacgggc ttgtctgctc ccggcatccg    2100
cttacagaca agctgtgacc gtctccggga gctgcatgtg tcagaggttt tcaccgtcat    2160
caccgaaacg cgcgaggcag ctgcggtaaa gctcatcagc gtggtcgtga agcgattcac    2220
agatgtctgc ctgttcatcc gcgtccagct cgttgagttt ctccagaagc gttaatgtct    2280
ggcttctgat aaagcgggcc atgttaaggg cggttttttc ctgtttggtc acttgatgcc    2340
tccgtgtaag ggggaatttc tgttcatggg ggtaatgata ccgatgaaac gagagaggat    2400
gctcacgata cgggttactg atgatgaaca tgcccggtta ctggaacgtt gtgagggtaa    2460
acaactggcg gtatggatgc ggcgggacca gagaaaaatc actcagggtc aatgccagcg    2520
cttcgttaat acagatgtag gtgttccaca gggtagccag cagcatcctg cgatgcagat    2580
ccggaacata atggtgcagg cgctgactt  ccgcgtttcc agactttacg aaacacggaa    2640
accgaagacc attcatgttg ttgctcaggt cgcagacgtt ttgcagcagc agtcgcttca    2700
cgttcgctcg cgtatcggtg attcattctg ctaaccagta aggcaacccc gccagcctag    2760
ccgggtcctc aacgacagga gcacgatcat gcgcacccgt ggccaggacc caacgctgcc    2820
cgagatgcgc cgcgtgcggc tgctggagat ggcggacgcg atggatatgt tctgccaagg    2880
gttggtttgc gcattcacag ttctccgcaa gaattgattg gctccaattc ttggagtggt    2940
gaatccgtta gcgaggtgcc gccggcttcc attcaggtcg aggtggcccg gctccatgca    3000
ccgcgacgca acgcggggag gcagacaagg tataggcgg  cgcctacaat ccatgccaac    3060
ccgttccatg tgctcgccga ggcggcataa atcgccgtga cgatcagcgg tccagtgatc    3120
gaagttaggc tggtaagagc cgcgagcgat ccttgaagct gtccctgatg gtcgtcatct    3180
acctgcctgg acagcatggc ctgcaacgcg ggcatcccga tgccgccgga agcgagaaga    3240
atcataatgg ggaaggccat ccagcctcgc gtcgcgaacg ccagcaagac gtagcccagc    3300
gcgtcggcca gcttgcaatt cgcgctaact tacattaatt gcgttgcgct cactgcccgc    3360
tttccagtcg ggaaacctgt cgtgccagct gcattaatga atcggccaac gcgcggggag    3420
```

```
aggcggtttg cgtattgggc gccagggtgg ttttctttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200 gcgacgcgc gtgcagggcc agactggagg tggcaacgcc aatcagcaac gactgtttgc   4260
ccgccagttg ttgtgccacg cggttgggaa tgtaattcag ctccgccatc gccgcttcca   4320 cttttcccg cgttttcgca gaaacgtggc tggcctggtt caccacgcgg gaaacggtct   4380
gataagagac accggcatac tctgcgacat cgtataacgt tactggtttc acattcacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag cgcactccc   4680 gttctggata atgttttttg cgccgacatc ataacggttc tggcaaatat tctgaaatga   4740
gctgttgaca attaatcatc ggctcgtata atgtgtggaa ttgtgagcgg ataacaattt   4800
cacacaggaa acagaattcc atatgaaata cctattacca acagcagcag ctgggttatt   4860
attgctcgct gcgcagccgg ccatggccca ggtcaccgtc tcctcacgta cggtggctgc   4920
accatctgtc ttcatcttcc cgccatctga tgagcagttg aaatctggaa ctgcctctgt   4980
tgtgtgcctg ctgaataact tctatcccag agaggccaaa gtacagtgga aggtggataa   5040
cgccctccaa tcgggtaact cccaggagag tgtcacagag caggacagca aggacagcac   5100
ctacagcctc agcagcaccc tgacgctgag caaagcagac tacgagaaac acaaagtcta   5160
cgcctgcgaa gtcaccccatc agggcctgag ctcgccggtg acaaagagct tcaaccgcgg   5220
agagtgttaa taaacaggaa acagaagtcc atatgaaata tctttttacct acggcagccg   5280 caggtttgtt gttactcgcg gcccagccgg ccatggccgc tagcaccaag ggcccatcgg   5340
tcttccccct ggcaccctcc tccaagagca cctctggggg cacagcggcc ctgggctgcc   5400
tggtcaagga ctacttcccc gaaccggtga cggtgtcgtg gaactcaggc gccctgacca   5460
gcggcgtgca caccttcccg gctgtcctac agtcctcagg actctactcc ctcagcagcg   5520
tagtgaccgt gccctccagc agcttgggca cccagaccta catctgcaac gtgaatcaca   5580
agcccagcaa caccaaggtg gacaagaaag ttgagcccaa atcttgtgac aaaactcaca   5640
catgcccacc gtgcccataa gcttggctgt tttggcggat gagagaagat tttcagcctg   5700
atacagatta aatcagaacg cagaagcggt ctgataaaac agaatttgcc tggcggcagt   5760
agcgcggtgg tcccacctga ccccatgccg aactcagaag tgaaacgccg tagcgccgat   5820
```

```
ggtagtgtgg ggtctcccca tgcgagagta gggaactgcc aggcatcaaa taaaacgaaa    5880
ggctcagtcg aaagactggg cctttcgttt tatctgttgt ttgtcggtga acgctctcct    5940
gagtaggaca aatccgccgg gagcggattt gaacgttgcg aagcaacggc ccggaggacc    6000
ctggcgggca ggacgccgc cataaactgc caggcatcaa attaagcaga aggccatcct     6060
gacggatggc cttttgcgt ttctacaaac tctt                                 6094

<210> SEQ ID NO 116
<211> LENGTH: 6745
<212> TYPE: DNA
<213> ORGANISM: Artificial sequence
<220> FEATURE:
<223> OTHER INFORMATION: plasmid pMabyl*

<400> SEQUENCE: 116
ttgtttattt ttctaaatac attcaaatat gtatccgctc atgagacaat aaccctgata      60
aatgcttcaa taatattgaa aaaggaagag tatgagtatt caacatttcc gtgtcgccct    120
tattcccttt tttgcggcat tttgccttcc tgttttgct cacccagaaa cgctggtgaa     180
agtaaaagat gctgaagatc agttgggtgc acgagtgggt tacatcgaac tggatctcaa    240
cagcggtaag atccttgaga gttttcgccc cgaagaacgt tttccaatga tgagcacttt    300
taaagttctg ctatgtggcg cggtattatc ccgtgttgac gccgggcaag agcaactcgg    360
tcgccgcata cactattctc agaatgactt ggttgagtac tcaccagtca cagaaaagca    420
tcttacggat ggcatgacag taagagaatt atgcagtgct gccataacca tgagtgataa    480
cactgcggcc aacttacttc tgacaacgat cggaggaccg aaggagctaa ccgcttttt     540 gcacaacatg gggatcatg taactcgcct tgatcgttgg gaaccggagc tgaatgaagc     600
cataccaaac gacgagcgtg acaccacgat gcctgtagca atggcaacaa cgttgcgcaa    660
actattaact ggcgaactac ttactctagc ttcccggcaa caattaatag actggatgga    720
ggcggataaa gttgcaggac cacttctgcg ctcggccctt ccggctggct ggtttattgc    780
tgataaatct ggagccggtg agcgtgggtc tcgcggtatc attgcagcac tggggccaga    840
tggtaagccc tcccgtatcg tagttatcta cacgacgggg agtcaggcaa ctatggatga    900
acgaaataga cagatcgctg agataggtgc ctcactgatt aagcattggt aactgtcaga    960
ccaagtttac tcatatatac tttagattga tttaaaactt catttttaat ttaaaaggat   1020
ctaggtgaag atcctttttg ataatctcat gaccaaaatc ccttaacgtg agttttcgtt   1080
ccactgagcg tcagaccccg tagaaaagat caaaggatct tcttgagatc ctttttttct   1140
gcgcgtaatc tgctgcttgc aaacaaaaaa accaccgcta ccagcggtgg tttgtttgcc   1200
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
```

```
cctggcctttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatgcatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg cgctgacttc cgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt ctgccaagg   2880
gttggtttgc gcattcacag ttctccgcaa gaattgattg ctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg ttttttcttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
```

-continued

```
tcgacaccac cacgctggca cccagttgat cggcgcgaga tttaatcgcc gcgacaattt    4200
gcgacggcgc gtgcagggcc agactggagg tggcaacgcc aatcagcaac gactgtttgc    4260
ccgccagttg ttgtgccacg cggttgggaa tgtaattcag ctccgccatc gccgcttcca    4320
cttttcccg  cgttttcgca gaaacgtggc tggcctggtt caccacgcgg gaaacggtct    4380
gataagagac accggcatac tctgcgacat cgtataacgt tactggtttc acattcacca    4440
ccctgaattg actctcttcc gggcgctatc atgccatacc gcgaaaggtt ttgcgccatt    4500
cgatggtgtc aacgtaaatg catgccgctt cgccttcgcg cgcgaattgc aagctgatcc    4560
ggagcttatc gactgcacgg tgcaccaatg cttctggcgt caggcagcca tcggaagctg    4620
tggtatggct gtgcaggtcg taaatcactg cataattcgt gtcgctcaag gcgcactccc    4680
gttctggata tgttttttg  cgccgacatc ataacggttc tggcaaatat tctgaaatga    4740
gctgttgaca attaatcatc ggctcgtata atgtgtggaa ttgtgagcgg ataacaattt    4800
cacacaggaa acagaattcc atatgaaata cctattacca acagcagcag ctgggttatt    4860
attgctcgct gcgcagccgg ccatggccca ggtcaccgtc tcctcacgta cggtggctgc    4920
accatctgtc ttcatcttcc cgccatctga tgagcagttg aaatctggaa ctgcctctgt    4980
tgtgtgcctg ctgaataact ctatcccag  agaggccaaa gtacagtgga aggtggataa    5040
cgccctccaa tcgggtaact cccaggagag tgtcacagag caggacagca aggacagcac    5100
ctacagcctc agcagcaccc tgacgctgag caaagcagac tacgagaaac acaaagtcta    5160
cgcctgcgaa gtcacccatc agggcctgag ctcgccggtg acaaagagct caaccgcgg    5220
agagtgttaa taaacaggaa acagaagtcc atatgaaata tcttttacct acggcagccg    5280
caggtttgtt gttactcgcg gcccagccgg ccatggccgc tagcaccaag ggcccatcgg    5340
tcttcccct  ggcacccctcc tccaagagca cctctggggg cacagcggcc ctgggctgcc    5400
tggtcaagga ctacttcccc gaaccggtga cggtgtcgtg gaactcaggc gccctgacca    5460
gcggcgtgca caccttcccg gctgtcctac agtcctcagg actctactcc ctcagcagcg    5520
tggtgaccgt gccctccagc agcttgggca cccagaccta catctgcaac gtgaatcaca    5580
agcccagcaa caccaaggtg gacaagaaag ttgagcccaa atcttgtgac aaaactcaca    5640
catgcccacc gtgcccagca cctgaactcc tggggggacc gtcagtcttc ctcttccccc    5700
caaaacccaa ggacaccctc atgatctccc ggacccctga ggtcacatgc gtggtggtgg    5760
acgtgagcca cgaagaccct gaggtcaagt tcaactggta cgtggacggc gtggaggtgc    5820
ataatgccaa gacaaagccg cgggaggagc agtacaacag cacgtaccgg gtggtcagcg    5880
tcctcaccgt cctgcaccag gactggctga atggcaagga gtacaagtgc aaggtctcca    5940
acaaagccct cccagccccc atcgagaaaa ccatctccaa agccaaaggg cagccccgag    6000
aaccacaggt gtacaccctg cccccatccc gggatgagct gaccaagaac caggtcagcc    6060
tgacctgcct ggtcaaaggc ttctatccca gcgacatcgc cgtggagtgg gagagcaatg    6120
ggcagccgga gaacaactac aagaccacgc ctcccgtgct ggactccgac ggctccttct    6180
tcctctacag caagctcacc gtggacaaga gcaggtggca gcagggggaac gtcttctcat    6240
gctccgtgat gcatgaggct ctgcacaacc actacacgca gaagagcctc tccctgtctc    6300
cgggtaaata agcttggctg ttttggcgga tgagagaaga ttttcagcct gatacagatt    6360
aaatcagaac gcagaagcgg tctgataaaa cagaatttgc ctggcggcag tagcgcggtg    6420
gtcccacctg accccatgcc gaactcagaa gtgaaacgcc gtagcgccga tggtagtgtg    6480
```

```
gggtctcccc atgcgagagt agggaactgc caggcatcaa ataaaacgaa aggctcagtc      6540
gaaagactgg gcctttcgtt ttatctgttg tttgtcggtg aacgctctcc tgagtaggac      6600
aaatccgccg ggagcggatt tgaacgttgc gaagcaacgg cccggaggac cctggcgggc      6660
aggacgcccg ccataaactg ccaggcatca aattaagcag aaggccatcc tgacggatgg      6720 ccttttgcg tttctacaaa ctctt                                             6745

<210> SEQ ID NO 117
<211> LENGTH: 119
<212> TYPE: DNA
<213> ORGANISM: Artificial sequence
<220> FEATURE:
<223> OTHER INFORMATION: oligonuclotide 5'Flag/RBS/35-sup

<400> SEQUENCE: 117
ggagagtgtg caggtgatta caaagacgat gacgataagt aataaacagg aaacagaagt        60
ccatatgaaa tatcttttac ctacggcagc cgcaggtttg ttgttactcg cggcccagc        119

<210> SEQ ID NO 118
<211> LENGTH: 118
<212> TYPE: DNA
<213> ORGANISM: Artificial sequence
<220> FEATURE:
<223> OTHER INFORMATION: oligonucleotide 5'Flag/RBS/35-inf

<400> SEQUENCE: 118
gggccgcgag taacaacaaa cctgcggctg ccgtaggtaa aagatatttc atatggactt        60
ctgtttcctg tttattactt atcgtcatcg tctttgtaat cacctgcaca ctctccgc        118

<210> SEQ ID NO 119
<211> LENGTH: 59
<212> TYPE: DNA
<213> ORGANISM: Artificial sequence
<220> FEATURE:
<223> OTHER INFORMATION: oligonuclotide 5'Ck

<400> SEQUENCE: 119
ggggccaggg gacccaggtc accgtctcct cacgtacggt ggctgcacca tctgtcttc        59

<210> SEQ ID NO 120
<211> LENGTH: 89
<212> TYPE: DNA
<213> ORGANISM: Artificial sequence
<220> FEATURE:
<223> OTHER INFORMATION: oligonucleotide 5'RBS/35-sup

<400> SEQUENCE: 120
ggagagtgtt aataaacagg aaacagaagt ccatatgaaa tatcttttac ctacggcagc        60
cgcaggtttg ttgttactcg cggcccagc                                         89

<210> SEQ ID NO 121
<211> LENGTH: 88
<212> TYPE: DNA
<213> ORGANISM: Artificial sequence
<220> FEATURE:
<223> OTHER INFORMATION: oligonucleotide 3'RBS/35-inf

<400> SEQUENCE: 121
gggccgcgag taacaacaaa cctgcggctg ccgtaggtaa aagatatttc atatggactt        60
ctgtttcctg tttattaaca ctctccgc                                          88
```

```
<210> SEQ ID NO 122
<211> LENGTH: 18
<212> TYPE: DNA
<213> ORGANISM: Artificial sequence
<220> FEATURE:
<223> OTHER INFORMATION: oligonucleotide 3' inf-Pst1+ 71

<400> SEQUENCE: 122
gttaaacggc gagcaccg                                                    18
```